(12) United States Patent
Wu et al.

(10) Patent No.: US 11,345,678 B2
(45) Date of Patent: May 31, 2022

(54) BENZOPYRAZOLE COMPOUND USED AS RHO KINASE INHIBITOR

(71) Applicant: MEDSHINE DISCOVERY INC., Jiangsu (CN)

(72) Inventors: Lingyun Wu, Shanghai (CN); Jun Yin, Shanghai (CN); Cailin Wang, Shanghai (CN); Zheming Xiao, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/047,840

(22) PCT Filed: Apr. 18, 2019

(86) PCT No.: PCT/CN2019/083210
§ 371 (c)(1),
(2) Date: Oct. 15, 2020

(87) PCT Pub. No.: WO2019/201297
PCT Pub. Date: Oct. 24, 2019

(65) Prior Publication Data
US 2021/0371393 A1   Dec. 2, 2021

(30) Foreign Application Priority Data

Apr. 18, 2018 (CN) .......................... 201810349362.X
Oct. 19, 2018 (CN) .......................... 201811221303.0

(51) Int. Cl.
| | |
|---|---|
| *C07D 403/04* | (2006.01) |
| *C07D 403/12* | (2006.01) |
| *C07D 401/04* | (2006.01) |
| *A61P 11/00* | (2006.01) |
| *C07D 231/56* | (2006.01) |

(52) U.S. Cl.
CPC ............ *C07D 401/04* (2013.01); *A61P 11/00* (2018.01); *C07D 231/56* (2013.01); *C07D 403/04* (2013.01); *C07D 403/12* (2013.01)

(58) Field of Classification Search
CPC ...... C07D 403/04; C07D 403/12; A61P 11/00
USPC .................................................. 514/254.06
See application file for complete search history.

(56) References Cited

U.S. PATENT DOCUMENTS 8,822,478 B2 * 9/2014 Hood .................... A61K 31/541
514/256

FOREIGN PATENT DOCUMENTS

| | | |
|---|---|---|
| CN | 101903349 A | 12/2010 |
| CN | 105358547 A | 2/2016 |
| WO | WO-2005074643 A2 | 8/2005 |
| WO | WO-2006105081 A2 | 10/2006 |
| WO | WO-2007084667 A2 | 7/2007 |
| WO | WO-2008054599 A2 | 5/2008 |
| WO | WO-2010104851 A1 | 9/2010 |
| WO | WO-2011050245 A1 | 4/2011 |
| WO | WO-2012135697 A2 | 10/2012 |
| WO | WO-201 4055996 A2 | 4/2014 |
| WO | WO-2014134388 A1 | 9/2014 |
| WO | WO-2016028971 A1 | 2/2016 |

OTHER PUBLICATIONS

International Search Report and Written Opinion regarding International Application No. PCT/CN2019/083210, dated Jun. 27, 2019.
Extended European Search Report regarding EP 19788388.7 dated Apr. 20, 2021.
Feb. 18, 2022 Chinese Office Action issued in Chinese Patent Application No. 201980026510.7.

* cited by examiner

*Primary Examiner* — Niloofar Rahmani

(57) ABSTRACT

The invention relates to a benzopyrazole compound used as RHO kinase inhibitor, a pharmaceutical composition and uses thereof for preparing an RHO kinase inhibiting drug, and more specifically to said compound of formula (I-1), a pharmaceutically acceptable salt and isomer thereof.

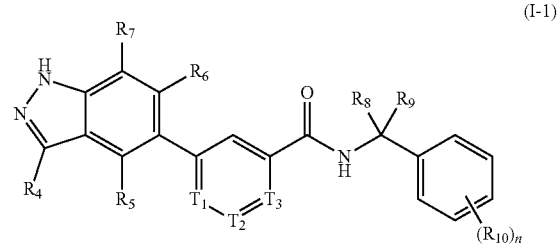

19 Claims, 3 Drawing Sheets

BENZOPYRAZOLE COMPOUND USED AS RHO KINASE INHIBITOR

CROSS REFERENCES TO RELATED APPLICATIONS

The present application is a U.S. National Phase Application under 35 U.S.C. 371 of International Application No. PCT/CN2019/083210, filed Apr. 18, 2019, which claims the benefits of: CN201810349362.X, filed Apr. 18, 2018 and CN201811221303.0, filed Oct. 19, 2018. The entire disclosures of the above applications are incorporated herein by reference.

TECHNICAL FIELD

The present disclosure relates to the field of medicament, in particular to a class of benzopyrazole compounds used as RHO kinase inhibitors, pharmaceutically acceptable salts thereof, isomers thereof, pharmaceutical compositions thereof and a use thereof in manufacturing a medicament used as RHO inhibitor.

PRIOR ART

RHO associated protein kinase (abbreviated as ROCK) belonging to serine/threonine protein kinase, is a downstream target effector of RHO, and is widely expressed in human body. RHO associated protein kinase (ROCK) is involved in the regulation of myosin light chain (MLC) and is suitable for the treatment of vasodilation. New research supports that ROCK kinase is involved in the regulation of TH17 cell immune response and the activation of fibroblasts, thereby the adaptation diseases thereof can be expanded to lung diseases including pulmonary fibrosis, asthma, and the like, and further expanded to autoimmune diseases. The ROCK kinase family includes two subtypes of ROCK1 and ROCK2, and ROCK2 kinase is related to the actions of inflammation and fibrosis. Since selective ROCK2 inhibitors did not cause vasodilation at high concentrations in isolated vasodilation experiments, they can reduce cardiovascular side effects. Although mice with ROCK1 knocked out have low embryonic mortality, most of them die after birth due to cytoskeletal mutations caused by reduced MLC phosphorylation. Although 90% of the mice with ROCK2 knocked out die in embryonic stage, there's no difference between the survived mice and wild-type mice, thus selective inhibition of ROCK2 activity may have higher safety. Therefore, selective ROCK2 protein kinase inhibitor can avoid cardiovascular side effects of drugs.

KD025 (WO2006105081; WO2008054599; WO2010104851; WO2014055996) is an oral selective inhibitor of ROCK2 kinase developed by Kadmon company. Studies have shown that KD025 is a representative of a new mechanism to treat idiopathic pulmonary fibrosis (IPF) by inhibiting protein (such as RHO kinase) that regulates fibrosis. The cause of idiopathic pulmonary fibrosis (IPF) may be body damage. The body's response to injury involves reorganization of actin cytoskeleton of a variety of cells (such as epithelial cells, fibroblasts, endothelial cells, and macrophages), and the assembly of actin filaments and the contraction of actomyosin are regulated by proteins of RHO kinase family (including ROCK1 and ROCK2). Previous studies have shown that the proteins of RHO kinase family are activated in the lungs of IPF patients and animal models of this disease, and RHO kinase inhibitors can prevent tissue fibrosis in these models and induce the regression of the established fibrosis. Phase II clinical trials for the treatment of moderate to severe psoriasis have been completed, and phase II clinical trials for the treatment of idiopathic pulmonary fibrosis (IPF) are now implemented.

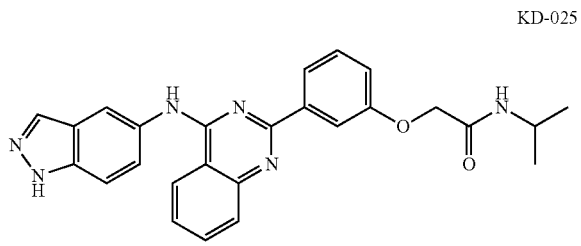 [SMILES: CC(C)NC(=O)COc1cccc(-c2nc(Nc3ccc4[nH]ncc4c3)c3ccccc3n2)c1]

KD-025

WO2014134388 and WO2016028971 also disclose a class of compounds with general formula thereof represented by formula (a) and formula (b), such compounds can also be used for cardiovascular diseases, neuropathological diseases, tumors, autoimmune diseases, pulmonary fibrosis, inflammatory diseases, etc.

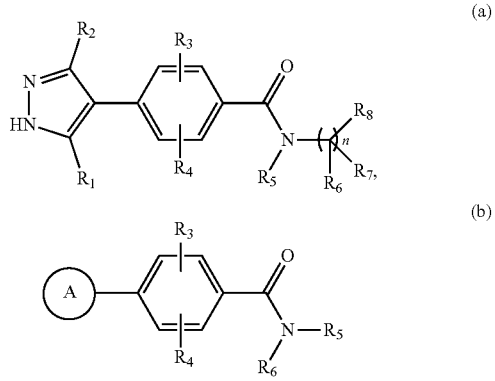

CONTENT OF THE INVENTION

The present disclosure provides compounds with a new core structure, which can inhibit the activity of ROCK2, thus can be used to treat ROCK2 related diseases.

In one aspect, the present disclosure provides a compound represented by formula (I-1), a pharmaceutically acceptable salt thereof or an isomer thereof,

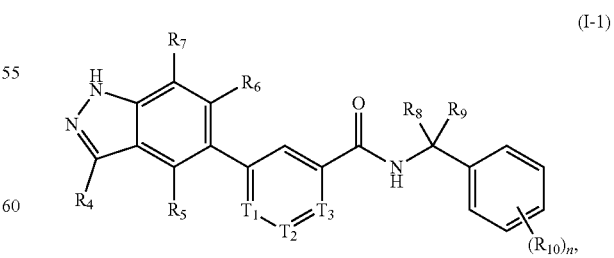

(I-1)

wherein, $T_1$ is N or $CR_1$; $T_2$ is N or $CR_2$; $T_3$ is N or $CR_3$;

$R_1$, $R_2$ and $R_3$ are each independently H, F, Cl, Br, CN, $-OR_a$, $-C(=O)NR_bR_c$ or $C_{1-6}$ alkyl, wherein the $C_{1-6}$ alkyl is optionally substituted by 1, 2 or 3 substituents independently selected from F, Cl, Br, I, —OH, —OCH$_3$, —CN, —NH$_2$, —NO$_2$ or 5-membered heterocycloalkyl;

or, $R_2$ and $R_3$ with the carbon atoms to which they are attached are linked together so that the moiety

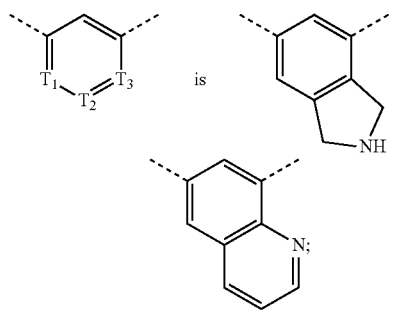 is 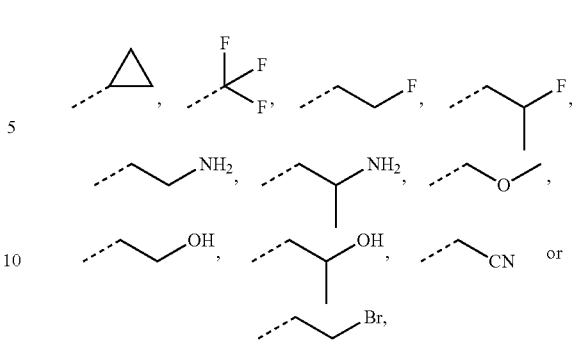 or $R_4$, $R_5$, $R_6$ and $R_7$ are each independently H, F, Cl, Br, CN, —OR$_a$, —C(=O)NR$_b$R$_c$, —NR$_d$R$_e$, $C_{1-6}$ alkyl or $C_{3-6}$ cycloalkyl, wherein the $C_{1-6}$ alkyl and $C_{3-6}$ cycloalkyl are optionally substituted by 1, 2 or 3 substituents independently selected from F, Cl, Br, I, —OH, —OCH$_3$, —CN, —NH$_2$, —NO$_2$ or $C_{1-4}$ alkyl;

$R_8$ and $R_9$ are each independently H, F, Cl, $C_{1-6}$ alkyl, or $R_8$ and $R_9$ together with the carbon atom to which they are attached form a 5- to 6-membered heterocycloalkyl, wherein the $C_{1-6}$ alkyl and 5- to 6-membered heterocycloalkyl are optionally substituted by 1, 2 or 3 substituents independently selected from F, Cl, Br, CN, —OR$_a$ or —NR$_d$R$_e$;

each of $R_{10}$ is independently F, Cl, Br, CN, —OR$_a$, $C_{1-6}$ alkyl or $C_{3-6}$ cycloalkyl, wherein the $C_{1-6}$ alkyl and $C_{3-6}$ cycloalkyl are optionally substituted by 1, 2 or 3 substituents independently selected from F, Cl, Br, I, —OH, —OCH$_3$, —CN, —NH$_2$, —NO$_2$ or $C_{1-4}$ alkyl;

$R_a$, $R_b$ and $R_c$ are each independently H, $C_{1-6}$ alkyl or $C_{3-4}$ cycloalkyl, wherein the $C_{1-6}$ alkyl and $C_{3-4}$ cycloalkyl are optionally substituted by 1, 2 or 3 substituents independently selected from F, Cl, Br, —OH, —OCH$_3$, —CN, —NH$_2$ or —NO$_2$;

$R_d$ and $R_e$ are each independently H, $C_{1-6}$ alkyl, —S(=O)$_2$C$_{1-3}$ alkyl, or $R_d$ and $R_e$ together with the N atom to which they are attached form a 4- to 8-membered heterocycloalkyl, wherein the $C_{1-6}$ alkyl and 4- to 8-membered heterocycloalkyl are optionally substituted by 1, 2 or 3 substituents independently selected from F, Cl, Br, —OH, —OCH$_3$, —CN, —NH$_2$, $C_{1-6}$ alkylamino or —NO$_2$;

n is 0, 1, 2, 3 or 4;

the 5-membered heterocycloalkyl, 5- to 6-membered heterocycloalkyl and 4- to 8-membered heterocycloalkyl contains 1, 2, 3 or 4 heteroatoms or heteroatomic groups independently selected from N, —O—, —S— and —NH—.

In some embodiments of the present disclosure, $R_a$, $R_b$ and $R_c$ are each independently H, methyl, ethyl, n-propyl, isopropyl or cyclopropyl, wherein the methyl, ethyl, n-propyl, isopropyl and cyclopropyl are optionally substituted by 1, 2 or 3 substituents independently selected from F, Cl, Br, I, —OH, —OCH$_3$, CN, —NH$_2$ or —NO$_2$, the other variables are as defined in the present disclosure.

In some embodiments of the present disclosure, $R_a$, $R_b$ and $R_c$ are each independently H, methyl, ethyl, n-propyl, isopropyl

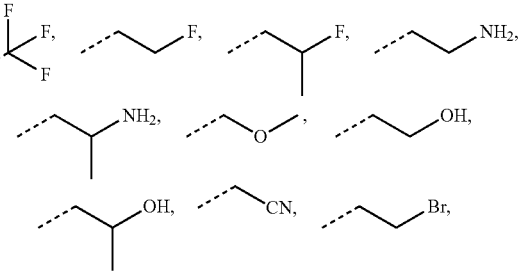

the other variables are as defined in the present disclosure.

In some embodiments of the present disclosure, $R_4$, $R_5$, $R_6$ and $R_7$ are each independently H, F, Cl, Br, CN, —OH, —OCH$_3$, —OCH$_2$CH$_3$, —C(=O)NH$_2$, —NH$_2$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, $R_4$, $R_5$, $R_6$ and $R_7$ are each independently H, F, Cl, Br, CN, —OH, —OCH$_3$, —OCH$_2$CH$_3$, —C(=O)NH$_2$, —NH$_2$, methyl, ethyl, n-propyl, isopropyl,

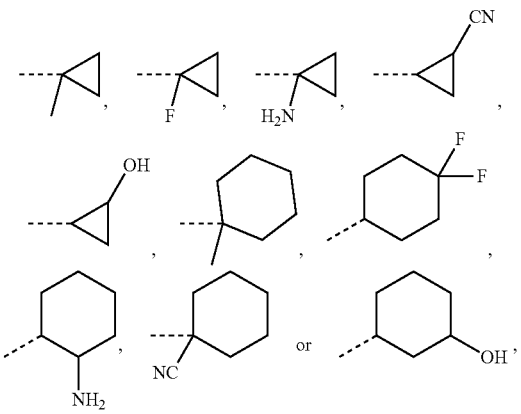

cyclopropyl, cyclopentyl, cyclohexyl, the other variables are as defined in the present disclosure.

In some embodiments of the present disclosure, $R_1$, $R_2$ and $R_3$ are each independently H, F, Cl, Br, CN, —OH, —OCH$_3$, —OCHF$_2$, —OCF$_3$, —C(=O)NH$_2$, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH₃, CN, —NH₂, —NO₂, or pyrrolidyl, the other variables are as defined in the present disclosure.

In some embodiments of the present disclosure, $R_1$, $R_2$ and $R_3$ are each independently H, F, Cl, Br, CN, —OH, —OCH₃, —OCHF₂, —OCF₃, —C(=O)NH₂, methyl, ethyl, n-propyl, isopropyl,

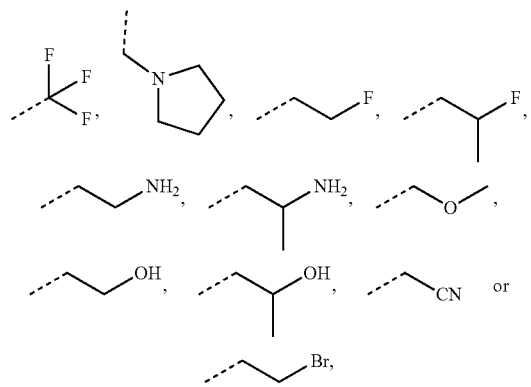

the other variables are as defined in the present disclosure.

In some embodiments of the present disclosure, the moiety

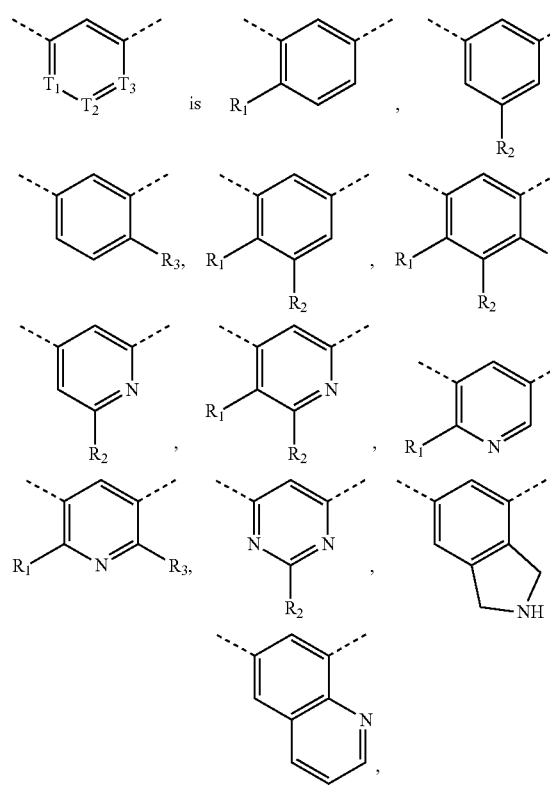

$R_1$, $R_2$, $R_3$ and the other variables are as defined in the present disclosure.

In some embodiments of the present disclosure, the moiety

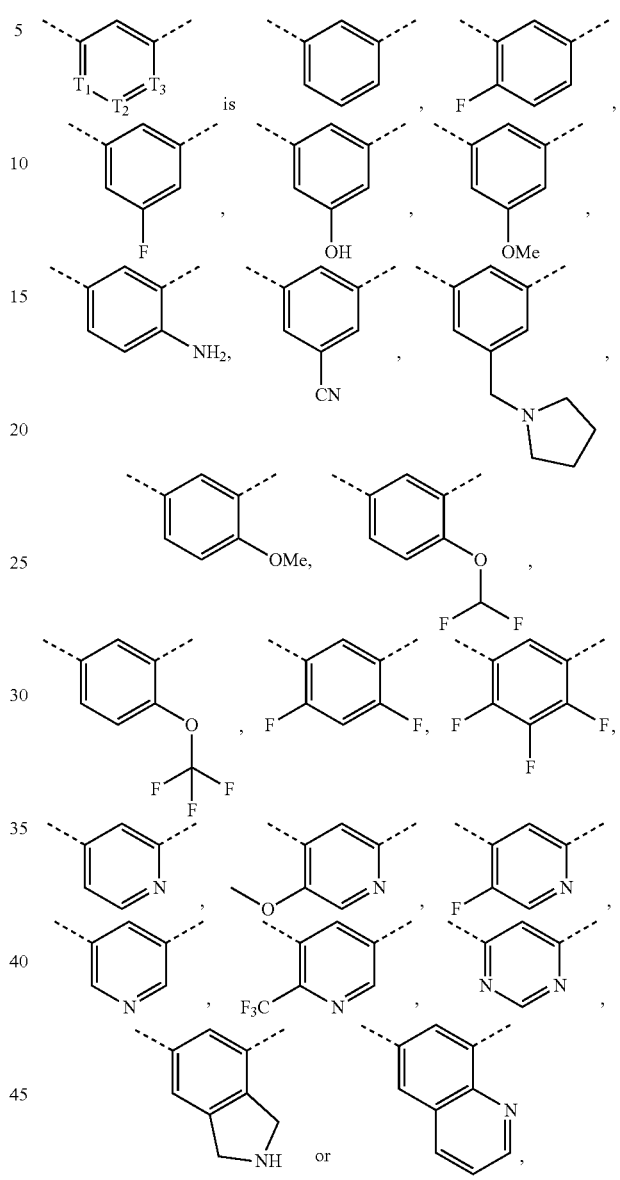

the other variables are as defined in the present disclosure.

In some embodiments of the present disclosure, $R_d$ and $R_e$ are each independently H, methyl, ethyl, n-propyl, isopropyl,

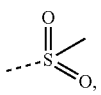

or $R_d$ and $R_e$ together with the N atom to which they are attached form a 5- to 6-membered heterocycloalkyl, wherein the methyl, ethyl, n-propyl, isopropyl, and 5- to 6-membered heterocycloalkyl are optionally substituted by 1, 2 or 3 substituents independently selected from F, Cl, Br, I, —OH, —OCH₃, CN, —NH₂, $C_{1-3}$ alkylamino or —NO₂, the other variables are as defined in the present disclosure.

In some embodiments of the present disclosure, $R_d$ and $R_e$ are each independently H, methyl, ethyl, n-propyl, isopropyl,

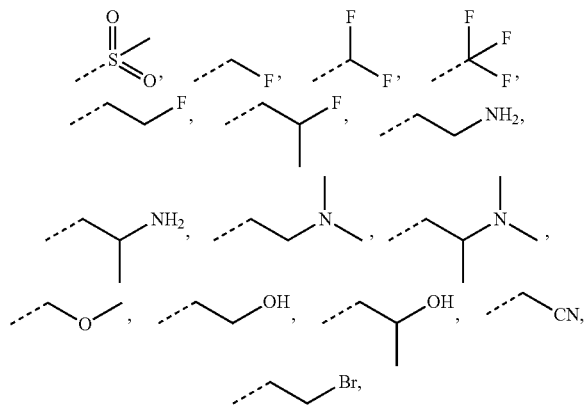

or $R_d$ and $R_e$ together with the N atom to which they are attached form a pyrrolidyl, piperazinyl or piperidyl, wherein the pyrrolidyl, piperazinyl and piperidyl are optionally substituted by 1, 2 or 3 substituents independently selected from F, Cl, Br, I, —OH, —OCH$_3$, CN, —NH$_2$, C$_{1-3}$ alkylamino or —NO$_2$, the other variables are as defined in the present disclosure.

In some embodiments of the present disclosure, $R_8$ and $R_9$ are each independently H, F, Cl, methyl, ethyl, n-propyl, isopropyl,

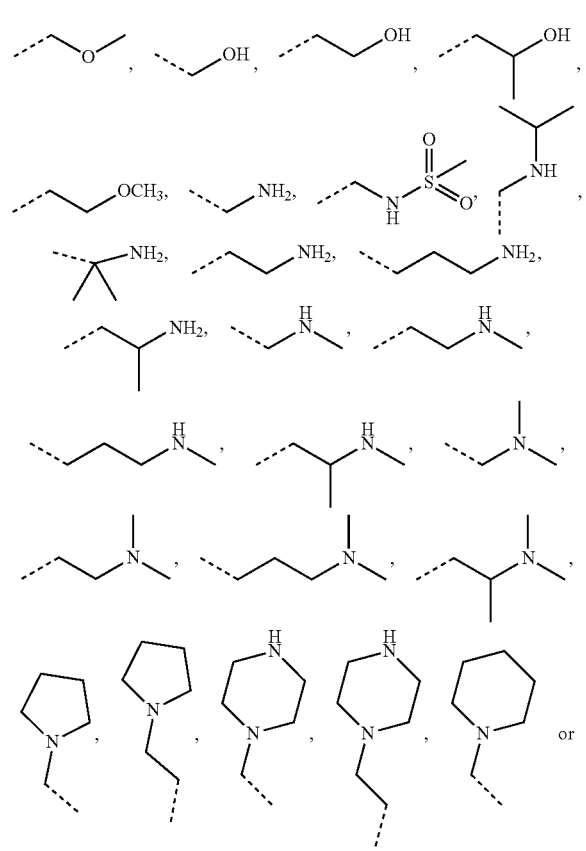

the other variables are as defined in the present disclosure.

In some embodiments of the present disclosure, $R_8$ and $R_9$ together with the carbon atom to which they are attached form

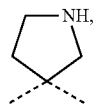

the other variables are as defined in the present disclosure.

In some embodiments of the present disclosure, each of $R_{10}$ is independently F, Cl, Br, CN, —OH, —OCH$_3$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, each of $R_{10}$ is independently F, Cl, Br, CN, —OH, —OCH$_3$, —OCH$_2$CH$_3$,

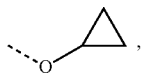

methyl, ethyl, n-propyl, isopropyl,

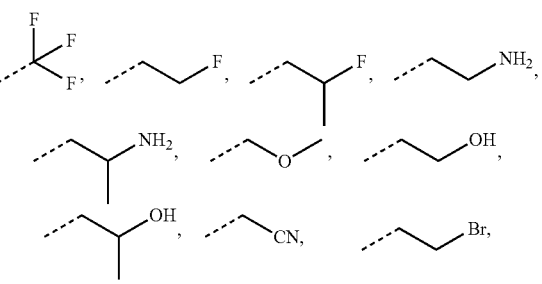

cyclopropyl cyclopentyl, cyclohexyl,

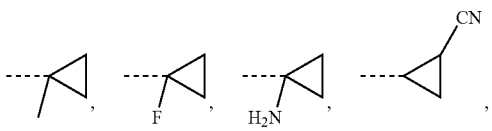

-continued
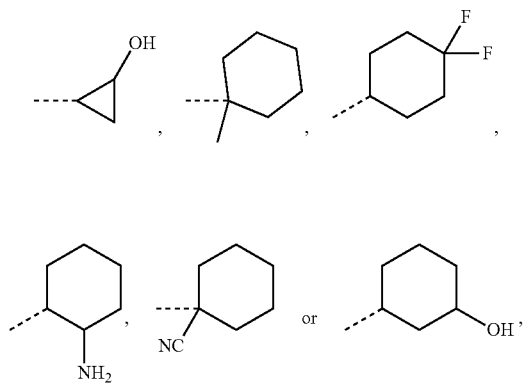
the other variables are as defined in the present disclosure.
In some embodiments of the present disclosure, the moiety
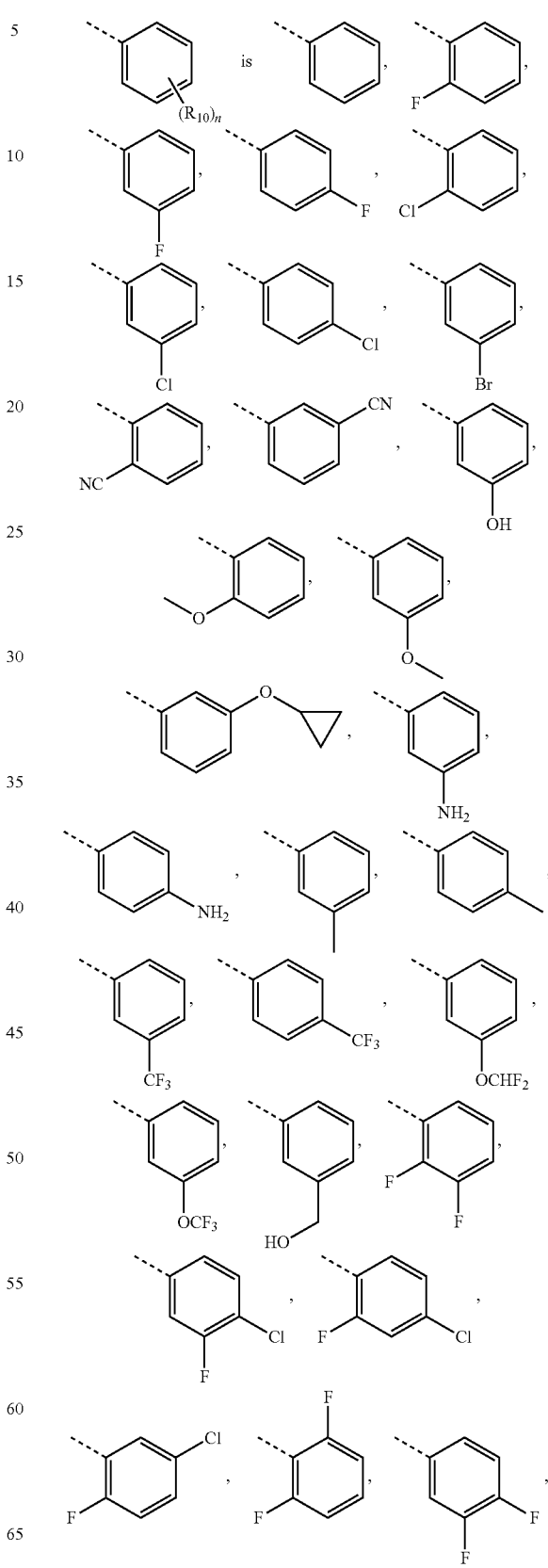
$R_{10}$ and the other variables are as defined in the present disclosure.
In some embodiments of the present disclosure, the moiety

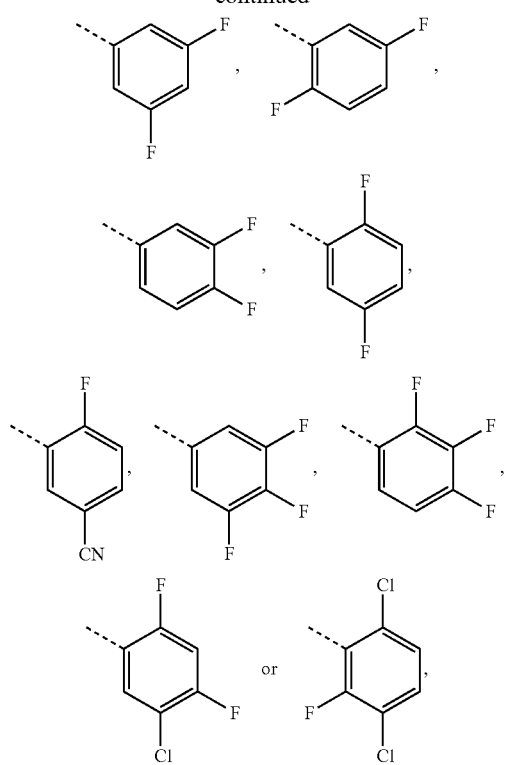
the other variables are as defined in the present disclosure.
In some embodiments of the present disclosure, the compound is represented by formula (I-2') to (I-5'),
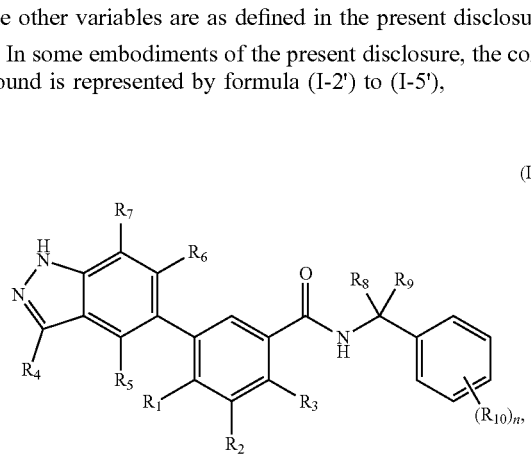
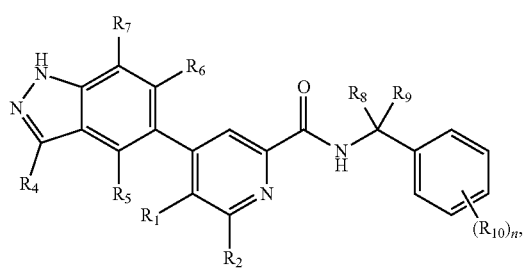
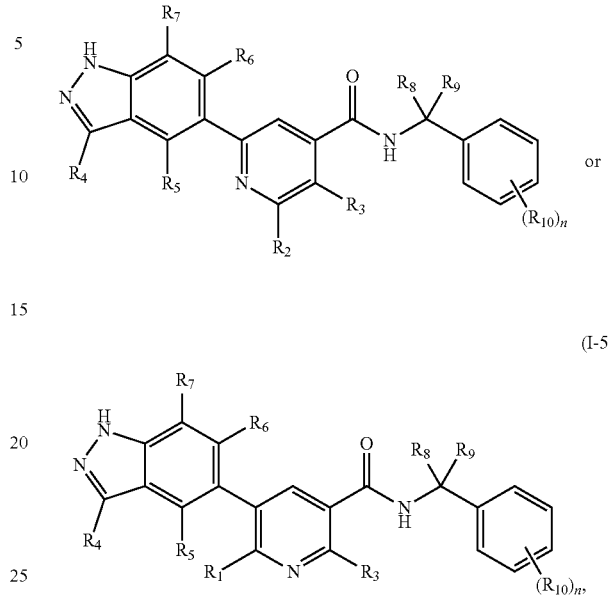
wherein, $R_1$, $R_2$, $R_3$, $R_4$, $R_5$, $R_6$, $R_7$, $R_8$, $R_9$, $R_{10}$ and n are as defined in the present disclosure.
In some embodiments of the present disclosure, the compound is represented by formula (I-2) to (I-5),
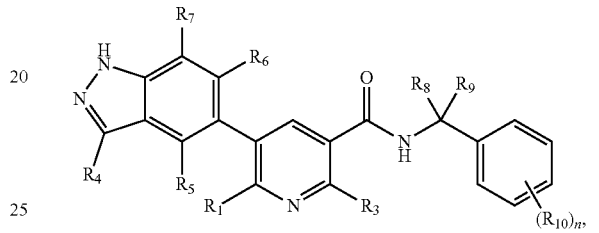
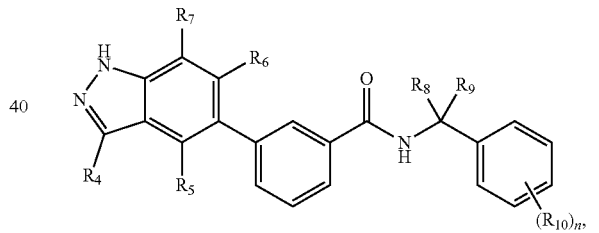
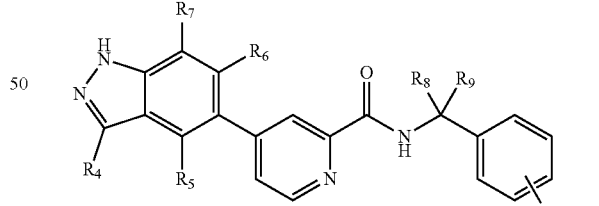
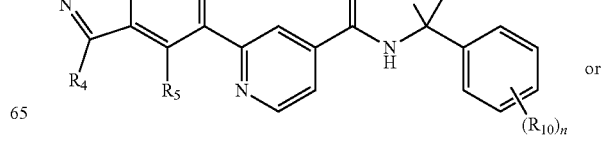

-continued (I-5)

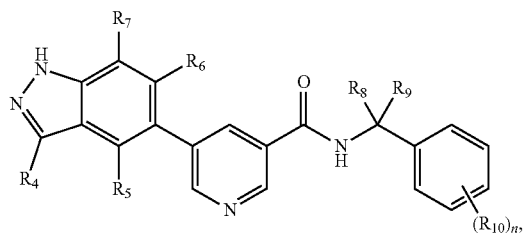

wherein, $R_4$, $R_5$, $R_6$, $R_7$, $R_8$, $R_9$, $R_{10}$ and n are as defined in the present disclosure.

In some embodiments of the present disclosure, the compound is represented by formula (II-1) to (II-4), (II-1)

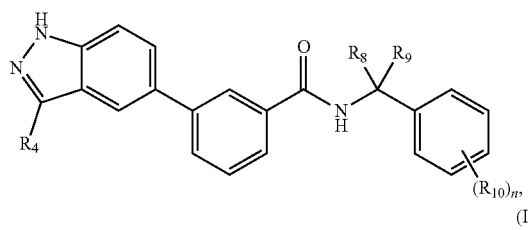

(II-2)

(II-3)

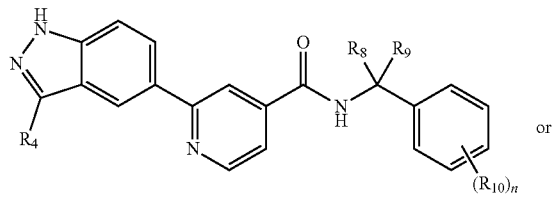

(II-4)

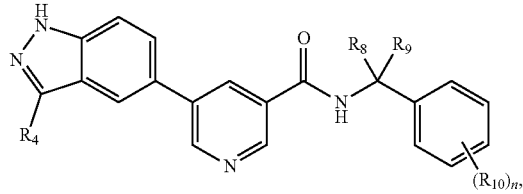

wherein, $R_4$, $R_8$, $R_9$, $R_{10}$ and n are as defined in the present disclosure.

In some embodiments of the present disclosure, the compound is represented by formula (I-6) to (I-9), (I-6)

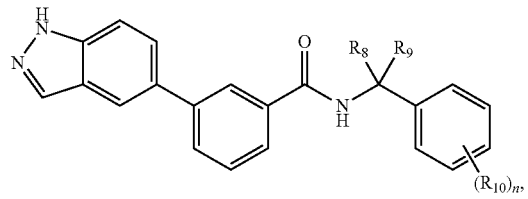

(I-7)

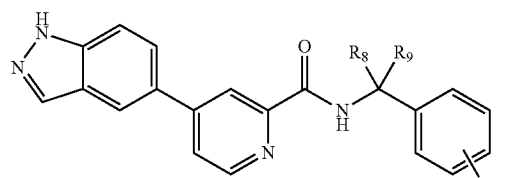

(I-8)

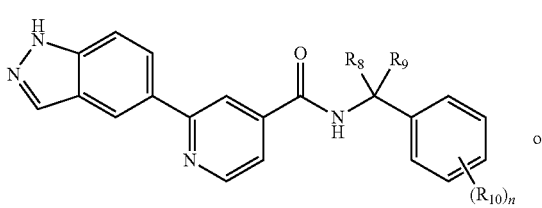

or (I-9)

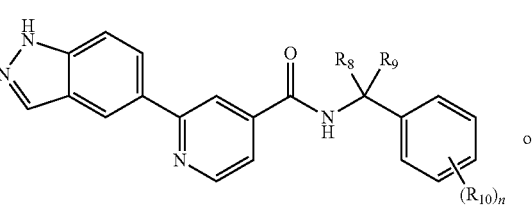

wherein, $R_8$, $R_9$, $R_{10}$ and n are as defined in the present disclosure.

In some embodiments of the present disclosure, the compound is represented by formula (I-10) to (I-13), (I-10)

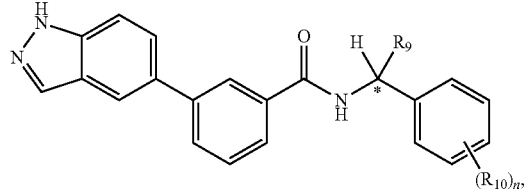

(I-11)

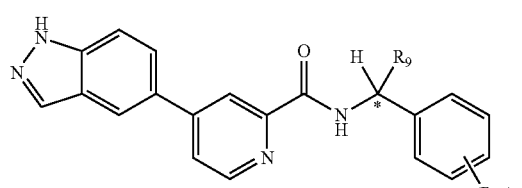

(I-12)

(I-13)

wherein, the carbon atom labeled with "*" is a chiral carbon atom, and exists in the form of (R) or (S) single enantiomer or enriched in one enantiomer;

R$_9$ is F, Cl, methyl, ethyl, n-propyl, isopropyl, or $R_{10}$ and n are as defined in the present disclosure.

In some embodiments of the present disclosure, the compound is represented by formula (I-14) to (I-17), (I-14)

(I-15)

(I-16)

or (I-17)

wherein, $R_8$, $R_9$, $R_{10}$ and n are as defined in the present disclosure.

In some embodiments of the present disclosure, the compound is represented by formula (I-18) to (I-21), (I-18)

-continued (I-19)
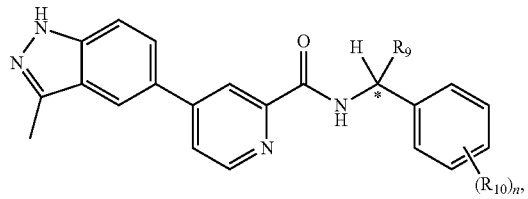

(I-20)
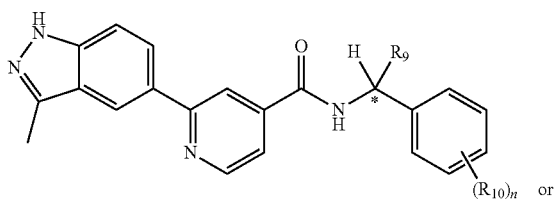

(I-21)
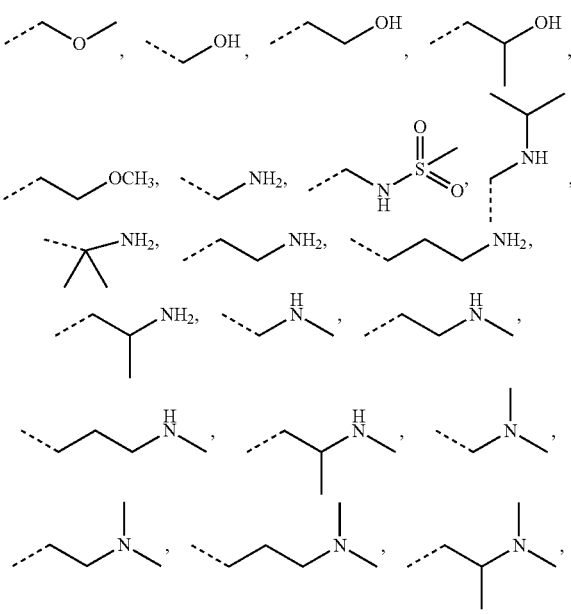

wherein, the carbon atom labeled with "*" is a chiral carbon atom, and exists in the form of (R) or (S) single enantiomer or enriched in one enantiomer;

$R_9$ is F, Cl, methyl, ethyl, n-propyl, isopropyl,

-continued
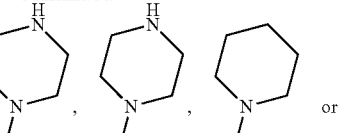
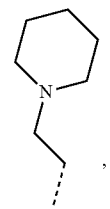

$R_{10}$ and n are as defined in the present disclosure.

Some embodiments of the present disclosure provide a compound represented by formula (I-1), a pharmaceutically acceptable salt thereof or an isomer thereof, (I-1)
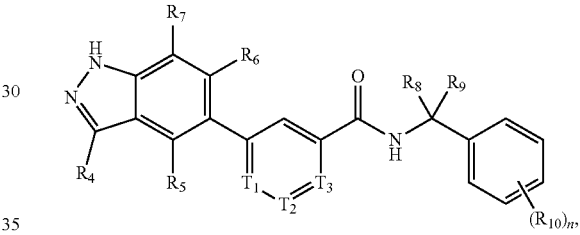

wherein, $T_1$ is N or $CR_1$; $T_2$ is N or $CR_2$; $T_3$ is N or $CR_3$;

$R_1$, $R_2$ and $R_3$ are each independently H, F, Cl, Br, CN, —$OR_a$, —C(=O)$NR_bR_c$ or $C_{1-6}$ alkyl, wherein the $C_{1-6}$ alkyl is optionally substituted by 1, 2 or 3 substituents independently selected from F, Cl, Br, I, —OH, —$OCH_3$, —CN, —$NH_2$ or —$NO_2$;

$R_4$, $R_5$, $R_6$ and $R_7$ are each independently H, F, Cl, Br, CN, —$OR_a$, —C(=O)$NR_bR_c$, —$NR_dR_e$, $C_{1-6}$ alkyl or $C_{3-6}$ cycloalkyl, wherein the $C_{1-6}$ alkyl and $C_{3-6}$ cycloalkyl are optionally substituted by 1, 2 or 3 substituents independently selected from F, Cl, Br, I, —OH, —$OCH_3$, —CN, —$NH_2$, —$NO_2$ or $C_{1-4}$ alkyl;

$R_8$ and $R_9$ are each independently H, F, Cl or $C_{1-6}$ alkyl, wherein the $C_{1-6}$ alkyl is optionally substituted by 1, 2 or 3 substituents independently selected from F, Cl, Br, CN, —$OR_a$ or —$NR_dR_e$;

each of $R_{10}$ is independently F, Cl, Br, CN, —$OR_a$, $C_{1-6}$ alkyl or $C_{3-6}$ cycloalkyl, wherein the $C_{1-6}$ alkyl and $C_{3-6}$ cycloalkyl are optionally substituted by 1, 2 or 3 substituents independently selected from F, Cl, Br, I, —OH, —$OCH_3$, —CN, —$NH_2$, —$NO_2$ or $C_{1-4}$ alkyl;

$R_a$, $R_b$ and $R_c$ are each independently H or $C_{1-6}$ alkyl, wherein the $C_{1-6}$ alkyl is optionally substituted by 1, 2 or 3 substituents independently selected from F, Cl, Br, —OH, —$OCH_3$, —CN, —$NH_2$ or —$NO_2$;

$R_d$ and $R_e$ are each independently H, $C_{1-6}$ alkyl, or $R_d$ and $R_e$ together with the N atom to which they are attached form a 4- to 8-membered heterocycloalkyl, wherein the $C_{1-6}$ alkyl and 4- to 8-membered heterocycloalkyl are optionally substituted by 1, 2 or 3 substituents independently selected from F, Cl, Br, —OH, —OCH$_3$, —CN, —NH$_2$, C$_{1-6}$ alkylamino or —NO$_2$;

n is 0, 1, 2, 3 or 4;

the 4- to 8-membered heterocycloalkyl contains 1, 2, 3 or 4 heteroatoms or heteroatomic groups independently selected from N, —O—, —S— and —NH—.

In some embodiments of the present disclosure, R$_a$, R$_b$ and R$_c$ are each independently H, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH$_3$, CN, —NH$_2$ or —NO$_2$, the other variables are as defined in the present disclosure.

In some embodiments of the present disclosure, R$_a$, R$_b$ and R$_c$ are each independently H, methyl, ethyl, n-propyl, isopropyl,

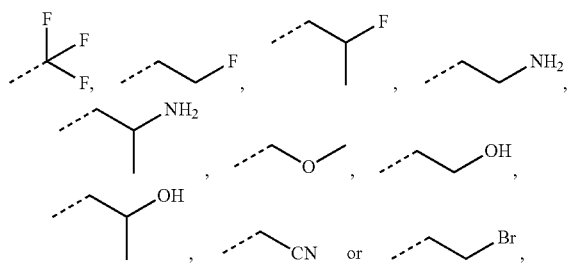

the other variables are as defined in the present disclosure.

In some embodiments of the present disclosure, R$_4$, R$_5$, R$_6$ and R$_7$ are each independently H, F, Cl, Br, CN, —OH, —OCH$_3$, —OCH$_2$CH$_3$, —C(=O)NH$_2$, —NH$_2$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, R$_4$, R$_5$, R$_6$ and R$_7$ are each independently H, F, Cl, Br, CN, —OH, —OCH$_3$, —OCH$_2$CH$_3$, —C(=O)NH$_2$, —NH$_2$, methyl, ethyl, n-propyl, isopropyl,

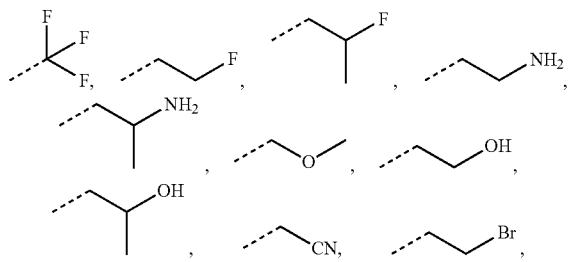

cyclopropyl, cyclopentyl, cyclohexyl,

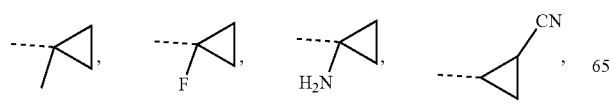

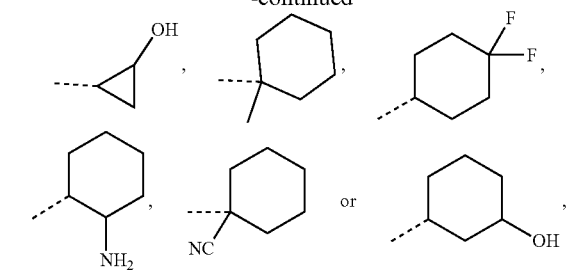

the other variables are as defined in the present disclosure.

In some embodiments of the present disclosure, R$_1$, R$_2$ and R$_3$ are each independently H, F, Cl, Br, CN, —OH, —OCH$_3$, —C(=O)NH$_2$, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, R$_1$, R$_2$ and R$_3$ are each independently H, F, Cl, Br, CN, —OH, —OCH$_3$, —OCH$_2$CH$_3$, —C(=O)NH$_2$, methyl, ethyl, n-propyl, isopropyl,

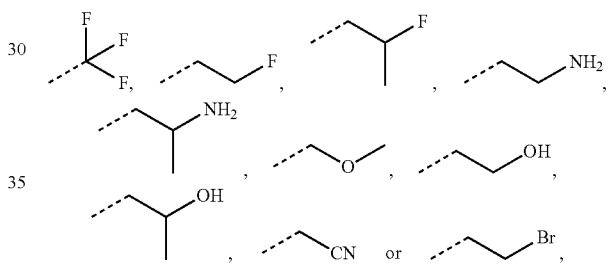

the other variables are as defined in the present disclosure.

In some embodiments of the present disclosure, the moiety

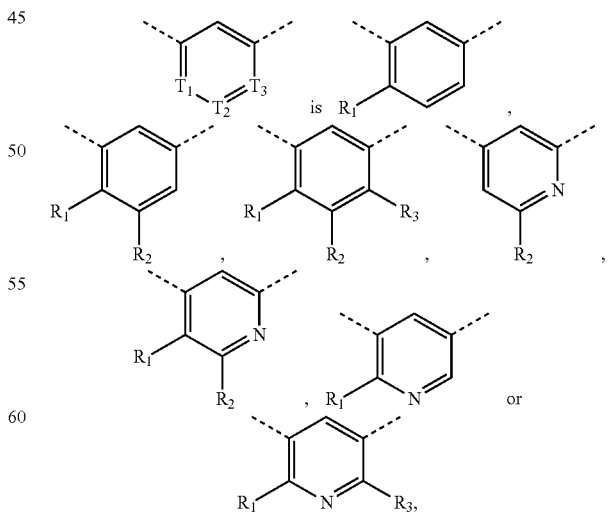

R$_1$, R$_2$, R$_3$ and the other variables are as defined in the present disclosure.

In some embodiments of the present disclosure, the moiety

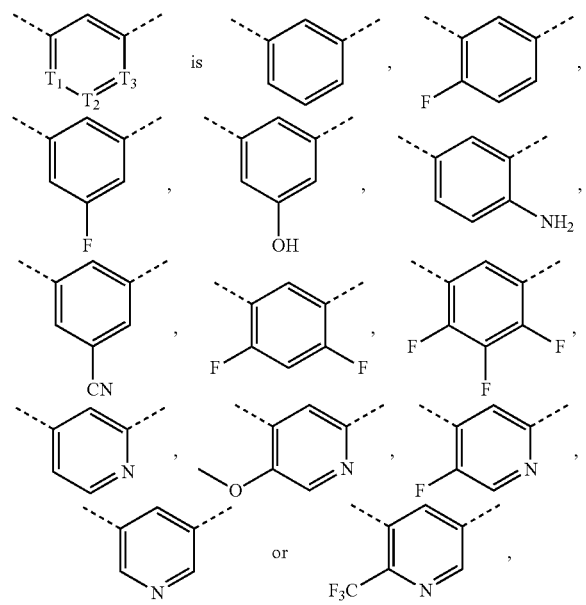

is the other variables are as defined in the present disclosure.

In some embodiments of the present disclosure, $R_d$ and $R_e$ are each independently H, methyl, ethyl, n-propyl, isopropyl, or $R_d$ and $R_e$ together with the N atom to which they are attached form a 5- to 6-membered heterocycloalkyl, wherein the methyl, ethyl, n-propyl, isopropyl, and 5- to 6-membered heterocycloalkyl are optionally substituted by 1, 2 or 3 substituents independently selected from F, Cl, Br, I, —OH, —OCH$_3$, CN, —NH$_2$, C$_{1-3}$ alkylamino or —NO$_2$, the other variables are as defined in the present disclosure.

In some embodiments of the present disclosure, $R_d$ and $R_e$ are each independently H, methyl, ethyl, n-propyl, isopropyl,

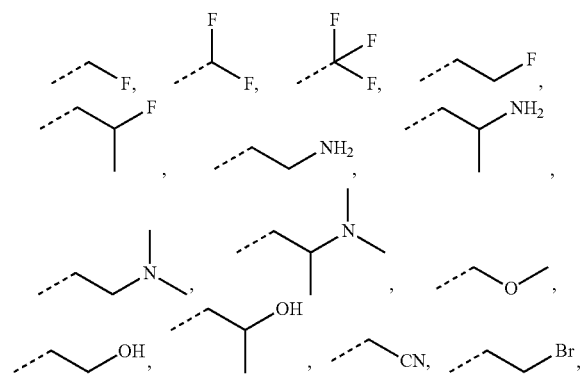

or $R_d$ and $R_e$ together with the N atom to which they are attached form a pyrrolidyl or piperidyl, wherein the pyrrolidyl and piperidyl are optionally substituted by 1, 2 or 3 substituents independently selected from F, Cl, Br, I, —OH, —OCH$_3$, CN, —NH$_2$, C$_{1-3}$ alkylamino or —NO$_2$, the other variables are as defined in the present disclosure.

In some embodiments of the present disclosure, $R_8$ and $R_9$ are each independently H, F, Cl, —OH, —OCH$_3$, —NH$_2$,

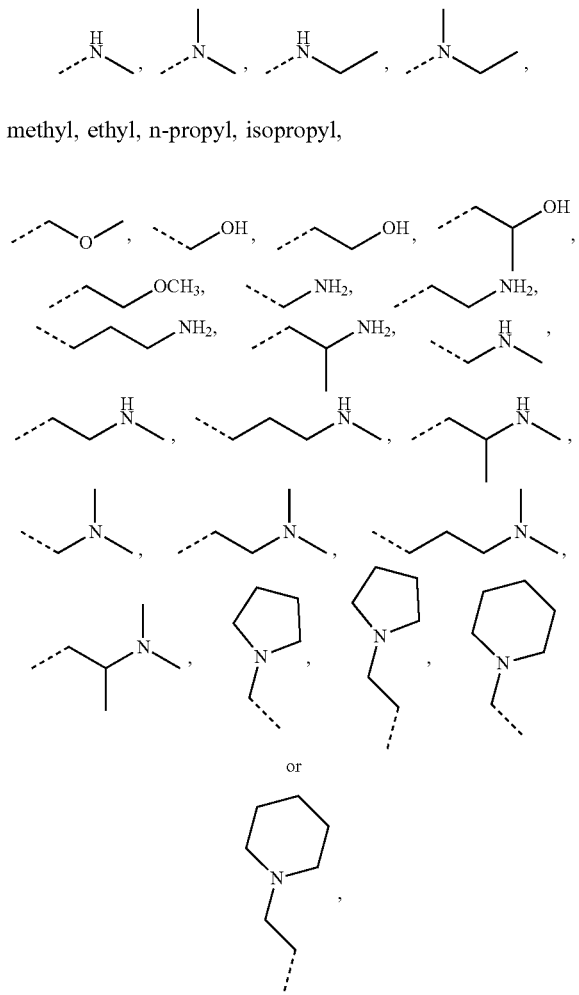

methyl, ethyl, n-propyl, isopropyl, the other variables are as defined in the present disclosure.

In some embodiments of the present disclosure, each of $R_{10}$ is independently F, Cl, Br, CN, —OH, —OCH$_3$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, each of $R_{10}$ is independently F, Cl, Br, CN, —OH, —OCH$_3$, —OCH$_2$CH$_3$, methyl, ethyl, n-propyl, isopropyl,

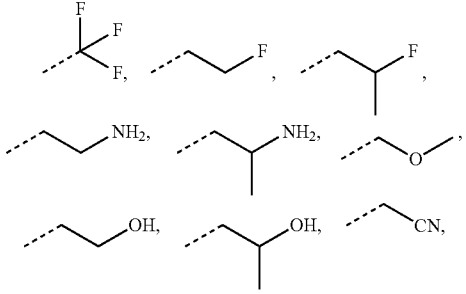

-continued
cyclopropyl, cyclopentyl, cyclohexyl,
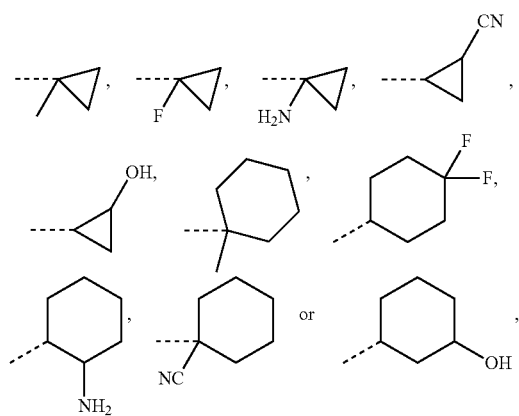
the other variables are as defined in the present disclosure.
In some embodiments of the present disclosure, the moiety
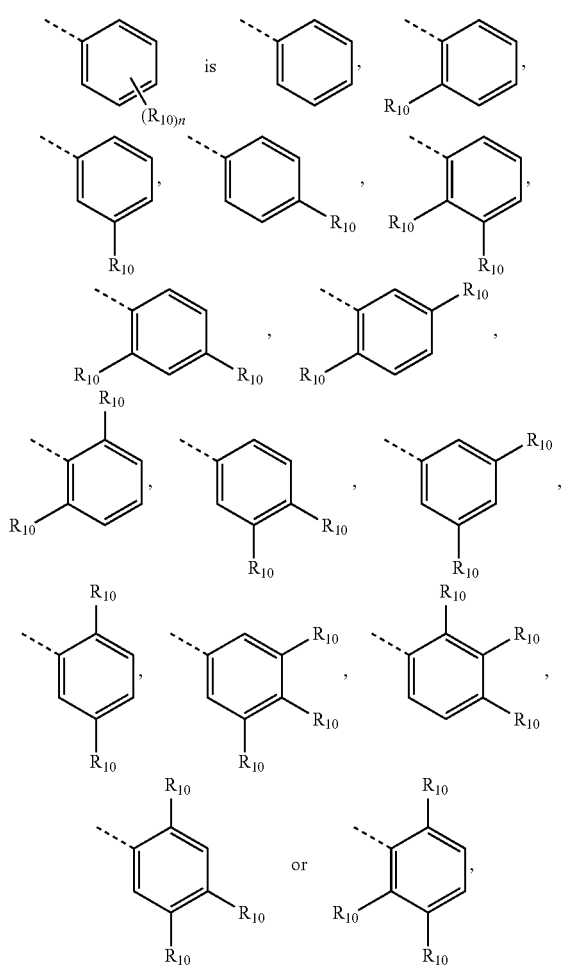
$R_{10}$ and the other variables are as defined in the present disclosure.
In some embodiments of the present disclosure, the moiety
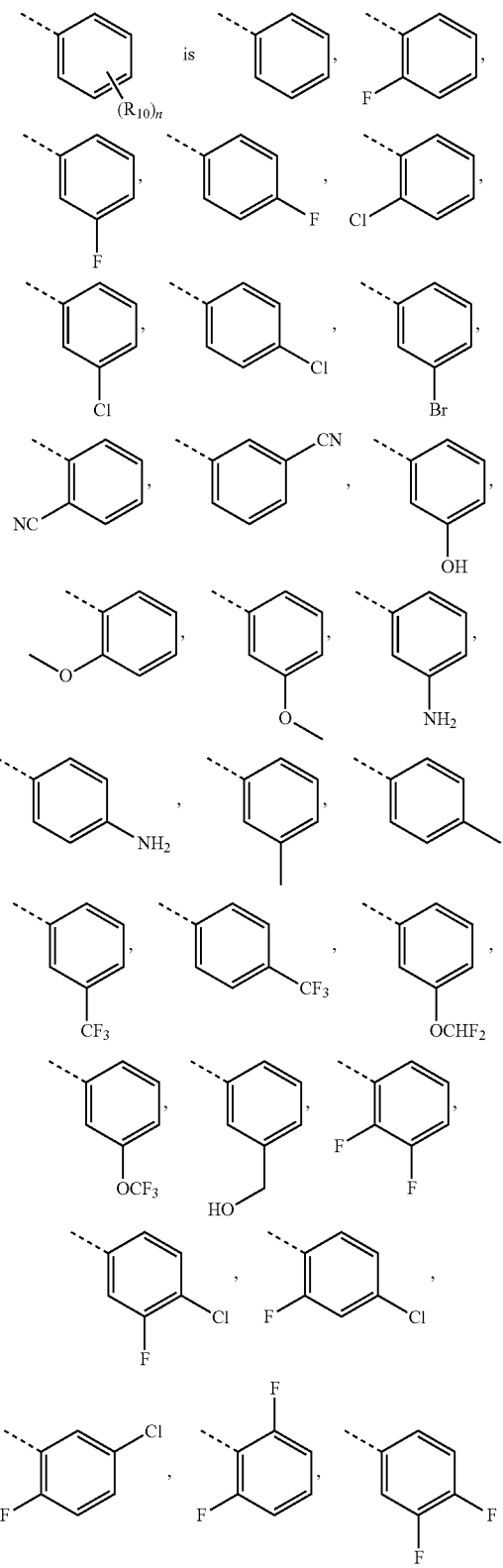

-continued

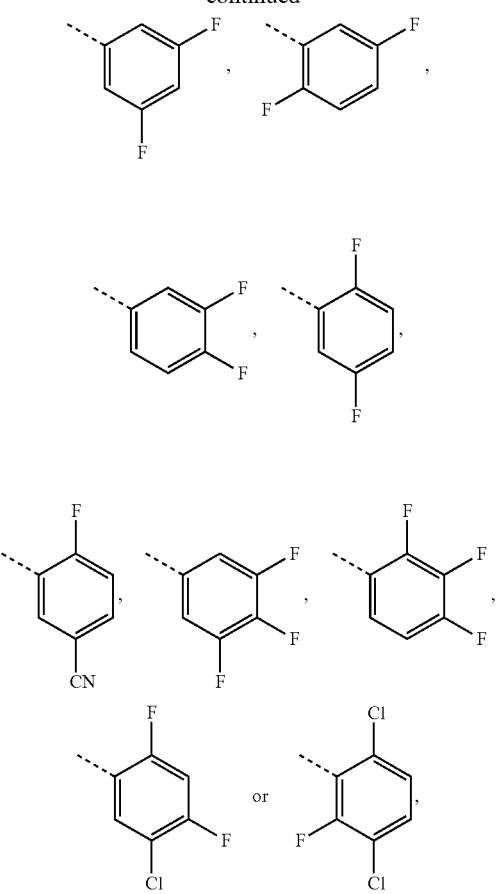

the other variables are as defined in the present disclosure.

In some embodiments of the present disclosure, the compound, the pharmaceutically acceptable salt thereof or the isomer thereof, the compound is represented by formula (I-2) to (I-5),

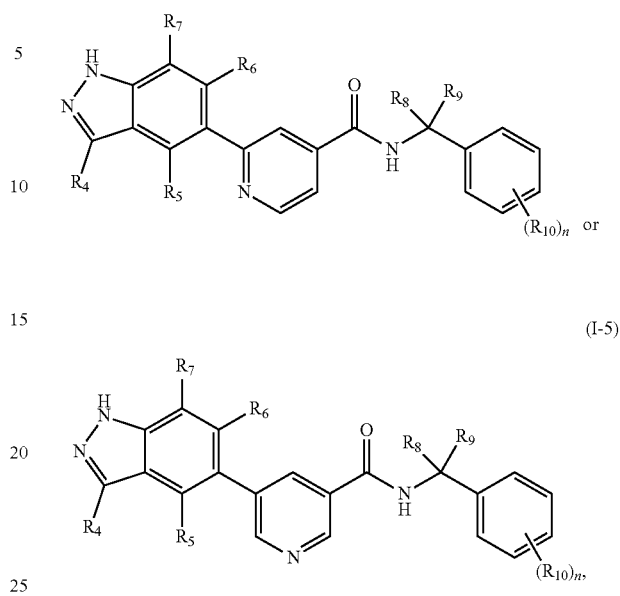

(I-2)

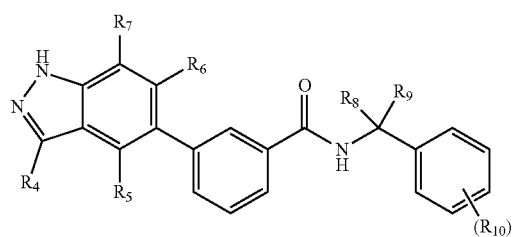

(I-3)

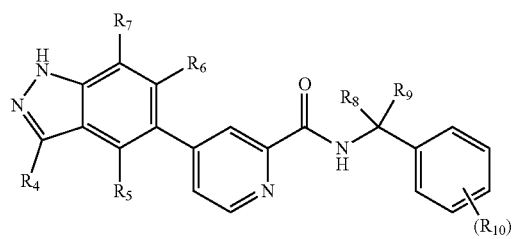

-continued (I-4)

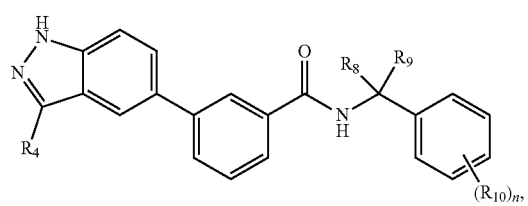

(I-5)

wherein, $R_4$, $R_5$, $R_6$, $R_7$, $R_8$, $R_9$, $R_{10}$ and n are as defined in the present disclosure.

In some embodiments of the present disclosure, the compound, the pharmaceutically acceptable salt thereof or the isomer thereof, the compound is represented by formula (II-1) to (II-4), (II-1)

(II-2)

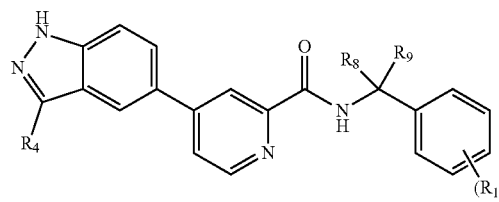

(II-3)

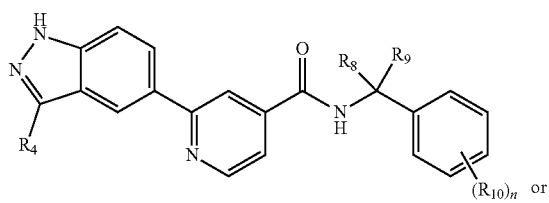

-continued (II-4)
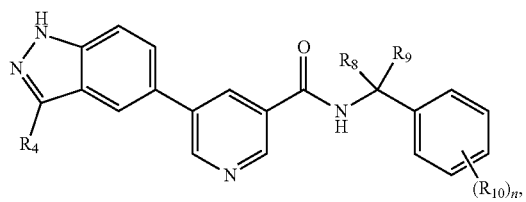

wherein, $R_4$, $R_8$, $R_9$, $R_{10}$ and n are as defined in the present disclosure.

In some embodiments of the present disclosure, the compound, the pharmaceutically acceptable salt thereof or the isomer thereof, the compound is represented by formula (I-6) to (I-9), (I-6)
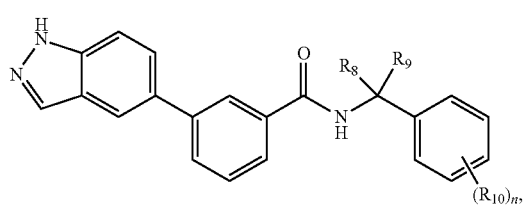

(I-7)
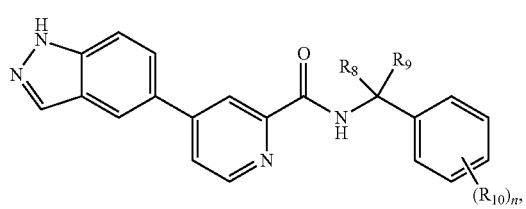

(I-8)
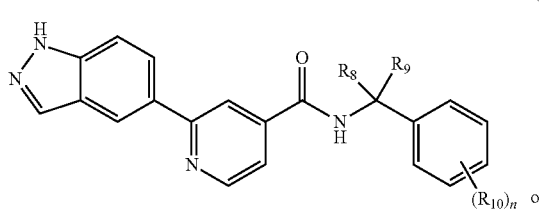

(I-9)
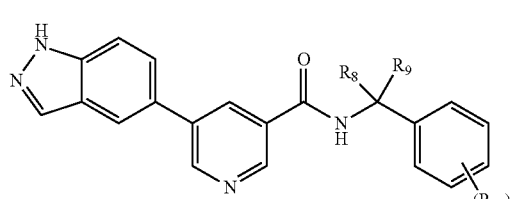

wherein, $R_8$, $R_9$, $R_{10}$ and n are as defined in the present disclosure.

In some embodiments of the present disclosure, the compound, the pharmaceutically acceptable salt thereof or the isomer thereof, the compound is represented by formula (I-10) to (I-13), (I-10)
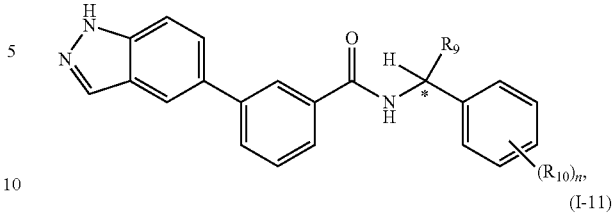

(I-11)
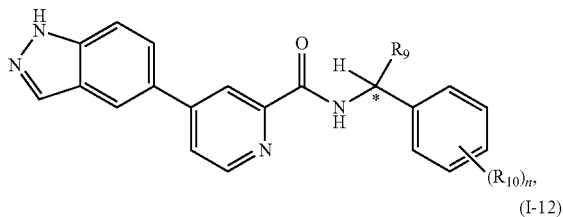

(I-12)
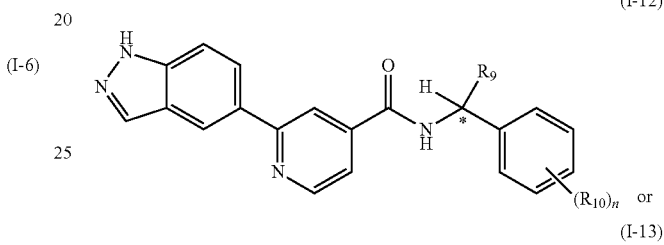

(I-13)
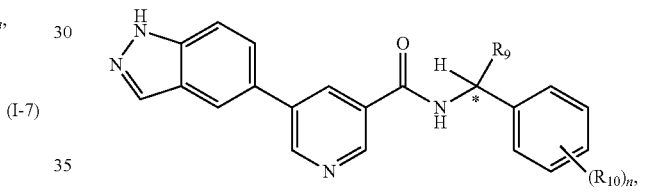

wherein, the carbon atom labeled with "*" is a chiral carbon atom, and exists in the form of (R) or (S) single enantiomer or enriched in one enantiomer;

$R_9$ is F, Cl, —OH, —OCH$_3$, —NH$_2$,

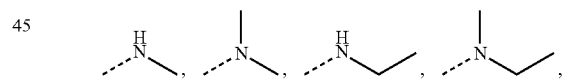

methyl, ethyl, n-propyl, isopropyl,

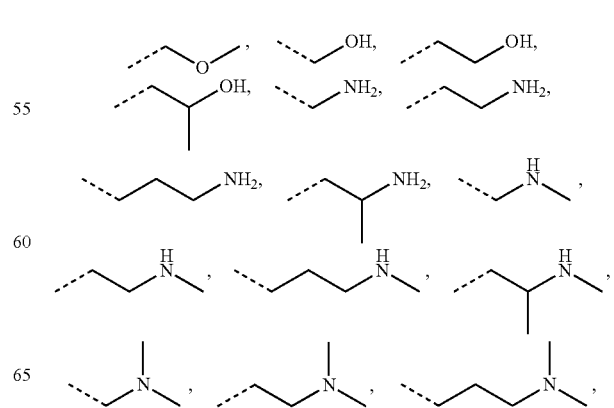

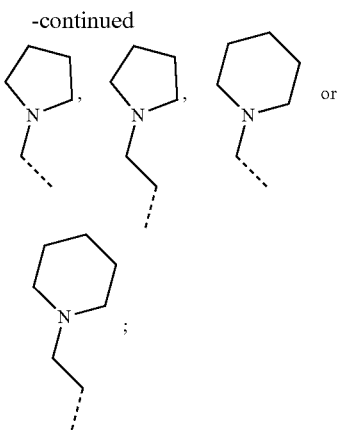

R$_{10}$ and n are as defined in the present disclosure.

Some embodiments of the present disclosure provide a compound represented by formula (I-1), a pharmaceutically acceptable salt thereof or an isomer thereof,

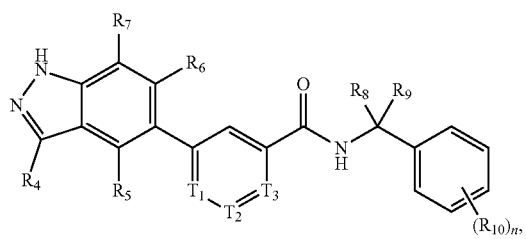
(I-1)

wherein,

T$_1$ is N or CR$_1$; T$_2$ is N or CR$_2$; T$_3$ is N or CR$_3$;

R$_1$, R$_2$ and R$_3$ are each independently H, F, Cl, Br, CN, —OR$_a$, —C(=O)NR$_b$R$_c$ or C$_{1-6}$ alkyl, wherein the C$_{1-6}$ alkyl is optionally substituted by 1, 2 or 3 substituents independently selected from F, Cl, Br, I, —OH, —OCH$_3$, —CN, —NH$_2$ or —NO$_2$;

R$_4$, R$_5$, R$_6$ and R$_7$ are each independently H, F, Cl, Br, CN, —OR$_a$, —C(=O)NR$_b$R$_c$, C$_{1-6}$ alkyl or C$_{3-6}$ cycloalkyl, wherein the C$_{1-6}$ alkyl and C$_{3-6}$ cycloalkyl are optionally substituted by 1, 2 or 3 substituents independently selected from F, Cl, Br, I, —OH, —OCH$_3$, —CN, —NH$_2$, —NO$_2$ or C$_{1-4}$ alkyl;

R$_8$ and R$_9$ are each independently H, F, Cl or C$_{1-6}$ alkyl, wherein the C$_{1-6}$ alkyl is optionally substituted by 1, 2 or 3 substituents independently selected from F, Cl, Br, CN, —OR$_a$ or —NR$_d$R$_e$;

each of R$_{10}$ is independently F, Cl, Br, CN, —OR$_a$, C$_{1-6}$ alkyl or C$_{3-6}$ cycloalkyl, wherein the C$_{1-6}$ alkyl and C$_{3-6}$ cycloalkyl are optionally substituted by 1, 2 or 3 substituents independently selected from F, Cl, Br, I, —OH, —OCH$_3$, —CN, —NH$_2$, —NO$_2$ or C$_{1-4}$ alkyl;

R$_a$, R$_b$ and R$_c$ are each independently H or C$_{1-6}$ alkyl, wherein the C$_{1-6}$ alkyl is optionally substituted by 1, 2 or 3 substituents independently selected from F, Cl, Br, —OH, —OCH$_3$, —CN, —NH$_2$ or —NO$_2$;

R$_d$ and R$_e$ are each independently H, C$_{1-6}$ alkyl, or R$_d$ and R$_e$ together with the N atom to which they are attached form a 4- to 8-membered heterocycloalkyl, wherein the C$_{1-6}$ alkyl and 4- to 8-membered heterocycloalkyl are optionally substituted by 1, 2 or 3 substituents independently selected from F, Cl, Br, —OH, —OCH$_3$, —CN, —NH$_2$, C$_{1-6}$ alkylamino or —NO$_2$;

n is 0, 1, 2, 3 or 4;

the 4- to 8-membered heterocycloalkyl contains 1, 2, 3 or 4 heteroatoms or heteroatomic groups independently selected from N, —O—, —S— and —NH—.

In some embodiments of the present disclosure, R$_a$, R$_b$ and R$_c$ are each independently H, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH$_3$, CN, —NH$_2$ or —NO$_2$, the other variables are as defined in the present disclosure.

In some embodiments of the present disclosure, R$_a$, R$_b$ and R$_c$ are each independently H, methyl, ethyl, n-propyl, isopropyl,

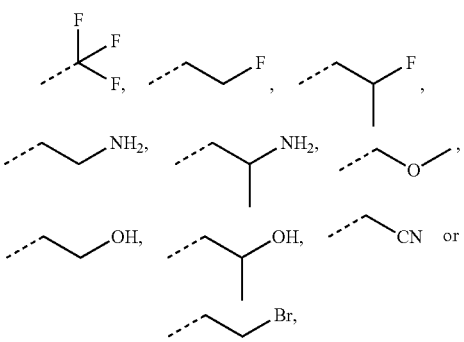

the other variables are as defined in the present disclosure.

In some embodiments of the present disclosure, R$_4$, R$_5$, R$_6$ and R$_7$ are each independently H, F, Cl, Br, CN, —OH, —OCH$_3$, —OCH$_2$CH$_3$, —C(=O)NH$_2$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, R$_4$, R$_5$, R$_6$ and R$_7$ are each independently H, F, Cl, Br, CN, —OH, —OCH$_3$, —OCH$_2$CH$_3$, —C(=O)NH$_2$, methyl, ethyl, n-propyl, isopropyl, cyclopropyl, cyclopentyl, cyclohexyl,

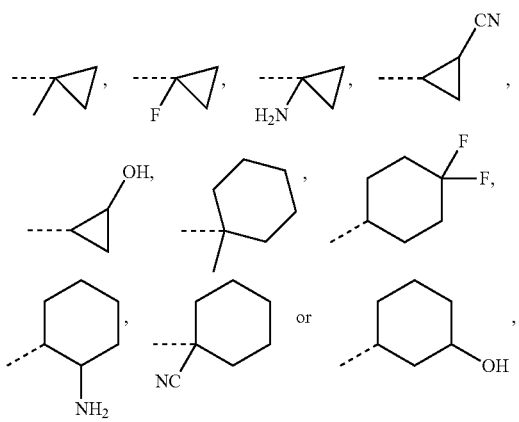

the other variables are as defined in the present disclosure.

In some embodiments of the present disclosure, $R_1$, $R_2$ and $R_3$ are each independently H, F, Cl, Br, CN, —OH, —OCH$_3$, —C(=O)NH$_2$, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, $R_1$, $R_2$ and $R_3$ are each independently H, F, Cl, Br, CN, —OH, —OCH$_3$, —OCH$_2$CH$_3$, —C(=O)NH$_2$, methyl, ethyl, n-propyl, isopropyl,

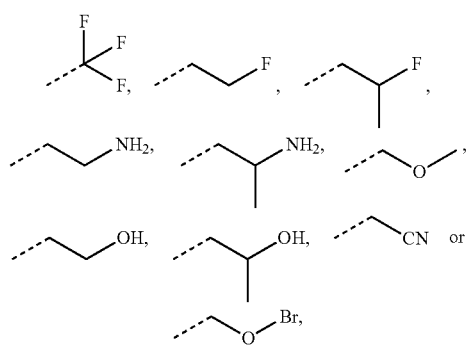

the other variables are as defined in the present disclosure.

In some embodiments of the present disclosure, the moiety

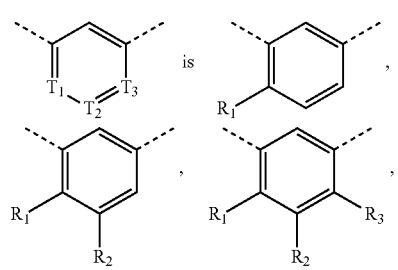

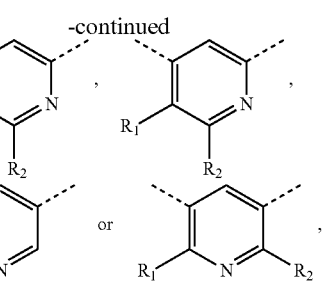

$R_1$, $R_2$, $R_3$ and the other variables are as defined in the present disclosure.

In some embodiments of the present disclosure, the moiety

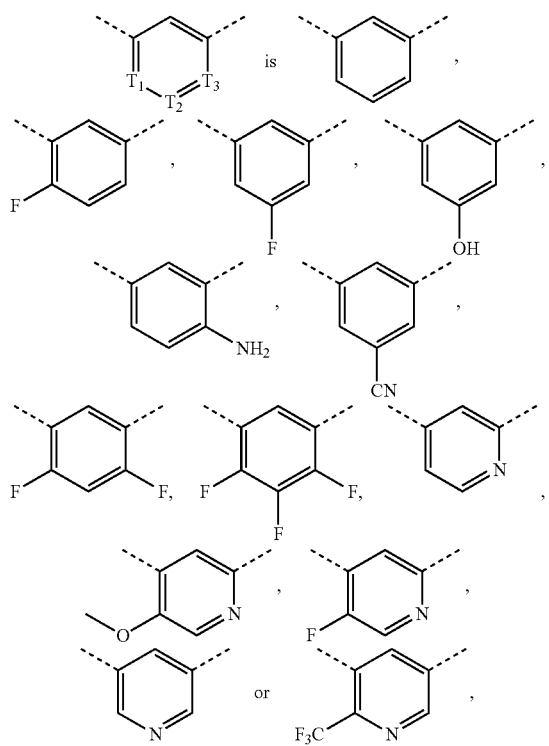

the other variables are as defined in the present disclosure.

In some embodiments of the present disclosure, $R_d$ and $R_e$ are each independently H, methyl, ethyl, n-propyl, isopropyl, or $R_d$ and $R_e$ together with the N atom to which they are attached form a 5- to 6-membered heterocycloalkyl, wherein the methyl, ethyl, n-propyl, isopropyl, and 5- to 6-membered heterocycloalkyl are optionally substituted by 1, 2 or 3 substituents independently selected from F, Cl, Br, I, —OH, —OCH$_3$, CN, —NH$_2$, C$_{1-3}$ alkylamino or —NO$_2$, the other variables are as defined in the present disclosure.

In some embodiments of the present disclosure, $R_d$ and $R_e$ are each independently H, methyl, ethyl, n-propyl, isopropyl,

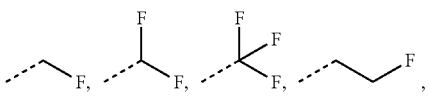

-continued

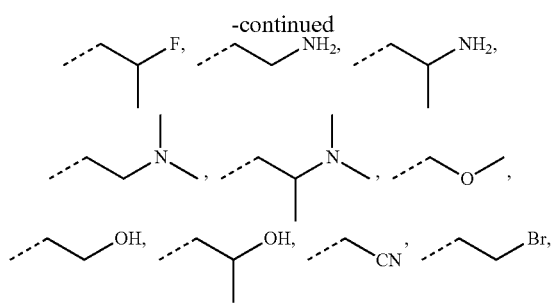

or $R_d$ and $R_e$ together with the N atom to which they are attached form a pyrrolidyl or piperidyl, wherein the pyrrolidyl and piperidyl are optionally substituted by 1, 2 or 3 substituents independently selected from F, Cl, Br, I, —OH, —OCH$_3$, CN, —NH$_2$, $C_{1-3}$ alkylamino or —NO$_2$, the other variables are as defined in the present disclosure.

In some embodiments of the present disclosure, $R_8$ and $R_9$ are each independently H, F, Cl, —OH, —OCH$_3$, —NH$_2$,

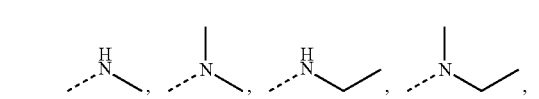

methyl, ethyl, n-propyl, isopropyl,

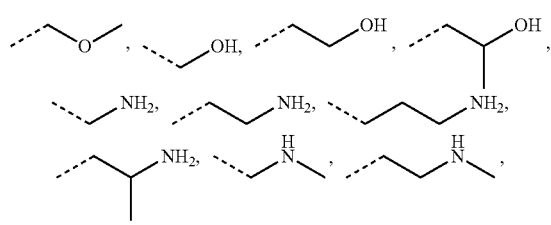

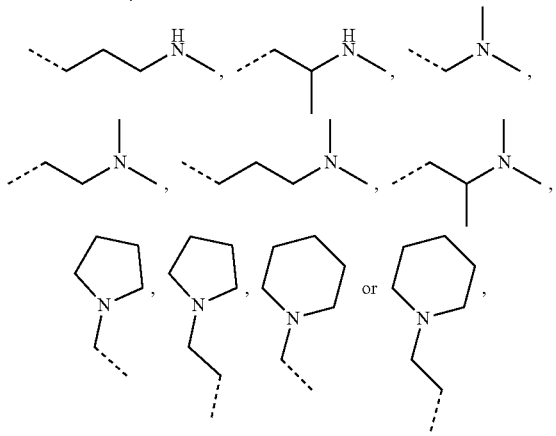

or the other variables are as defined in the present disclosure.

In some embodiments of the present disclosure, each of $R_{10}$ is independently F, Cl, Br, CN, —OH, —OCH$_3$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl, the other variables are as defined in the present disclosure.

In some embodiments of the present disclosure, each of $R_{10}$ is independently F, Cl, Br, CN, —OH, —OCH$_3$, —OCH$_2$CH$_3$, methyl, ethyl, n-propyl, isopropyl,

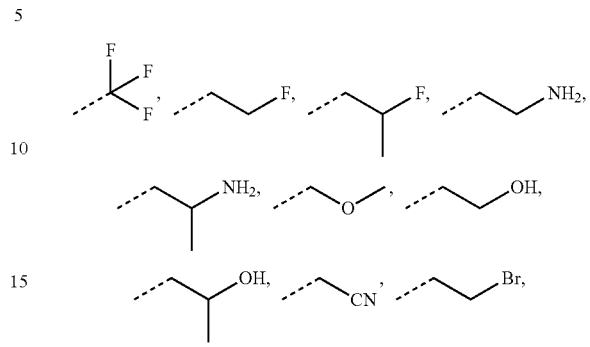

cyclopropyl, cyclopentyl, cyclohexyl,

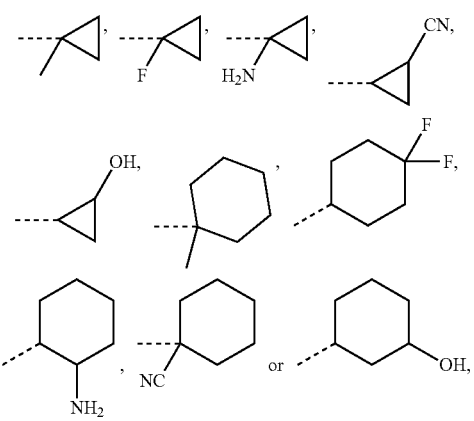

the other variables are as defined in the present disclosure.

In some embodiments of the present disclosure, the moiety

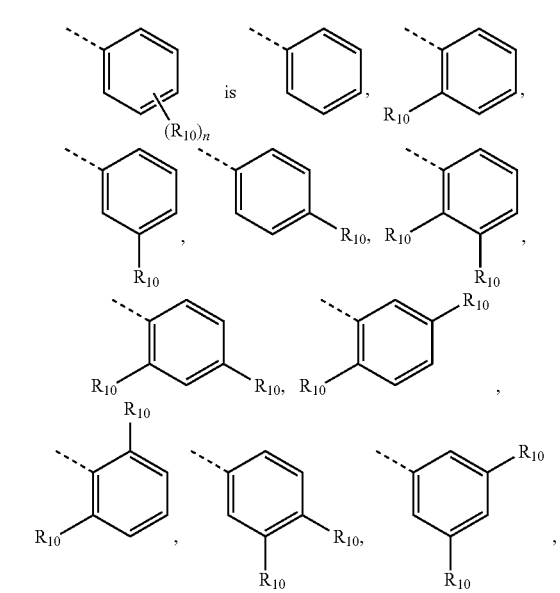

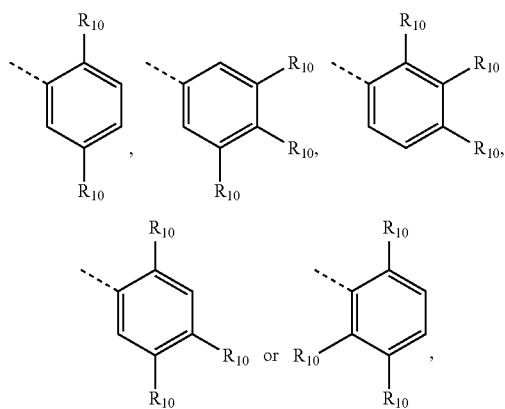

$R_{10}$ and the other variables are as defined in the present disclosure.

In some embodiments of the present disclosure, the moiety

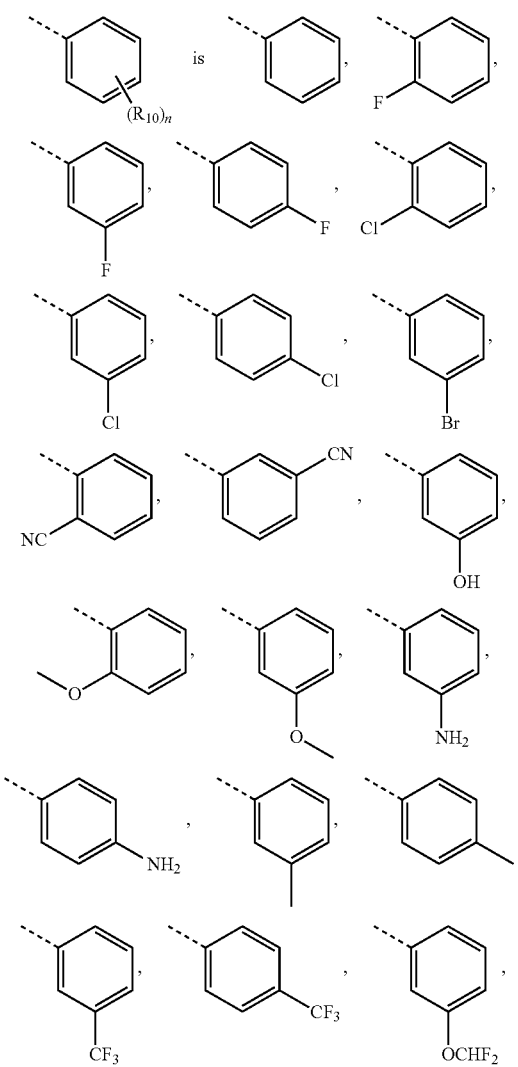

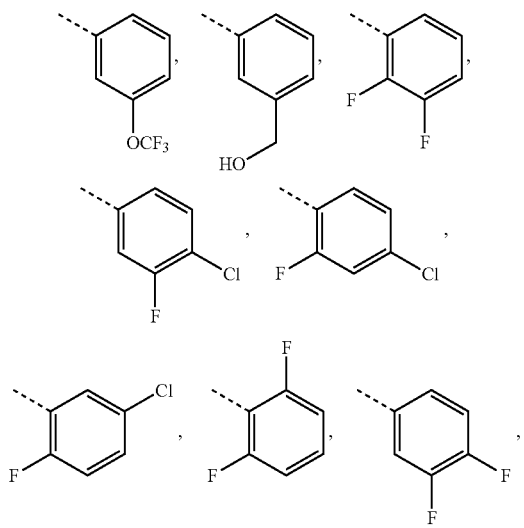

the other variables are as defined in the present disclosure.

In some embodiments of the present disclosure, the compound, the pharmaceutically acceptable salt thereof or the isomer thereof, the compound is represented by formula (I-2) to (I-5),

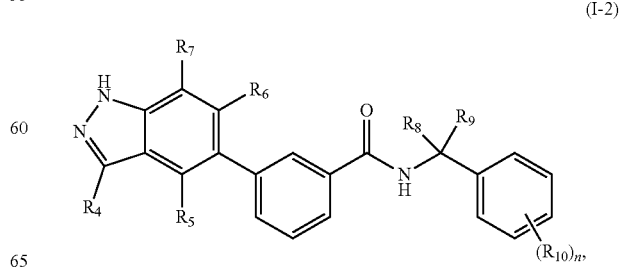

(I-3)

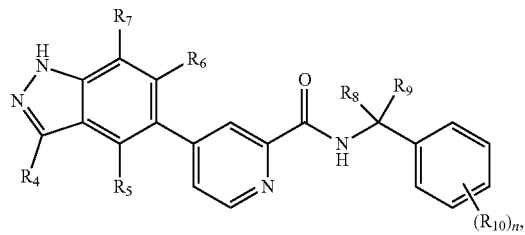

(I-4)

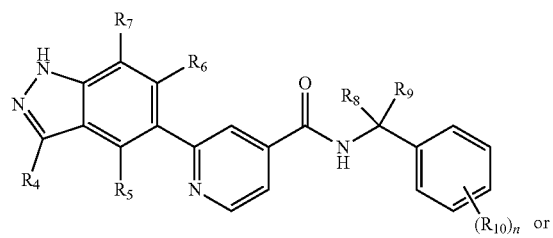
or (I-5)

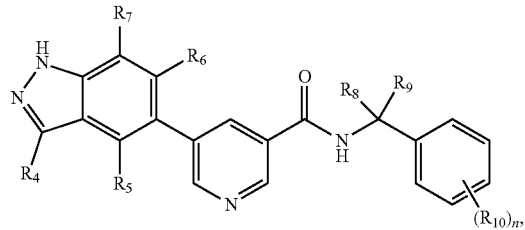

wherein, $R_4$, $R_5$, $R_6$, $R_7$, $R_8$, $R_9$, $R_{10}$ and n are as defined in the present disclosure.

In some embodiments of the present disclosure, the compound, the pharmaceutically acceptable salt thereof or the isomer thereof, the compound is represented by formula (I-6) to (I-9), (I-6)

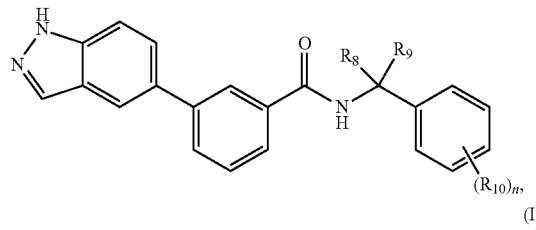

(I-7)

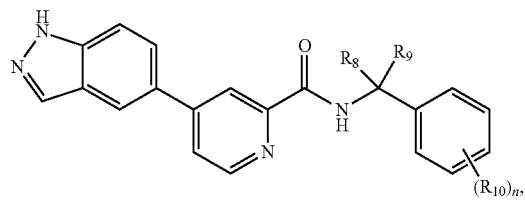

(I-8)

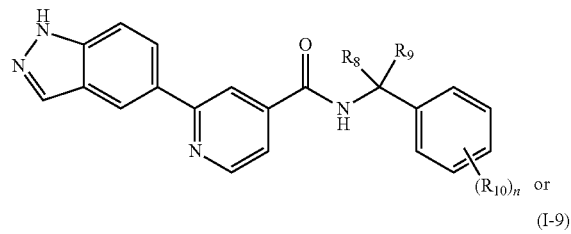
or (I-9)

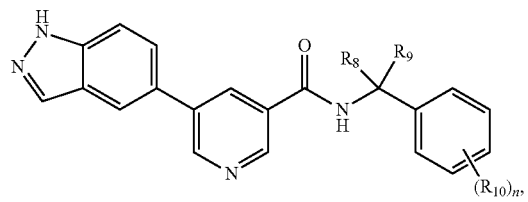

wherein, $R_8$, $R_9$, $R_{10}$ and n are as defined in the present disclosure.

In some embodiments of the present disclosure, the compound, the pharmaceutically acceptable salt thereof or the isomer thereof, the compound is represented by formula (I-10) to (I-13), (I-10)

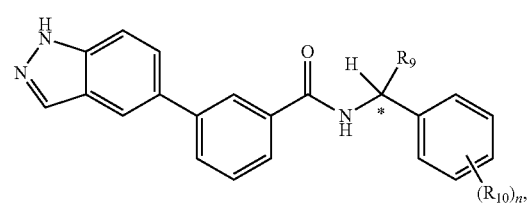

(I-11)

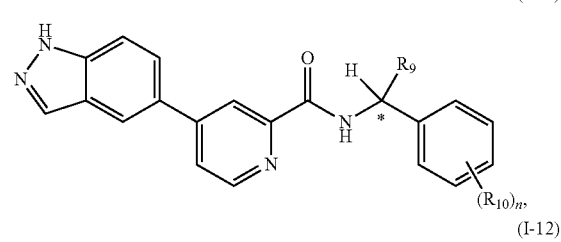

(I-12)

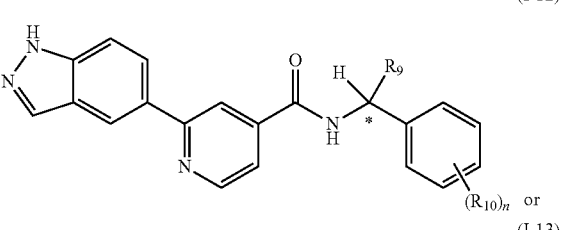
or (I-13)

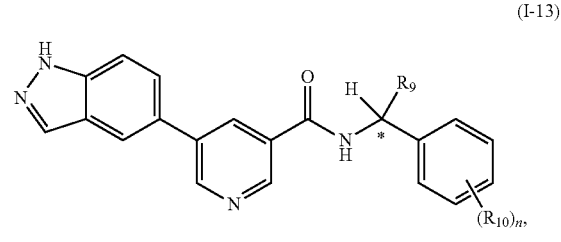

wherein, the carbon atom labeled with "*" is a chiral carbon atom, and exists in the form of (R) or (S) single enantiomer or enriched in one enantiomer;

R₉ is F, Cl, —OH, —OCH₃, —NH₂,

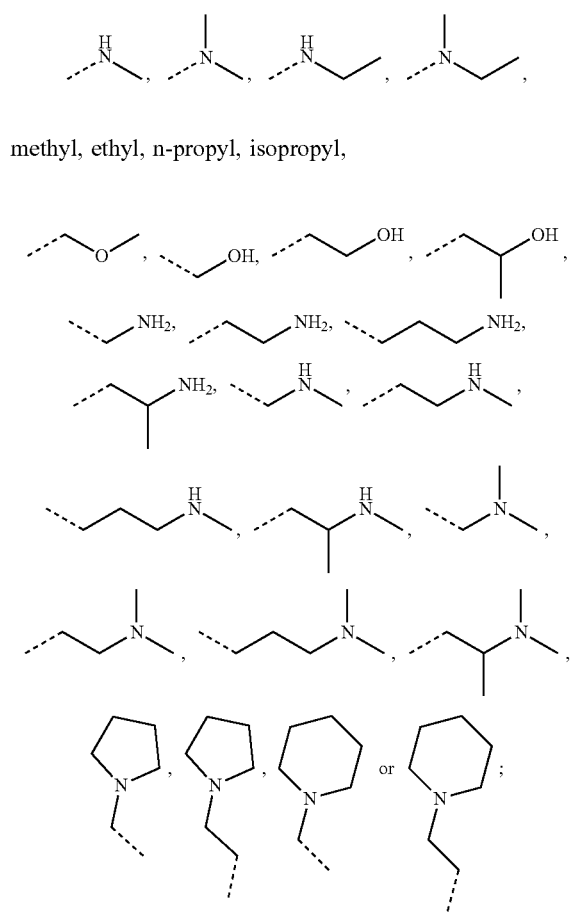

methyl, ethyl, n-propyl, isopropyl,

R₁₀ and n are as defined in the present disclosure.

Some embodiments of the present disclosure are obtained from arbitrary combinations of the above variables.

In some embodiments of the present disclosure, the compound is:

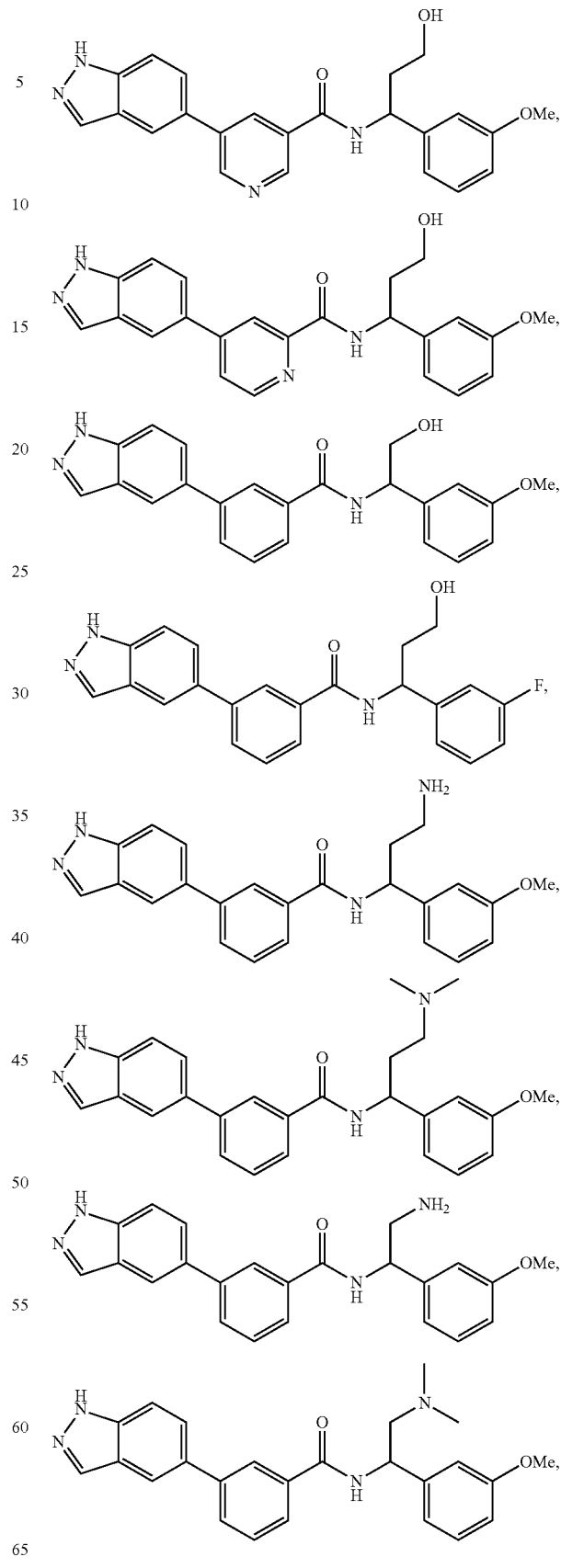

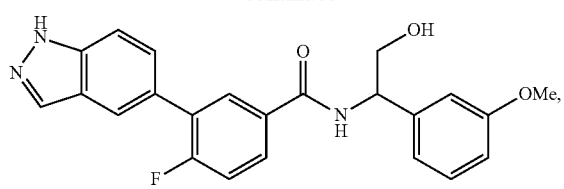
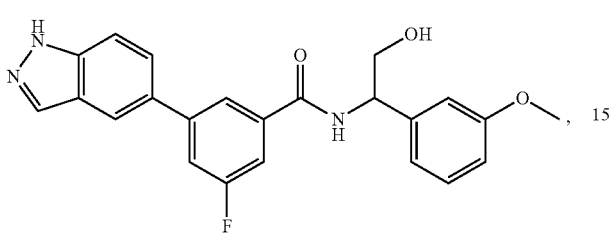
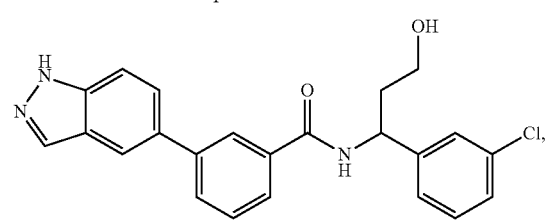
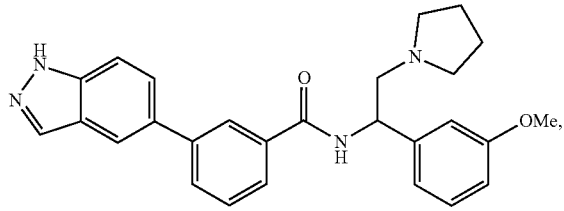
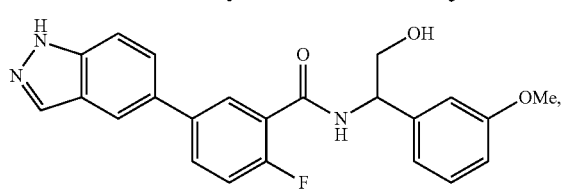
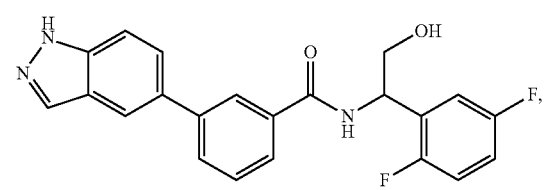
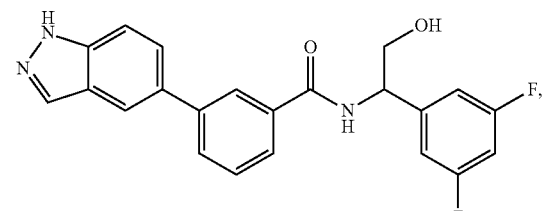
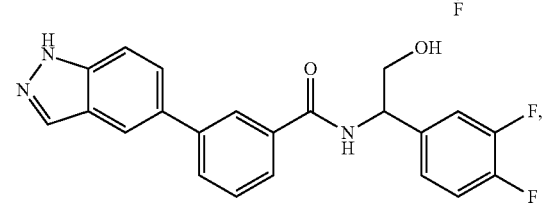
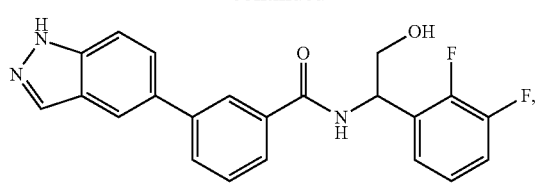
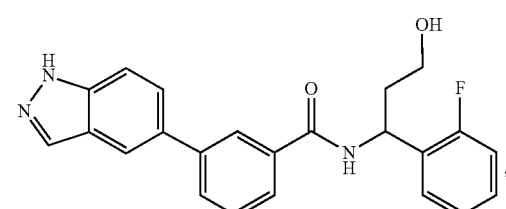
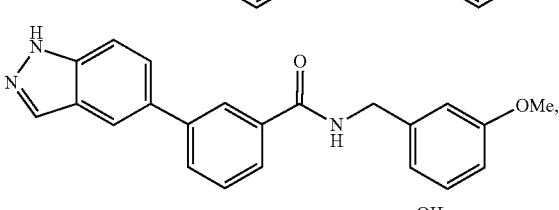
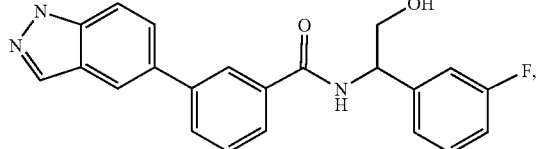
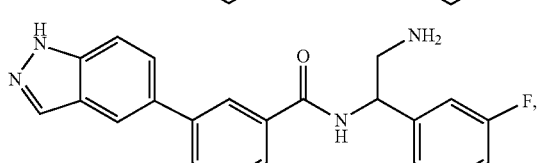
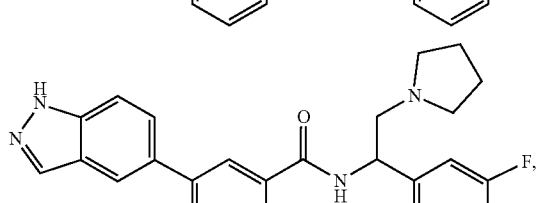
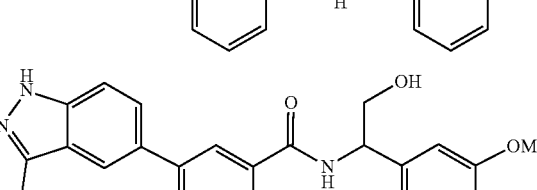
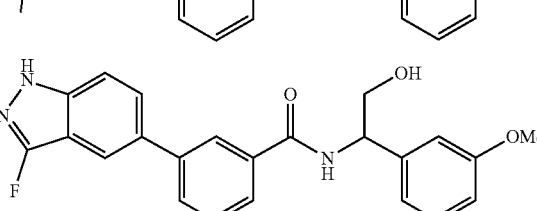
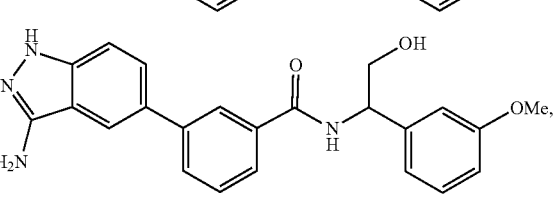

43
-continued
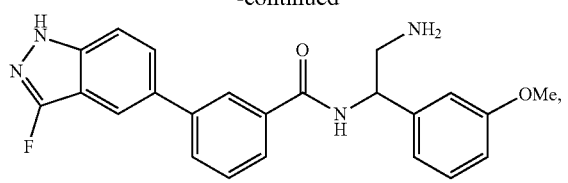
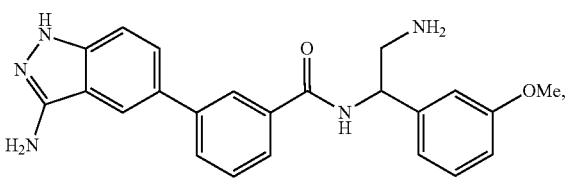
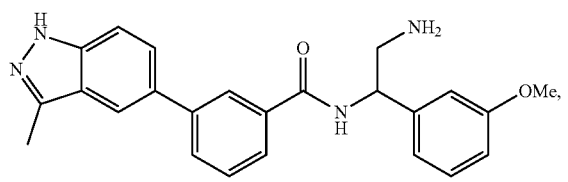
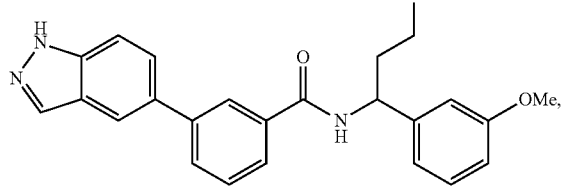
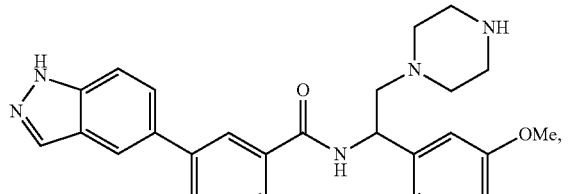
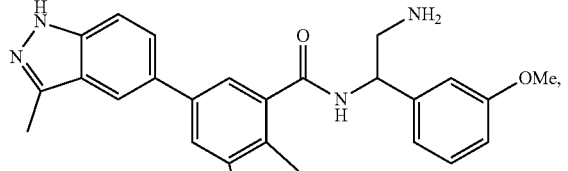
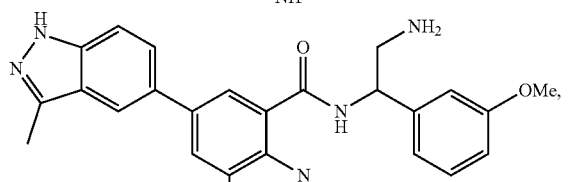
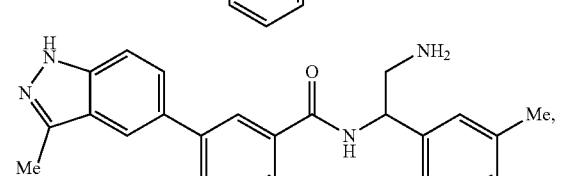
44
-continued
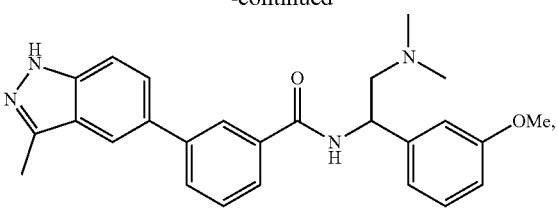
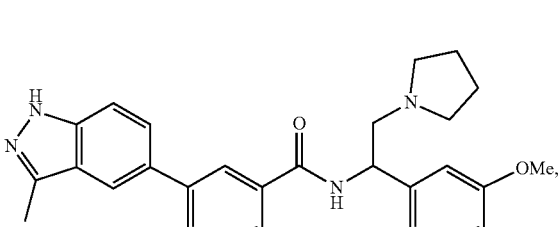
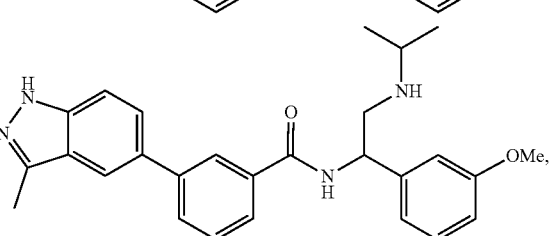
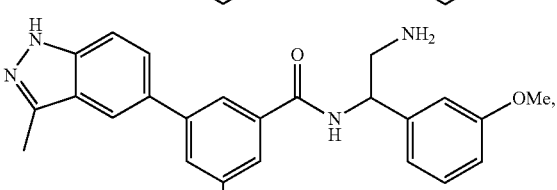
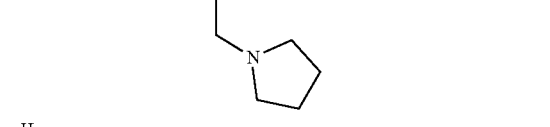
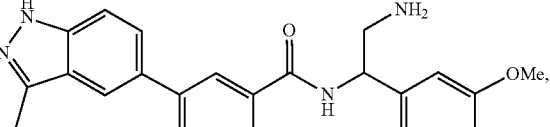
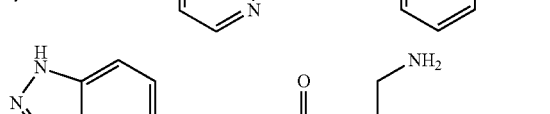
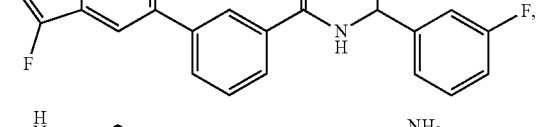
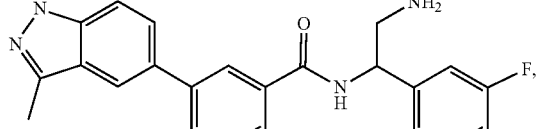
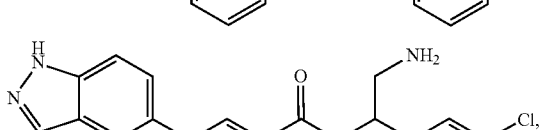
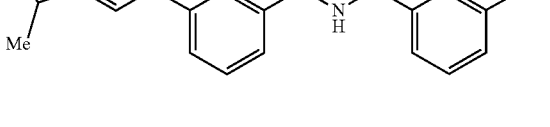

-continued
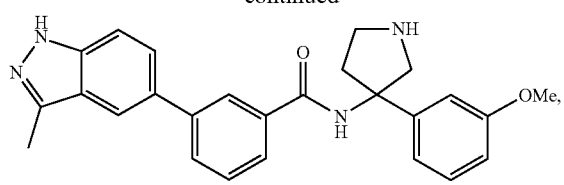
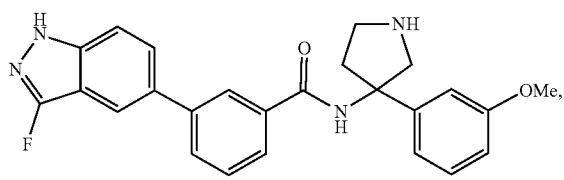
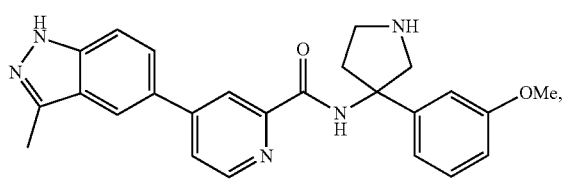
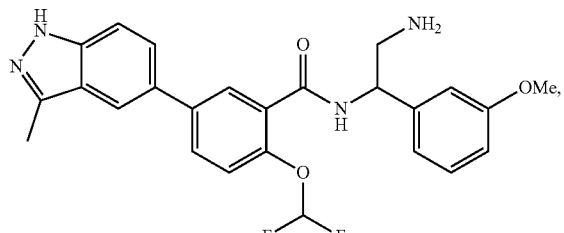
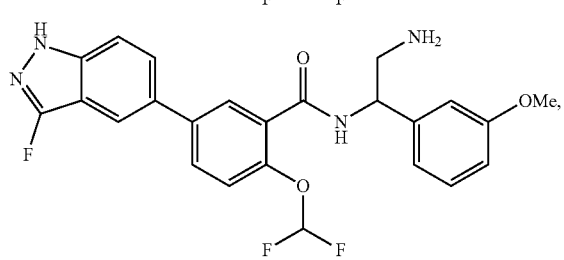
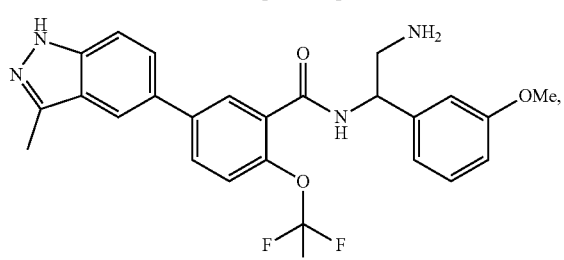
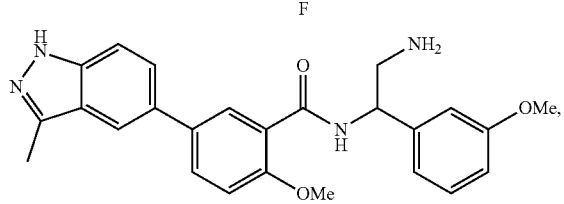
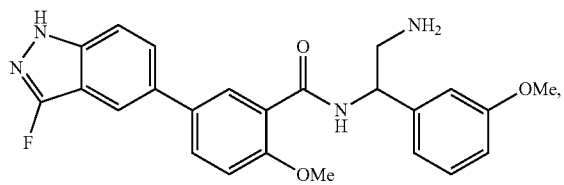
-continued
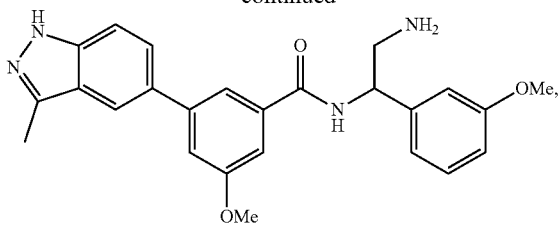
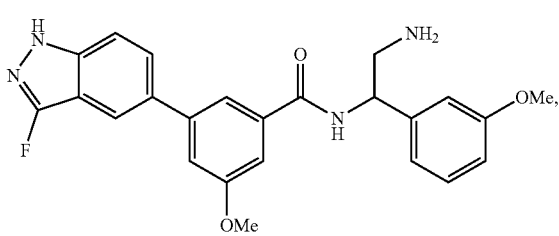
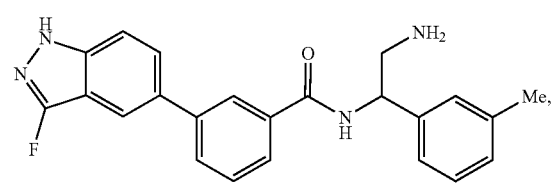
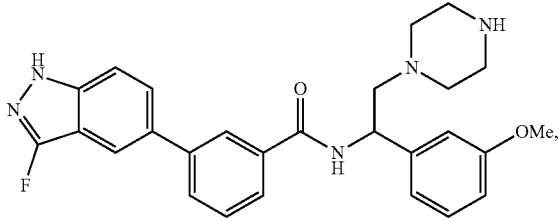
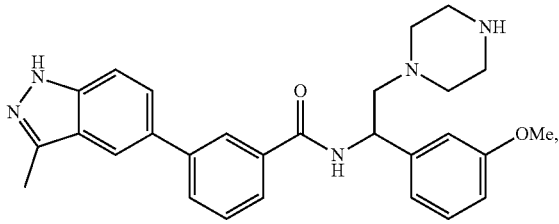
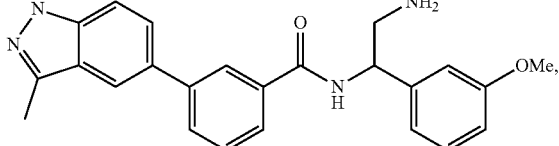
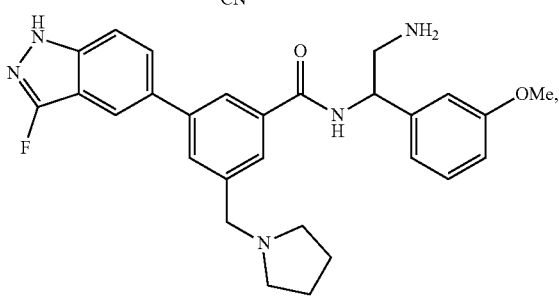

-continued
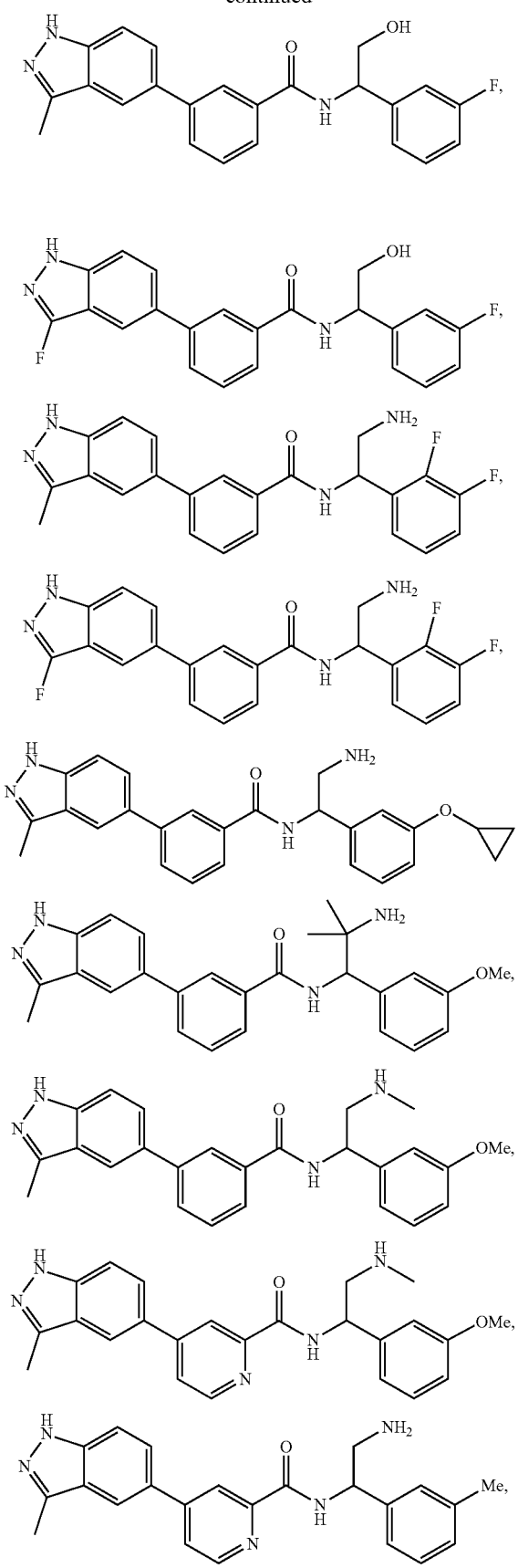
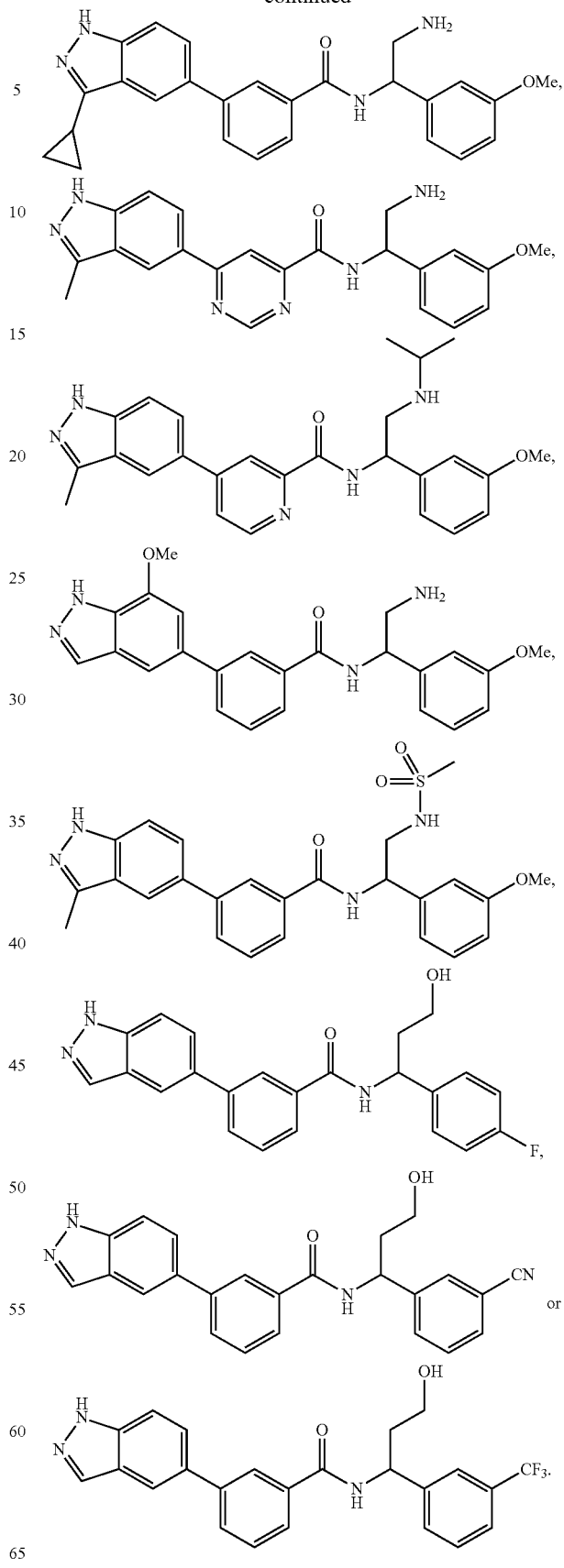

In some embodiments of the present disclosure, the compound is:
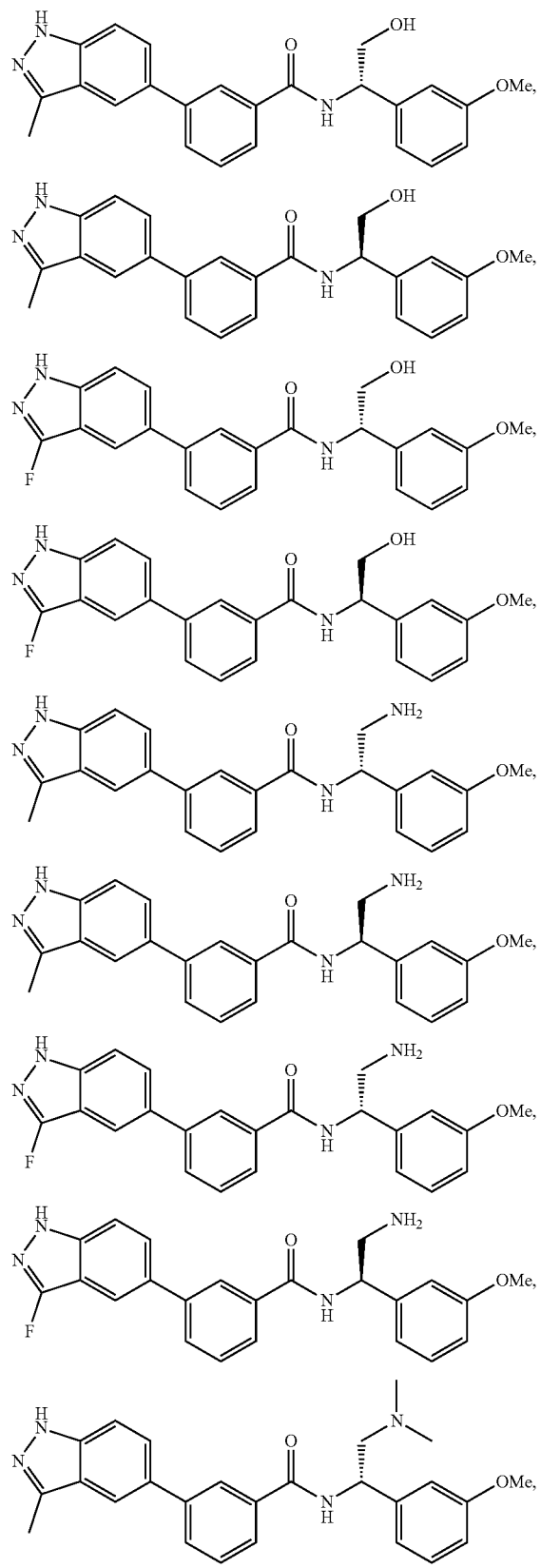
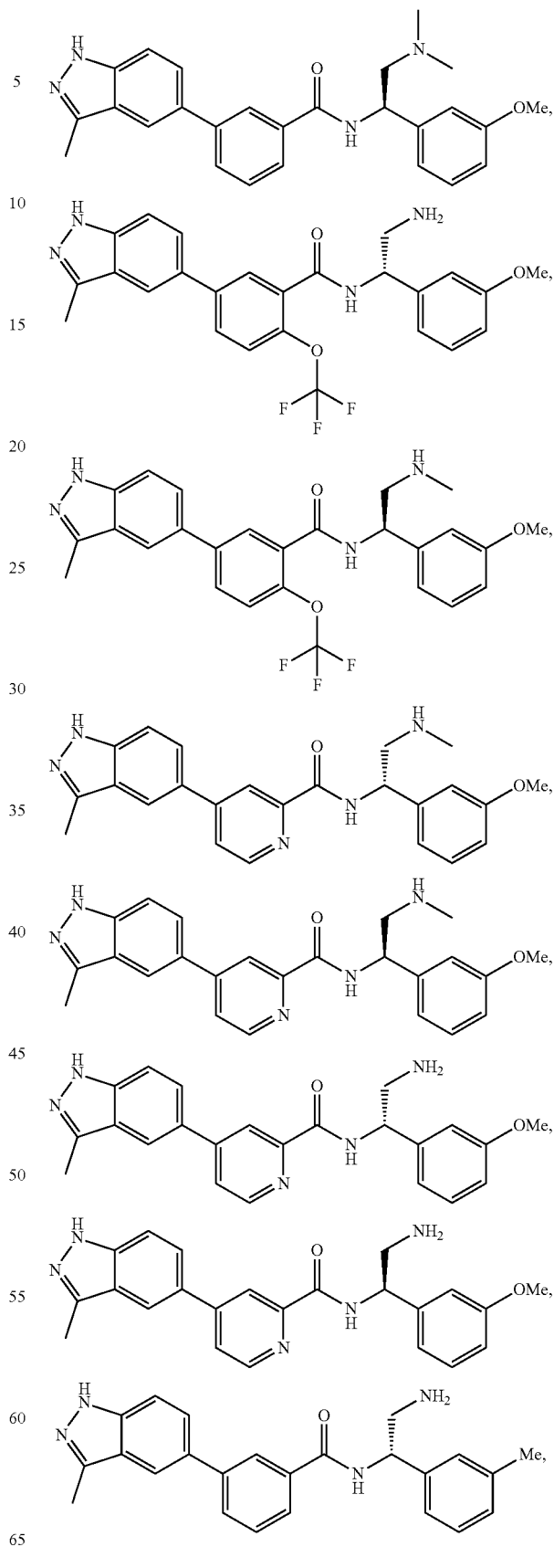

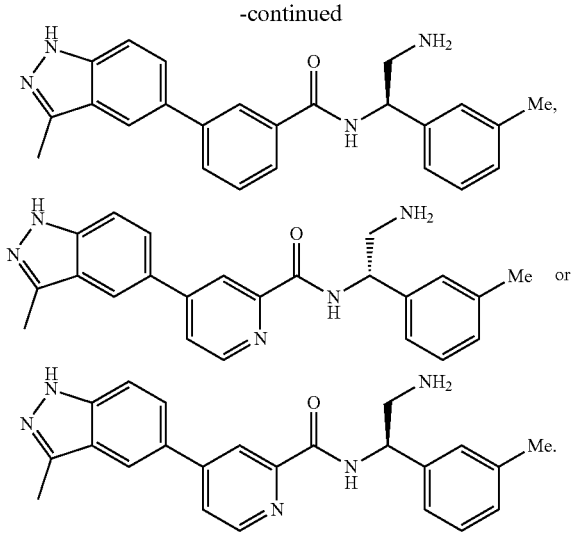

In some embodiments of the present disclosure, the pharmaceutically acceptable salts of the compounds are formate or hydrochloride.

In another aspect, the present disclosure provides a pharmaceutical composition comprising a therapeutically effective amount of the compound, the pharmaceutically acceptable salt thereof or the isomer thereof as an active ingredient, and a pharmaceutically acceptable carrier.

The present disclosure also provides a use of the compound, the pharmaceutically acceptable salt thereof or the isomer thereof, and the pharmaceutical composition in the manufacture of a medicament used as RHO inhibitor.

The present disclosure also provides a use of the compound, the pharmaceutically acceptable salt thereof or the isomer thereof, and the pharmaceutical composition in the manufacture of a medicament for treating pulmonary fibrosis and radiation pulmonary fibrosis.

Technical Effect

The compounds of the present disclosure have good inhibitory activity against ROCK2. In some embodiments, the compounds show certain selectivity to ROCK2. In some embodiments, the compounds show excellent pharmacokinetic and pharmacodynamic properties, and have significant kinase inhibitory activity, membrane permeability and solubility simultaneously.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

Unless otherwise specified, the term "isomer" is intended to include geometric isomers, cis-trans isomers, stereoisomers, enantiomers, optical isomers, diastereomers and tautomers.

The compounds of the disclosure may exist in specific geometric or stereoisomeric forms. The present disclosure contemplates all such compounds, including cis and trans isomers, (−)-and (+)-enantiomers, (R)-and (S)-enantiomers, diastereomers isomers, (D)-isomers, (L)-isomers, and racemic and other mixtures thereof, such as enantiomers or diastereomeric enriched mixtures, all of which are within the scope of the disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond ( ◆ ) and a wedged dashed bond ( ◆ ), and the relative configuration of a stereogenic center is represented by a straight solid bond ( ◆ ) and a straight dashed bond ( ◆ ), a wave line ( ◆ ) is used to represent a wedged dashed bond ( ◆ ) or a wedged dashed bond ( ◆ ), or the wave line ( ◆ ) is used to represent a straight solid bond ( ◆ ) and a straight dashed bond ( ◆ ).

Unless otherwise specified, when double bond structure, such as carbon-carbon double bond, carbon-nitrogen double bond, and nitrogen=nitrogen double bond, exists in the compound, and each of the atom on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ◆ ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

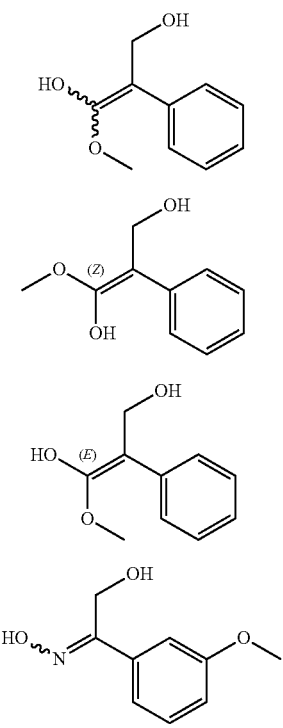

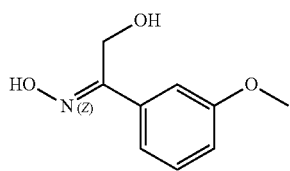

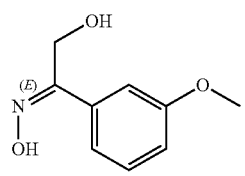

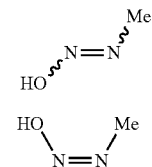

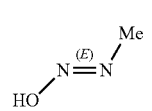

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

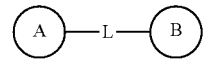

is -M-W-, then -M-W- can link ring A and ring B to form

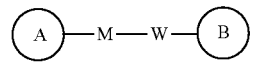

in the direction same as left-to-right reading order, and form

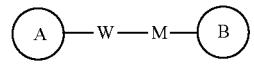

in the direction contrary to left-to-right reading order. A combination of the linking groups, substituents and/or variants thereof is allowed only when such combination can result in a stable compound.

Unless otherwise specified, when a group has one or more linkable sites, any one or more sites of the group can be linked to other groups through chemical bonds. The chemical bond between the site and other groups can be represented by a straight solid bond ( 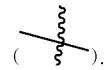 ), a straight dashed bond (  ), or a wave line

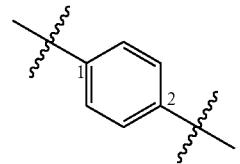 [SMILES: *c1ccc(*)cc1].

For example, the straight solid bond in —OCH$_3$ means that it is linked to other groups through the oxygen atom in the group; the straight dashed bond in means that it is linked to other groups through the two ends of the nitrogen atom in the group; the wave line in means that it is linked to other groups through the 1 and 2 carbon atoms in the phenyl group.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), or —N(H)—.

Unless otherwise specified, the number of atoms in a ring is generally defined as the number of ring members. For example, "5- to 7-membered ring" refers to a "ring" in which 5-7 atoms are arranged around.

Unless otherwise specified, the term "ring" refers to a cycloalkyl, heterocycloalkyl, cycloalkenyl, heterocycloalkenyl, cycloalkynyl, heterocycloalkynyl, aryl or heteroaryl. The ring includes single ring and double ring or multiple ring system such as spiral ring, fused ring, and bridged ring. The number of the atom on the ring is usually defined as the member number of the ring, for example, a "5- to 7-membered ring" means that 5 to 7 atoms are arranged on a ring. Unless otherwise specified, the ring optionally contains 1 to 3 heteroatoms. Therefore, a "5- to 7-membered ring" includes, for example, phenyl, pyridinyl and piperidyl; on the other hand, the term "5- to 7-membered heterocycloalkyl" includes piperidyl, but excluding phenyl. The term "ring" also includes a ring system containing at least one ring, wherein each "ring" independently meets the above definition.

Unless otherwise specified, the term "$C_{1-6}$ alkyl" refers to a linear or branched saturated hydrocarbon group containing 1 to 6 carbon atoms. The $C_{1-6}$ alkyl group includes $C_{1-5}$, $C_{1-4}$, $C_{1-3}$ and $C_{1-2}$ alkyl groups and the like. It can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-4}$ alkyl" refers to a linear or branched saturated hydrocarbon group composed of 1 to 4 carbon atoms. The $C_{1-4}$ alkyl group includes $C_{1-2}$, $C_{1-3}$ and $C_{2-3}$ alkyl groups and the like; it can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl) etc.

Unless otherwise specified, the term "$C_{1-3}$ alkyl" refers to a linear or branched saturated hydrocarbon group composed of 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "heteroalkyl" by itself or in combination with another term refers to a stable linear or branched alkyl group or a combination thereof composed of a certain number of carbon atoms and at least one heteroatom or heteroatomic group. In some embodiments, the heteroatoms are selected from O, N, and S, wherein the N and S atoms are optionally oxidized, and the N heteroatoms are optionally quaternized. In some embodiments, the heteroalkyl is $C_{1-6}$ heteroalkyl; in other embodiments, the heteroalkyl is $C_{1-3}$ heteroalkyl. The heteroatom or heteroatomic group can be located in any internal position of the heteroalkyl, including the attachment position of the alkyl to the rest of the molecule, but the term "$C_{1-6}$ alkylamino" refers to the alkyl group containing 1-6 carbon atoms whose amino group is attached to the rest of the molecule. The $C_{1-6}$ alkylamino includes $C_{1-5}$, $C_{1-4}$, $C_{1-3}$, $C_{1-2}$, $C_1$, $C_2$, $C_3$, $C_4$, $C_5$, $C_6$ alkylamino, etc. Examples of alkylamino includes, but are not limited to, —NHCH$_3$, —N(CH$_3$)$_2$, —NHCH$_2$CH$_3$, —N(CH$_3$)(CH$_2$CH$_3$), etc. Examples of heteroalkyl includes, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, etc. At most two heteroatoms can be continuous, for example —CH$_2$—NH—OCH$_3$.

But the term "$C_{1-3}$ alkylamino" refers to the alkyl group containing 1-3 carbon atoms whose amino group is attached to the rest of the molecule. The $C_{1-3}$ alkylamino includes $C_{1-2}$, $C_1$, $C_2$, $C_3$, alkylamino, etc. Examples of alkylamino includes, but are not limited to, —NHCH$_3$, —N(CH$_3$)$_2$, —NHCH$_2$CH$_3$, —N(CH$_3$)(CH$_2$CH$_3$), etc.

Unless otherwise specified, the term "$C_{3-6}$ cycloalkyl" refers to any stable cyclic alkyl group containing 3 to 6 carbon atoms. The $C_{3-6}$ cycloalkyl is a monocyclic ring system. The $C_{3-6}$ cycloalkyl includes $C_{3-5}$, $C_{3-4}$, $C_{4-6}$, $C_{5-6}$, $C_3$ and $C_6$ cycloalkyl groups and the like, and it may be monovalent, divalent, or multivalent. Examples of $C_{3-6}$ cycloalkyl include, but are not limited to, cyclopropyl, cyclobutyl, cyclopentyl, cyclohexyl and the like.

Unless otherwise specified, the term "$C_{3-4}$ cycloalkyl" refers to any stable cyclic alkyl group containing 3 to 4 carbon atoms. The $C_{3-4}$ cycloalkyl is a monocyclic ring system, and may be monovalent, divalent, or multivalent. Examples of $C_{3-4}$ cycloalkyl include cyclopropyl and cyclobutyl.

Unless otherwise specified, the term "4- to 8-membered heterocycloalkyl" by itself or in combination with other terms refers to cyclized "heteroalkyl", and the "4- to 8-membered heterocycloalkyl" contains 4 to 8 ring atoms, and it includes monocyclic and bicyclic ring systems, wherein bicyclic ring includes spiro ring, fused ring, and bridged ring. In addition, with regard to the "4- to 8-membered heterocycloalkyl", a heteroatom may occupy the linking position of the heterocycloalkyl with the rest of the molecule. The 4- to 8-membered heterocycloalkyl includes 4- to 5-membered, 4- to 6-membered, 5- to 6-membered, 5-membered, and 6-membered heterocycloalkyl groups. Examples of 4- to 8-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidyl or oxepanyl.

Unless otherwise specified, the term "5- to 6-membered heterocycloalkyl" by itself or in combination with other terms refers to a saturated cyclic group consisting of 5 to 6 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and S(O)$_p$, p is 1 or 2). Monocyclic and bicyclic ring systems are included, wherein the bicyclic ring system includes spiro, fused and bridged rings. In addition, with regard to the "5- to 6-membered heterocycloalkyl", a heteroatom may occupy the connection position of the heterocycloalkyl with the rest of the molecule. The 5- to 6-membered heterocycloalkyl includes 5- and 6-membered heterocycloalkyl groups. Examples of 5- to 6-membered heterocycloalkyl include, but are not limited to, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl), morpholinyl (including 3-morpholinyl and 4-morpholinyl, etc.), dioxanyl, dithiazyl, isoxazolidinyl, isothiazolidinyl, 1,2-oxazinyl, 1,2-thiazinyl, hexahydropyridazinyl, homopiperazinyl or homopiperidyl, etc.

Unless otherwise specified, the term "5-membered heterocycloalkyl" by itself or in combination with other terms refers to a saturated cyclic group consisting of 5 ring atoms, of which 1, 2, 3 or 4 ring atoms are independently selected from O, S and N, the rest are carbon atoms, wherein the N atom is optionally quaternized, and the N and S heteroatoms can be optionally oxidized (i.e. NO and $S(O)_p$, p is 1 or 2), which is a single ring system. In addition, with regard to the "5-membered heterocycloalkyl", a heteroatom may occupy the connection position of the heterocycloalkyl with the rest of the molecule. Examples of 5-membered heterocycloalkyl include but are not limited to pyrrolidinyl, pyrazolidinyl, imidazolidinyl, tetrahydrothienyl (including tetrahydrothiophen-2-yl and tetrahydrothiophen-3-yl, etc.), tetrahydrofuryl (including tetrahydrofuran-2-yl, etc.) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n-membered to n+m-membered means that the number of atoms in the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl, and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvent used in the present disclosure is commercially available.

The present disclosure uses the following abbreviating words: $CD_3OD$ represents for deuterated methanol; $CDCl_3$ represents for deuterated chloroform; DMSO represents for dimethyl sulfoxide; Boc represents for tert-butoxycarbonyl.

The compounds of the present disclosure are named according to the conventional naming principles in the field or using ChemDraw® software, and the commercially available compounds use the supplier catalog names.

SPECIFIC EMBODIMENTS

Figure 1:
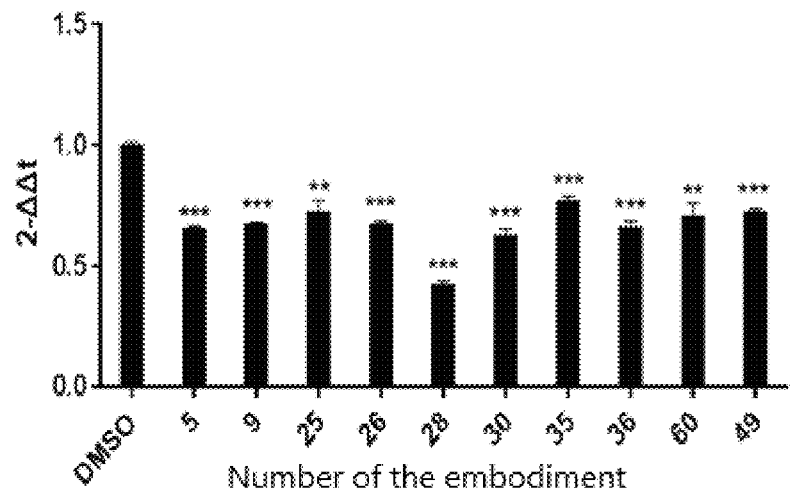
FIG. 1 shows the inhibitory effect of the embodiments 5, 9, 25, 26, 28, 30, 35, 36, 49 and 60 of the present disclosure on the expression of α-SMA gene.

The following examples further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure. The pH value of the hydrochloride or formate of the compound of the present disclosure can be adjusted to neutral by adding saturated sodium bicarbonate solution, and then purified by high performance liquid chromatography (neutral, ammonium bicarbonate system) to obtain the free base of the compound.

Embodiment 1

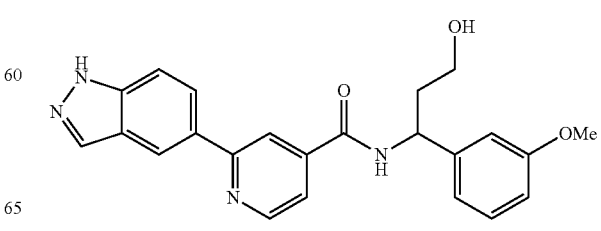

1

Synthetic Route:

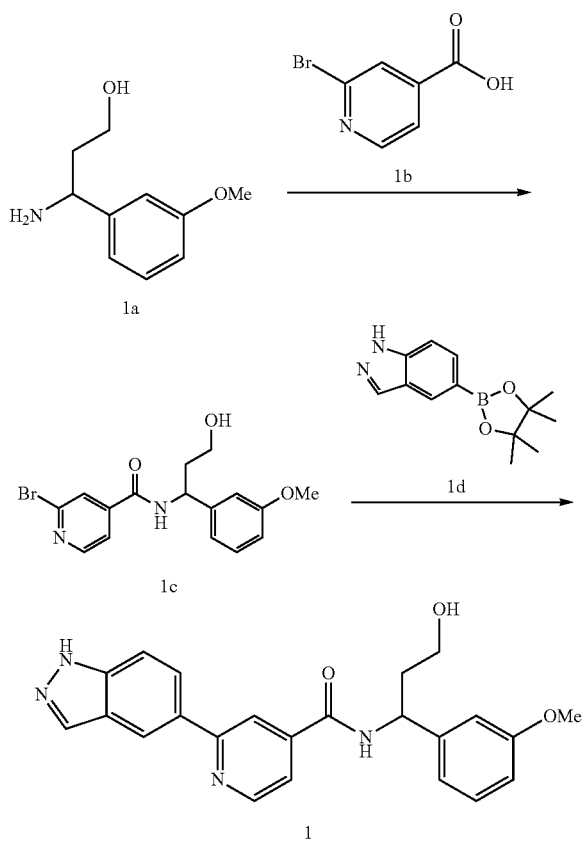

Step 1

Compound 1b (184 mg, 910 μmol) was dissolved in N,N-dimethylformamide (5 mL), and O-(7-azabenzotriazol-1-yl)-N,N,N',N'-tetramethyluronium hexafluorophosphate (629 mg, 1.66 mmol) and N,N-diisopropylethylamine (214 mg, 1.66 mmol, 288 μL) was added to the reaction mixture. The reaction mixture was stirred at 25° C. for 0.5 hour, and then compound 1a (150 mg, 828 μmol) was added to the reaction mixture and stirred at 25° C. for 12 hours. After the completion of the reaction, the reaction mixture was concentrated under reduced pressure, the residue was added with water (10 mL) and then extracted with ethyl acetate (10 mL×3), the combined organic phase was washed with saturated brine (20 mL×1), and dried over anhydrous sodium sulfate, filtered, the filtrate was concentrated under reduced pressure, and the obtained crude product was purified by thin-layer chromatography to give compound 1c. MS-ESI calculated values [M+H]$^+$ 365 and 367, measured values 365 and 367.

Step 2

Compound 1c (150 mg, 305 μmol), compound 1d (112 mg, 457 μmol), tris(dibenzylideneacetone) dipalladium (27.9 mg, 30.6 μmol), 2-dicyclohexylphosphino-2',4',6'-triisopropylbiphenyl (14.5 mg, 30.5 μmol) and cesium carbonate (298 mg, 914 μmol) were dissolved in dioxane (2.5 mL) and water (0.5 mL), and the air in the reaction flask was replaced with nitrogen gas for three times and then the reaction mixture was stirred for 12 hours at 90° C. under nitrogen protection. After the completion of the reaction, the reaction mixture was filtered, and the filtrate was concentrated under reduced pressure. The residue was added with water (10 mL) and extracted with ethyl acetate (10 mL×3), the combined organic phase was washed with saturated brine (20 mL×1), dried over anhydrous sodium sulfate, filtered, and the filtrate was concentrated under reduced pressure. The residue was purified by preparative high performance liquid chromatography (hydrochloric acid condition) to give the hydrochloride salt of compound 1. MS-ESI calculated value [M+H]$^+$ 403, measured value 403.

$^1$H NMR (400 MHz, CD$_3$OD) δ 8.91 (d, J=6.2 Hz, 1H), 8.72 (d, J=1.8 Hz, 1H), 8.55-8.52 (m, 1H), 8.32 (d, J=1.8 Hz, 1H), 8.24 (dd, J=1.8, 6.2 Hz, 1H), 8.00 (dd, J=1.8, 8.8 Hz, 1H), 7.85 (d, J=8.8 Hz, 1H), 7.33-7.25 (m, 1H), 7.06-7.00 (m, 2H), 6.88-6.82 (m, 1H), 5.36-5.29 (m, 1H), 3.80 (s, 3H), 3.71-3.58 (m, 2H), 2.28-2.07 (m, 2H) ppm.

Embodiment 2

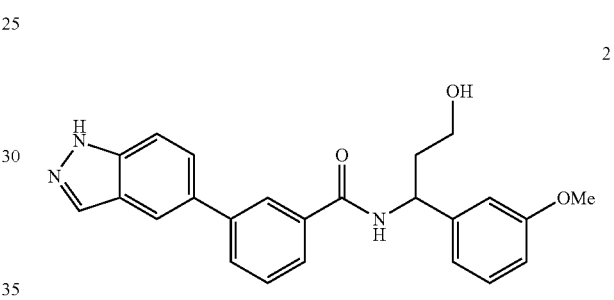

Synthetic Route:

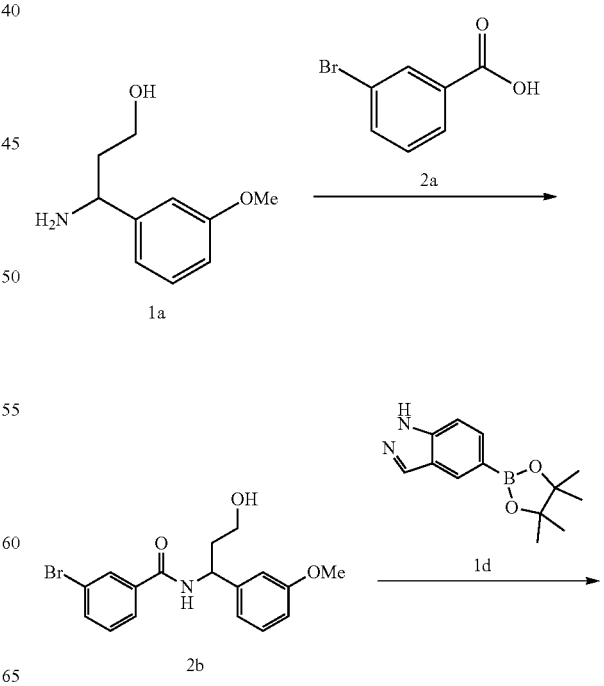

-continued

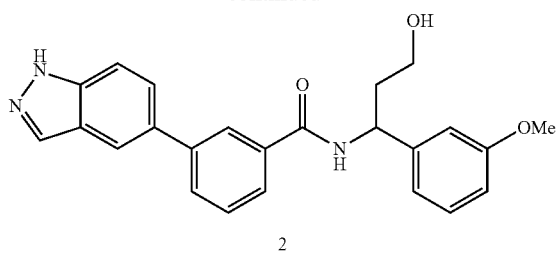

2

Compound 2b was obtained by referring to Step 1 of Embodiment 1. MS-ESI calculated values [M+H]$^+$ 364 and 366, and measured values: 364 and 366.

Step 2

Hydrochloride of compound 2 was obtained by referring to Step 2 of Embodiment 1. MS-ESI calculated value [M+H]$^+$ 402, measured value 402.

$^1$H NMR (400 MHz, CD$_3$OD) δ 8.30 (s, 1H), 8.18-8.10 (m, 2H), 7.89-7.79 (m, 3H), 7.69 (d, J=8.8 Hz, 1H), 7.61-7.54 (m, 1H), 7.26 (t, J=8.2 Hz, 1H), 7.05-6.98 (m, 2H), 6.85-6.78 (m, 1H), 5.33-5.26 (m, 1H), 3.79 (s, 3H), 3.72-3.60 (m, 2H), 2.19-2.07 (m, 2H) ppm.

Embodiment 3

3

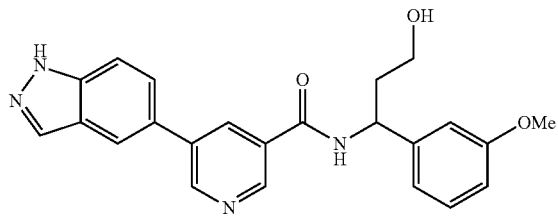

Synthetic Route:

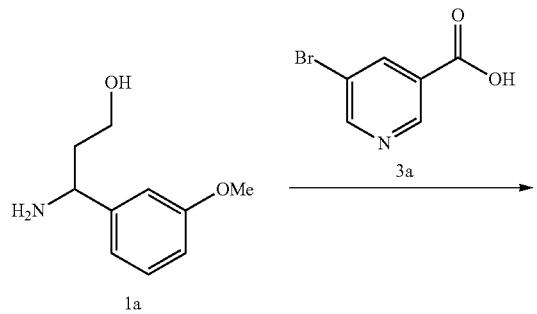

-continued

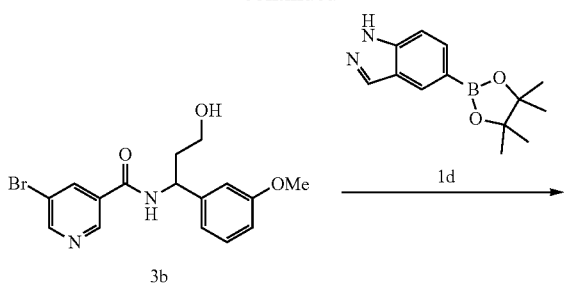

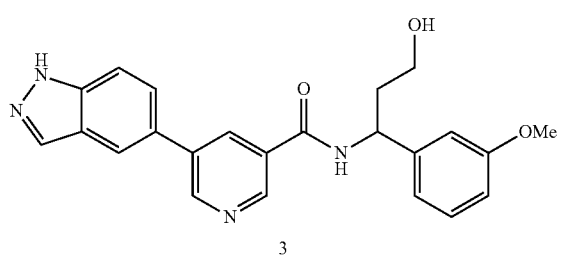

3

Step 1

Compound 3b was obtained by referring to Step 1 of Embodiment 1. MS-ESI calculated value [M+H]$^+$ 365 and 367, measured value 365 and 367.

Step 2

Hydrochloride of compound 3 was obtained by referring to Step 2 of Embodiment 1. MS-ESI calculated value [M+H]$^+$ 403, measured value 403.

$^1$H NMR (400 MHz, CD$_3$OD) δ 9.29 (d, J=1.8 Hz, 1H), 9.20-9.18 (m, 1H), 9.13 (d, J=1.8 Hz, 1H), 8.33 (s, 1H), 8.22 (s, 1H), 7.89 (dd, J=1.8, 8.8 Hz, 1H), 7.78 (d, J=8.8 Hz, 1H), 7.28 (t, J=7.8 Hz, 1H), 7.06-7.01 (m, 2H), 6.89-6.83 (m, 1H), 5.36-5.30 (m, 1H), 3.80 (s, 3H), 3.75-3.58 (m, 2H), 2.27-2.08 (m, 2H) ppm.

Embodiment 4

4

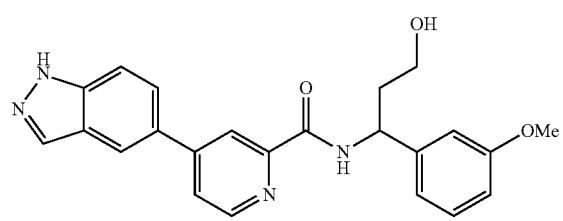

Synthetic Route:

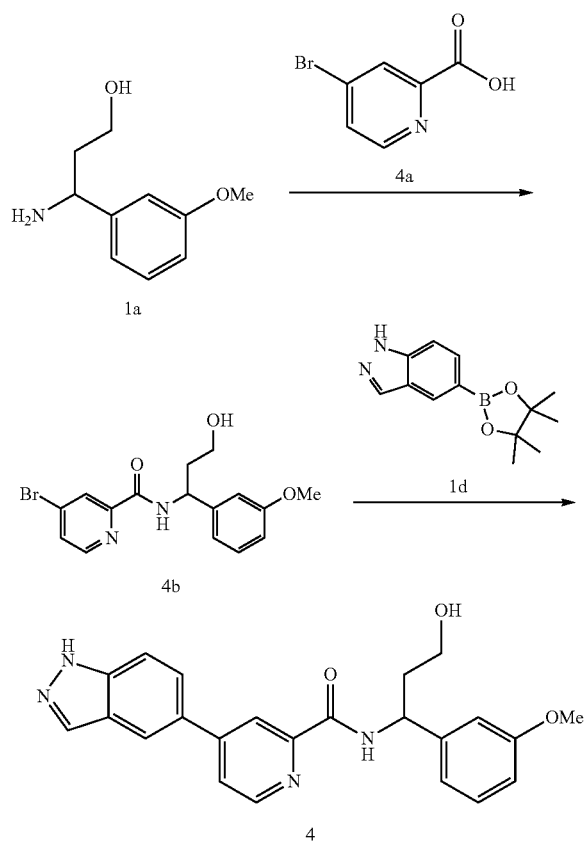

Step 1

Compound 4b was obtained by referring to Step 1 of Embodiment 1. MS-ESI calculated value [M+H]$^+$ 365 and 367, measured value 365 and 367.

Step 2

Hydrochloride of compound 4 was obtained by referring to Step 2 of Embodiment 1. MS-ESI calculated value [M+H]$^+$ 403, measured value 403.

$^1$H NMR (400 MHz, CD$_3$OD) δ 8.76-8.63 (m, 2H), 8.38 (s, 1H), 8.21 (s, 1H), 8.17-8.10 (m, 1H), 7.92 (d, J=8.8 Hz, 1H), 7.71 (d, J=8.8 Hz, 1H), 7.26 (t, J=8.2 Hz, 1H), 7.06-7.00 (m, 2H), 6.86-6.77 (m, 1H), 5.38-5.30 (m, 1H), 3.78 (s, 3H), 3.72-3.59 (m, 2H), 2.30-2.10 (m, 2H) ppm.

Embodiment 5

5

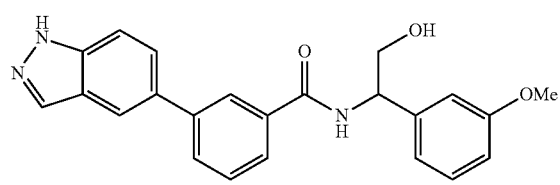

Synthetic Route:

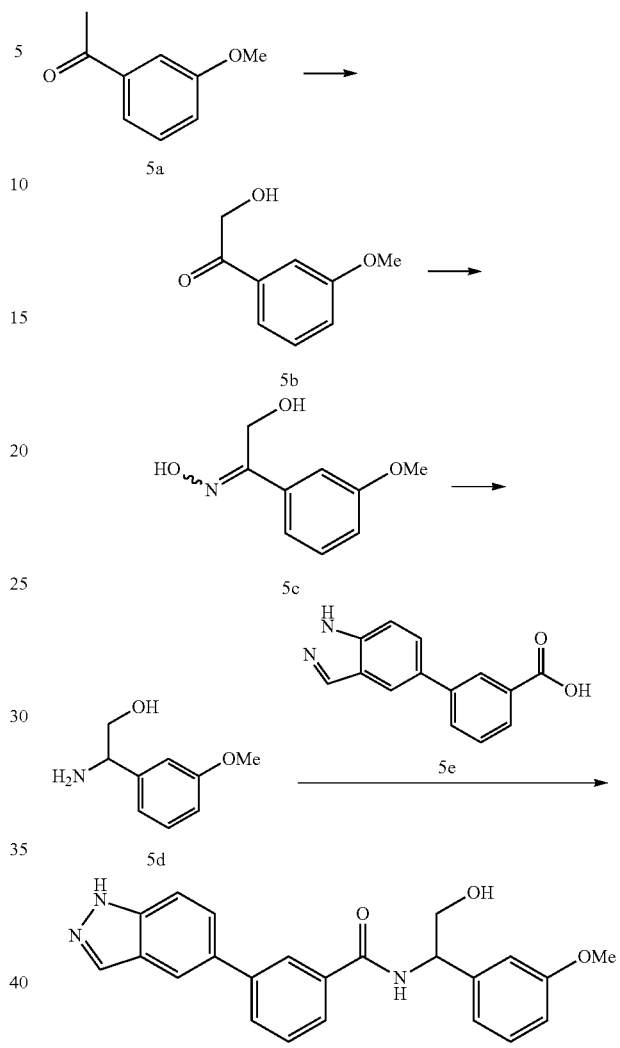

Step 1

Compound 5a (5.00 g, 33.3 mmol, 4.59 mL) was dissolved in acetonitrile (150 mL) and water (30 mL), bis(trifluoroacetoxy)iodobenzene (28.6 g, 66.6 mmol) and trifluoroacetic acid (7.59 g, 66.6 mmol, 4.93 mL) were added to the reaction mixture. The reaction mixture was stirred at 100° C. for 3 hours, after the completion of the reaction, the reaction mixture was concentrated under reduced pressure, the residue was diluted with water (50 mL) and extracted with dichloromethane (80 mL×3), the combined organic phase was washed with saturated sodium bicarbonate (80 mL×1), dried over anhydrous sodium sulfate, filtered, and the filtrate was concentrated under reduced pressure. The residue was purified by column chromatography to give compound 5b.

$^1$H NMR (400 MHz, CDCl$_3$) δ 7.41-7.36 (m, 2H), 7.35-7.29 (m, 1H), 7.13-7.05 (m, 1H), 4.78 (s, 2H), 3.79 (s, 3H), 3.42 (br s, 1H) ppm.

Step 2

Compound 5b (1.50 g, 9.03 mmol) was dissolved in ethanol (30 mL), then hydroxylamine hydrochloride (753 mg, 10.8 mmol) and sodium carbonate (1.44 g, 13.5 mmol) were added, and the resulting mixture was stirred at 50° C. for 12 hours. After the completion of the reaction, the reaction mixture was filtered and the filtrate was concentrated. The residue was purified by column chromatography to give compound 5c. MS-ESI calculated value $[M+H]^+$ 182, measured value 182.

$^1$H NMR (400 MHz, $CDCl_3$) δ 7.39-7.30 (m, 1H), 7.25-7.17 (m, 2H), 7.02-6.95 (m, 1H), 4.77 (s, 2H), 3.85 (s, 3H) ppm.

Step 3

Compound 5c (500 mg, 2.74 mmol) was dissolved in methanol (15 mL), and wet palladium-carbon (50.0 mg, purity 10%) was added under nitrogen protection, hydrogen gas replacement was performed for 3 times, and the reaction mixture was allowed to react at 30° C. under a hydrogen pressure of 50 Psi for 12 hours. After the completion of the reaction, the mixture was filtered, and the filtrate was concentrated under reduced pressure to give compound 8d, which was directly used in the next step without purification.

$^1$H NMR (400 MHz, $CDCl_3$) δ 7.28 (t, J=8.0 Hz, 1H), 6.95-6.87 (m, 2H), 6.83 (dd, J=2.3, 8.0 Hz, 1H), 4.03 (dd, J=4.2, 8.2 Hz, 1H), 3.82 (s, 3H), 3.74 (dd, J=4.2, 10.8 Hz, 1H), 3.56 (dd, J=8.2, 10.8 Hz, 1H), 2.28 (br s, 3H) ppm.

Step 4

Compound 5e (85.5 mg, 359 μmol) was dissolved in N,N-dimethylformamide (8 mL), and O-(7-azabenzotriazol-1-yl)-N,N,N',N'-tetramethyluronium hexafluorophosphate (177 mg, 466 μmol) and N,N-diisopropylethylamine (139 mg, 1.08 mmol, 188 μL) were added to the reaction mixture, the resulting mixture was stirred at 20° C. for 0.5 hour. Then compound 5d (60.0 mg, 359 μmol) was added to the mixture and stirred for 11.5 hours. After the completion of the reaction, the mixture was diluted with water (40 mL) and extracted with ethyl acetate (30 mL×2). The combined organic phase was washed with saturated brine (30 mL×1), dried over anhydrous sodium sulfate, filtered, and the filtrate was concentrated under reduced pressure. The residue was purified by high performance liquid chromatography (formic acid condition) to give compound 5.

MS-ESI calculated value $[M+H]^+$ 388, measured value 388.

$^1$H NMR (400 MHz, $CD_3OD$) δ 8.28-8.04 (m, 3H), 7.92-7.83 (m, 2H), 7.79 (dd, J=1.6, 8.8 Hz, 1H), 7.66 (d, J=8.8 Hz, 1H), 7.58 (t, J=7.8 Hz, 1H), 7.34-7.21 (m, 1H), 7.08-6.98 (m, 2H), 6.85 (dd, J=2.0, 7.8 Hz, 1H), 5.24 (t, J=6.4 Hz, 1H), 3.90 (d, J=6.4 Hz, 2H), 3.81 (s, 3H) ppm.

Embodiment 6

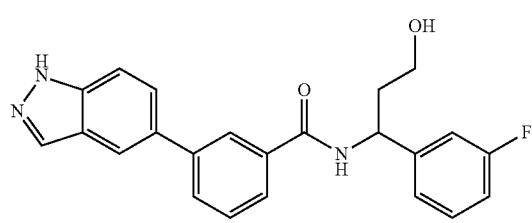

Synthetic Route:

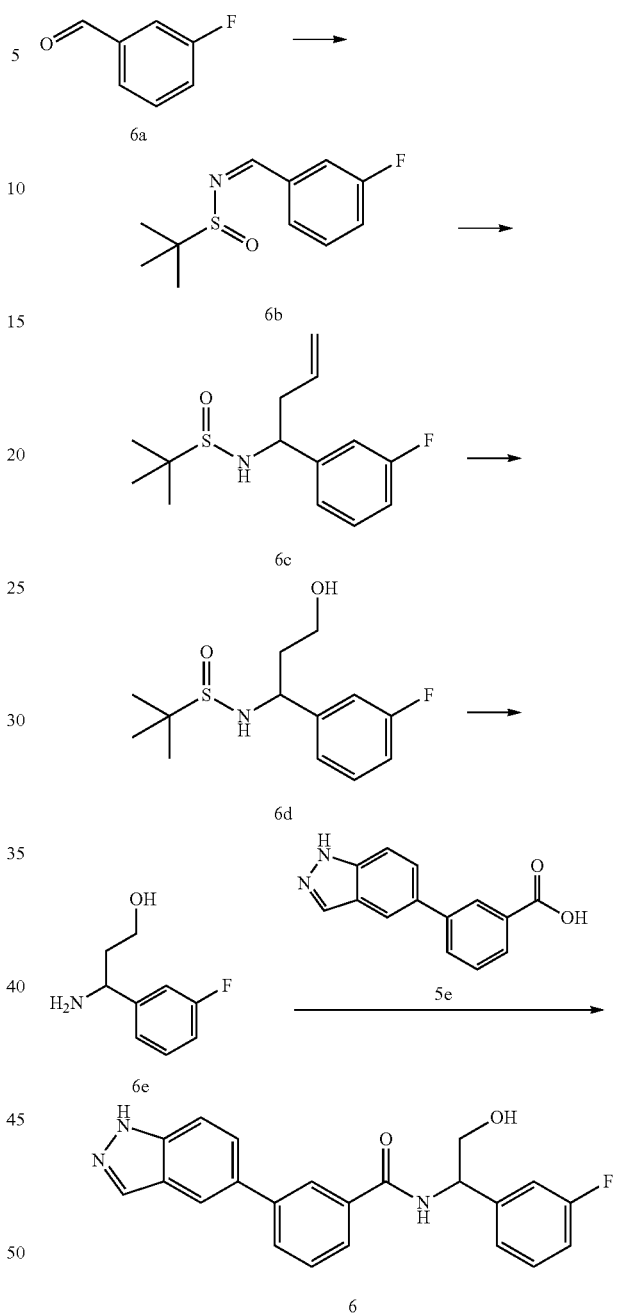

Step 1

Compound 6a (1.50 g, 12.1 mmol, 1.27 mL) was dissolved in dichloromethane (20 mL), and tert-butylsulfinamide (1.90 g, 15.7 mmol) and cesium carbonate (7.88 g, 24.2 mmol) were added to the reaction mixture. The reaction mixture was stirred at 20° C. for 16 hours, after the completion of the reaction, the reaction mixture was concentrated under reduced pressure to give a crude product of compound 6b. MS-ESI calculated value $[M+H]^+$ 228, measured value 228.

¹H NMR (400 MHz, CDCl₃) δ 8.58 (d, J=1.2 Hz, 1H), 7.64-7.58 (m, 2H), 7.51-7.44 (m, 1H), 7.27-7.21 (m, 1H), 1.29 (s, 9H) ppm.

Step 2

Compound 6b (1.00 g, 4.40 mmol) was dissolved in tetrahydrofuran (10 mL), the temperature was reduced to −78° C., allylmagnesium bromide (1 M, 8.80 mL) was added dropwise, and the mixture was stirred at −78° C. for 1 hour. After the completion of the reaction, the reaction mixture was quenched with saturated ammonium chloride (20 mL) at 0° C., and then extracted with ethyl acetate (20 mL×3). The combined organic phase was dried over anhydrous magnesium sulfate and filtered; the filtrate was concentrated under reduced pressure. The residue was purified by column chromatography to give compound 6c. MS-ESI calculated value [M+H]⁺ 270, measured value 270.

Step 3

Compound 6c (1.00 g, 3.71 mmol) was dissolved in dichloromethane (25 mL) and methanol (5 mL), and ozone (15 Psi) was introduced at −78° C. until the reaction mixture turned blue, and then at 0° C., sodium borohydride (281 mg, 7.42 mmol) was added and the reaction was carried out at 25° C. for 12 hours. After the completion of the reaction, saturated ammonium chloride solution (25 mL) was added to quench the reaction, and then the mixture was extracted with dichloromethane (30 mL×3), the combined organic phase was dried over anhydrous magnesium sulfate, filtered, and the filtrate was concentrated under reduced pressure. The residue was purified by column chromatography to give compound 6d. Calculated value [M+H]⁺ 274, measured value 274.

Step 4

Compound 6d (200 mg, 732 μmol) was dissolved in dichloromethane (3 mL), a solution (4 M, 3 mL) of hydrogen chloride in dioxane was added thereto, and the mixture was stirred at 20° C. for 1 hour. After the completion of the reaction, the reaction mixture was concentrated to give a crude product of compound 6e. MS-ESI calculated value [M+H]⁺ 170, measured value 170.

Step 5

Compound 5e (204 mg, 857 μmol) was dissolved in N,N-dimethylformamide (5 mL), O-(7-azabenzotriazol-1-yl)-N,N,N',N'-tetramethyluronium hexafluorophosphate (402 mg, 1.06 mmol) and N,N-diisopropylethylamine (273 mg, 2.12 mmol, 368 μL) were added to the reaction mixture, and the mixture was stirred at 20° C. for 0.5 hour. Then compound 6e (145 mg, 705 μmol) was added thereto, and stirred for 1.5 hours. After the completion of the reaction, the mixture was diluted with water (20 mL), and extracted with a mixed solvent (20 mL×3) of ethyl acetate and 2-methyltetrahydrofuran (with a ratio of 1:1), the combined organic phase was washed once with saturated sodium chloride solution (30 mL), then dried over anhydrous sodium sulfate, filtered, and the filtrate was concentrated under reduced pressure. The residue was purified by high performance liquid chromatography (formic acid condition) to give compound 6. MS-ESI calculated value [M+H]⁺ 390, measured value 390.

¹H NMR (400 MHz, CD₃OD) δ 8.14 (s, 1H), 8.12 (s, 1H), 8.09 (s, 1H), 7.88 (d, J=7.8 Hz, 1H), 7.83 (d, J=7.8 Hz, 1H), 7.77 (d, J=9.2 Hz, 1H), 7.68-7.64 (m, 1H), 7.61-7.55 (m, 1H), 7.42-7.35 (m, 1H), 7.28 (d, J=7.8 Hz, 1H), 7.23-7.18 (m, 1H), 7.03-6.95 (m, 1H), 5.44-5.29 (m, 1H), 3.76-3.62 (m, 2H), 2.26-2.05 (m, 2H) ppm.

Embodiment 7

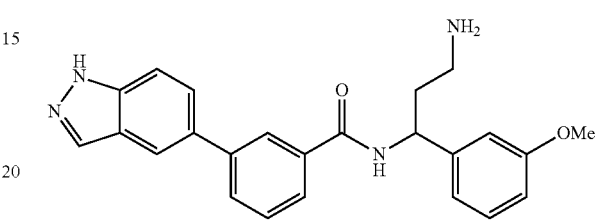

Synthetic Route:

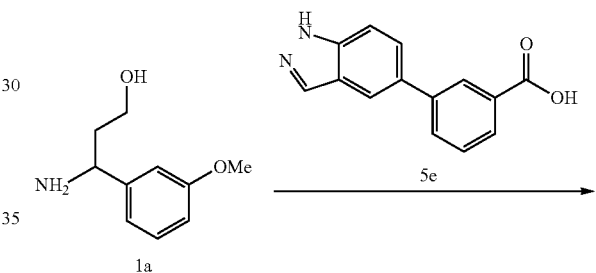

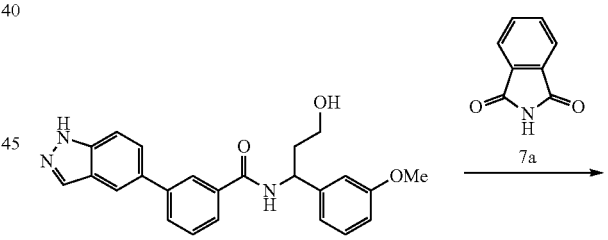

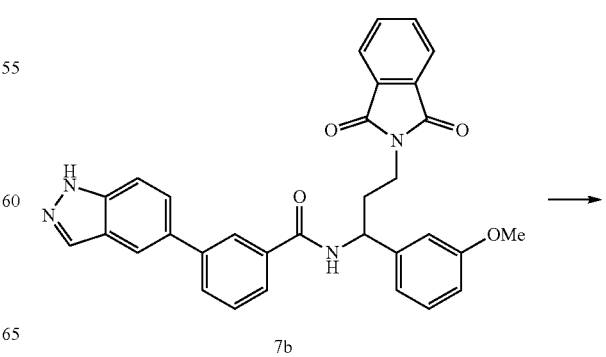

-continued

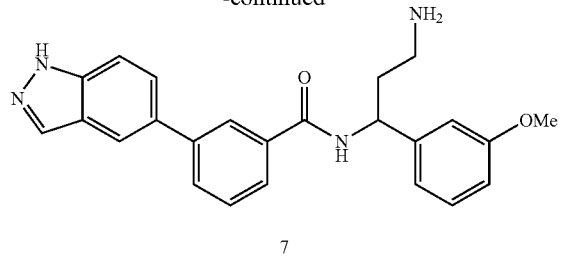

7

Step 1

Compound 5e (2.50 g, 10.5 mmol) was dissolved in N,N-dimethylformamide (15 mL), and O-(7-azabenzotriazol-1-yl)-N,N,N',N'-tetramethyluronium hexafluorophosphate (5.98 g, 15.7 mmol) and N,N-diisopropylethylamine (4.06 g, 31.5 mmol, 5.48 mL) were added to the reaction mixture, and stirred at 20° C. for 0.5 hour. Then compound 1a (1.90 g, 10.5 mmol) was added to the mixture and stirred for 11.5 hours. After the completion of the reaction, the mixture was diluted with a saturated aqueous solution of ammonium chloride (30 mL) and extracted with a mixed solvent (40 mL×3) of ethyl acetate and tetrahydrofuran (with a ratio of 4:1), the combined organic phase was dried over anhydrous sodium sulfate, filtered, and the filtrate was concentrated under reduced pressure. The residue was purified by column chromatography to give compound 2.

MS-ESI calculated value [M+H]$^+$ 402, measured value 402.

Step 2

Compound 2 (300 mg, 747 μmol), compound 7a (143 mg, 971 μmol) and triphenylphosphine (392 mg, 1.49 mmol) were dissolved in tetrahydrofuran (8 mL), diisopropyl azodicarboxylate (302 mg, 1.49 mmol, 291 μL) was added dropwise at 0° C., after the addition, the reaction was performed at 0 to 20° C. for 12 hours. After the completion of the reaction, a saturated sodium bicarbonate aqueous solution (20 mL) was added to the reaction mixture, and the mixture was diluted with water (10 mL), extracted with ethyl acetate (30 mL×2), the combined organic phase was washed with saturated brine (30 mL×1), dried over anhydrous sodium sulfate, filtered, and the filtrate was concentrated under reduced pressure. The residue was purified by column chromatography to give compound 7b. MS-ESI calculated value [M+H]$^+$ 531, measured value 531.

Step 3

Compound 7b (200 mg, 158 μmol) was dissolved in ethanol (6 mL), 85% hydrazine monohydrate (74.4 mg, 1.26 mmol, 72.3 μL) was added and the reaction was performed at 55° C. for 12 hours. After the completion of the reaction, the reaction mixture was concentrated under reduced pressure, and the residue was purified by high performance liquid chromatography (formic acid condition) to give the formate of compound 7. MS-ESI calculated value [M+H]$^+$ 401, measured value 401.

$^1$H NMR (400 MHz, CD$_3$OD) δ 8.54 (br s, 1H), 8.17 (s, 1H), 8.13 (s, 1H), 8.08 (s, 1H), 7.91-7.81 (m, 2H), 7.76 (dd, J=1.6, 8.8 Hz, 1H), 7.69-7.63 (m, 1H), 7.58 (t, J=7.8 Hz, 1H), 7.34 (t, J=8.0 Hz, 1H), 7.11-7.04 (m, 2H), 6.91 (dd, J=1.8, 8.0 Hz, 1H), 5.29 (dd, J=6.4, 8.8 Hz, 1H), 3.83 (s, 3H), 3.18-2.91 (m, 2H), 2.44-2.22 (m, 2H) ppm.

Embodiment 8

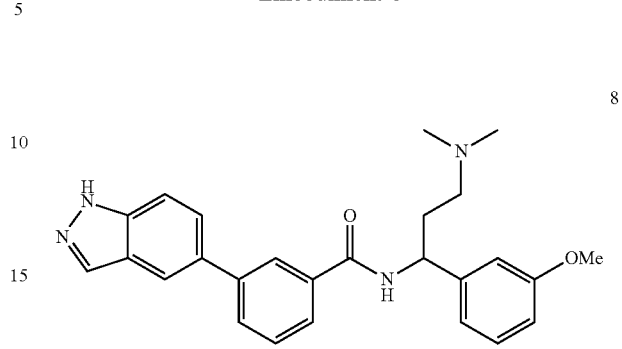

8

Synthetic Route:

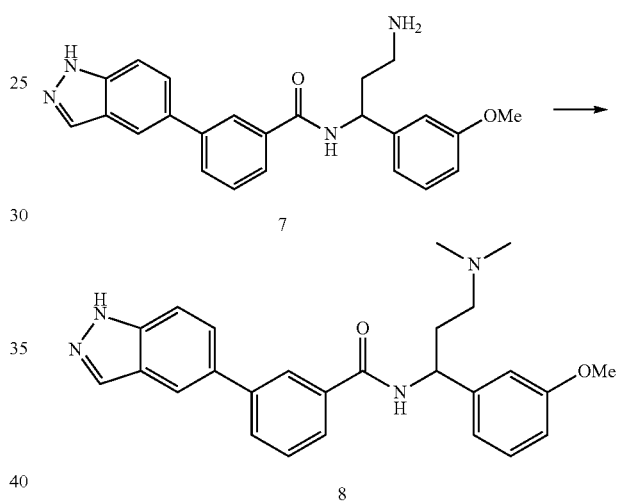

Compound 7 (400 mg, 999 μmol) was dissolved in methanol (10 mL), 37% aqueous formaldehyde solution (1.22 g, 15.0 mmol, 1.12 mL) and acetic acid (60.0 mg, 999 μmol, 57.1 μL) were added, the mixture was stirred at 20° C. for 0.5 hour. Sodium cyanoborohydride (942 mg, 15.0 mmol) was added to the reaction mixture and the mixture was stirred for 11.5 hours at 20° C. After the completion of the reaction, water (20 mL) was added to quench the reaction, and then the mixture was diluted with water (20 mL) and extracted with ethyl acetate (30 mL×2), the combined organic phase was washed with saturated brine (30 mL×1), dried over anhydrous sodium sulfate, filtered, and the filtrate was concentrated under reduced pressure. The residue was purified by high performance liquid chromatography (formic acid condition) to give the formate of compound 8.

MS-ESI calculated value [M+H]$^+$ 429, measured value 429.

$^1$H NMR (400 MHz, CD$_3$OD) δ 8.46 (br s, 1H), 8.17 (s, 1H), 8.14 (s, 1H), 8.11 (s, 1H), 7.91-7.81 (m, 2H), 7.76 (dd, J=1.6, 8.8 Hz, 1H), 7.71-7.55 (m, 2H), 7.34 (br t, J=7.8 Hz, 1H), 7.13-7.02 (m, 2H), 6.97-6.84 (m, 1H), 5.26 (dd, J=6.4, 8.8 Hz, 1H), 3.87-3.78 (m, 3H), 3.27-3.10 (m, 2H), 2.87 (s, 6H), 2.46-2.27 (m, 2H) ppm.

Embodiment 9

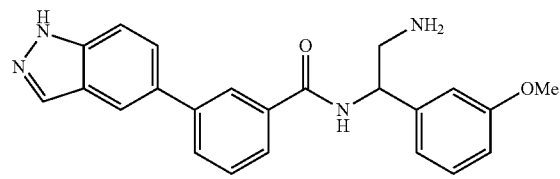

Synthetic Route:

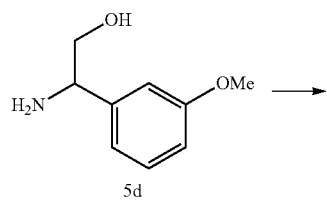

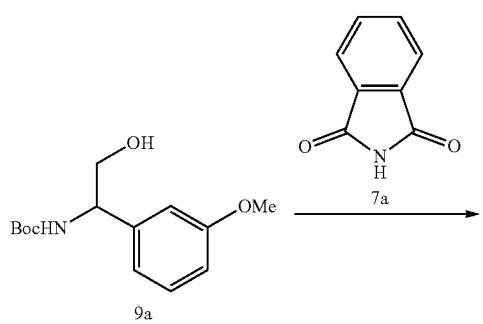

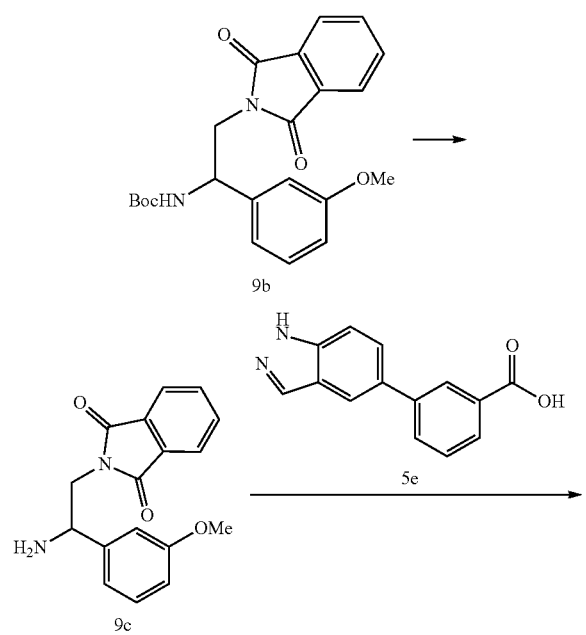

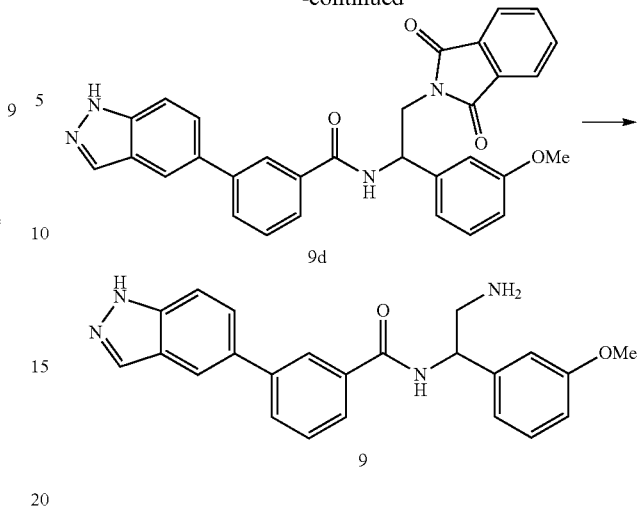

Step 1

Compound 5d (500 mg, 2.99 mmol) was dissolved in dichloromethane (15 mL), triethylamine (757 mg, 7.48 mmol, 1.04 mL) and di-tert-butyl dicarbonate (848 mg, 3.89 mmol, 893 μL) were added, the reaction was performed at 20° C. for 6 hours. After the completion of the reaction, the reaction mixture was concentrated under reduced pressure, and the residue was purified by column chromatography to give compound 9a.

$^1$H NMR (400 MHz, CDCl$_3$) δ 7.23-7.18 (m, 1H), 6.85-6.72 (m, 3H), 5.20-5.10 (m, 1H), 4.72-4.62 (m, 1H), 3.80-3.75 (m, 2H), 3.74 (s, 3H), 2.22 (br, 1H), 1.37 (s, 9H) ppm.

Step 2

Compound 9a (200 mg, 748 μmol), compound 7a (165 mg, 1.12 mmol) and triphenylphosphine (392 mg, 1.50 mmol) were dissolved in tetrahydrofuran (10 mL), diisopropyl azodicarboxylate (303 mg, 1.50 mmol, 291 μL) was added dropwise at 0° C., and the mixture was stirred at 20° C. for 12 hours. After the completion of the reaction, a saturated sodium bicarbonate solution (10 mL) was added to quench the reaction, and the mixture was diluted with water (10 mL), and extracted with ethyl acetate (20 mL×2), the combined organic phase was washed with saturated brine (20 mL×1), dried over anhydrous sodium sulfate, filtered, and the filtrate was concentrated under reduced pressure. The residue was purified by thin-layer chromatography to give compound 9b. MS-ESI calculated value [M-Boc+H]$^+$ 297, measured value 297.

Step 3

Compound 9b (90.0 mg, 227 μmol) was dissolved in dioxane (2 mL), a solution of hydrogen chloride in dioxane (4 M, 3 mL) was added thereto, and the reaction was performed at 20° C. for 0.5 hour. After the completion of the reaction, the reaction mixture was concentrated under reduced pressure to give crude compound 9c.

MS-ESI calculated value [M+H]$^+$ 297, measured value 297.

Step 4

Compound 5e (78.8 mg, 331 μmol) was dissolved in N,N-dimethylformamide (6 mL), and O-(7-azabenzotriazol- 1-yl)-N,N,N',N'-tetramethyluronium hexafluorophosphate (163 mg, 430 μmol) and N,N-diisopropylethylamine (171 mg, 1.32 mmol, 230 μL) were added to the reaction mixture, then compound 9c (110 mg, 331 μmol) was added thereto, the mixture was stirred for 12 hours. After the completion of the reaction, the mixture was diluted with water (40 mL) and extracted with ethyl acetate (20 mL×2), the combined organic phase was washed with saturated brine (30 mL×1), dried over anhydrous sodium sulfate and filtered, and the filtrate was concentrated under reduced pressure. The residue was purified by thin-layer chromatography to give compound 9d. MS-ESI calculated value [M+H]+ 517, measured value 517.

Step 5

Compound 9d (100 mg, 125 μmol) was dissolved in ethanol (5 mL), hydrazine monohydrate (50.0 mg, 998 μmol, 48.5 μL) was added thereto, and the mixture was stirred at 55° C. for 12 hours. After the completion of the reaction, the mixture was concentrated under reduced pressure and purified by high performance liquid chromatography (neutral condition) to give compound 9.

MS-ESI calculated value [M+H]+ 387, measured value 387.

$^1$H NMR (400 MHz, CD$_3$OD) δ 8.22 (s, 1H), 8.14 (s, 1H), 8.11 (s, 1H), 7.91-7.83 (m, 2H), 7.78 (dd, J=1.2, 8.6 Hz, 1H), 7.66 (d, J=8.6 Hz, 1H), 7.59 (t, J=7.8 Hz, 1H), 7.31 (t, J=8.0 Hz, 1H), 7.07-6.99 (m, 2H), 6.91-6.84 (m, 1H), 5.22-5.17 (m, 1H), 3.85-3.79 (m, 3H), 3.18-3.03 (m, 2H) ppm.

Embodiment 10

Compound 9 (150 mg, 388 μmol) was dissolved in methanol (8 mL), 37% aqueous formaldehyde solution (472 mg, 5.82 mmol, 433 μL) and acetic acid (23.3 mg, 388 μmol, 22.2 μL) were added, and then sodium cyanoborohydride (366 mg, 5.82 mmol) was added thereto, and the mixture was stirred at 20° C. for 1 hour. Then potassium carbonate (1.07 g, 7.76 mmol) was added and the mixture was stirred at 60° C. for 11 hours. After the completion of the reaction, the reaction was quenched with water (20 mL), the reaction mixture was diluted with water (20 mL), and extracted with ethyl acetate (40 mL×2), the combined organic phases were washed with saturated brine (30 mL×1) and dried over sodium sulfate, filtered, and the filtrate was concentrated under reduced pressure. The residue was purified by high performance liquid chromatography (formic acid condition) to give the formate of compound 10.

MS-ESI calculated value [M+H]+ 415, measured value 415.

$^1$H NMR (400 MHz, CD$_3$OD) δ 8.42 (br s, 1H), 8.25 (t, J=1.6 Hz, 1H), 8.14 (s, 1H), 8.10 (s, 1H), 7.93-7.86 (m, 2H), 7.77 (dd, J=1.6, 8.8 Hz, 1H), 7.67 (d, J=8.8 Hz, 1H), 7.60 (t, J=7.8 Hz, 1H), 7.38-7.32 (m, 1H), 7.11-7.05 (m, 2H), 6.95-6.90 (m, 1H), 5.61 (dd, J=4.0, 10.8 Hz, 1H), 3.83 (s, 3H), 3.51 (dd, J=10.8, 12.8 Hz, 1H), 3.26 (br dd, J=4.0, 12.8 Hz, 1H), 2.82 (s, 6H) ppm.

Embodiment 11

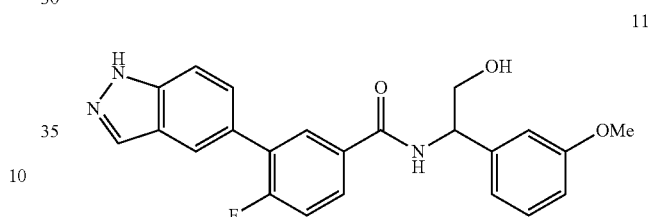

Synthetic Route:

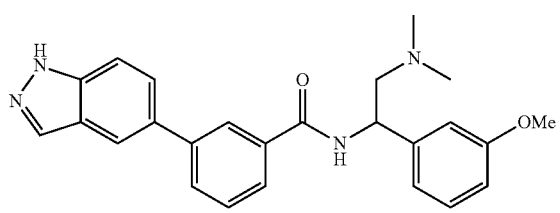

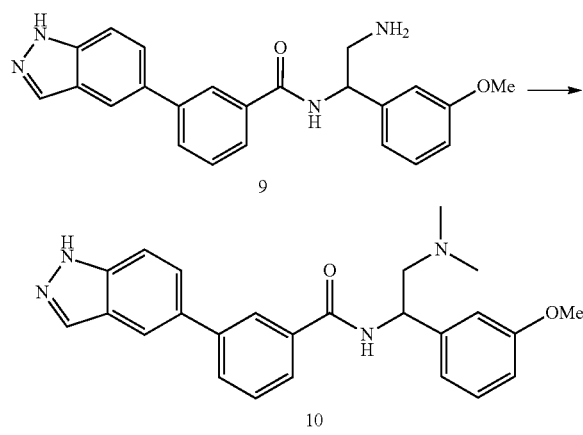

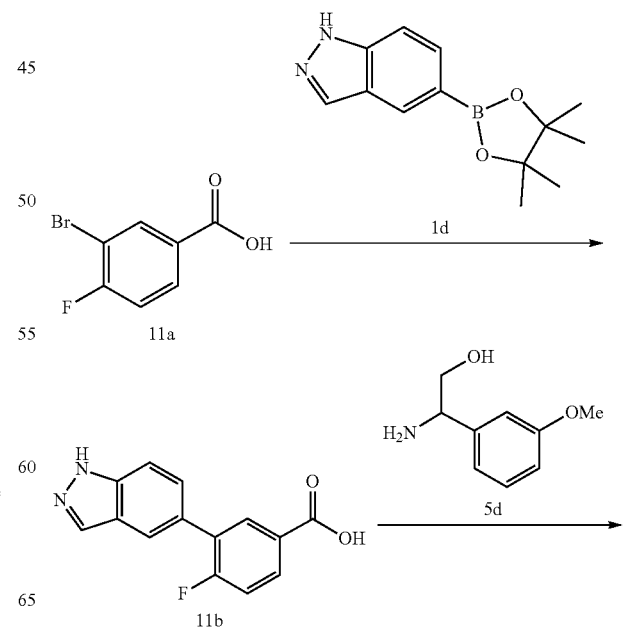

-continued

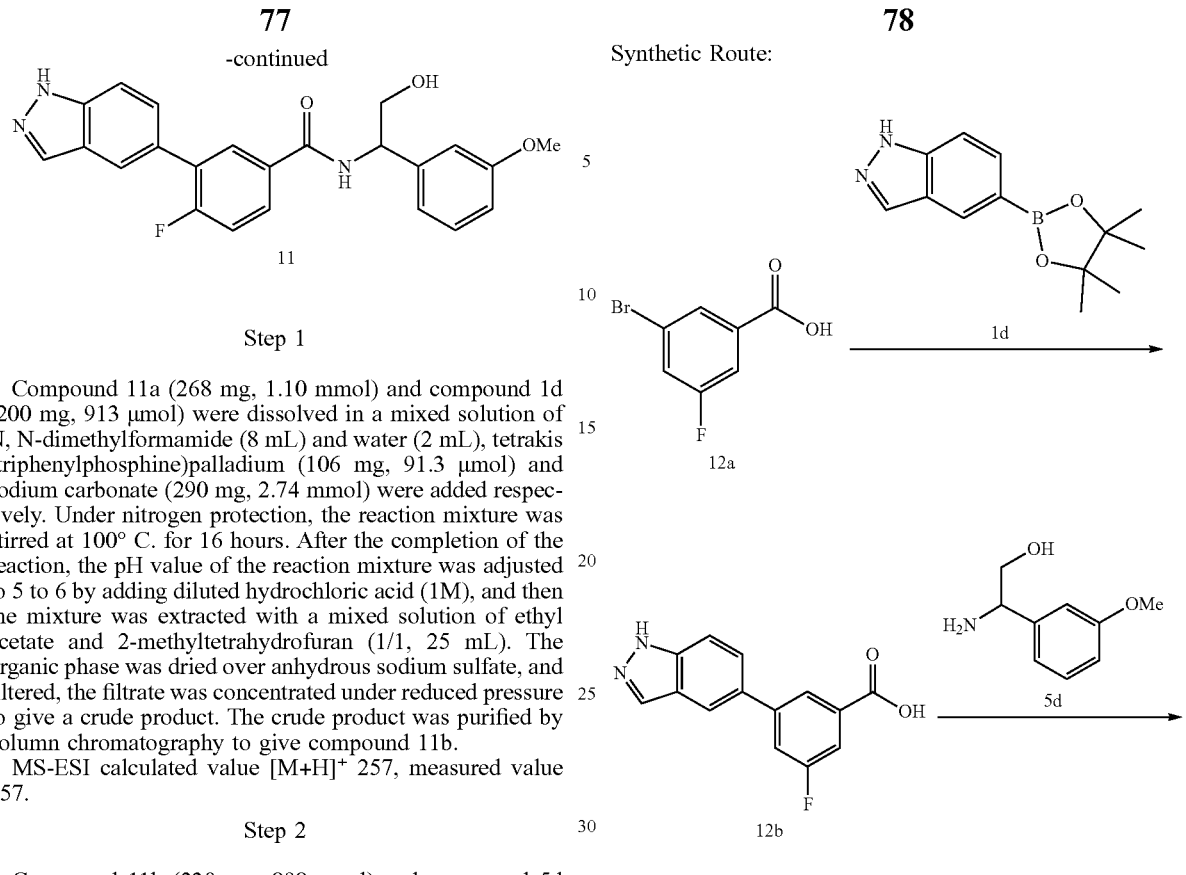

Step 1

Compound 11a (268 mg, 1.10 mmol) and compound 1d (200 mg, 913 μmol) were dissolved in a mixed solution of N, N-dimethylformamide (8 mL) and water (2 mL), tetrakis (triphenylphosphine)palladium (106 mg, 91.3 μmol) and sodium carbonate (290 mg, 2.74 mmol) were added respectively. Under nitrogen protection, the reaction mixture was stirred at 100° C. for 16 hours. After the completion of the reaction, the pH value of the reaction mixture was adjusted to 5 to 6 by adding diluted hydrochloric acid (1M), and then the mixture was extracted with a mixed solution of ethyl acetate and 2-methyltetrahydrofuran (1/1, 25 mL). The organic phase was dried over anhydrous sodium sulfate, and filtered, the filtrate was concentrated under reduced pressure to give a crude product. The crude product was purified by column chromatography to give compound 11b.

MS-ESI calculated value [M+H]$^+$ 257, measured value 257.

Step 2

Compound 11b (230 mg, 898 μmol) and compound 5d (150 mg, 898 μmol) were dissolved in N, N-dimethylformamide (4 mL), N, N-diisopropyl ethylamine (232 mg, 1.80 mmol, 313 μL) and O-(7-azabenzotriazol-1-yl)-N,N,N',N'-tetramethyluronium hexafluorophosphate (410 mg, 1.08 mmol) were added to the reaction mixture. Under the protection of nitrogen, the reaction mixture was stirred at 20° C. for 16 hours. After the completion of the reaction, the reaction mixture was concentrated under reduced pressure. The residue was purified by column chromatography to give a crude product. The crude product was purified by high performance liquid chromatography (hydrochloric acid condition) to give product 11.

MS-ESI calculated value [M+H]$^+$ 406, measured value 406.

$^1$H NMR (400 MHz, DMSO-d$_6$) δ 8.83 (d, J=8.0 Hz, 1H), 8.26-8.10 (m, 2H), 8.02 (s, 1H), 7.94 (m, 1H), 7.72-7.64 (m, 1H), 7.63-7.56 (m, 1H), 7.43 (dd, J=8.8, 10.4 Hz, 1H), 7.28-7.20 (m, 1H), 7.06-6.91 (m, 2H), 6.87-6.77 (m, 1H), 5.07 (m, 1H), 3.74 (s, 3H), 3.71 (m, 1H), 3.68 (m, 1H) ppm.

Embodiment 12

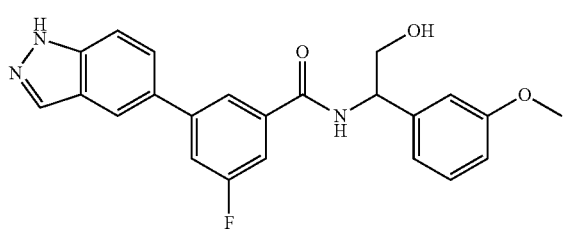

Synthetic Route:

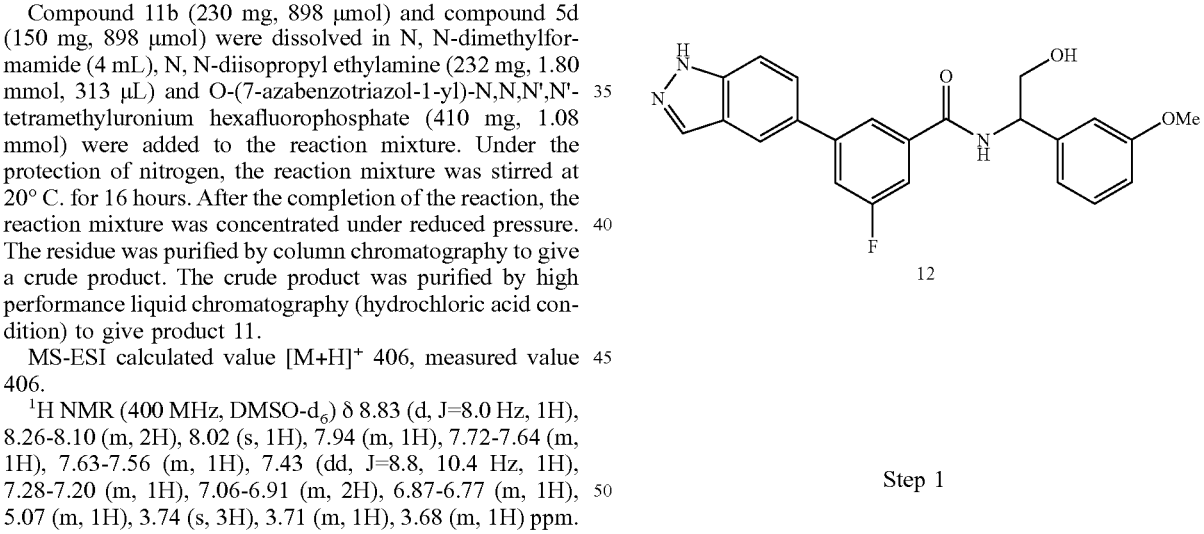

Step 1

Compound 12b was obtained by referring to Step 1 of Embodiment 11.

Step 2

Compound 12 was obtained by referring to Step 2 of Embodiment 11.

MS-ESI calculated value [M+H]$^+$ 406, measured value 406.

$^1$H NMR (400 MHz, DMSO-d$_6$) δ 8.97 (d, J=8.0 Hz, 1H), 8.41-8.03 (m, 3H), 7.80 (dd, J=1.6, 8.8 Hz, 1H), 7.77-7.72 (m, 1H), 7.71-7.59 (m, 2H), 7.25 (t, J=8.0 Hz, 1H), 7.12-6.92 (m, 2H), 6.91-6.75 (m, 1H), 5.18-5.01 (m, 1H), 3.74 (s, 3H), 3.72 (m, 1H), 3.70 (m, 1H) ppm.

Embodiment 13

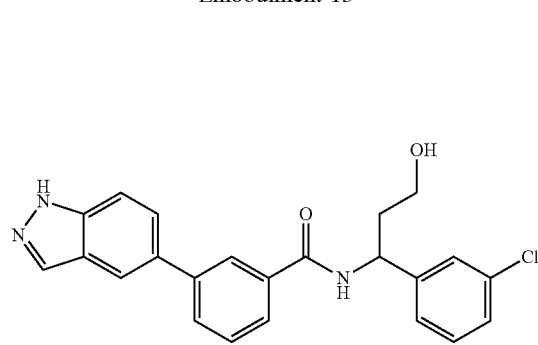

Synthetic Route:

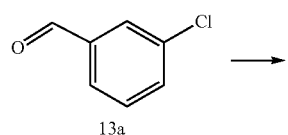

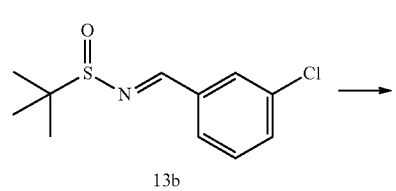

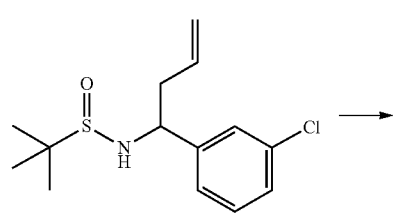

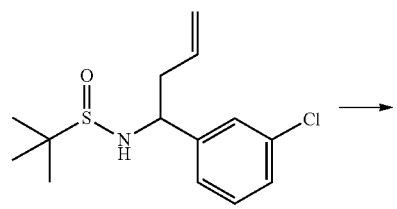

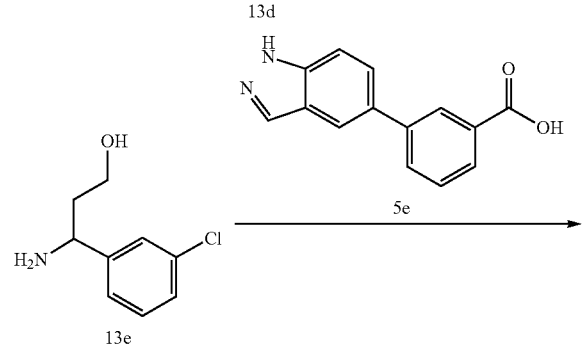

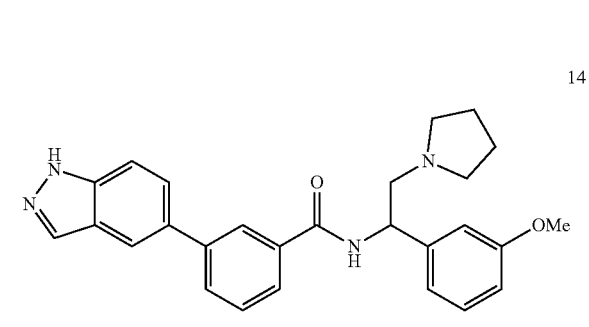 [SMILES: COc1cccc(C(CN2CCCC2)NC(=O)c2cccc(-c3ccc4[nH]ncc4c3)c2)c1]

Step 1

Compound 13b was obtained by referring to Step 1 of Embodiment 6.

Step 2

Compound 13c was obtained by referring to Step 2 of Embodiment 6.

Step 3

Compound 13d was obtained by referring to Step 3 of Embodiment 6.

Step 4

Compound 13e was obtained by referring to Step 4 of Embodiment 6.

Step 5

Compound 13 was obtained by referring to Step 5 of Embodiment 6.

MS-ESI calculated value [M+H]$^+$ 406, measured value 406.

$^1$H NMR (400 MHz, CD$_3$OD) δ 8.16 (s, 1H), 8.14 (s, 1H), 8.05 (s, 1H), 7.90-7.70 (m, 3H), 7.65-7.60 (m, 1H), 7.58-7.52 (m, 1H), 7.48 (s, 1H), 7.43-7.32 (m, 2H), 7.30-7.25 (m, 1H), 5.35-5.25 (m, 1H), 3.75-3.60 (m, 2H), 2.25-2.05 (m, 2H) ppm.

Embodiment 14

Synthetic Route:

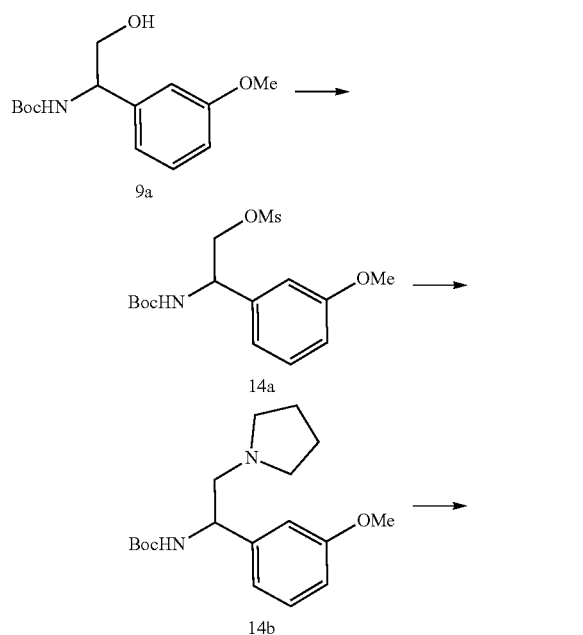

Step 1

Compound 9a (200 mg, 748 μmol) was dissolved in dichloromethane (8 mL), triethylamine (151 mg, 1.50 mmol, 208 μL) was added thereto, and methanesulfonyl chloride (103 mg, 898 μmol, 69.5 μL) was added at 0° C., then the reaction mixture was stirred at 20° C. for 0.5 hour. After the completion of the reaction as monitored by TLC, the reaction mixture was diluted with water (15 mL), extracted with dichloromethane (20 mL×2), and the combined organic phase was washed with saturated brine (20 mL×1), dried over anhydrous sodium sulfate, filtered, the filtrate was concentrated under reduced pressure to give a crude product of compound 14a.

$^1$H NMR (400 MHz, CDCl$_3$) δ 7.26-7.18 (m, 1H), 6.93-6.66 (m, 3H), 5.21-5.00 (m, 1H), 4.96-4.80 (m, 1H), 4.45-4.26 (m, 2H), 3.74 (s, 3H), 2.83 (s, 3H), 1.45-1.30 (m, 9H) ppm.

Step 2

Compound 14a (280 mg, 811 μmol) was dissolved in tetrahydropyrrole (4 mL), nitrogen replacement was performed for 3 times, and the mixture was stirred at 50° C. for 10 hours. After the completion of the reaction, the reaction mixture was concentrated under reduced pressure, and diluted with water (30 mL), extracted with ethyl acetate (30 mL×2), the combined organic phase was washed with saturated brine (30 mL×1), dried over anhydrous sodium sulfate, filtered, and the filtrate was concentrated under reduced pressure to give a crude product. The crude product was purified by thin layer chromatography to give compound 14b.

MS-ESI calculated value [M+H]$^+$ 321, measured value 321.

Step 3

Compound 14b (120 mg, 375 μmol) was dissolved in 1,4-dioxane (2 mL), a solution (4 M, 4 mL) of hydrogen chloride in 1,4-dioxane was added thereto, and the reaction was performed at 20° C. for 0.5 hour. After the completion of the reaction, the reaction mixture was concentrated under reduced pressure to give crude product of compound 14c.

MS-ESI calculated value [M+H]$^+$ 221, measured value 221.

Step 4

Compound 5e (130 mg, 545 μmol) was dissolved in N,N-dimethylformamide (10 mL), and O-(7-azabenzotriazol-1-yl)-N,N,N',N'-tetramethyluronium hexafluorophosphate (270 mg, 709 μmol) and N,N-diisopropylethylamine (282 mg, 2.18 mmol, 379.9 μL) were added to the reaction mixture, and then compound 14c (140 mg, 545 μmol) was added thereto, and the mixture was stirred at 20° C. for 12 hours. After the completion of the reaction, the mixture was diluted with water (50 mL) and extracted with ethyl acetate (30 mL×2), the combined organic phase was washed with saturated brine (40 mL×1), dried over anhydrous sodium sulfate, filtered, and the filtrate was concentrated under reduced pressure. The residue was purified by high performance liquid chromatography (neutral condition) to give compound 14.

MS-ESI calculated value [M+H]$^+$ 441, measured value 441.

$^1$H NMR (400 MHz, CD$_3$OD) δ 8.26 (s, 1H), 8.14 (s, 1H), 8.11 (s, 1H), 7.92-7.85 (m, 2H), 7.78 (dd, J=1.6, 8.8 Hz, 1H), 7.67 (d, J=8.8 Hz, 1H), 7.59 (t, J=7.8 Hz, 1H), 7.36-7.27 (m, 1H), 7.10-7.03 (m, 2H), 6.89 (dd, J=2.0, 7.8 Hz, 1H), 5.50-5.40 (m, 1H), 3.82 (s, 3H), 3.51-3.38 (m, 1H), 3.53-3.38 (m, 1H), 3.17-2.79 (m, 5H), 1.98-1.90 (m, 4H) ppm.

Embodiment 15

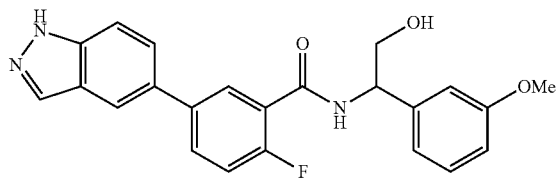

Synthetic Route:

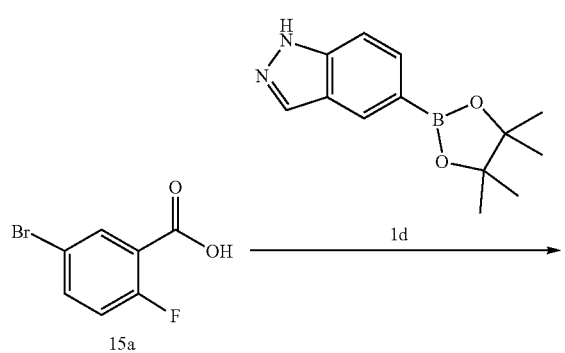

Step 1

Compound 15b was obtained by referring to Step 1 of Embodiment 11.

MS-ESI calculated value [M+H]$^+$ 257, measured value 257.

Step 2

Compound 15 was obtained by referring to Step 2 of Embodiment 11.

MS-ESI calculated value [M+H]$^+$ 406, measured value 406.

$^1$H NMR (400 MHz, CD$_3$OD) δ 8.18 (s, 1H), 8.09-7.99 (m, 2H), 7.88-7.83 (m, 1H), 7.77-7.63 (m, 2H), 7.38-7.27 (m, 2H), 7.07-6.99 (m, 2H), 6.89-6.84 (m, 1H), 5.28-5.17 (m, 1H), 3.93-3.85 (m, 2H), 3.82 (s, 3H) ppm.

Embodiment 16

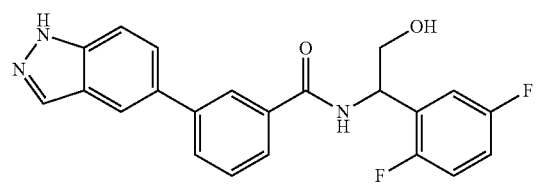

Synthetic Route:

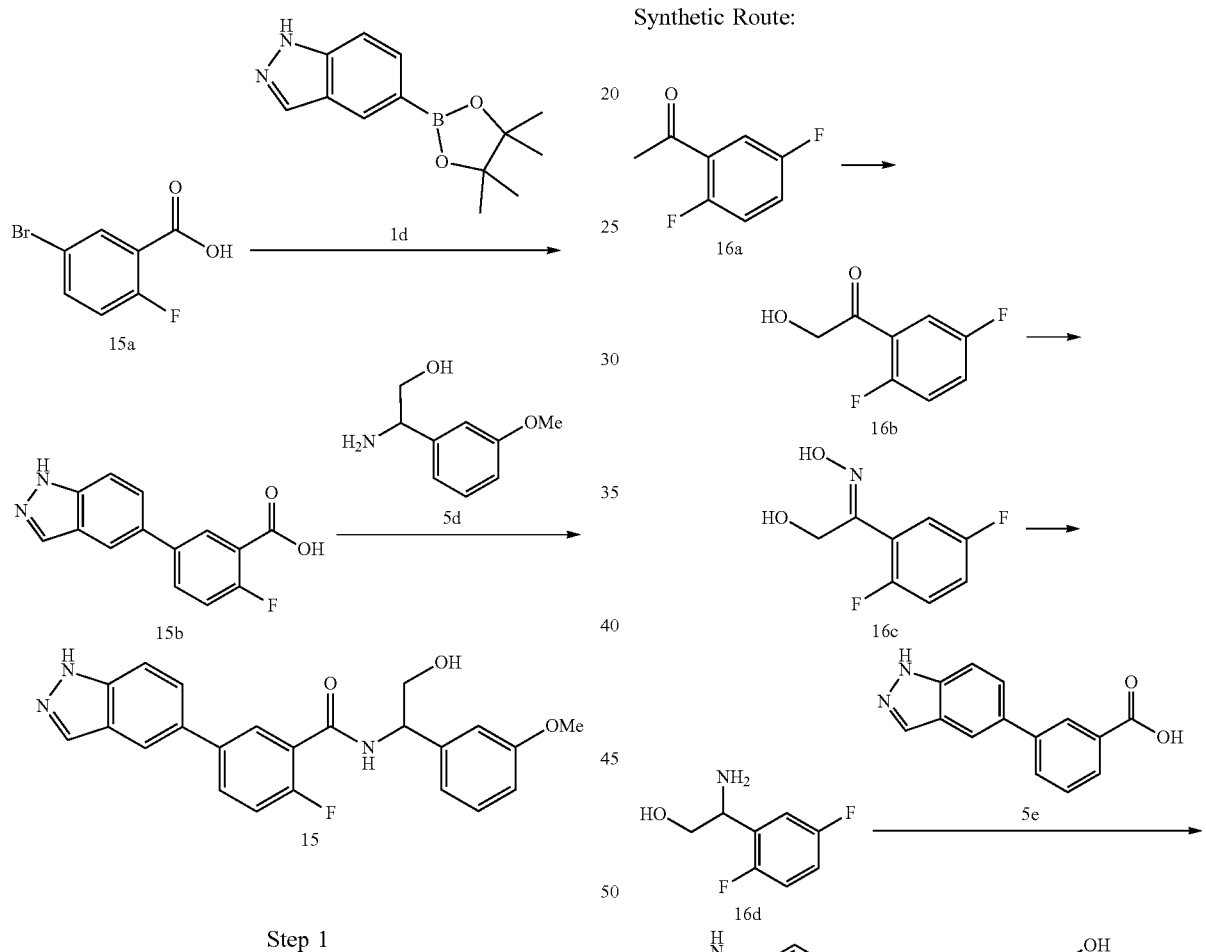

Step 1

Compound 16a (5 g, 32.0 mmol, 4.1 mL) was dissolved in acetonitrile (100 mL) and water (20 mL), and bis(trifluoroacetoxy)iodobenzene (27.5 g, 64.1 mmol) and trifluoroacetic acid (7.30 g, 64.1 mmol, 4.74 mL) were added to the reaction mixture. The reaction mixture was stirred at 100° C. for 12 hours. After the completion of the reaction was monitored by TLC, the reaction mixture was diluted with water (50 mL) and the pH value of the reaction mixture was adjusted to 7 by adding sodium carbonate aqueous solution, the mixture was then extracted with ethyl acetate (150 mL×3), the combined organic phase was washed with saturated brine (200 mL×1), dried over anhydrous sodium sulfate, filtered, and the filtrate was concentrated under reduced pressure. The residue was purified by column chromatography to give compound 16b.

Step 2

Compound 16b (2 g, 11.6 mmol) was dissolved in ethanol (50 mL), hydroxylamine hydrochloride (969 mg, 13.9 mmol) and sodium carbonate (1.85 g, 17.4 mmol) were added, and the mixture was stirred at 50° C. for 3 hours. After the completion of the reaction was monitored by TLC, the reaction mixture was diluted with water (100 mL) and extracted with ethyl acetate (60 mL×2), the combined organic phase was washed with saturated brine (100 mL×1) and dried over anhydrous sodium sulfate, filtered, and the filtrate was concentrated under reduced pressure. The compound 16c was purified by column chromatography.

MS-ESI calculated value [M+H]$^+$ 188, measured value 188.

Step 3

Compound 16c (200 mg, 1.07 mmol, 1 eq) was dissolved in methanol (20 mL), and wet Pd/C (50 mg, 10% purity) was added under nitrogen protection, the reaction was performed at 25° C. under a hydrogen pressure of 50 (Psi) for 12 hours. After the completion of the reaction, the mixture was filtered with celite, and the filtrate was concentrated under reduced pressure to give a crude product of compound 16d.

Step 4

Compound 16d (100 mg, 578 μmol) and compound 5e (138 mg, 578 μmol) were dissolved in N,N-dimethylformamide (8 mL), and O-(7-azabenzotriazol-1-yl)-N,N,N',N'-tetramethyluronium hexafluorophosphate (285 mg, 751 μmol) and N,N-diisopropylethylamine (224 mg, 1.73 mmol, 302 μL) were added to the reaction mixture, the mixture was stirred at 25° C. for 3 hours. After the completion of the reaction, the mixture was diluted with water (80 mL) and extracted with ethyl acetate (60 mL×2), the combined organic phase was washed with saturated brine (60 mL), dried over anhydrous sodium sulfate, filtered, and the filtrate was concentrated under reduced pressure. The residue was purified by high performance liquid chromatography (hydrochloric acid condition) to give compound 16.

MS-ESI calculated value [M+H]$^+$ 394, measured value 394.

$^1$H NMR (400 MHz, DMSO-d$_6$) δ 8.87 (d, J=7.8 Hz, 1H), 8.24 (s, 1H), 8.17 (s, 1H), 8.13 (s, 1H), 7.90-7.82 (m, 2H), 7.78-7.73 (m, 1H), 7.70-7.64 (m, 1H), 7.58 (t, J=7.8 Hz, 1H), 7.41-7.34 (m, 1H), 7.30-7.20 (m, 1H), 7.19-7.11 (m, 1H), 5.45-5.35 (m, 1H), 3.72-3.67 (m, 2H) ppm.

Embodiment 17

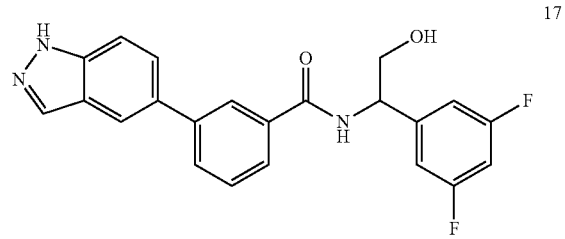 [SMILES: O=C(NC(CO)c1cc(F)cc(F)c1)c1cccc(-c2ccc3[nH]ncc3c2)c1]

Synthetic Route:

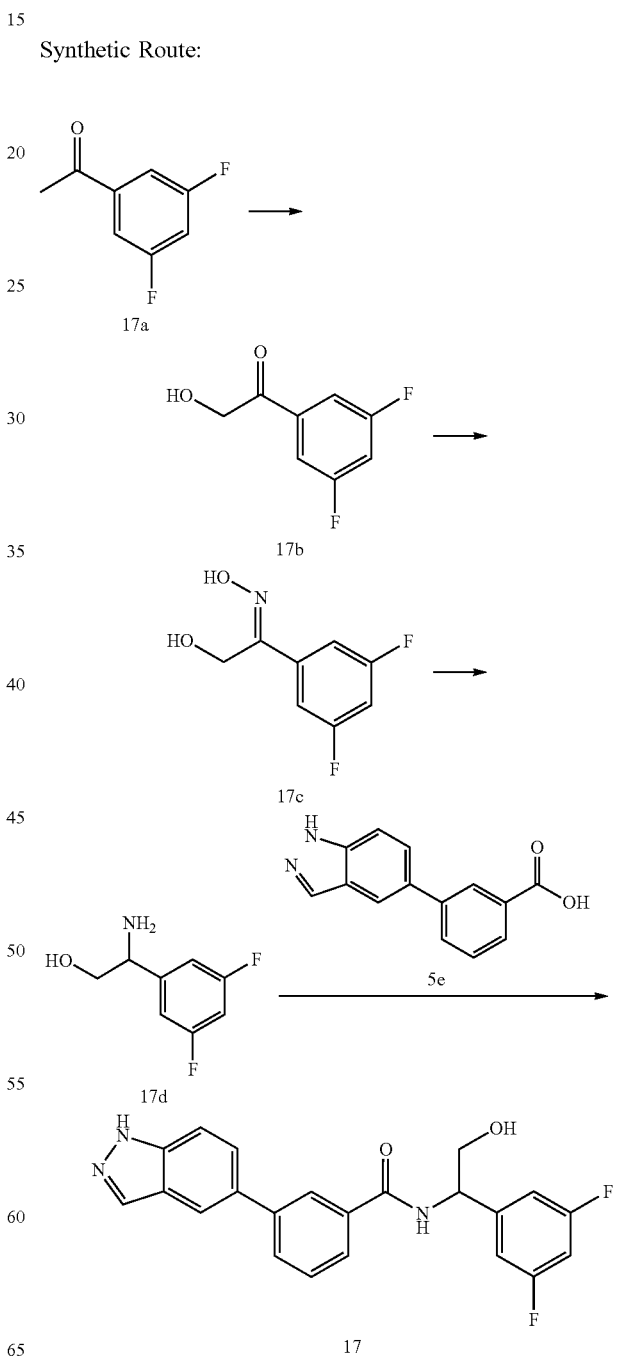

Step 1

Compound 17b was obtained by referring to Step 1 of Embodiment 16.

Step 2

Compound 17c was obtained by referring to Step 2 of Embodiment 16.
MS-ESI calculated value [M+H]⁺ 188, measured value 188.

Step 3

Compound 17d was obtained by referring to Step 3 of Embodiment 16.

Step 4

Compound 17 was obtained by referring to Step 4 of Embodiment 16.
MS-ESI calculated value [M+H]⁺ 394, measured value 394.
$^1$H NMR (400 MHz, CD$_3$OD) δ 8.24-8.17 (m, 2H), 8.13 (s, 1H), 7.93-7.85 (m, 2H), 7.84-7.78 (m, 1H), 7.68 (d, J=8.4 Hz, 1H), 7.60 (t, J=7.8 Hz, 1H), 7.08 (dd, J=2.0, 8.4 Hz, 2H), 6.95-6.80 (m, 1H), 5.24 (t, J=6.4 Hz, 1H), 3.91 (d, J=6.4 Hz, 2H) ppm.

Embodiment 18

Synthetic Route:

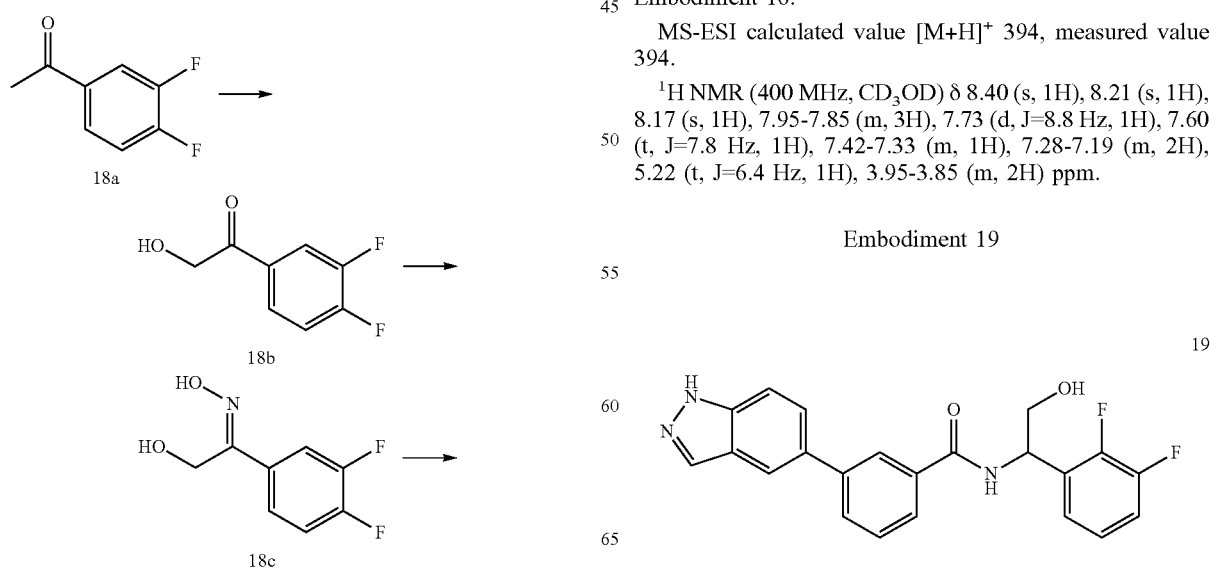

Step 1

Compound 18b was obtained by referring to Step 1 of Embodiment 16.

Step 2

Compound 18c was obtained by referring to Step 2 of Embodiment 16.

Step 3

Compound 18d was obtained by referring to Step 3 of Embodiment 16.

Step 4

Compound 18 was obtained by referring to Step 4 of Embodiment 16.
MS-ESI calculated value [M+H]⁺ 394, measured value 394.
$^1$H NMR (400 MHz, CD$_3$OD) δ 8.40 (s, 1H), 8.21 (s, 1H), 8.17 (s, 1H), 7.95-7.85 (m, 3H), 7.73 (d, J=8.8 Hz, 1H), 7.60 (t, J=7.8 Hz, 1H), 7.42-7.33 (m, 1H), 7.28-7.19 (m, 2H), 5.22 (t, J=6.4 Hz, 1H), 3.95-3.85 (m, 2H) ppm.

Embodiment 19

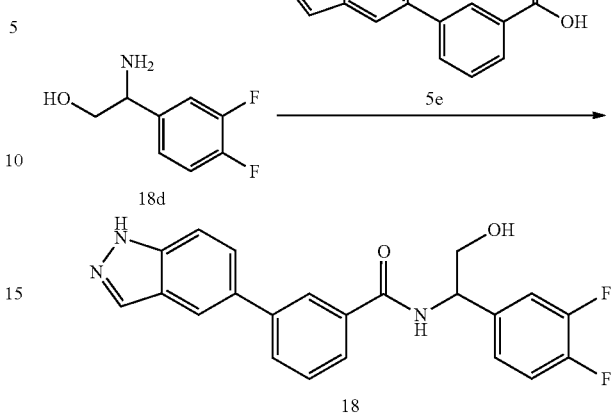

Synthetic Route:

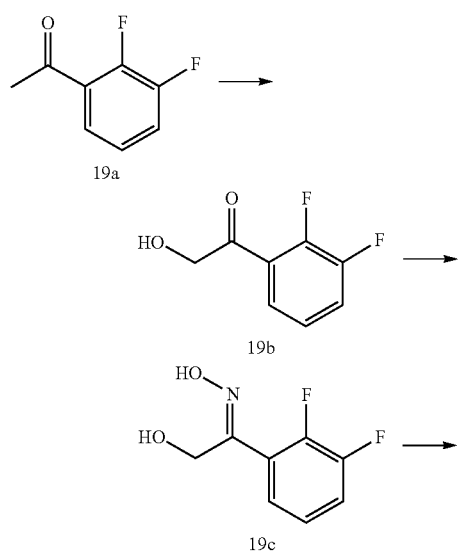

Step 1

Compound 19b was obtained by referring to Step 1 of Embodiment 16.

Step 2

Compound 19c was obtained by referring to Step 2 of Embodiment 16.
MS-ESI calculated value [M+H]$^+$ 188, measured value 188.

Step 3

Compound 19d was obtained by referring to Step 3 of Embodiment 16.
MS-ESI calculated value [M+H]$^+$ 174, measured value 174.

Step 4

Compound 19 was obtained by referring to Step 4 of Embodiment 16.
MS-ESI calculated value [M+H]$^+$ 394, measured value 394.

$^1$H NMR (400 MHz, DMSO-d$_6$) δ 8.96 (d, J=7.8 Hz, 1H), 8.27-8.22 (m, 1H), 8.17 (d, J=0.8 Hz, 1H), 8.13 (d, J=0.8 Hz, 1H), 7.90-7.83 (m, 2H), 7.78-7.73 (m, 1H), 7.70-7.64 (m, 1H), 7.57 (t, J=7.8 Hz, 1H), 7.39-7.28 (m, 2H), 7.24-7.16 (m, 1H), 5.48-5.38 (m, 1H), 3.80-3.70 (m, 2H) ppm.

Embodiment 20

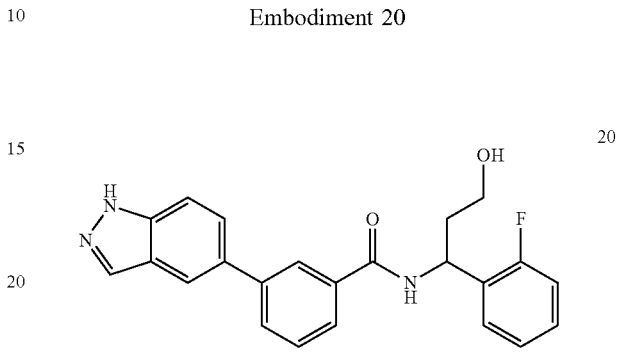

Synthetic Route:

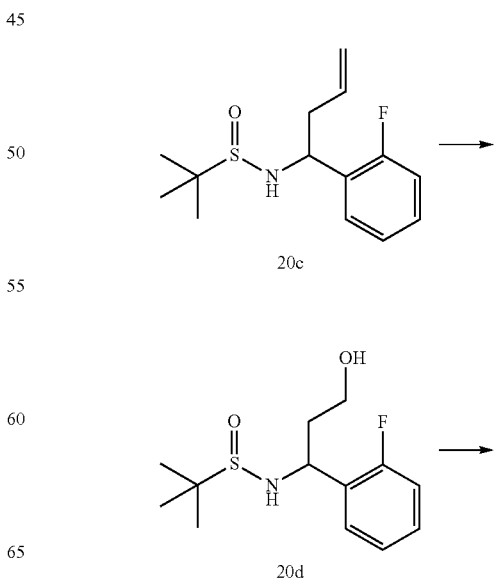

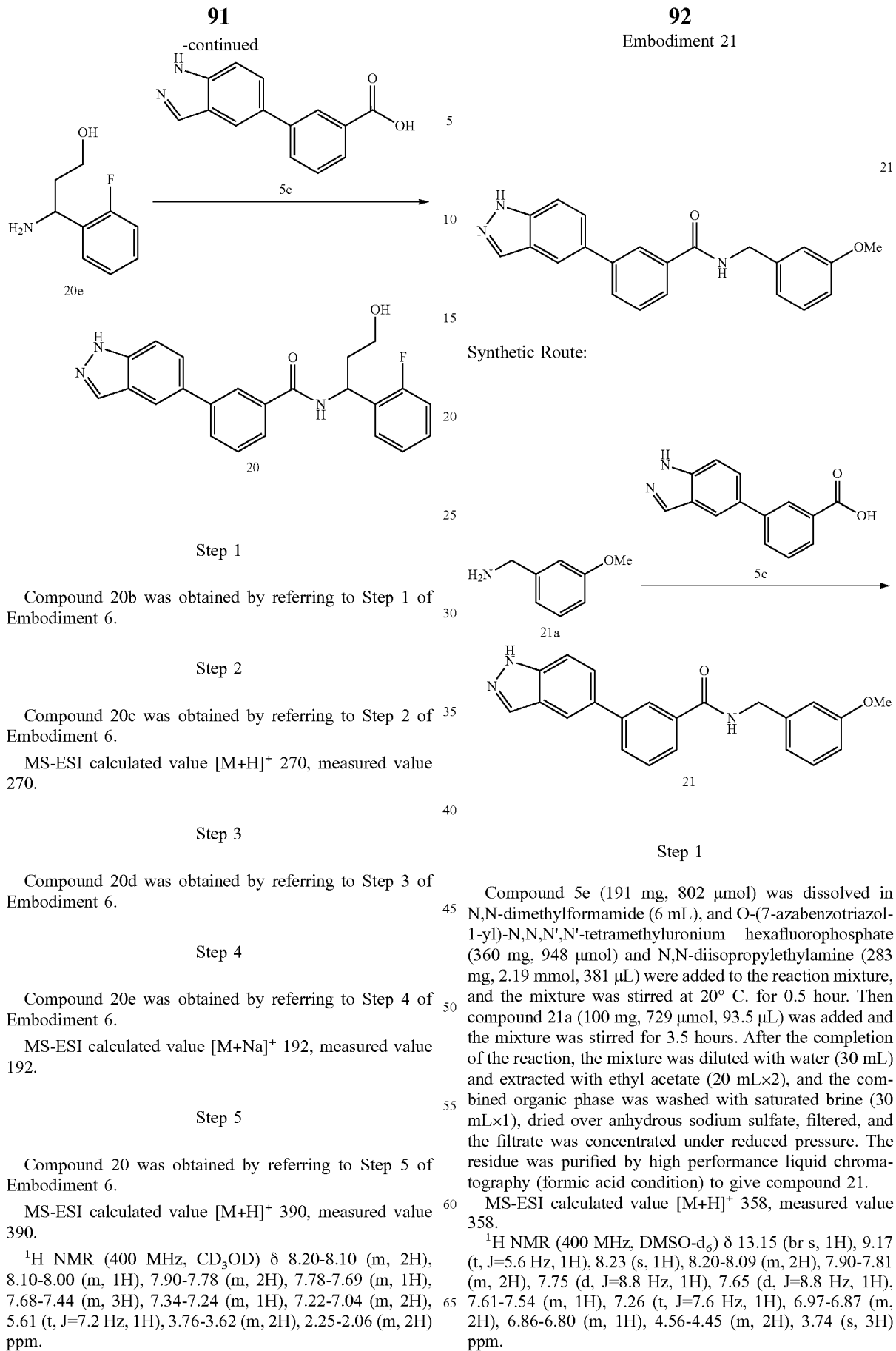

Step 1

Compound 20b was obtained by referring to Step 1 of Embodiment 6.

Step 2

Compound 20c was obtained by referring to Step 2 of Embodiment 6.

MS-ESI calculated value [M+H]$^+$ 270, measured value 270.

Step 3

Compound 20d was obtained by referring to Step 3 of Embodiment 6.

Step 4

Compound 20e was obtained by referring to Step 4 of Embodiment 6.

MS-ESI calculated value [M+Na]$^+$ 192, measured value 192.

Step 5

Compound 20 was obtained by referring to Step 5 of Embodiment 6.

MS-ESI calculated value [M+H]$^+$ 390, measured value 390.

$^1$H NMR (400 MHz, CD$_3$OD) δ 8.20-8.10 (m, 2H), 8.10-8.00 (m, 1H), 7.90-7.78 (m, 2H), 7.78-7.69 (m, 1H), 7.68-7.44 (m, 3H), 7.34-7.24 (m, 1H), 7.22-7.04 (m, 2H), 5.61 (t, J=7.2 Hz, 1H), 3.76-3.62 (m, 2H), 2.25-2.06 (m, 2H) ppm.

Embodiment 21

Synthetic Route:

Step 1

Compound 5e (191 mg, 802 μmol) was dissolved in N,N-dimethylformamide (6 mL), and O-(7-azabenzotriazol-1-yl)-N,N,N',N'-tetramethyluronium hexafluorophosphate (360 mg, 948 μmol) and N,N-diisopropylethylamine (283 mg, 2.19 mmol, 381 μL) were added to the reaction mixture, and the mixture was stirred at 20° C. for 0.5 hour. Then compound 21a (100 mg, 729 μmol, 93.5 μL) was added and the mixture was stirred for 3.5 hours. After the completion of the reaction, the mixture was diluted with water (30 mL) and extracted with ethyl acetate (20 mL×2), and the combined organic phase was washed with saturated brine (30 mL×1), dried over anhydrous sodium sulfate, filtered, and the filtrate was concentrated under reduced pressure. The residue was purified by high performance liquid chromatography (formic acid condition) to give compound 21.

MS-ESI calculated value [M+H]$^+$ 358, measured value 358.

$^1$H NMR (400 MHz, DMSO-d$_6$) δ 13.15 (br s, 1H), 9.17 (t, J=5.6 Hz, 1H), 8.23 (s, 1H), 8.20-8.09 (m, 2H), 7.90-7.81 (m, 2H), 7.75 (d, J=8.8 Hz, 1H), 7.65 (d, J=8.8 Hz, 1H), 7.61-7.54 (m, 1H), 7.26 (t, J=7.6 Hz, 1H), 6.97-6.87 (m, 2H), 6.86-6.80 (m, 1H), 4.56-4.45 (m, 2H), 3.74 (s, 3H) ppm.

Embodiment 22

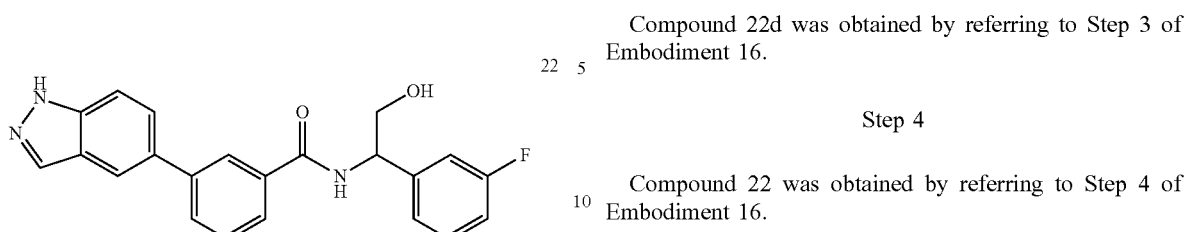

Synthetic Route:

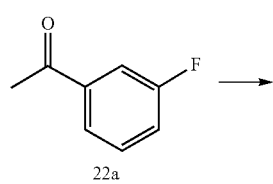

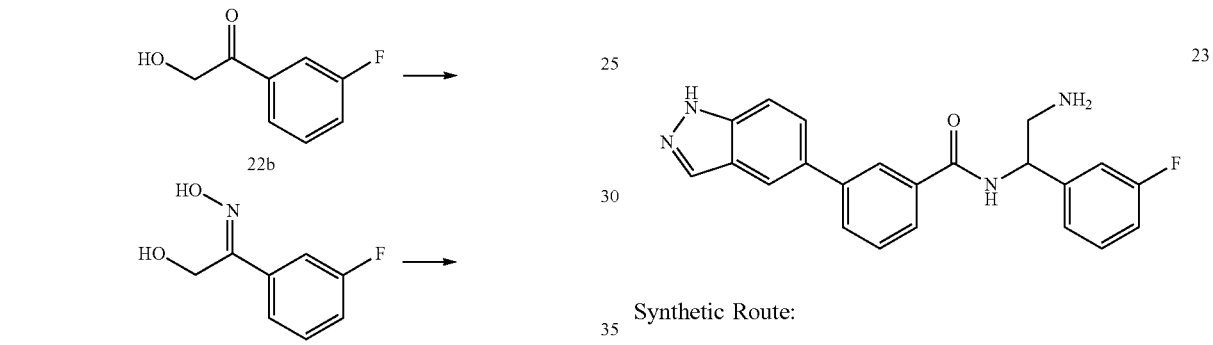

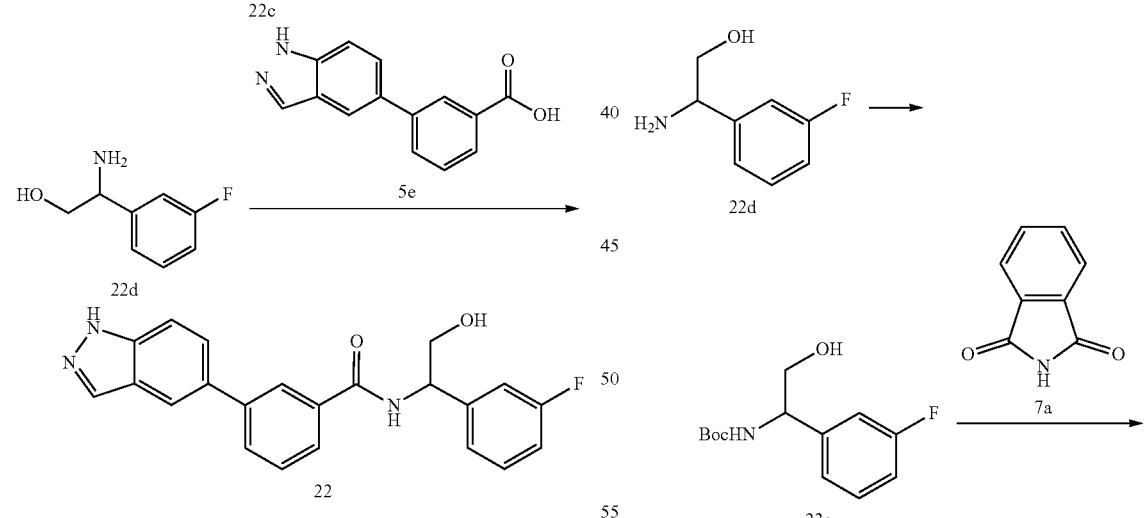

Step 1

Compound 22b was obtained by referring to Step 1 of Embodiment 16.

Step 2

Compound 22c was obtained by referring to Step 2 of Embodiment 16.

Step 3

Compound 22d was obtained by referring to Step 3 of Embodiment 16.

Step 4

Compound 22 was obtained by referring to Step 4 of Embodiment 16.

MS-ESI calculated value [M+H]$^+$ 376, measured value 376.

$^1$H NMR (400 MHz, CD$_3$OD) δ 8.37 (s, 1H), 8.21 (s, 1H), 8.17 (s, 1H), 7.92-7.85 (m, 3H), 7.72 (d, J=8.8 Hz, 1H), 7.59 (t, J=7.8 Hz, 1H), 7.42-7.32 (m, 1H), 7.26 (d, J=7.8 Hz, 1H), 7.23-7.15 (m, 1H), 7.05-6.95 (m, 1H), 5.24 (t, J=6.4 Hz, 1H), 3.90 (d, J=6.4 Hz, 2H) ppm.

Embodiment 23

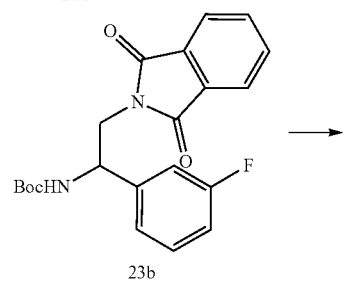

Synthetic Route:

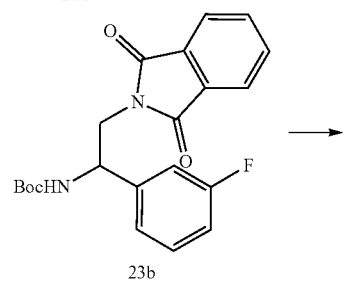

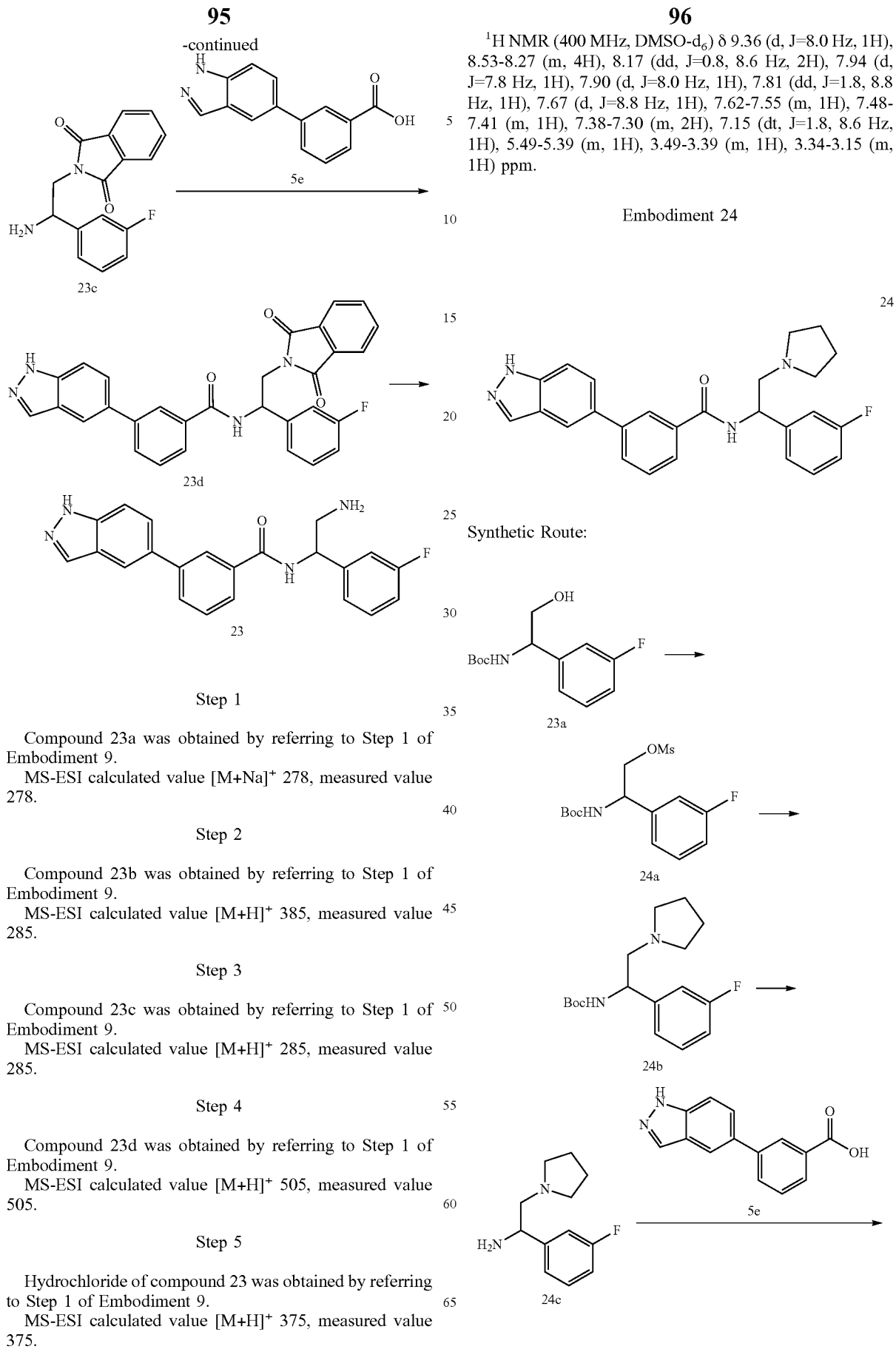

$^1$H NMR (400 MHz, DMSO-d$_6$) δ 9.36 (d, J=8.0 Hz, 1H), 8.53-8.27 (m, 4H), 8.17 (dd, J=0.8, 8.6 Hz, 2H), 7.94 (d, J=7.8 Hz, 1H), 7.90 (d, J=8.0 Hz, 1H), 7.81 (dd, J=1.8, 8.8 Hz, 1H), 7.67 (d, J=8.8 Hz, 1H), 7.62-7.55 (m, 1H), 7.48-7.41 (m, 1H), 7.38-7.30 (m, 2H), 7.15 (dt, J=1.8, 8.6 Hz, 1H), 5.49-5.39 (m, 1H), 3.49-3.39 (m, 1H), 3.34-3.15 (m, 1H) ppm.

Embodiment 24

Synthetic Route:

Step 1

Compound 23a was obtained by referring to Step 1 of Embodiment 9.
MS-ESI calculated value [M+Na]$^+$ 278, measured value 278.

Step 2

Compound 23b was obtained by referring to Step 1 of Embodiment 9.
MS-ESI calculated value [M+H]$^+$ 385, measured value 285.

Step 3

Compound 23c was obtained by referring to Step 1 of Embodiment 9.
MS-ESI calculated value [M+H]$^+$ 285, measured value 285.

Step 4

Compound 23d was obtained by referring to Step 1 of Embodiment 9.
MS-ESI calculated value [M+H]$^+$ 505, measured value 505.

Step 5

Hydrochloride of compound 23 was obtained by referring to Step 1 of Embodiment 9.
MS-ESI calculated value [M+H]$^+$ 375, measured value 375.

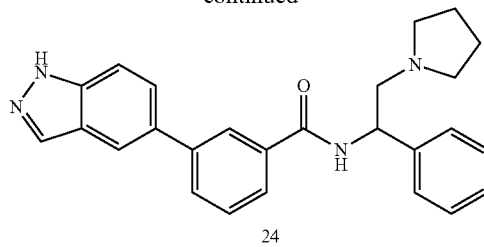

Step 1

Compound 24a was obtained by referring to Step 1 of Embodiment 14.

MS-ESI calculated value [M+Na]$^+$ 356, measured value 356.

Step 2

Compound 24b was obtained by referring to Step 2 of Embodiment 14.

MS-ESI calculated value [M+H]$^+$ 309, measured value 309.

Step 3

Compound 24c was obtained by referring to Step 3 of Embodiment 14.

MS-ESI calculated value [M+H]$^+$ 209, measured value 209.

Step 4

Hydrochloride of compound 24 was obtained by referring to Step 4 of Embodiment 14.

MS-ESI calculated value [M+H]$^+$ 429, measured value 429.

$^1$H NMR (400 MHz, DMSO-d$_6$) δ 10.15 (s, 1H), 9.44 (d, J=8.4 Hz, 1H), 8.37 (s, 1H), 8.20-8.10 (m, 2H), 7.97 (d, J=7.6 Hz, 1H), 7.90 (d, J=7.6 Hz, 1H), 7.80 (d, J=8.8 Hz, 1H), 7.66 (d, J=8.8 Hz, 1H), 7.59 (t, J=7.6 Hz, 1H), 7.49-7.42 (m, 2H), 7.42-7.37 (m, 1H), 7.20-7.10 (m, 1H), 5.62 (t, J=8.4 Hz, 1H), 3.93-3.82 (m, 1H), 3.54-3.47 (m, 3H), 3.40-3.09 (m, 2H), 2.10-1.84 (m, 4H) ppm.

Embodiment 25

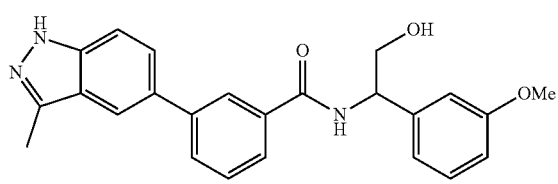

Synthetic Route:

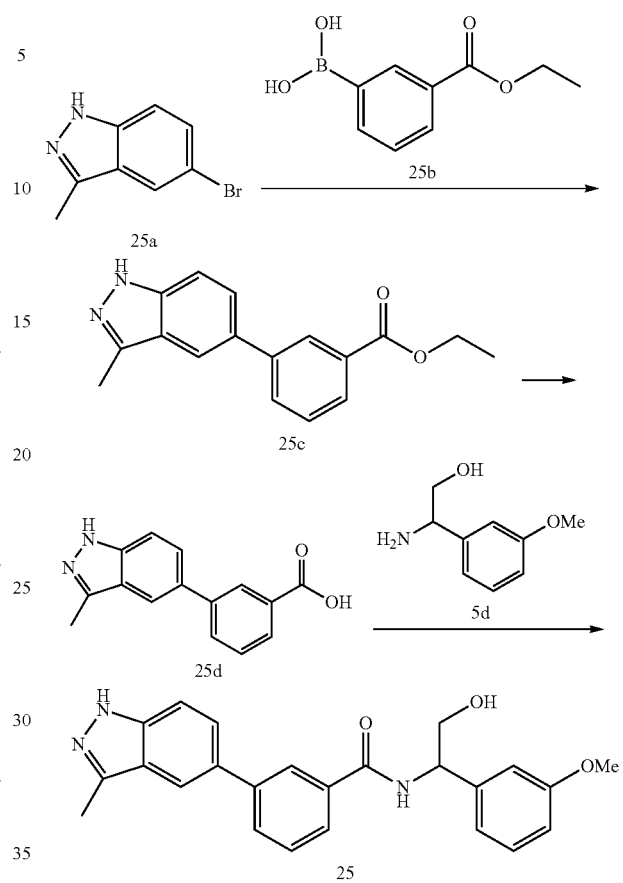

Step 1

Compound 25a (3.45 g, 16.4 mmol), compound 25b (4.76 g, 24.5 mmol), tris(dibenzylideneacetone)dipalladium (1.50 g, 1.63 mmol), 2-dicyclohexylphosphino-2',4',6'-triisopropylbiphenyl (779 mg, 1.63 mmol), potassium carbonate (6.78 g, 49.0 mmol) were dissolved in dioxane (80 mL) and water (20 mL), the reaction mixture was stirred at 95° C. for 12 hours. After the completion of the reaction, the reaction mixture was directly filtered, the filtrate was concentrated under reduced pressure, and the residue was purified by column chromatography to give compound 25c.

MS-ESI calculated value [M+H]$^+$ 281, measured value 281.

Step 2

Compound 25c (3 g, 9.55 mmol) was dissolved in tetrahydrofuran (32 mL), water (8 mL) and methanol (8 mL), lithium hydroxide monohydrate (1.20 g, 28.7 mmol) was added thereto, the mixture was stirred at 28° C. for 12 hours. After the completion of the reaction, the reaction mixture was concentrated under reduced pressure to remove tetrahydrofuran and methanol, diluted with water (100 mL), and extracted with methyl tert-butyl ether (60 mL×1). The pH value of the aqueous phase was adjusted to 3 with dilute aqueous hydrochloric acid solution (1 M), and a white solid precipitated. After suction filtration, the filter cake was washed with water and dried to give compound 25d.

MS-ESI calculated value [M+H]⁺ 253, measured value 253.

Step 3

Compound 25d (1.25 g, 4.96 mmol) and compound 5d (829 mg, 4.96 mmol) were dissolved in N,N-dimethylformamide (40 mL), and 1-(3-dimethylaminopropyl)-3-ethylcarbodiimide hydrochloride (1.14 g, 5.95 mmol), 1-hydroxybenzotriazole (803 mg, 5.95 mmol) and N,N-diisopropylethylamine (1.92 g, 14.9 mmol, 2.59 mL) were added to the reaction mixture and stirred at 28° C. for 8 hours. After the completion of the reaction, the mixture was diluted with water (500 mL) and extracted with ethyl acetate (300 mL×2), the combined organic phase was washed with saturated brine (300 mL×1), then dried over anhydrous sodium sulfate, filtered, and the filtrate was concentrated under reduced pressure. The residue was purified by column chromatography and then purified by high performance liquid chromatography (hydrochloric acid condition) to give compound 25.

MS-ESI calculated value [M+H]⁺ 402, measured value 402.

$^1$H NMR (400 MHz, CD$_3$OD) δ 8.25-8.22 (m, 1H), 8.18-8.14 (m, 1H), 7.97-7.86 (m, 3H), 7.68 (d, J=8.8 Hz, 1H), 7.60 (t, J=8.0 Hz, 1H), 7.28 (t, J=8.0 Hz, 1H), 7.07-6.99 (m, 2H), 6.88-6.82 (m, 1H), 5.24 (t, J=6.6 Hz, 1H), 3.94-3.88 (m, 2H), 3.81 (s, 3H), 2.74 (s, 3H) ppm.

Embodiment 26

26

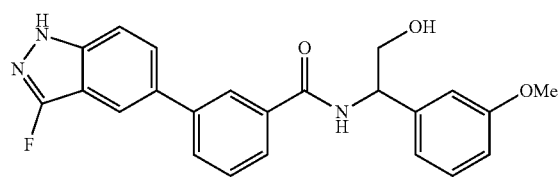

Synthetic Route:

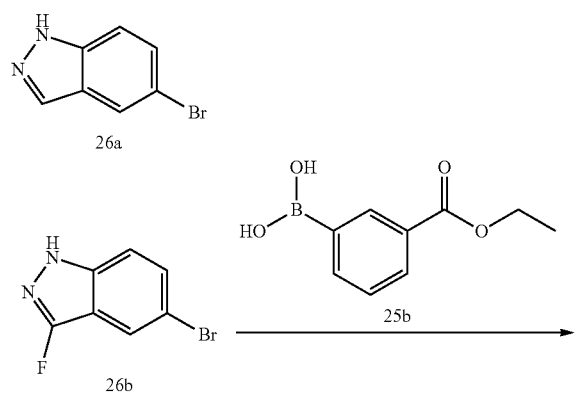

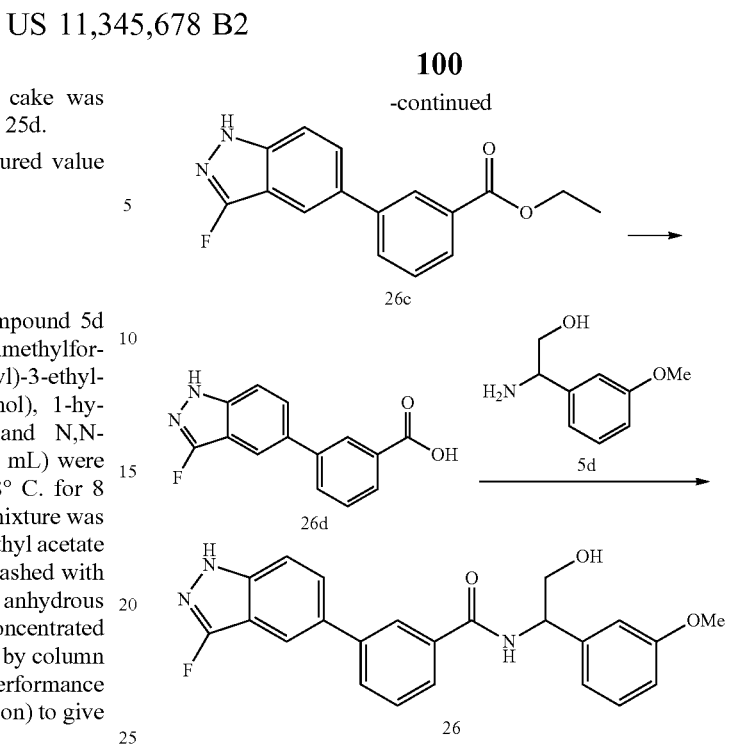

Step 1

Compound 26a (4 g, 20.3 mmol) was dissolved in N,N-dimethylacetamide (50 mL), and 1-chloromethyl-4-fluoro-1,4-diazoniabicyclo[2.2.2]octane bis(tetrafluoroborate) (14.38 g, 40.60 mmol) to the reaction mixture under nitrogen, the mixture was stirred at 60° C. for 18 hours. After the completion of the reaction, the reaction mixture was concentrated under reduced pressure, and the residue was purified by column chromatography to give compound 26b.

MS-ESI calculated value [M+Na]⁺ 215 and 217, measured value 215 and 217.

Step 2

Compound 26c was obtained by referring to Step 1 of Embodiment 25.

MS-ESI calculated value [M+H]⁺ 285 measured value 285.

Step 3

Compound 26d was obtained by referring to Step 2 of Embodiment 25.

MS-ESI calculated value [M+H]⁺ 257, measured value 257.

Step 4

Compound 26 was obtained by referring to Step 3 of Embodiment 25.

MS-ESI calculated value [M+H]⁺ 406, measured value 406.

$^1$H NMR (400 MHz, DMSO-d$_6$) δ 12.66 (br, 1H), 8.90-8.70 (m, 1H), 8.23 (s, 1H), 8.05 (s, 1H), 7.93-7.79 (m, 3H), 7.68-7.52 (m, 2H), 7.24 (t, J=7.6 Hz, 1H), 7.02-6.85 (m, 2H), 6.81 (d, J=7.6 Hz, 1H), 5.15-5.00 (m, 1H), 3.74 (s, 3H), 3.72-3.60 (m, 2H) ppm.

Embodiment 27

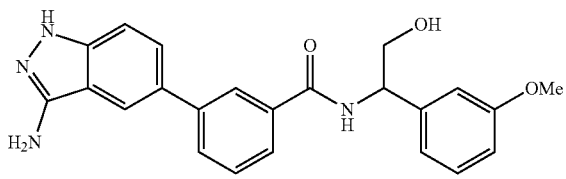

Synthetic Route:

Step 1 (Preparation of Intermediate 27b)

Compound 2a (793 mg, 3.95 mmol) was dissolved in N,N-dimethylformamide (30 mL), and O-(7-azabenzotriazol-1-yl)-N,N,N',N'-tetramethyluronium hexafluorophosphate (1.77 g, 4.66 mmol) and N,N-diisopropylethylamine (1.39 g, 10.8 mmol, 1.88 mL), then compound 5d (600 mg, 3.59 mmol) was added thereto, the mixture was stirred at 25° C. for 6 hours. After the completion of the reaction, the mixture was diluted with water (200 mL) and extracted with ethyl acetate (100 mL×2). The combined organic phases were washed with saturated brine (150 mL×1), dried over anhydrous sodium sulfate, filtered, and the filtrate was concentrated under reduced pressure. The residue was purified by column chromatography to give compound 27b.

MS-ESI calculated value [M+H]$^+$ 350, 352, measured value 350, 352.

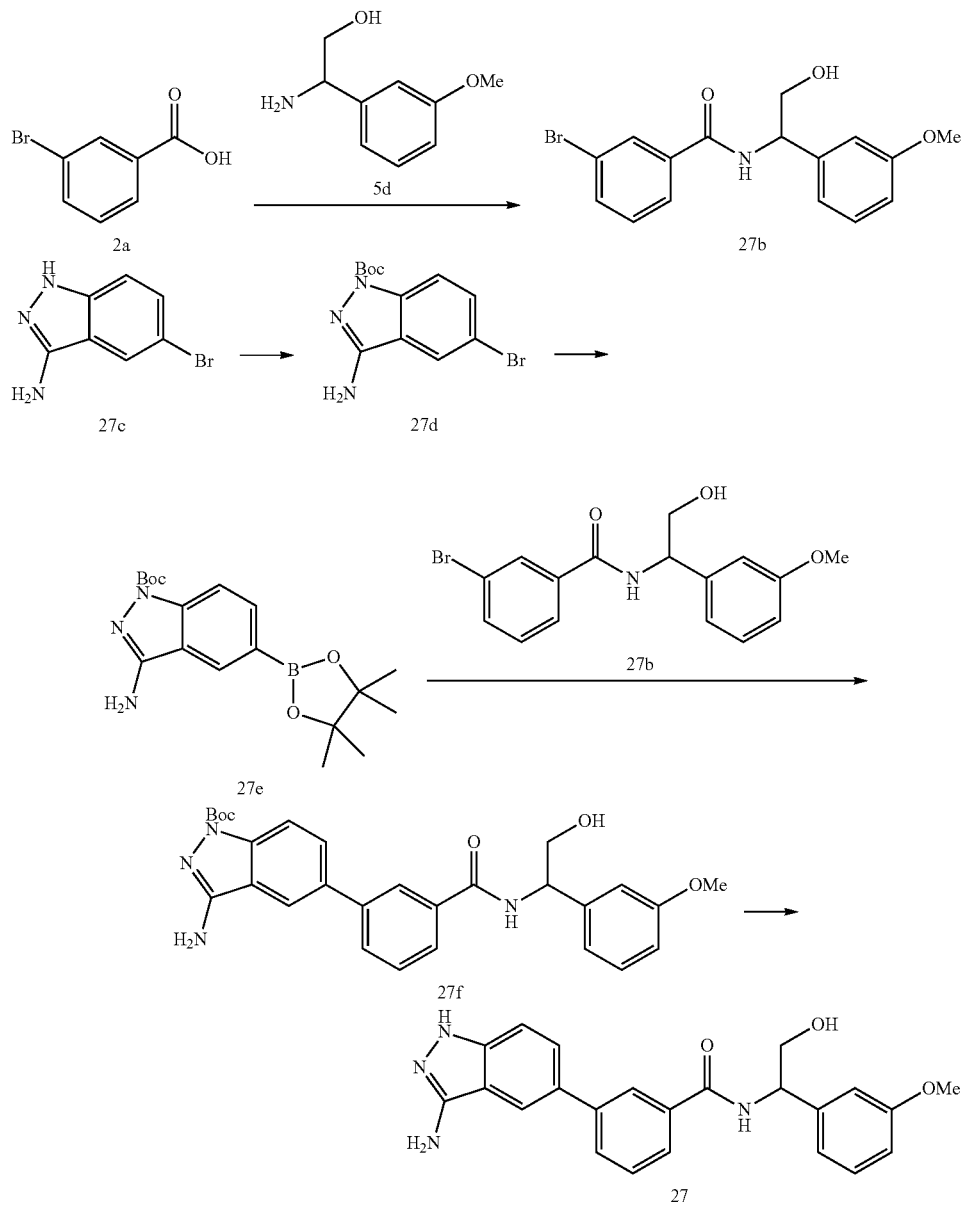

Step 2

Compound 27c (2.5 g, 11.8 mmol) was dissolved in dichloromethane (50 mL), di-tert-butyl dicarbonate (3.35 g, 15.3 mmol, 3.5 mL), triethylamine (2.39 g, 23.6 mmol, 3.3 mL) and 4-dimethylaminopyridine (288 mg, 2.36 mmol) were added. The reaction mixture was stirred at 25° C. for 12 hours. After the completion of the reaction, the reaction mixture was directly concentrated under reduced pressure, and purified by column chromatography to give compound 27d.

Step 3

Compound 27d (1.50 g, 4.38 mmol) and bis(pinacolato)diboron (2.23 g, 8.76 mmol) were dissolved in dioxane (50 mL), [1,1'-bis(diphenylphosphino)ferrocene]palladium(II) dichloride (321 mg, 438 μmol) and potassium acetate (1.08 g, 11.0 mmol, 2.5) were added, the reaction mixture was stirred at 95° C. for 12 hours. After the completion of the reaction, the mixture was diluted with water (120 mL) and extracted with ethyl acetate (80 mL×2). The combined organic phase was washed with saturated brine (100 mL×), dried over anhydrous sodium sulfate, filtered, and concentrated under reduced pressure. The residue was purified by column chromatography to give compound 27e.

MS-ESI calculated value [M+H]+ 360, measured value 360.

Step 4

Compound 27b (100 mg, 286 μmol) and compound 27e (154 mg, 428 μmol) were dissolved in dioxane (16 mL) and water (4 mL), and tris(dibenzylideneacetone)dipalladium (52.3 mg, 57.1 μmol), 2-dicyclohexylphosphino-2',4',6'-triisopropylbiphenyl (27.2 mg, 57.1 μmol), potassium carbonate (118 mg, 857 μmol) were added, the reaction mixture was stirred at 95° C. for 4 hours. After the completion of the reaction, the mixture was diluted with water (60 mL) and extracted with ethyl acetate (60 mL×2). The combined organic phase was washed with saturated brine (60 mL×1), dried over anhydrous sodium sulfate and filtered, the filtrate was concentrated under reduced pressure. The residue was purified by column chromatography to give compound 27f.

Step 5

Compound 27f (190 mg, 195 μmol) was dissolved in methanol (5 mL), a solution of hydrogen chloride in ethyl acetate (4 M, 5 mL) was added thereto, and the mixture was stirred at 25° C. for 3 hours. After the completion of the reaction, the reaction mixture was concentrated under reduced pressure, then purified by high performance liquid chromatography (hydrochloric acid condition) to give compound 27.

MS-ESI calculated value [M+H]+ 403, measured value 403.

1H NMR (400 MHz, CD3OD) δ 8.29 (s, 1H), 8.21-8.19 (m, 1H), 8.10-8.05 (m, 1H), 7.97-7.82 (m, 2H), 7.66-7.51 (m, 2H), 7.28 (t, J=8.0 Hz, 1H), 7.10-6.95 (m, 2H), 6.93-6.77 (m, 1H), 5.24 (t, J=6.6 Hz, 1H), 3.98-3.85 (m, 2H), 3.81 (s, 3H) ppm.

Embodiment 28

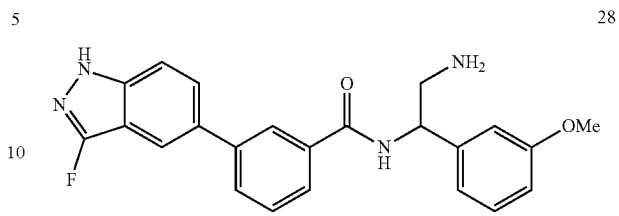

Synthetic Route:

Step 1

Compound 26d (182 mg, 711 μmol) was dissolved in tetrahydrofuran (16 mL) and N,N-dimethylformamide (4 mL), and 1-(3-dimethylaminopropyl)-3-ethylcarbodiimide hydrochloride (272 mg, 1.42 mmol) and 1-hydroxybenzotriazole (144 mg, 1.07 mmol) were added to the reaction mixture, then compound 9c (250 mg, 711 μmol) and N,N-diisopropylethylamine (551 mg, 4.26 mmol, 743 μL) were added sequentially, the mixture was stirred at 20° C. for 4 hours. After the completion of the reaction, the reaction mixture was concentrated under reduced pressure and purified by column chromatography to give compound 28a.

MS-ESI calculated value [M+H]+ 535, measured value 535.

Step 2

Compound 28a (300 mg, 561 μmol) was dissolved in ethanol (10 mL), hydrazine hydrate (421 mg, 8.42 mmol, 409 μL) was added to the reaction mixture, and the mixture was stirred at 55° C. for 2 hours. After the completion of the reaction, the reaction mixture was filtered and concentrated, and the residue was purified by high performance liquid chromatography (hydrochloric acid condition) to give the hydrochloride of compound 28.

MS-ESI calculated value [M+H]⁺ 405, measured value 405.

¹H NMR (400 MHz, DMSO-d₆) δ 12.72 (s, 1H), 9.30-9.15 (m, 1H), 8.34 (s, 1H), 8.28-8.15 (m, 3H), 8.08 (s, 1H), 7.95-7.85 (m, 3H), 7.66-7.53 (m, 2H), 7.30 (t, J=8.0 Hz, 1H), 7.10-6.98 (m, 2H), 6.90-6.80 (m, 1H), 5.43-5.32 (m, 1H), 3.75 (s, 3H), 3.28-3.20 (m, 2H) ppm.

Embodiment 29

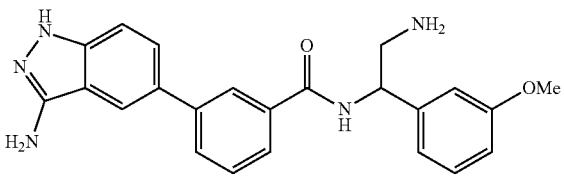

Synthetic Route:

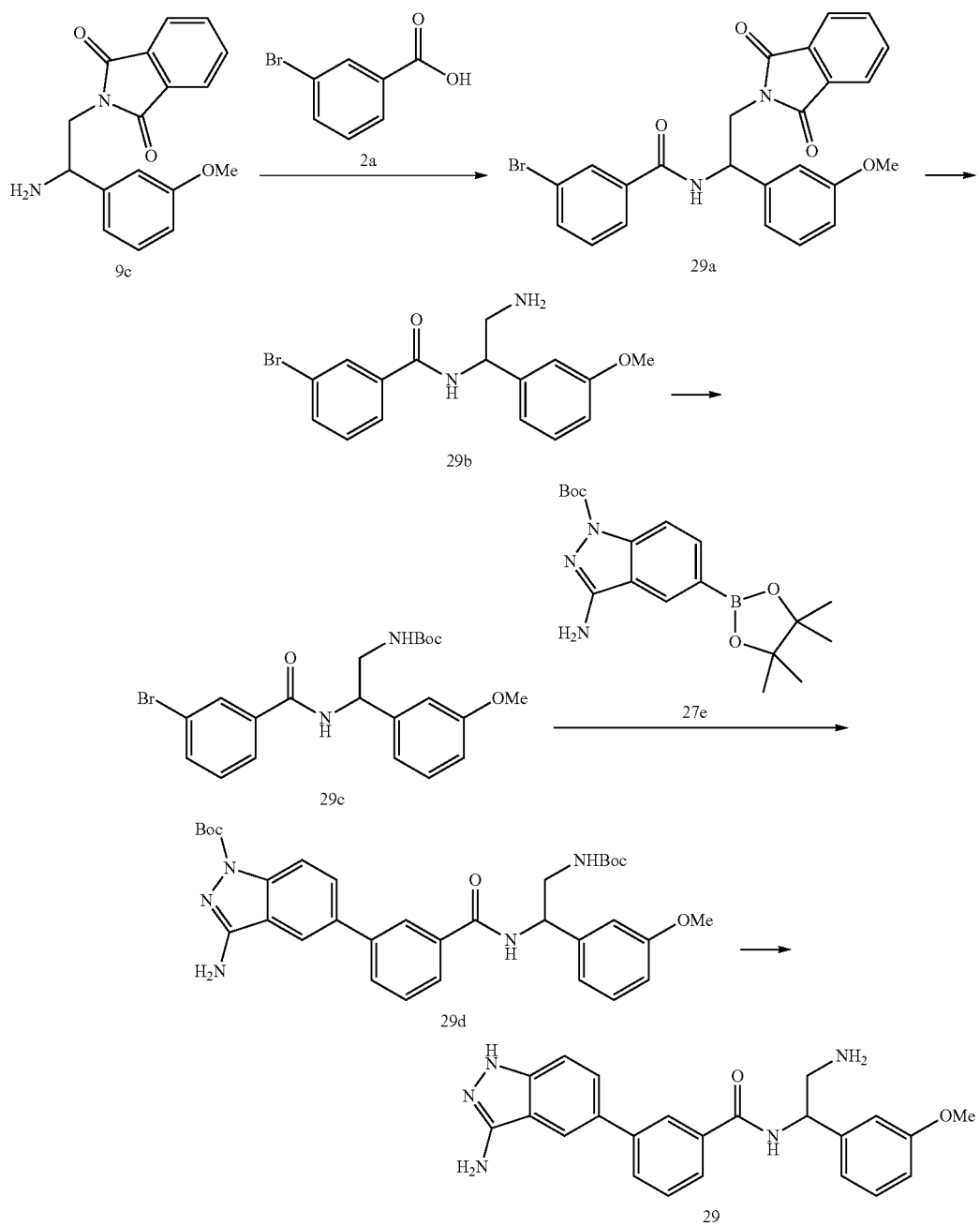

Step 1

Compound 2a (174 mg, 865 μmol) was dissolved in tetrahydrofuran (4 mL) and N,N-dimethylformamide (1 mL), and 1-(3-dimethylaminopropyl)-3-ethylcarbodiimide hydrochloride (332 mg, 1.73 mmol) and 1-hydroxybenzotriazole (175 mg, 1.30 mmol) were added to the reaction mixture, and then compound 9c (300 mg, 865 μmol) and N,N-diisopropylethylamine (671 mg, 5.19 mmol, 904 μL) were added sequentially, and the mixture was stirred at 20° C. for 2.5 hours. After the completion of the reaction, the reaction mixture was concentrated under reduced pressure and purified by column chromatography to give compound 29a.

MS-ESI calculated value $[M+H]^+$ 479 and 481, measured value 479 and 481.

Step 2

Compound 29a (360 mg, 751 μmol) was dissolved in ethanol (10 mL), hydrazine hydrate (664 mg, 11.3 mmol, 644 μL) was added to the reaction mixture, and the mixture was stirred at 55° C. for 2 hours. After the completion of the reaction, the reaction mixture was filtered and concentrated to give a crude product of compound 29b.

MS-ESI calculated value $[M+H]^+$ 349 and 351, measured value 349 and 351.

Step 3

Compound 29b (280 mg, 802 μmol) was dissolved in dichloromethane (5 mL), di-tert-butyl dicarbonate (175 mg, 802 μmol, 184 μL) was added to the reaction mixture, and the mixture was stirred at 25° C. for 16 hours. After the completion of the reaction, the reaction mixture was concentrated under reduced pressure to give a crude product of compound 29c.

MS-ESI calculated value $[M+H]^+$ 449 and 451, measured value 449 and 451.

Step 4

Compound 29c (360 mg, 801 μmol) and compound 27e (432 mg, 1.20 mmol) were dissolved in dioxane (8 mL) and water (2 mL), then tris(dibenzylideneacetone) dipalladium (73.4 mg, 80.1 μmol), 2-dicyclohexylphosphino-2',4',6'-triisopropylbiphenyl (76.4 mg, 160 μmol) and potassium carbonate (332 mg, 2.40 mmol) were added under nitrogen atmosphere, the reaction mixture was stirred at 100° C. for 5 hours. After the completion of the reaction, the reaction mixture was concentrated under reduced pressure and purified by column chromatography to give compound 29d.

MS-ESI calculated value $[M+H]^+$ 602, measured value 602.

Step 5

Compound 29d (50 mg, 72.3 μmol) was dissolved in DCM (3 mL), TFA (4.62 g, 40.5 mmol, 3 mL) was added thereto, the reaction mixture was stirred at 0° C. for 1 hour, and then at 25° C. for 1 hour. After the completion of the reaction, the reaction mixture was concentrated under reduced pressure, and the residue was purified by high performance liquid chromatography (hydrochloric acid condition) to give the hydrochloride of compound 29.

MS-ESI calculated value $[M+H]^+$ 402, measured value 402.

$^1$H NMR (400 MHz, DMSO-$d_6$) δ 13.57-11.77 (m, 1H), 9.29 (d, J=8.2 Hz, 1H), 8.55 (s, 1H), 8.36 (s, 1H), 8.28 (m, 3H), 8.05-7.95 (m, 2H), 7.87 (d, J=7.8 Hz, 1H), 7.61 (t, J=7.8 Hz, 1H), 7.53 (d, J=8.8 Hz, 1H), 7.30 (t, J=7.8 Hz, 1H), 7.09 (s, 1H), 7.04 (d, J=7.8 Hz, 1H), 7.00-6.76 (m, 1H), 5.42-5.34 (m, 1H), 3.76 (s, 3H), 3.51-3.39 (m, 1H), 3.26-3.13 (m, 1H) ppm.

Embodiment 30

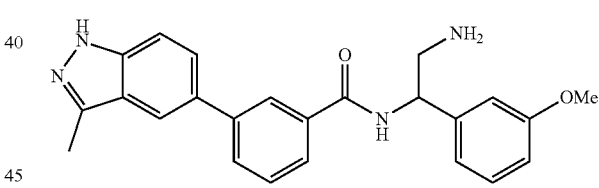

Synthetic Route:

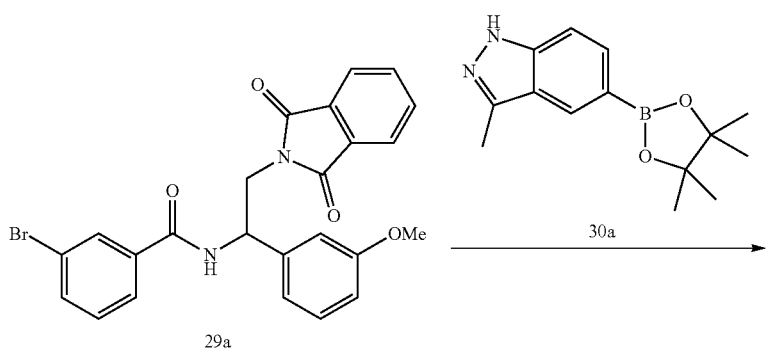

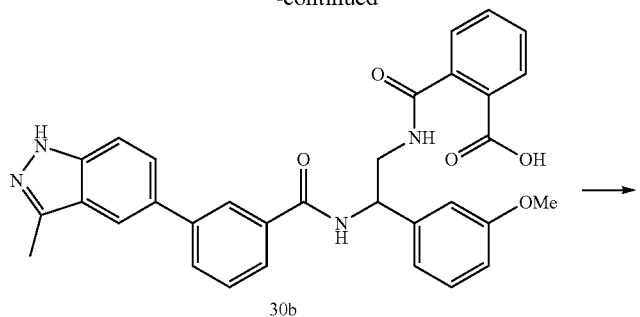

30b

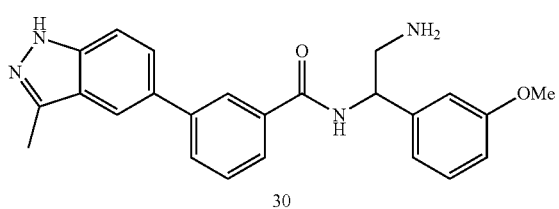

30

Step 1

Tris(dibenzylacetone)dipalladium (92.5 mg, 101 μmol), cesium carbonate (987 mg, 3.03 mmol) and 2-dicyclohexylphosphino-2',4',6'-triisopropylbiphenyl (48.1 mg, 101 μmol) were added to a solution of compound 29a (484 mg, 1.01 mmol) and compound 30a (391 mg, 1.51 mmol) in dioxane (10 mL) and water (2.5 mL), the mixture was stirred under the protection of nitrogen at 95° C. for 12 hours. After the completion of the reaction, the filtrate was filtered and subjected to rotary evaporation to dryness to give a crude product, the crude product was purified by thin-layer chromatography to give compound 30b.

MS-ESI calculated value [M+H]⁺ 549, measured value 549.

Step 2

Hydrazine hydrate (517 mg, 8.78 mmol, 502 μL, 85% purity) was added to a solution of compound 30b (340 mg, 585 μmol) in ethanol (5 mL). The reaction mixture was stirred at 50° C. for two hours and then stirred at 80° C. for 12 hours. After the completion of the reaction, the reaction mixture was subjected to rotary evaporation to dryness, and the crude product was purified by high performance liquid chromatography (neutral condition) to give compound 30.

MS-ESI calculated value [M+H]⁺ 401, measured value 401.

¹H NMR (400 MHz, DMSO-d₆) δ 12.70 (br, 1H), 8.77 (d, J=7.8 Hz, 1H), 8.21 (s, 1H), 8.04 (s, 1H), 7.91-7.84 (m, 2H), 7.75-7.71 (m, 1H), 7.60-7.54 (m, 2H), 7.28-7.22 (m, 1H), 6.99-6.94 (m, 2H), 6.83-6.79 (m, 1H), 5.08-4.85 (m, 1H), 3.75 (s, 3H), 2.84-2.96 (m, 2H), 2.56 (s, 3H) ppm.

Embodiment 31

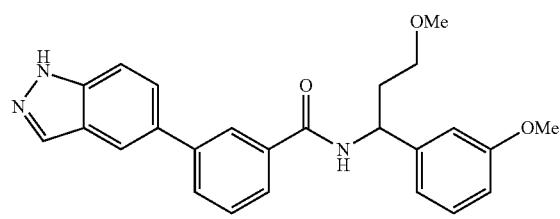

31

Synthetic Route:

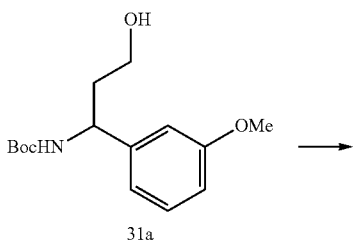

31a

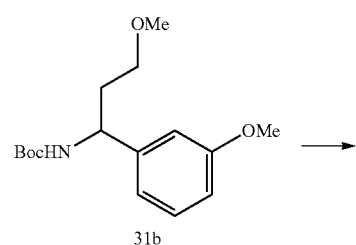

31b

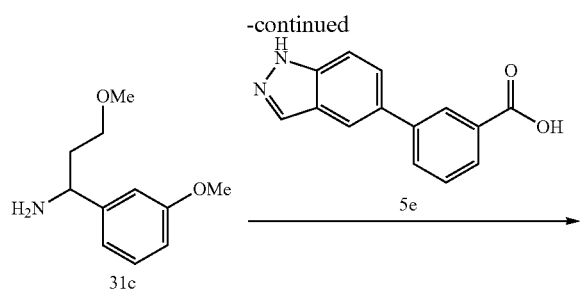

Step 1

At 0° C., compound 31a (300 mg, 1.07 mmol) was dissolved in tetrahydrofuran (5 mL), sodium hydride (51.2 mg, 1.28 mmol, purity 60%) was added to the reaction mixture in batches and stirred for 30 minutes, iodomethane (182 mg, 1.28 mmol, 79.7 L) was added dropwise to the reaction mixture. The reaction mixture was stirred at 20° C. for 16 hours. After the completion of the reaction, a saturated aqueous solution of ammonium chloride (2 mL) was added to the reaction mixture and the reaction mixture was extracted with ethyl acetate (10 mL). The organic phase was dried over anhydrous magnesium sulfate, filtered, and the filtrate was concentrated under reduced pressure to give a crude product. The crude product was purified by thin-layer chromatography to give compound 31b.

MS-ESI calculated value [M+Na]$^+$ 318, measured value 318.

Step 2

At room temperature, compound 31b (160 mg, 526 μmol) was dissolved in dichloromethane (4 mL), and a solution of hydrogen chloride in methanol (4 M, 2 mL) was added to the reaction mixture. The reaction mixture was stirred at 20° C. for 1 hour. After the completion of the reaction, the reaction mixture was concentrated under reduced pressure to give a crude product of compound 31c.

MS-ESI calculated value [M+H]$^+$ 196, measured value 196.

Step 3

At room temperature, compound 31c (150 mg, 647.3 μmol) and compound 5e (154 mg, 647.3 μmol) were dissolved in N, N-dimethylformamide (2 mL), and N, N-diisopropylethylamine (167 mg, 1.29 mmol, 226 μL) and O-(7-azabenzotriazol-1-yl)-N,N,N',N'-tetramethyluronium hexafluorophosphate (369 mg, 971 μmol) were added to the reaction mixture. The reaction mixture was stirred at 20° C. for 16 hours. After the completion of the reaction, the mixture was diluted with ethyl acetate (50 mL), and then washed with water (30 mL) and saturated brine (30 mL) sequentially. The organic phase was dried over anhydrous magnesium sulfate, filtered, the filtrate was concentrated under reduced pressure. The residue was purified by high performance liquid chromatography (hydrochloric acid condition) to give compound 31.

MS-ESI calculated value [M+H]$^+$ 416, measured value 416.

1H NMR (400 MHz, DMSO-d$_6$) δ 8.92-8.85 (m, 1H), 8.23-8.15 (m, 2H), 8.08 (s, 1H), 7.90-7.80 (m, 1H), 7.78-7.73 (m, 2H), 7.67-7.63 (m, 1H), 7.61-7.52 (m, 1H), 7.26 (t, J=8.2 Hz, 1H), 7.05-6.95 (m, 2H), 6.85-6.75 (m, 1H), 5.20-5.10 (m, 1H), 3.76 (s, 3H), 3.45-3.30 (m, 2H), 3.25 (s, 3H), 2.25-1.90 (m, 2H) ppm.

Embodiment 32

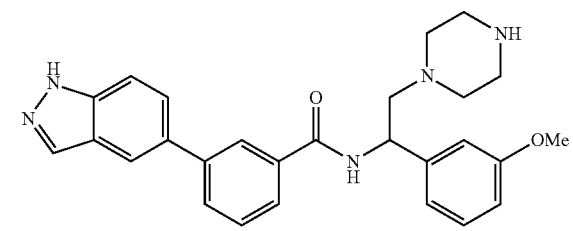

Synthetic Route:

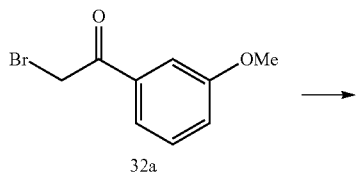

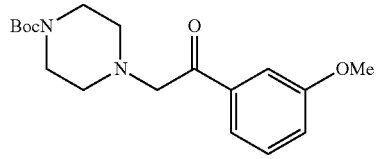

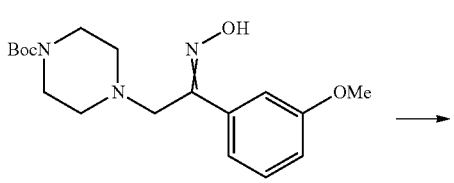

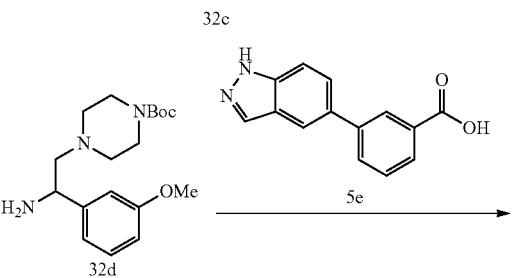

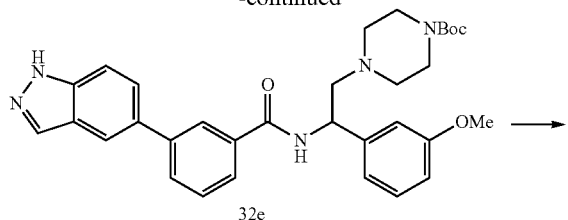

phase was washed with saturated brine (100 mL×1), dried over anhydrous sodium sulfate, filtered, and the filtrate was concentrated under reduced pressure. The residue was purified by column chromatography to give compound 32e.

MS-ESI calculated value [M+H]$^+$ 556, measured value 556.

Step 5

Compound 32e (130 mg, 180 mol) was dissolved in dioxane (4 mL), a solution of hydrogen chloride in dioxane (4 M, 4 mL) was added thereto, and the reaction mixture was stirred at 28° C. for 1 hour. After the completion of the reaction, the reaction mixture was concentrated under reduced pressure. The residue was purified by high performance liquid chromatography (formic acid condition) to give the formate of compound 32.

MS-ESI calculated value [M+H]$^+$ 456, measured value 456.

$^1$H NMR (400 MHz, CD$_3$OD) δ 8.51 (s, 1H), 8.18 (t, J=1.6 Hz, 1H), 8.14 (s, 1H), 8.09 (s, 1H), 7.91-7.82 (m, 2H), 7.79-7.73 (m, 1H), 7.70-7.64 (m, 1H), 7.63-7.56 (m, 1H), 7.30 (t, J=8.2 Hz, 1H), 7.11-6.99 (m, 2H), 6.94-6.80 (m, 1H), 5.45-5.35 (m, 1H), 3.82 (s, 3H), 3.26-3.13 (m, 4H), 3.05-2.95 (m, 1H), 2.96-2.86 (m, 2H), 2.83-2.71 (m, 3H) ppm.

Embodiment 33

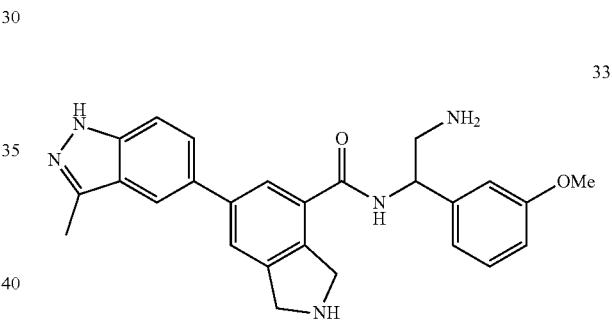

Step 1

Compound 32a (4.00 g, 17.5 mmol) and N-tert-butoxycarbonylpiperazine (3.25 g, 17.5 mmol) were dissolved in tetrahydrofuran (100 mL), and then potassium carbonate (6.03 g, 43.7 mmol) was added thereto. The reaction mixture was stirred at 28° C. for 12 hours. After the completion of the reaction, the mixture was filtered and the filtrate was subjected to rotary evaporation to dryness to give a crude product, which was purified by column chromatography to give compound 32b.

Step 2

Compound 32b (4.10 g, 12.3 mmol) was dissolved in ethanol (80 mL), and then hydroxylamine hydrochloride (1.02 g, 14.7 mmol) and sodium acetate (1.51 g, 18.4 mmol) were added. The reaction mixture was stirred at 50° C. for 12 hours. After the completion of the reaction, the reaction mixture was filtered and the filtrate was subjected to rotary evaporation to dryness. The crude product was purified by column chromatography to give compound 32c.

Step 3

Compound 32c (3.50 g, 10.0 mmol) was dissolved in methanol (105 mL), and then wet palladium on carbon (350 mg, 10% purity) was added thereto. The reaction mixture was stirred at 30° C. under a hydrogen pressure of 15 psi for 12 hours. After the completion of the reaction, the reaction mixture was filtered, and the filtrate was subjected to rotary evaporation to dryness to give the crude compound 32d.

Step 4

Compound 32d (250 mg, 745 μmol) and compound 5e (266 mg, 1.12 mmol) were dissolved in N,N-dimethylformamide (12 mL), and 1-(3-dimethylaminopropyl)-3-ethylcarbodiimide hydrochloride (157 mg, 820 μmol), 1-hydroxybenzotriazole (111 mg, 820 μmol) and N,N-diisopropylethylamine (578 mg, 4.47 mmol, 779 μL) were added to the reaction mixture, and the mixture was stirred at 25° C. for 4 hours. After the completion of the reaction, the reaction mixture was diluted with water (120 mL) and extracted with ethyl acetate (70 ml×2), the combined organic Synthetic Route of Intermediate 33d:

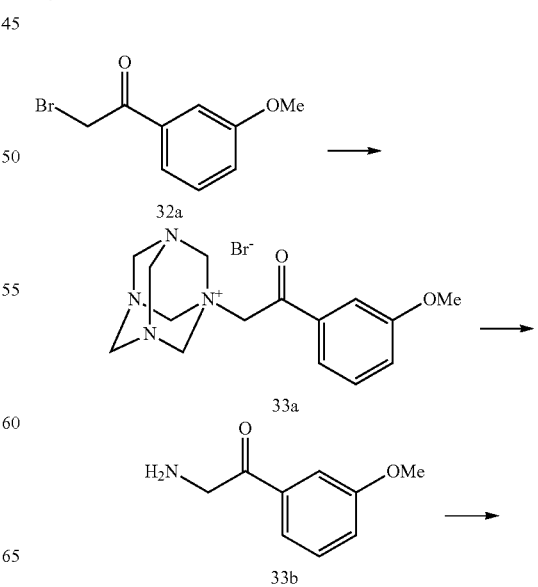

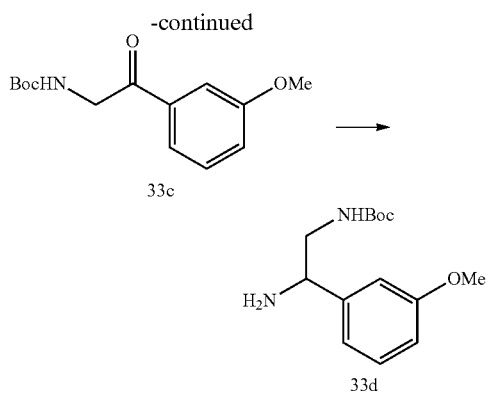

Step 1

Urotropine (82.6 g, 589 mmol) was added to a solution of compound 32a (135 g, 589 mmol) in dichloromethane (800 mL), and the reaction mixture was stirred at 10° C. for 1 hour. After the completion of the reaction, the reaction mixture was filtered, the filter cake was collected to give crude compound 33a.

Step 2

Compound 33a (76.0 g, 206 mmol) was dissolved in ethanol (500 mL), then 35% concentrated hydrochloric acid (62.0 mL) was added thereto, and reaction mixture was stirred at 80° C. for 1.5 hours. After the completion of the reaction, the mixture was filtered, concentrated under reduced pressure, and dried to give the hydrochloride of compound 33b.

Step 3

Hydrochloride of compound 33b (50 g, 248 mmol) was dissolved in water (400 mL), then sodium bicarbonate (52.1 g, 620 mmol), methanol (400 mL) and di-tert-butyl dicarbonate (81.2 g, 372 mmol, 85.5 mL) were added thereto. The reaction mixture was stirred at 10° C. for 1 hour. After the completion of the reaction, the reaction mixture was extracted with ethyl acetate (800 mL×3). The combined organic phase was dried over anhydrous sodium sulfate, filtered, and the filtrate was concentrated under reduced pressure. The residue was purified by column chromatography to give compound 33c.

Step 4

Ammonium acetate (158 g, 2.05 mol) and sodium cyanoborohydride (12.9 g, 205 mmol) were added to a solution of compound 33c (54.5 g, 205 mmol) in methanol (800 mL). The reaction mixture was stirred at 50° C. for 18 hours. After the completion of the reaction, the mixture was filtered and the filtrate was concentrated by evaporation to dryness. The residue was purified by a reverse-phase preparative chromatography column (ammonium hydroxide system) to give compound 33d.

MS-ESI calculated value $[M+H]^+$ 267, measured value 267.

Synthetic Route of Compound 33:

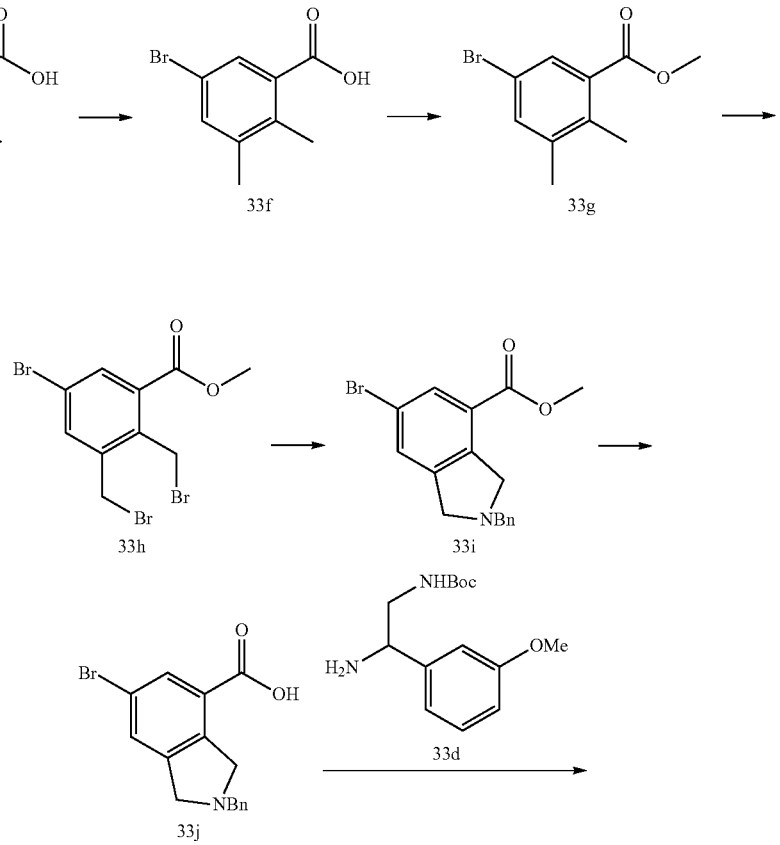

-continued

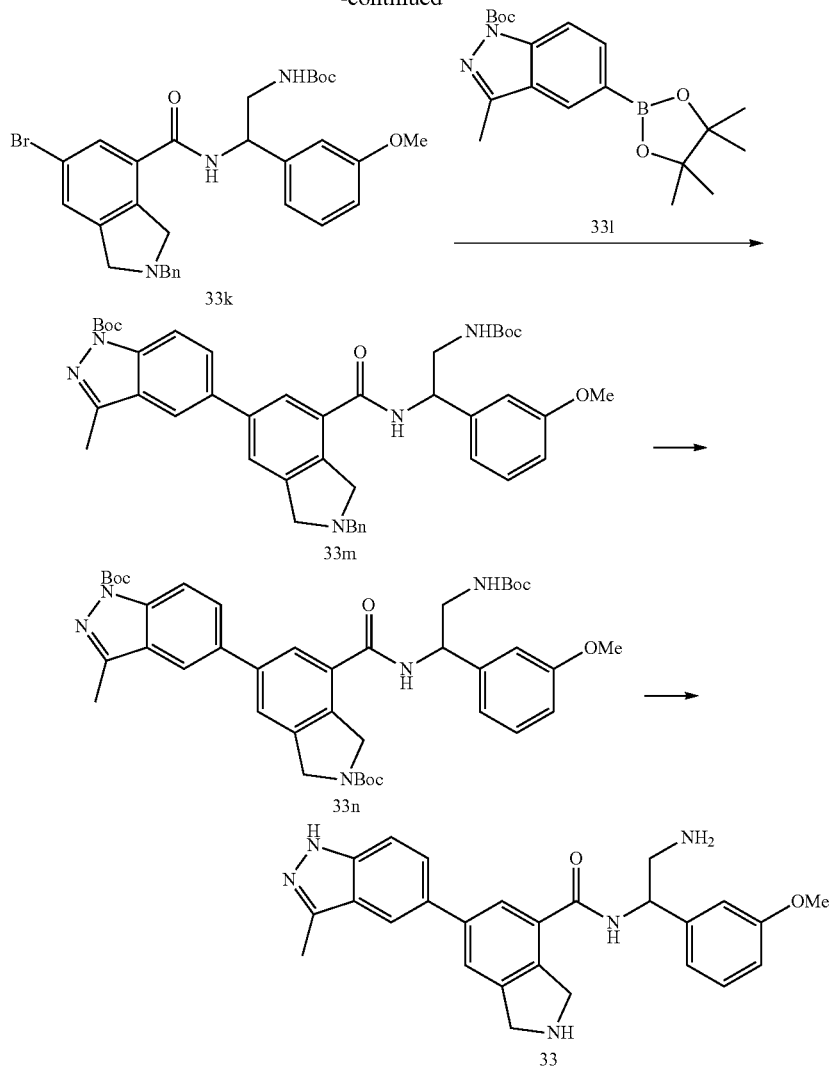

Step 1

Nitric acid (77.5 g, 799 mmol, 55.3 mL, 65% purity), water (30 mL) and liquid bromine (11.7 g, 73.3 mmol, 3.78 mL) were sequentially added to a solution of compound 33e (10.0 g, 66.6 mmol) in acetic acid (334 mL) at 30° C., and then the aqueous solution (86 mL) with silver nitrate (14.7 g, 86.6 mmol) dissolved in it was added dropwise to the reaction mixture within half an hour. After the addition was completed, the reaction mixture was stirred at 30° C. for 1 hour. After the completion of the reaction, the reaction mixture was poured into a mixture of ethyl acetate (300 mL) and water (200 mL). Then the mixture was extracted with ethyl acetate (300 mL×3). The organic phase was washed with water (300 mL×1), dried over anhydrous sodium sulfate, filtered, and the filtrate was concentrated under reduced pressure to give crude compound 33f.

Step 2

A concentrated sulfuric acid solution (9.20 g, 89.1 mmol, 5.00 mL, 95% purity) was added to a solution of compound 33f (5.00 g, 21.8 mmol) in methanol (238 mL). The reaction mixture was stirred at 70° C. for 6 hours. After the completion of the reaction, the reaction mixture was concentrated by evaporation, the residue was quenched with saturated sodium bicarbonate solution (50 mL), and then extracted with ethyl acetate (50 mL×2), the combined organic phase was dried over anhydrous sodium sulfate, filtered, and the filtrate was concentrated under reduced pressure. The residue was purified by column chromatography to give compound 33g.

Step 3

Compound 33g (3.40 g, 14.0 mmol) was dissolved in carbon tetrachloride (30 mL), and then N-bromosuccinimide (5.23 g, 29.4 mmol) and benzoyl peroxide (339 mg, 1.40 mmol) were added thereto. The reaction mixture was stirred at 80° C. under nitrogen protection for 2 hours. After the completion of the reaction, the reaction mixture was filtered, and the filtrate was concentrated under reduced pressure to give the crude compound 33h.

Step 4

Compound 33h (2.00 g, 4.99 mmol) was dissolved in dioxane (20 mL), then benzylamine (535 mg, 4.99 mmol, 543.82 µL) and sodium hydroxide (479 mg, 12.0 mmol) were added thereto. The reaction mixture was stirred at 28° C. for 16 hours. After the completion of the reaction, the reaction mixture was evaporated to dryness, ethyl acetate (30 mL) and water (20 mL) were added, the liquid phases were separated, and the organic phase was concentrated under reduced pressure. The crude product was purified by thin layer chromatography to give compound 33i.

MS-ESI calculated value [M+H]$^+$ 346 and 348, measured value 346 and 348.

Step 5

Compound 33i (0.35 g, 1.01 mmol) was dissolved in water (7 mL) and tetrahydrofuran (7 mL), and then sodium hydroxide (121 mg, 3.03 mmol) was added thereto. The reaction mixture was stirred at 20° C. for 1 hour. After the completion of the reaction, a dilute hydrochloric acid solution (2 M, 3 mL) was added to the mixture, and then the mixture was extracted with ethyl acetate (10 mL×3), the combined organic phase was dried over anhydrous sodium sulfate, filtered, and the filtrate was concentrated under reduced pressure to give the crude compound 33j.

Step 6

Compound 33j (317 mg, 954 µmol) was dissolved in tetrahydrofuran (10 mL), and then O-(7-azabenzotriazol-1-yl)-N,N,N',N'-tetramethyluronium hexafluorophosphate (381 mg, 1.00 mmol), N,N-diisopropylethylamine (370 mg, 2.86 mmol, 499 µL) and compound 33d (271 mg, 1.00 mmol) were added thereto. The reaction mixture was stirred at 25° C. for 16 hours. After the completion of the reaction, the reaction mixture was concentrated under reduced pressure. The residue was purified by thin layer chromatography to give compound 33k.

Step 7

Compound 33k (180 mg, 310 µmol) and compound 33l (133 mg, 372 µmol) were dissolved in dioxane (5 mL) and water (0.5 mL), and then 2-dicyclohexylphosphino-2',4',6'-triisopropylbiphenyl (14.8 mg, 31.0 µmol), tris(dibenzylideneacetone) dipalladium (28.4 mg, 31.0 µmol) and cesium carbonate (202 mg, 620 µmol) were added thereto. The reaction mixture was in stirred at 85° C. for 12 hours under nitrogen protection. After the completion of the reaction, the reaction mixture was evaporated to dryness. The residue was purified by thin layer chromatography to give compound 33m.

Step 8

Compound 33m (114 mg, 156 µmol) was dissolved in ethyl acetate (5 mL), then wet palladium on carbon (20.0 mg, 10% purity), di-tert-butyl dicarbonate (27.4 mg, 126 µmol, 28.84 µL) and glacial acetic acid (754 g, 12.6 µmol, 0.700 µL) were added thereto. The reaction mixture was stirred for 9 hours at 60° C. under a hydrogen pressure of 15 psi. After the completion of the reaction, the reaction mixture was filtered with celite, and the filtrate was concentrated under reduced pressure. The residue was purified by thin layer chromatography to give compound 33n.

Step 9

Compound 33n (64.0 mg, 86.3 µmol) was dissolved in dichloromethane (0.5 mL), then trifluoroacetic acid (193 mg, 1.69 mmol, 0.125 mL) was added thereto, and the reaction mixture was stirred at 15° C. for 1 hour. After the completion of the reaction, the reaction mixture was concentrated under reduced pressure. The residue was purified by high performance liquid chromatography (formic acid condition) to give the formate of compound 33.

MS-ESI calculated value [M+H]$^+$ 442, measured value 442.

$^1$H NMR (400 MHz, CD$_3$OD) δ 8.60-8.41 (m, 2H), 8.31 (s, 1H), 8.09 (s, 1H), 7.93 (s, 1H), 7.86-7.76 (m, 1H), 7.65-7.58 (m, 1H), 7.38-7.32 (m, 1H), 7.12-7.05 (m, 2H), 6.98-6.90 (m, 1H), 5.49-5.42 (m, 1H), 4.93 (s, 2H) 4.69 (s, 2H), 3.83 (s, 3H), 3.55-3.38 (m, 2H), 2.65 (s, 3H) ppm.

Embodiment 34

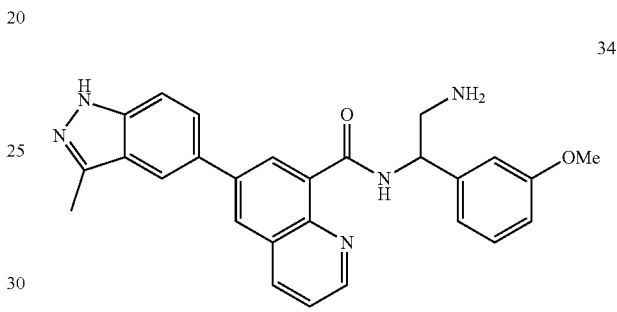

Synthetic Route:

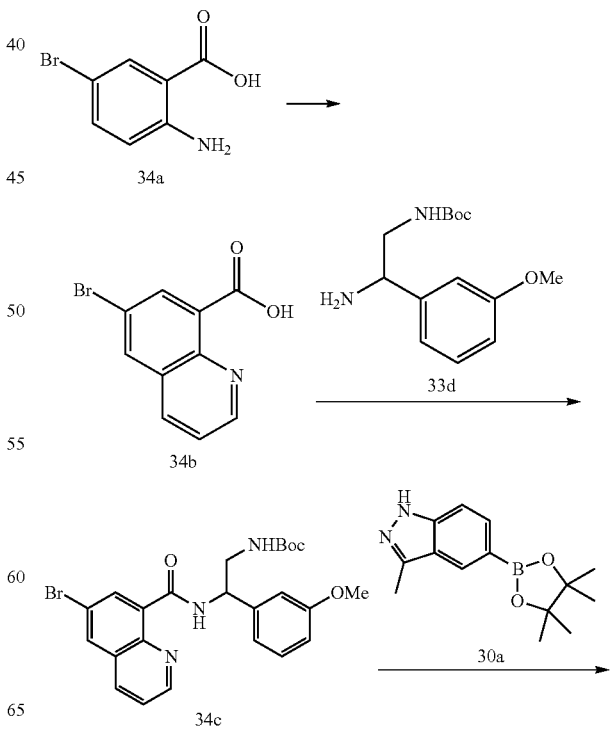

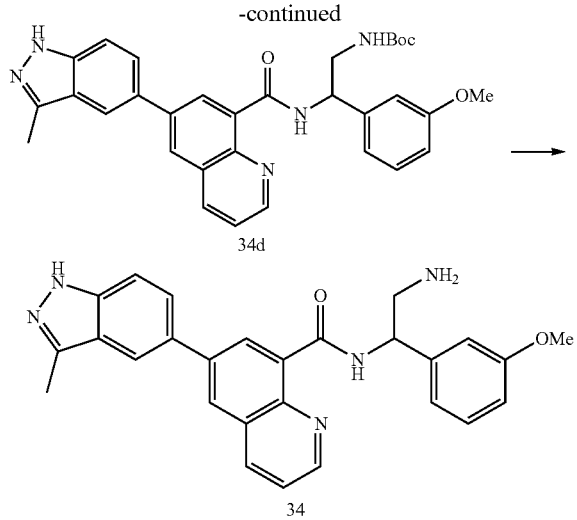

Step 1

Compound 34a (25.0 g, 116 mmol) and acrolein (6.49 g, 116 mmol, 7.74 mL) were dissolved in toluene (130 mL), then trifluoromethanesulfonic acid (868 mg, 5.79 mmol, 511 μL) and silver trifluoromethanesulfonate (1.49 g, 5.79 mmol) were added. The reaction mixture was stirred at 25° C. for 10 minutes, then heated to 110° C. and stirred for 4 hours under an oxygen gas pressure of 15 psi. Then acrolein (7.97 g, 142 mmol, 9.51 mL) was added to the reaction mixture, and stirred at 110° C. for 12 hours under an oxygen gas pressure of 15 psi. Acrolein (3.24 g, 57.9 mmol, 3.87 mL) was added and the reaction mixture was stirred at 110° C. for 1 hour under an oxygen gas pressure of 15 psi. After the completion of the reaction, the reaction mixture was concentrated under reduced pressure, the resulting solid was dissolved in tetrahydrofuran (500 mL), and then hydrochloric acid (2 M, 600 mL) was added thereto. The mixture was washed with ethyl acetate (500 mL×3), the pH value of the aqueous phase was neutralized to about a pH value of 8 to 9 by adding sodium carbonate, and extracted with ethyl acetate (500 mL×6). The combined organic phase was subjected to rotary evaporation to dryness to give the crude compound 34b.

Step 2

Compound 34b (800 mg, 3.17 mmol) was dissolved in tetrahydrofuran (10 mL), and then O-(7-azabenzotriazol-1-yl)-N,N,N',N'-tetramethyluronium hexafluorophosphate (1.27 g, 3.33 mmol), N,N-diisopropylethylamine (1.23 g, 9.52 mmol, 1.66 mL) and compound 33d (535 mg, 1.98 mmol) were added thereto, the reaction mixture was stirred at 14° C. for 16 hours After the completion of the reaction, the reaction mixture was concentrated under reduced pressure. The residue was purified by thin layer chromatography to give compound 34c.

Step 3

Compound 34c (350 g, 699 μmol) was dissolved in dioxane (5 mL) and water (0.5 mL), then compound 30a (276 mg, 769 μmol), [1,1'-bis(diphenylphosphino)ferrocene] palladium dichloride (51.2 mg, 70.0 μmol) and potassium acetate (206 mg, 2.10 mmol) were added thereto. The reaction mixture was stirred at 85° C. under nitrogen protection for 12 hours. After the completion of the reaction, the reaction mixture was diluted with water (10 mL), and then extracted with ethyl acetate (10 mL×2). The combined organic phase was concentrated under reduced pressure, and the residue was purified by thin layer chromatography to give compound 34d.

Step 5

Compound 34d (340 mg, 522 μmol) was dissolved in dichloromethane (1 mL), and then trifluoroacetic acid (385 mg, 3.38 mmol, 250 μL) was added thereto. The reaction mixture was stirred at 16° C. for 1 hour. After the completion of the reaction, the reaction mixture was quenched with a saturated aqueous solution of sodium bicarbonate (10 mL). Then the mixture was extracted with ethyl acetate (10 mL×6), and the combined organic phases were concentrated under reduced pressure. The residue was purified by thin layer chromatography and then separated by high-performance liquid chromatography (under neutral condition) to give compound 34.

MS-ESI calculated value $[M+H]^+$ 452, measured value 452.

$^1$H NMR (400 MHz, DMSO-$d_6$) δ 12.78 (br, 1H), 11.32 (m, 1H), 9.10-9.05 (m, 1H), 8.87 (d, J=2.4 Hz, 1H), 8.69-8.62 (dd, J=8.4, 1.6 Hz, 1H), 8.59-8.53 (m, 1H), 8.20 (s, 1H), 7.84 (dd, J=8.4, 1.6 Hz, 1H), 7.75-7.70 (m, 1H), 7.63 (d, J=8.8 Hz, 1H), 7.32-7.26 (m, 1H), 7.07-7.01 (m, 2H), 6.88-6.80 (m, 1H), 5.21-5.09 (m, 1H), 3.76 (s, 3H), 3.00 (d, J=6.24 Hz, 2H), 2.58 (s, 3H) ppm.

Embodiment 35

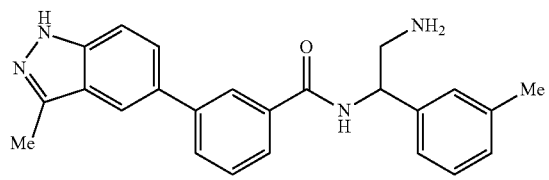

Synthetic Route:

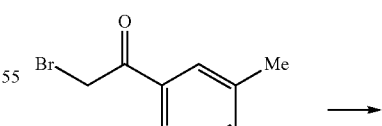

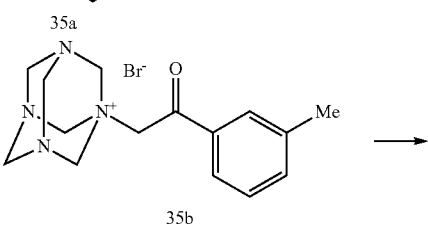

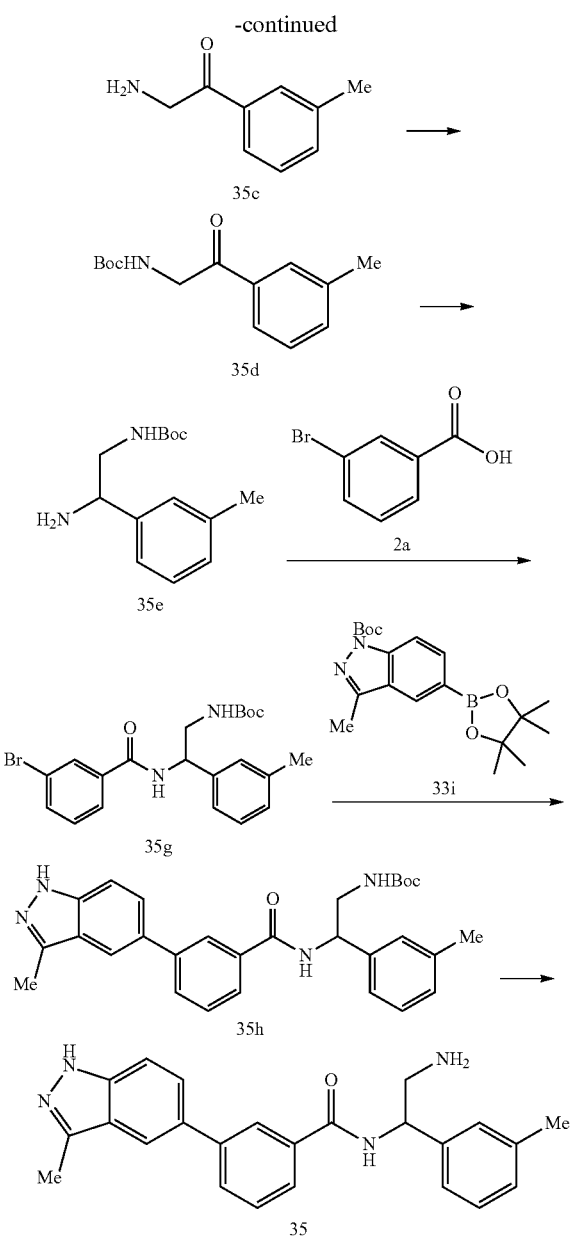

MS-ESI calculated value [M+H]⁺ 251, measured value 251.

Step 5

Compound 2a (225 mg, 1.12 mmol) was dissolved in N,N-dimethylformamide (15 mL), O-(7-azabenzotriazol-1-yl)-N,N,N',N'-tetramethyluronium hexafluorophosphate (553 mg, 1.45 mmol) and N,N-diisopropylethylamine (434 mg, 3.36 mmol, 584 μL) were added to the reaction mixture, the reaction mixture was stirred at 20° C. for 10 minutes. Then compound 35e (280 mg, 1.12 mmol) was added to the mixture and stirred at 20° C. for 12 hours. After the completion of the reaction, the mixture was concentrated under reduced pressure, and the residue was purified by column chromatography to give compound 35g.

Step 6

Compound 35g (50 mg, 115 μmol), compound 33l (62.00 mg, 173 μmol, 1.5 eq), [1,1'-bis(diphenylphosphino)ferrocene]palladium dichloride (18.9 mg, 23.1 μmol), 2-dicyclohexylphosphino-2',6'-dimethoxybiphenyl (11.0 mg, 26.8 μmol), potassium phosphate (73.5 mg, 346 μmol) were dissolved in dioxane (4 mL) and water (1 mL), the reaction mixture was stirred at 95° C. for 12 hours. After the completion of the reaction, the reaction mixture was filtered, and the filtrate was concentrated under reduced pressure. The residue was purified by column chromatography to give compound 35h.

MS-ESI calculated value [M+H]⁺ 485, measured value 485.

Step 7

Compound 35h (240 mg, 269 μmol) was dissolved in dichloromethane (5 mL), trifluoroacetic acid (2 mL) was added thereto, and the mixture was stirred at 20° C. for 1 hour. After the completion of the reaction, the reaction mixture was concentrated under reduced pressure, and the residue was purified by high performance liquid chromatography (hydrochloric acid condition) to give hydrochloride of compound 35.

MS-ESI calculated value [M+H]⁺ 385, measured value 385.

¹H NMR (400 MHz, DMSO-d₆) δ 9.39 (d, J=8.0 Hz, 1H), 8.42 (s, 1H), 8.38 (s, 3H), 8.21 (s, 1H), 7.92 (dd, J=8.0, 13.2 Hz, 2H), 7.82-7.80 (m, 1H), 7.61-7.53 (m, 2H), 7.32-7.23 (m, 3H), 7.14-7.08 (m, 1H), 5.42-5.34 (m, 1H), 3.55-3.41 (m, 1H), 3.25-3.11 (m, 1H), 2.59 (s, 3H), 2.31 (s, 3H) ppm.

Step 1

Intermediate 35b was obtained by referring to Step 1 of Embodiment 33.

Step 2

Intermediate 35c was obtained by referring to Step 2 of Embodiment 33.

Step 3

Intermediate 35d was obtained by referring to Step 3 of Embodiment 33.

Step 4

Intermediate 35e was obtained by referring to Step 4 of Embodiment 33.

Embodiment 36

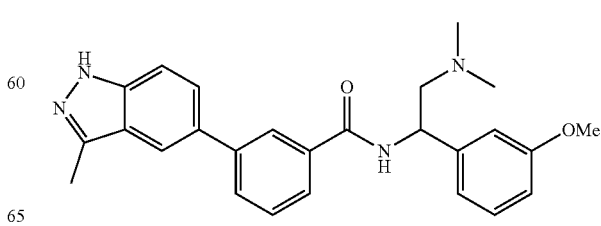

Synthetic Route:

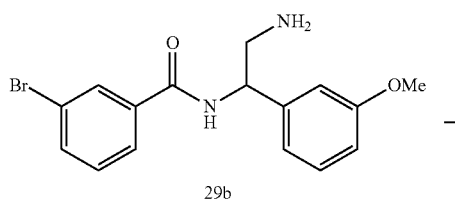

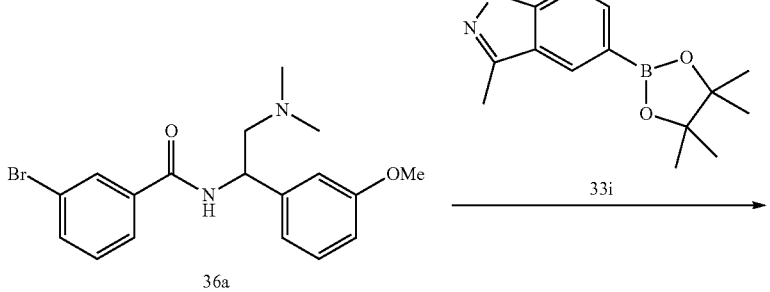

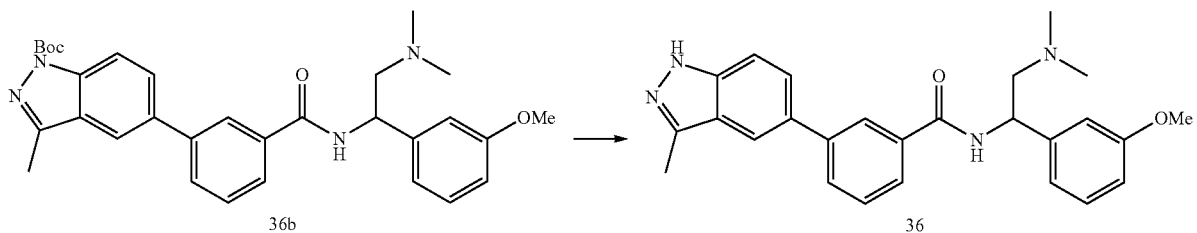

Step 1

Compound 29b (800 mg, 2.07 mmol) was dissolved in 1,2-dichloroethane (16 mL), and sodium cyanoborohydride (879 mg, 4.15 mmol), paraformaldehyde (1.68 g, 18.7 mmol) and acetic acid (42.0 mg, 699 μmol, 40.0 μL) were added thereto. The reaction mixture was stirred at 10° C. for 12 hours. After the completion of the reaction, the reaction mixture was filtered and the filtrate was concentrated under reduced pressure. The residue was purified by thin layer chromatography to give compound 36a.

Step 2

Compound 36a (608 mg, 1.70 mmol) and compound 33I (640 mg, 1.70 mmol) were dissolved in dioxane (15 mL) and water (1.5 mL), and then [1,1'-bis(diphenylphosphino)ferrocene]palladium dichloride (124 mg, 170 μmol) and potassium acetate (499 mg, 5.09 mmol) were added thereto. The reaction mixture was stirred at 85° C. under nitrogen protection for 4 hours. After the completion of the reaction, the mixture was filtered, and the filtrate was concentrated under reduced pressure. The residue was purified by thin-layer chromatography to give compound 36b.

Step 3

Compound 36b (250 mg, 473 μmol) was dissolved in dioxane (8 mL), and then a solution of hydrogen chloride (4 M, 8 mL) in dioxane was added thereto, the reaction mixture was stirred at 10° C. for 0.5 hour. After the completion of the reaction, the reaction mixture was concentrated under reduced pressure. The residue was purified by thin layer chromatography and high performance liquid chromatography (neutral condition) to give compound 36.

MS-ESI calculated value [M+H]$^+$ 429, measured value 429.

$^1$H NMR (400 MHz, DMSO-d$_6$) δ 12.73 (br, 1H), 8.81 (d, J=8.0 Hz, 1H), 8.18 (s, 1H), 8.03 (s, 1H), 7.91-7.81 (m, 2H), 7.75-7.69 (m, 1H), 7.61-7.54 (m, 2H), 7.29-7.21 (m, 1H), 7.06-6.99-7.06 (m, 2H), 6.85-6.78 (m, 1H), 5.27-5.16 (m, 1H), 3.76 (s, 3H), 2.86-2.76 (m, 1H), 2.56 (s, 3H), 2.48-2.40 (m, 1H), 2.23 (s, 6H) ppm.

Embodiment 37

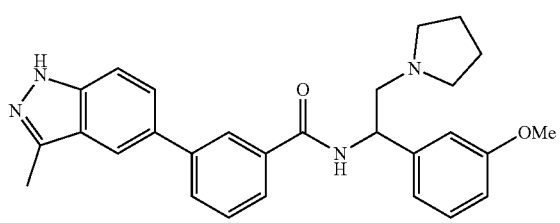

37

Synthetic Route:

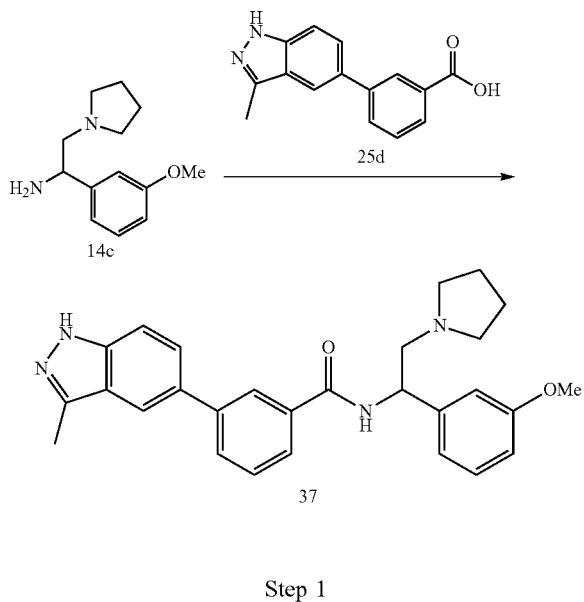

Step 1

Compound 14c (130 mg, 443 μmol) and compound 25d (112 mg, 443 μmol) were dissolved in N,N-dimethylformamide (5 mL), and O-(7-azabenzotriazol-1-yl)-N,N,N',N'-tetramethyluronium hexafluorophosphate (219 mg, 576 μmol) and N,N-diisopropylethylamine (229 mg, 1.77 mmol, 309 μL) were added to the reaction mixture, the mixture was stirred at 30° C. for 12 hours. After the completion of the reaction, the mixture was extracted with ethyl acetate (10 mL×2). The combined organic phases were washed with saturated brine (10 mL×1), dried over anhydrous sodium sulfate, and filtered, the filtrate was concentrated under reduced pressure. The residue was purified by high performance liquid chromatography (hydrochloric acid condition) to give the hydrochloride of compound 37.

MS-ESI calculated value $[M+H]^+$ 455, measured value 455.

$^1$H NMR (400 MHz, DMSO-$d_6$) δ 10.04 (br, 1H), 9.38 (d, J=8.8 Hz, 1H), 8.37 (s, 1H), 8.16 (s, 1H), 7.99-7.90 (m, 2H), 7.79-7.72 (m, 1H), 7.62-7.54 (m, 2H), 7.31 (t, J=8.0 Hz, 1H), 7.17 (s, 1H), 7.11 (d, J=7.7 Hz, 1H), 6.91-6.86 (m, 1H), 5.61-5.51 (m, 1H), 3.90-3.80 (m, 2H), 3.77 (s, 3H), 3.37-3.10 (m, 4H), 2.56 (s, 3H), 2.08-1.98 (m, 2H), 1.97-1.86 (m, 2H) ppm.

Embodiment 38

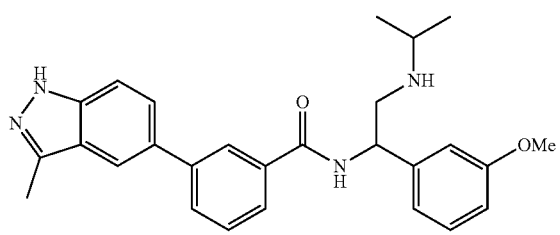

38

Synthetic Route:

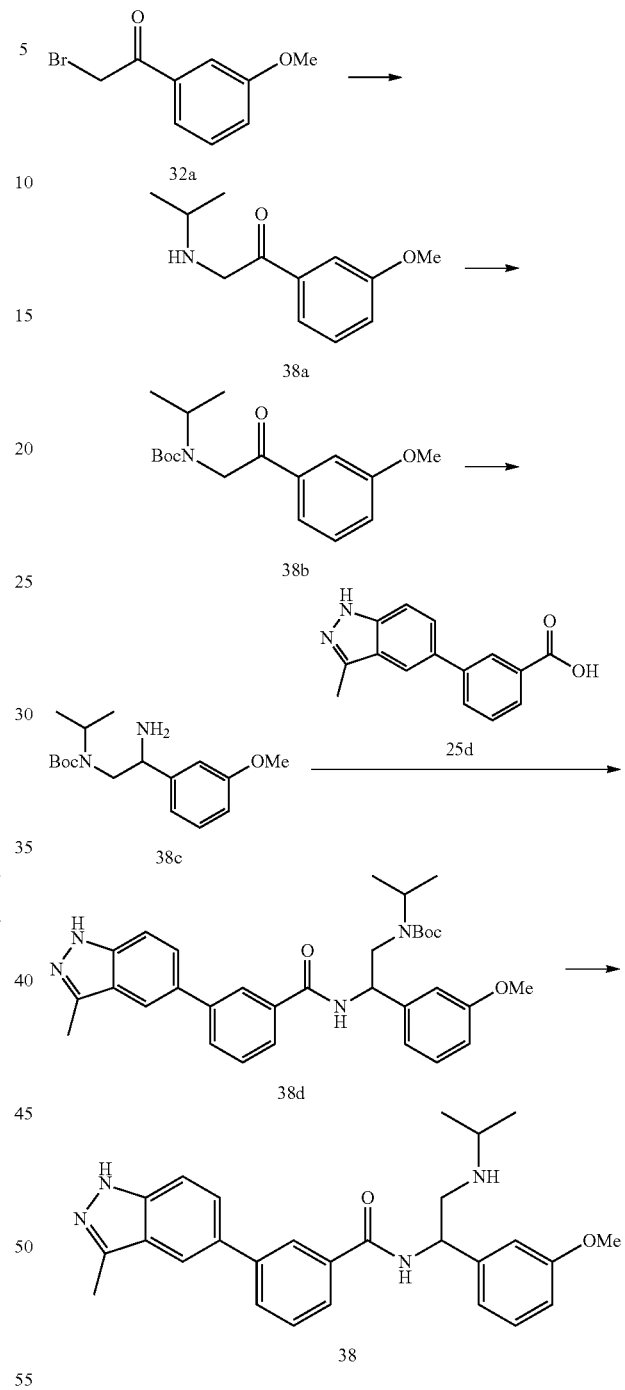

Step 1

Isopropylamine (774 mg, 13.1 mmol, 1.1 mL) was dissolved in ethanol (20 mL), then compound 32a (2.00 g, 8.73 mmol) was added to the reaction mixture, and the mixture was stirred at 20° C. for 1.5 hours. After the completion of the reaction, the mixture was diluted with water (40 mL) and the pH value of the reaction mixture was adjusted to about 5 with dilute aqueous hydrochloric acid solution (1 M), then extracted with ethyl acetate (50 mL×2), the liquid phases were separated, and the aqueous solution of compound 38a hydrochloride was collected and used directly in the next step.

MS-ESI calculated value [M+H]⁺ 208, measured value 208.

Step 2

Tetrahydrofuran (50 mL), di-tert-butyl dicarbonate (2.48 g, 11.4 mmol, 2.60 mL) and sodium bicarbonate (1.47 g, 17.5 mmol, 680 µL) were added to the aqueous solution (100 mL) of compound 38a hydrochloride obtained in Step 1, the reaction mixture was stirred at 20° C. for 12 hours. After the completion of the reaction, the reaction mixture was diluted with water (50 mL), and extracted with ethyl acetate (80 mL×2), the combined organic phase was washed with saturated brine (100 mL×1), dried over anhydrous sodium sulfate, filtered, and the filtrate was concentrated under reduced pressure. The residue was purified by column chromatography to give compound 38b.

Step 3

Compound 38b (600 mg, 1.95 mmol) was dissolved in methanol (20 mL), sodium cyanoborohydride (123 mg, 1.95 mmol) and ammonium acetate (1.50 g, 19.5 mmol) were added, and the reaction mixture was stirred at 65° C. for 72 hours. After the completion of the reaction, water (15 mL) was added to quench the reaction and the mixture was concentrated under reduced pressure. The residue was purified by high performance liquid chromatography (basic condition) to give compound 38c.

MS-ESI calculated value [M+H]⁺ 309, measured value 309.

Step 4

Compound 38d was obtained by referring to Step 1 of Embodiment 37.

MS-ESI calculated value [M+H]⁺ 543, measured value 543.

Step 5

Compound 38d (310 mg, 539 µmol) was dissolved in dichloromethane (3 mL), then a solution of hydrogen chloride in ethyl acetate (4M, 0.5 mL) was added thereto, the mixture was stirred at 20° C. for 4 hours. After the completion of the reaction, the reaction mixture was concentrated under reduced pressure, the residue was purified by high performance liquid chromatography (hydrochloric acid condition) to give hydrochloride of compound 38.

MS-ESI calculated value [M+H]⁺ 443, measured value 443.

¹H NMR (400 MHz, DMSO-d₆) δ 9.56 (d, J=8.0 Hz, 1H), 9.37 (s, 1H), 8.97 (s, 1H), 8.48 (s, 1H), 8.28 (s, 1H), 8.00-7.95 (m, 1H), 7.95-7.89 (m, 1H), 7.86-7.80 (m, 1H), 7.62-7.53 (m, 2H), 7.30 (t, J=8.0 Hz, 1H), 7.18-7.12 (m, 1H), 7.08 (d, J=8.0 Hz, 1H), 6.89-6.86 (m, 1H), 5.57-5.44 (m, 1H), 3.76 (s, 3H), 3.70-3.59 (m, 1H), 3.46-3.18 (m, 2H), 2.59 (s, 3H), 1.35-1.26 (m, 6H) ppm.

Embodiment 39

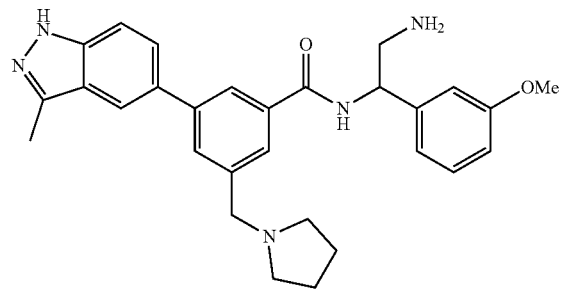

Synthetic Route:

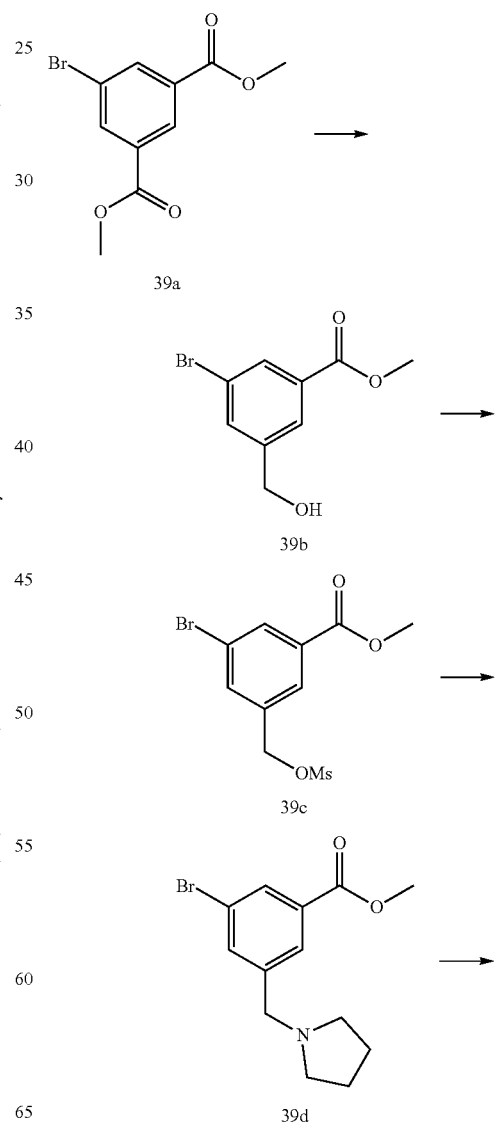

-continued

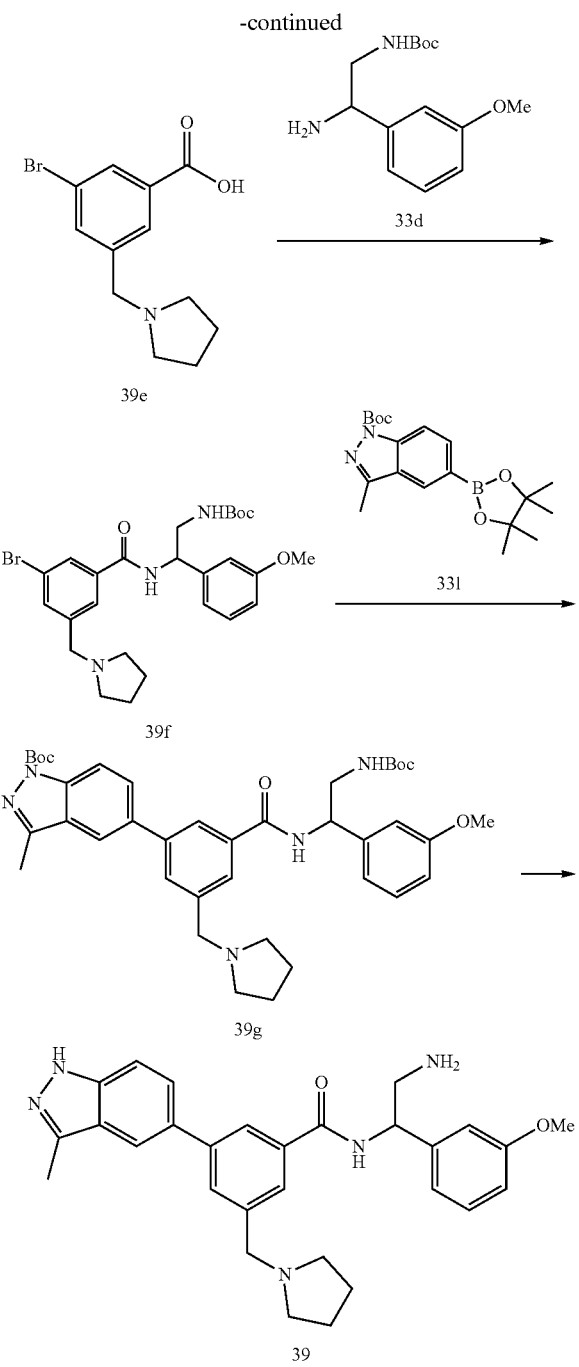

Step 1

Compound 39a (25.0 g, 91.6 mmol) was dissolved in tetrahydrofuran (225 mL), sodium borohydride (4.26 g, 113 mmol) was added at 0° C., and ethanol (25 mL) was added at 0° C., the reaction mixture was then stirred at 20° C. for 12 hours. After the completion of the reaction, water (20 mL) was slowly added to quench the reaction, the pH value of the solution was adjusted to about 7 with dilute aqueous hydrochloric acid solution (1M), and the mixture was extracted with ethyl acetate (30 mL×3), the combined organic phase was washed with saturated brine (100 mL×1), dried over anhydrous sodium sulfate, filtered, and the filtrate was concentrated under reduced pressure. The residue was purified by column chromatography to give compound 39b.

MS-ESI calculated value [M+H]$^+$ 245, measured value 245.

Step 2

Compound 39b (3.00 g, 12.0 mmol) was dissolved in tetrahydrofuran (40 mL), triethylamine (2.43 g, 24.0 mmol, 3.30 mL) was added to the reaction mixture, and methanesulfonyl chloride (2.66 g, 23.2 mmol, 1.80 mL) was added dropwise into the mixture at 0° C., the reaction mixture was stirred at 0° C. for 1 hour. After the completion of the reaction, a saturated aqueous solution of sodium bicarbonate (50 mL) was added to quench the reaction, and the mixture was extracted with ethyl acetate (80 mL×3), the combined organic phase was washed with saturated brine (200 mL×1), dried over anhydrous sodium sulfate, filtered, and the filtrate was concentrated under reduced pressure to give crude compound 39c.

Step 3

Compound 39c (3.82 g, 11.8 mmol) was dissolved in tetrahydrofuran (40 mL), cesium carbonate (7.70 g, 23.6 mmol) and tetrahydropyrrole (2.52 g, 35.5 mmol, 3.00 mL) were added thereto, the mixture was stirred at 20° C. for 12 hours. After the completion of the reaction, the mixture was filtered and the filter cake was washed with ethyl acetate (50 mL×2), the filtrate was concentrated under reduced pressure. The residue was diluted with dilute hydrochloric acid solution (1M) and the pH value was adjusted to about 3, then the mixture was extracted with ethyl acetate (100 mL×3), then the pH value of the aqueous phase was adjusted to about 9 with a saturated aqueous sodium bicarbonate solution, and extracted with ethyl acetate (100 mL×3). The combined organic phases were washed with saturated brine (200 mL×1), dried over anhydrous sodium sulfate, filtered, and the filtrate was concentrated under reduced pressure to give crude compound 39d.

MS-ESI calculated value [M+H]$^+$ 298 and 300, measured value 298 and 300.

Step 4

Compound 39d (4.26 g, 13.8 mmol) was dissolved in tetrahydrofuran (16 mL), water (8 mL) and methanol (8 mL), lithium hydroxide monohydrate (697 mg, 16.6 mmol) was added to the reaction mixture, and the reaction mixture was stirred at 20° C. for 12 hours. After the completion of the reaction, the reaction mixture was concentrated under reduced pressure, the pH value was adjusted to about 6 with dilute hydrochloric acid solution (1 M), and the mixture was extracted with ethyl acetate (50 mL×3), the aqueous phase was concentrated under reduced pressure to give crude compound 39e.

MS-ESI calculated value [M+H]$^+$ 284 and 286, measured value 284 and 286.

Step 5

Compound 33d (432 mg, 1.60 mmol) was dissolved in N,N-dimethylformamide (8 mL), and compound 39e (500 mg, 1.76 mmol), O-(7-azabenzotriazol-1-yl)-N,N,N',N'-tetramethyluronium hexafluorophosphate (912 mg, 2.40 mmol) and N,N-diisopropylethylamine (827 mg, 6.40 mmol, 1.10 mL) were added to the reaction mixture, and the mixture was stirred at 20° C. for 12 hours. After the completion of the reaction, water (80 mL) was added to quench the reaction, and the mixture was extracted with ethyl acetate (100 mL×3), the combined organic phases were washed with water (200 mL×1) and saturated brine (200 mL×1), dried over anhydrous sodium sulfate, filtered, and the filtrate was concentrated under reduced pressure. The residue was purified by column chromatography to give compound 39f.

MS-ESI calculated value [M+H]+ 532 and 534, measured value 532 and 534.

Step 6

The compound 39f (50.0 mg, 93.9 μmol), compound 33I (50.5 mg, 141 μmol), [1,1'-bis(diphenylphosphino)ferrocene]palladium dichloride dichloromethane complex (15.3 mg, 18.8 μmol), potassium phosphate (59.8 mg, 282 μmol) were dissolved in dioxane (4 mL) and water (1 mL), the reaction mixture was stirred at 95° C. for 12 hours. After the completion of the reaction, the mixture was filtered and the filtrate was concentrated under reduced pressure. The residue was purified by column chromatography to give compound 39g.

MS-ESI calculated value [M+H]+ 684, measured value 684

Step 7

Compound 39g (280 mg, 275 μmol) was dissolved in dichloromethane (5 mL), trifluoroacetic acid (2 mL) was added thereto, and the mixture was stirred at 20° C. for 0.5 hour. After the completion of the reaction, the reaction mixture was concentrated under reduced pressure, and the residue was purified by high performance liquid chromatography (hydrochloric acid condition) to give compound 39 hydrochloride.

MS-ESI calculated value [M+H]+ 484, measured value 484.

$^1$H NMR (400 MHz, DMSO-$d_6$) δ 11.46-11.27 (m, 1H), 9.61 (d, J=8.0 Hz, 1H), 8.53 (s, 1H), 8.50-8.40 (m, 4H), 8.34 (s, 1H), 8.15 (s, 1H), 7.95 (dd, J=1.6, 8.8 Hz, 1H), 7.58 (d, J=8.8 Hz, 1H), 7.33-7.25 (m, 1H), 7.14 (s, 1H), 7.07 (d, J=8.0 Hz, 1H), 6.87 (dd, J=2.0, 8.0 Hz, 1H), 5.43-5.36 (m, 1H), 4.48 (d, J=6.0 Hz, 2H), 3.76 (s, 3H), 3.58-3.45 (m, 1H), 3.44-3.34 (m, 2H), 3.25-3.08 (m, 3H), 2.59 (s, 3H), 2.08-1.97 (m, 2H), 1.96-1.86 (m, 2H) ppm.

Embodiment 40

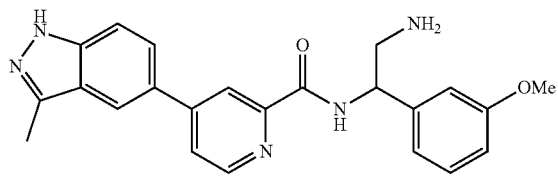

40

Synthetic Route:

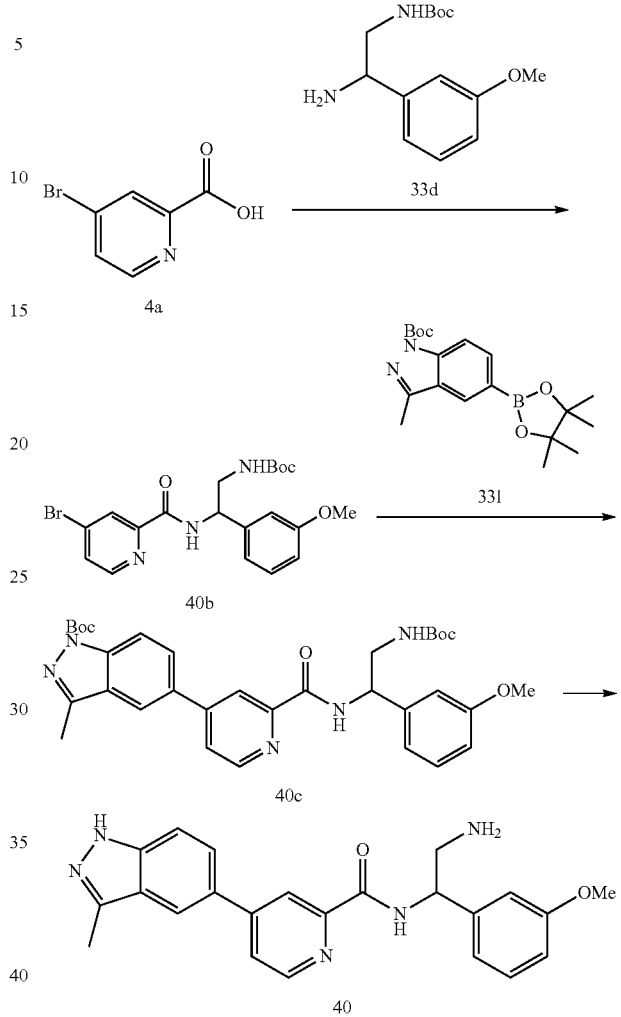

Step 1

Compound 40b was obtained by referring to Step 5 of Embodiment 39.

Step 2

Compound 40c was obtained by referring to Step 6 of Embodiment 39.

MS-ESI calculated value [M+H]+ 602, measured value 602.

Step 3

Compound 40c (700 mg, 1.16 mmol) was dissolved in dioxane (10 mL), then a solution of hydrogen chloride in dioxane (4 M, 10 mL) was added thereto, the reaction mixture was stirred at 10° C. for 12 hours. After the completion of the reaction, the mixture was concentrated under reduced pressure. The residue was purified by high performance liquid chromatography (neutral condition) to give compound 40.

MS-ESI calculated value [M+H]+ 402, measured value 402.

$^1$H NMR (400 MHz, DMSO-$d_6$) δ 12.88 (br, 1H), 9.26 (d, J=8.0 Hz, 1H), 8.83-8.75 (m, 1H), 8.40 (s, 1H), 8.33 (s, 1H), 8.10-8.05 (m, 1H), 7.89-7.84 (m, 1H), 7.66 (d, J=8.8 Hz,

1H), 7.35-7.28 (m, 1H), 7.07-7.01 (m, 2H), 6.92-6.80 (m, 1H), 5.12-4.99 (m, 1H), 3.80 (s, 3H), 3.17-2.96 (m, 2H), 2.63 (s, 3H) ppm.

Embodiments 40-1 and 40-2

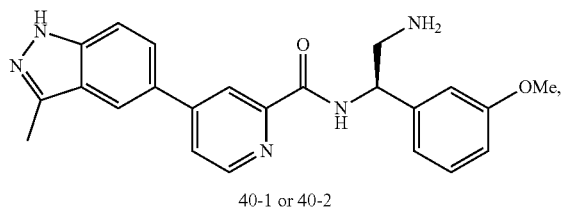

40-1 or 40-2

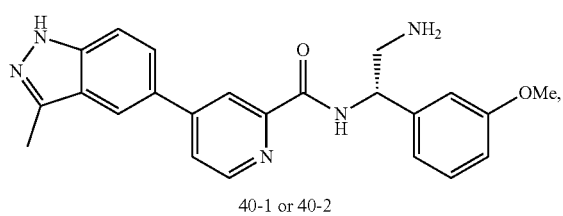

40-1 or 40-2

Synthetic Route:

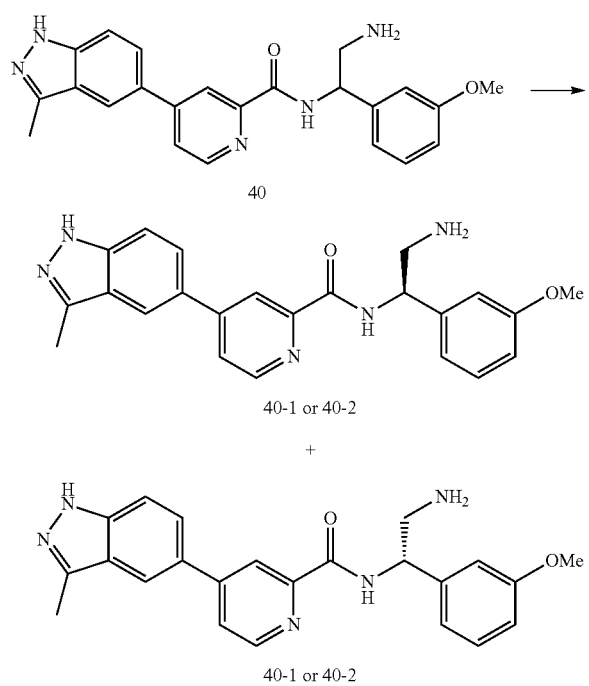

Compound 40 can be purified by chiral supercritical fluid chromatography to give 40-1 and 40-2 with retention times of 0.727 and 1.432 respectively. Separation method: Column: Chiralpak AD-3 50×4.6 mm I.D., 3 μm. Mobile phase: Phase A for $CO_2$, and Phase B for MeOH+ACN (0.05% DEA); gradient elution: 60% OMeOH+ACN (0.05% DEA) in $CO_2$. Flow rate: 3 mL/min; wavelength: 220 nm. Column temp: 35° C.; Back Pressure: 100 Bar.

Embodiment 41

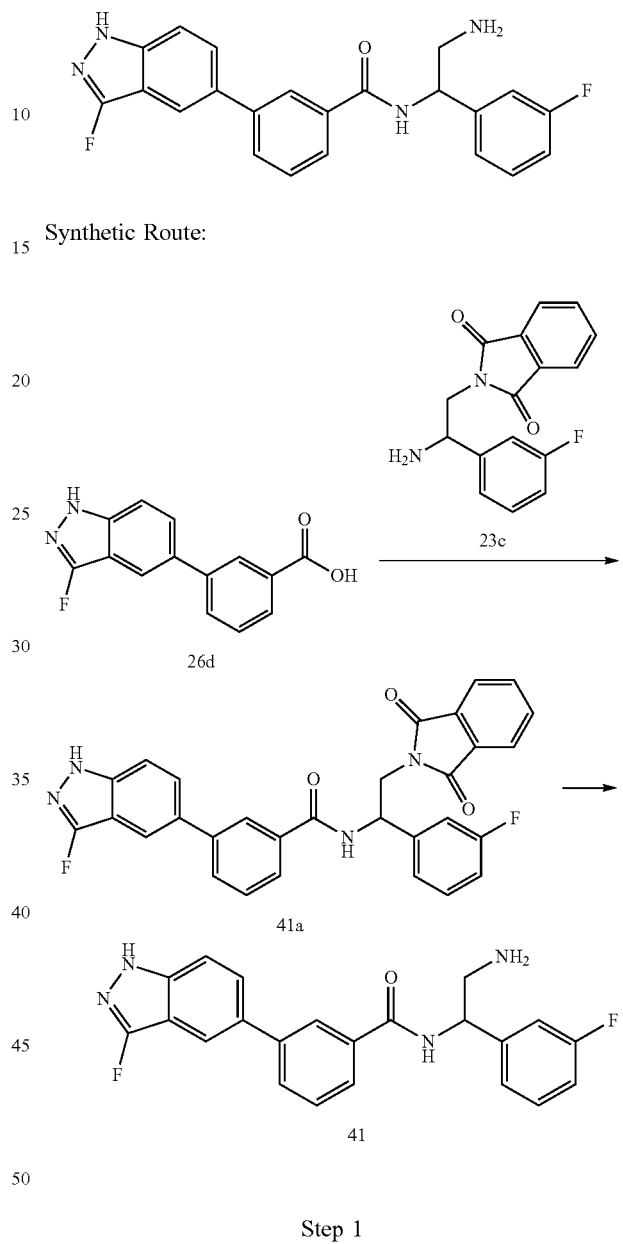

Synthetic Route:

Step 1

Compound 26d (200 mg, 781 μmol) and compound 23c (225 mg, 781 μmol) were dissolved in tetrahydrofuran (12 mL) and N,N-dimethylformamide (3 mL), and 1-ethyl-(3-dimethylaminopropyl)carbodiimide hydrochloride (165 mg, 859 μmol), 1-hydroxybenzotriazole (1161 mg, 859 μmol) and N,N-diisopropylethylamine (303 mg, 2.34 mmol, 408 μL) were added thereto. The reaction mixture was stirred at 25° C. for 1 hour. After the completion of the reaction, the reaction mixture was diluted with water (25 mL) and extracted with ethyl acetate (25 mL×2), the combined organic phase was washed with saturated brine (10 mL×1), dried over anhydrous sodium sulfate, filtered, and the filtrate was concentrated under reduced pressure. The residue was purified by column chromatography to give compound 41a.

MS-ESI calculated value [M+H]$^+$ 523, measured value 523.

Step 2

Compound 41a (200 mg, 383 μmol) was dissolved in absolute ethanol (12.5 mL), hydrazine monohydrate (451 mg, 7.66 mmol, 438 μL, 85% purity) was added to the reaction mixture, and the mixture was stirred at 50° C. or 12 hours. After the completion of the reaction, the mixture was filtered and the filtrate was concentrated under reduced pressure. The residue was purified by high performance liquid chromatography (hydrochloric acid condition) to give the hydrochloride of compound 41.

MS-ESI calculated value [M+H]$^+$ 393, measured value 393.

$^1$H NMR (400 MHz, DMSO-d$_6$) δ 12.74 (s, 1H), 9.34 (d, J=8.0 Hz, 1H), 8.38 (s, 1H), 8.30 (br, 3H), 8.11 (s, 1H), 7.97-7.87 (m, 3H), 7.67-7.56 (m, 2H), 7.48-7.41 (m, 1H), 7.37-7.29 (m, 2H), 7.19-7.11 (m, 1H), 5.47-5.39 (m, 1H), 3.35-3.17 (m, 2H) ppm.

Embodiment 42

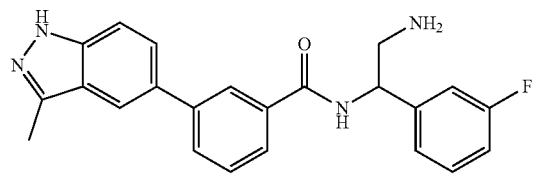

42

Synthetic Route:

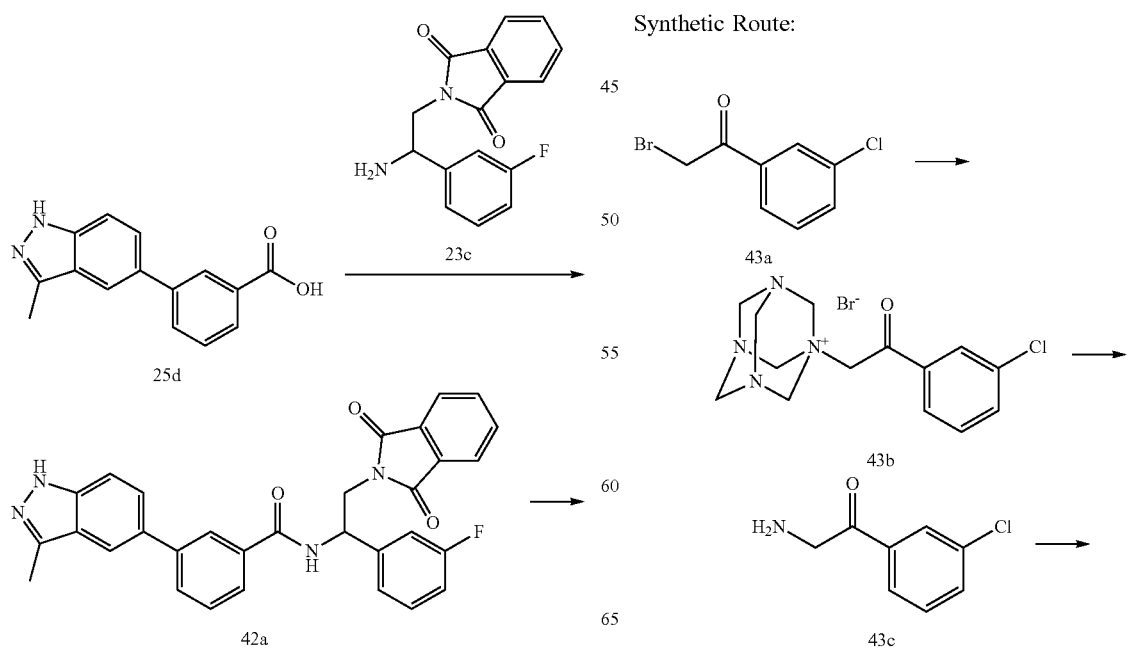

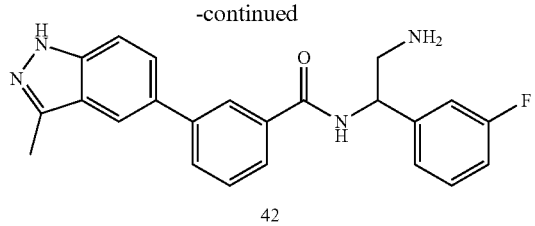

42

Step 1

Compound 42a was obtained by referring to Step 1 of Embodiment 41.

Step 2

Hydrochloride of compound 42 was obtained by referring to Step 2 of Embodiment 41.

MS-ESI calculated value [M+H]$^+$ 389, measured value 389.

$^1$H NMR (400 MHz, DMSO-d$_6$) δ 9.24 (d, J=8.0 Hz, 1H), 8.34 (s, 1H), 8.25-8.15 (m, 2H), 8.12 (s, 1H), 7.95-7.90 (m, 2H), 7.76 (dd, J=1.6, 8.8 Hz, 1H), 7.63-7.55 (m, 2H), 7.50-7.42 (m, 1H), 7.37-7.30 (m, 2H), 7.20-7.12 (m, 1H), 5.47-5.37 (m, 1H), 3.47-3.35 (m, 1H), 3.33-3.23 (m, 1H), 2.57 (s, 3H) ppm.

Embodiment 43

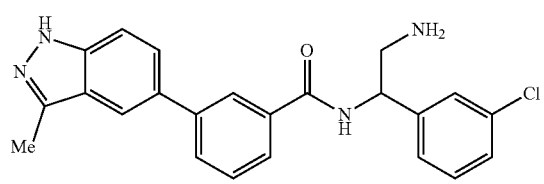

43

Synthetic Route:

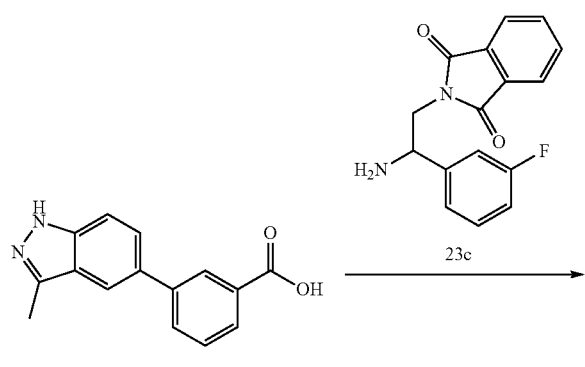

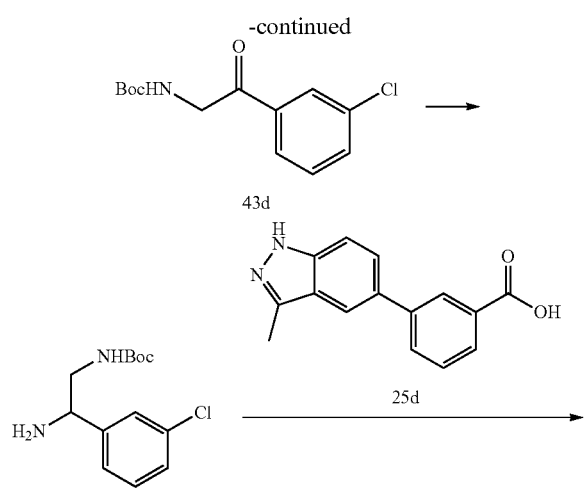

(4 M, 10 mL) was added thereto, and the reaction mixture was stirred at 25° C. for 1 hour. After the completion of the reaction, the mixture was concentrated under reduced pressure, the residue was purified by high performance liquid chromatography (hydrochloric acid condition) to give the hydrochloride of compound 43.

MS-ESI calculated value [M+H]$^+$ 405, measured value 405.

$^1$H NMR (400 MHz, DMSO-d$_6$) δ 9.38 (d, J=8.0 Hz, 1H), 8.38 (s, 1H), 8.30 (br, 2H), 8.16 (s, 1H), 7.95-7.90 (m, 2H), 7.78 (dd, J=1.6, 8.8 Hz, 1H), 7.62-7.54 (m, 3H), 7.48-7.35 (m, 3H), 5.45-5.5 (m, 1H), 3.40-3.20 (m, 2H), 2.57 (s, 3H) ppm.

Embodiment 44

Step 1

Compound 43b was obtained by referring to Step 1 of the preparation of Intermediate 33d in Embodiment 33.

Step 2

Compound 43c was obtained by referring to Step 2 of the preparation of Intermediate 33d in Embodiment 33.

Step 3

Compound 43d was obtained by referring to Step 3 of the preparation of Intermediate 33d in Embodiment 33.

Step 4

Compound 43e was obtained by referring to Step 4 of the preparation of Intermediate 33d in Embodiment 33.

MS-ESI calculated value [M+H]$^+$ 271, measured value 271.

Step 5

Compound 43f was obtained by referring to Step 1 of Embodiment 41.

Step 6

Compound 43f (300 mg, 594 μmol) was dissolved in dioxane (10 mL), a solution of hydrogen chloride in dioxane Synthetic Route:

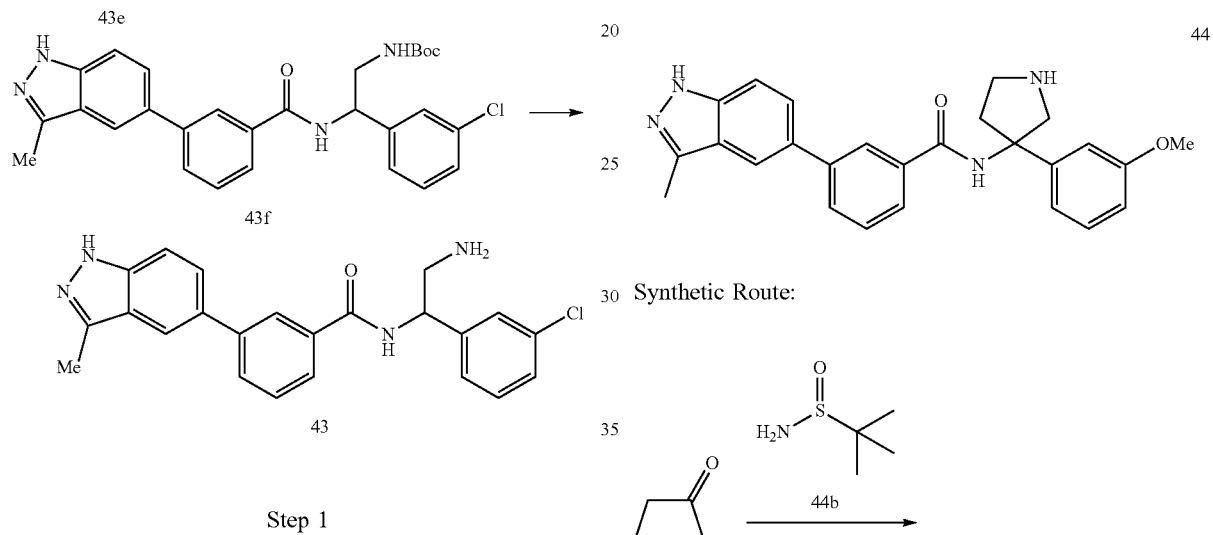

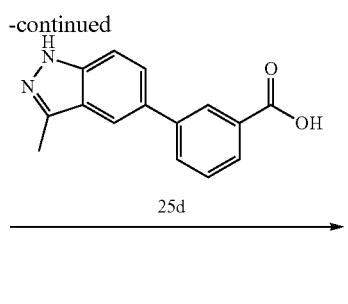

Step 1

Compound 44a (2.00 g, 10.8 mmol) was dissolved in dichloromethane (30 mL), and compound 44b (1.70 mg, 14.0 mmol) and tetraethyl titanate (7.39 g, 32.4 mmol, 6.72 mL) were added to the reaction mixture, the reaction mixture was stirred at 25° C. for 1.5 hours. After the completion of the reaction, saturated sodium bicarbonate aqueous solution (30 mL) was added to quench the reaction, then the mixture was filtered, and the filtrate was extracted with ethyl acetate (30 mL×3), the combined organic phase was washed with saturated brine (50 mL×1), dried over anhydrous sodium sulfate, filtered, and the filtrate was concentrated under reduced pressure. The residue was purified by column chromatography to give compound 44c.

Step 2

Compound 44d (2.98 g, 16.0 mmol, 2.02 mL) was dissolved in tetrahydrofuran (40 mL), the temperature was reduced to −72° C., and a solution of n-butyl lithium in n-hexane (2.50 M, 6.38 mL) was slowly added dropwise to the reaction mixture, after reacting for 0.5 hours, compound 44c (2.30 g, 7.97 mmol) was slowly added to the reaction mixture. After the addition, the temperature was raised to 25° C. and the mixture was stirred for 12 hours. After the completion of the reaction, saturated ammonium chloride aqueous solution (20 mL) was added to quench the reaction, the mixture was extracted with ethyl acetate (20 mL), dried over anhydrous sodium sulfate, filtered, and the filtrate was concentrated under reduced pressure. The residue was purified by column chromatography to give compound 44e.

MS-ESI calculated value [M+H]$^+$ 397, measured value 397.

Step 3

Compound 44e (230 mg, 580 μmol) was dissolved in tetrahydrofuran (10 mL) and water (1 mL), elemental iodine (29.4 mg, 116 μmol, 23.4 μL) was added to the reaction mixture, and the mixture was stirred at 50° C. for 12 hours. After the completion of the reaction, an aqueous solution of sodium sulfite (0.2 N, 5 mL) was added to quench the reaction, the mixture was concentrated under reduced pressure to remove tetrahydrofuran, and the aqueous phase was extracted with ethyl acetate (10 mL×2). The combined organic phases were washed with saturated brine (15 mL×1), dried over anhydrous sodium sulfate, filtered, and the filtrate was concentrated under reduced pressure to give crude compound 44f.

Step 4

Compound 44g was obtained referring to Step 1 of Embodiment 41.

MS-ESI calculated value [M+H]$^+$ 527, measured value 527.

Step 5

Hydrochloride of compound 44 was obtained by referring to Step 6 of Embodiment 43.

MS-ESI calculated value [M+H]$^+$ 427, measured value 427.

$^1$H NMR (400 MHz, CD$_3$OD) δ 8.24-8.16 (m, 2H), 8.00-7.85 (m, 3H), 7.96 (d, J=8.8 Hz, 1H), 7.61 (t, J=7.6 Hz, 1H), 7.34 (t, J=8.0 Hz, 1H), 7.14-7.05 (m, 2H), 6.91 (t, J=8.0, 2.2 Hz, 1H), 4.46 (d, J=12.4 Hz, 1H), 3.90 (d, J=12.4 Hz, 1H), 3.80 (s, 3H), 3.70-3.57 (m, 2H), 3.01-2.91 (m, 1H), 2.74 (s, 3H), 2.52-2.40 (m, 1H) ppm.

Embodiment 45

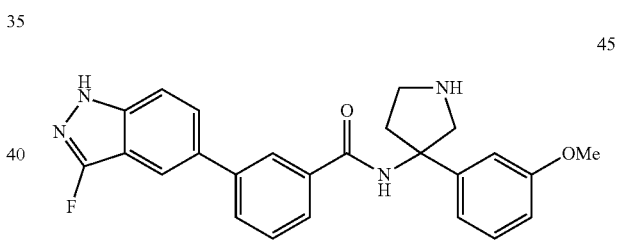

Synthetic Route:

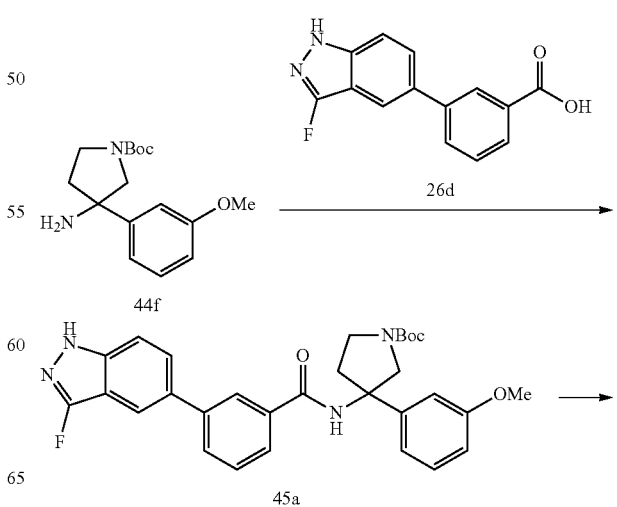

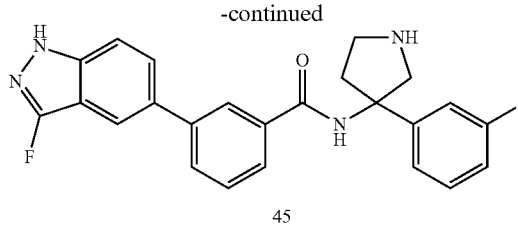

45

Step 1

Compound 45a was obtained by referring to Step 1 of Embodiment 41.

Step 2

Hydrochloride of compound 45 was obtained by referring to Step 6 of Embodiment 43.

MS-ESI calculated value $[M+H]^+$ 431, measured value 431.

$^1$H NMR (400 MHz, CD$_3$OD) δ 8.07 (s, 1H), 7.88 (s, 1H), 7.81-7.67 (m, 3H), 7.52-7.42 (m, 2H), 7.23 (t, J=8.0 Hz, 1H), 7.02-6.94 (m, 2H), 6.83-6.76 (m, 1H), 4.36 (dd, J=12.4 Hz, 1H), 3.80 (d, J=12.4 Hz, 1H), 3.70 (s, 3H), 3.56-3.48 (m, 2H), 2.88-2.78 (m, 1H), 2.41-2.29 (m, 1H) ppm.

Embodiment 46

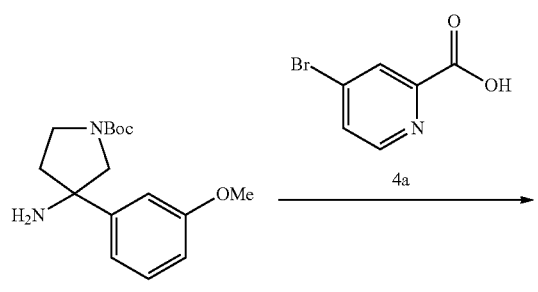

46

Synthetic Route:

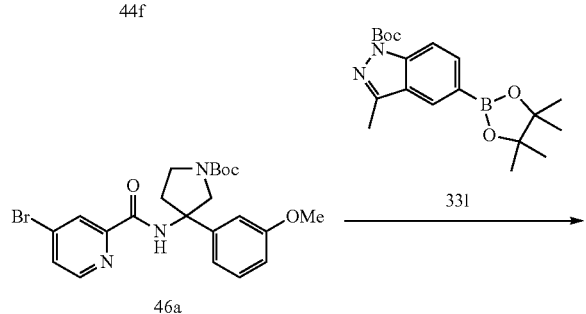

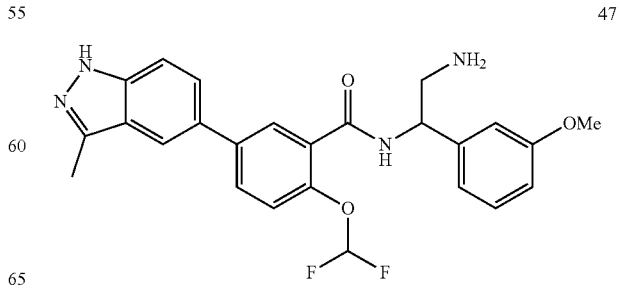

Step 1

Compound 46a was obtained by referring to Step 1 of Embodiment 41.

Step 2

Compound 46 was obtained by referring to Step 4 of Embodiment 27.

MS-ESI calculated value $[M+H]^+$ 628, measured value 628.

Step 3

Compound 46b (80.0 mg, 124 μmol) was dissolved in trifluoroacetic acid (5.00 mL), the mixture was stirred at 25° C. for 1 hour. After the completion of the reaction, the mixture was concentrated under reduced pressure, the residue was purified by high performance liquid chromatography (hydrochloric acid condition) to give the hydrochloride of compound 46.

MS-ESI calculated value $[M+H]^+$ 428, measured value 428.

$^1$H NMR (400 MHz, CD$_3$OD) δ 8.94 (s, 1H), 8.77 (d, J=6.0 Hz, 1H), 8.58 (s, 1H), 8.32 (dd, J=1.6, 6.0 Hz, 1H), 8.07 (dd, J=1.6, 8.8 Hz, 1H), 7.72 (d, J=8.8 Hz, 1H), 7.39-7.33 (m, 1H), 7.18-7.13 (m, 2H), 6.96-6.92 (m, 1H), 4.56 (dd, J=1.2, 12.4 Hz, 1H), 3.86 (d, J=12.4 Hz, 1H), 3.82 (s, 3H), 3.72-3.62 (m, 2H), 3.21-3.11 (m, 1H), 2.72 (s, 3H), 2.63-2.51 (m, 1H) ppm.

Embodiment 47

47

Synthetic Route:

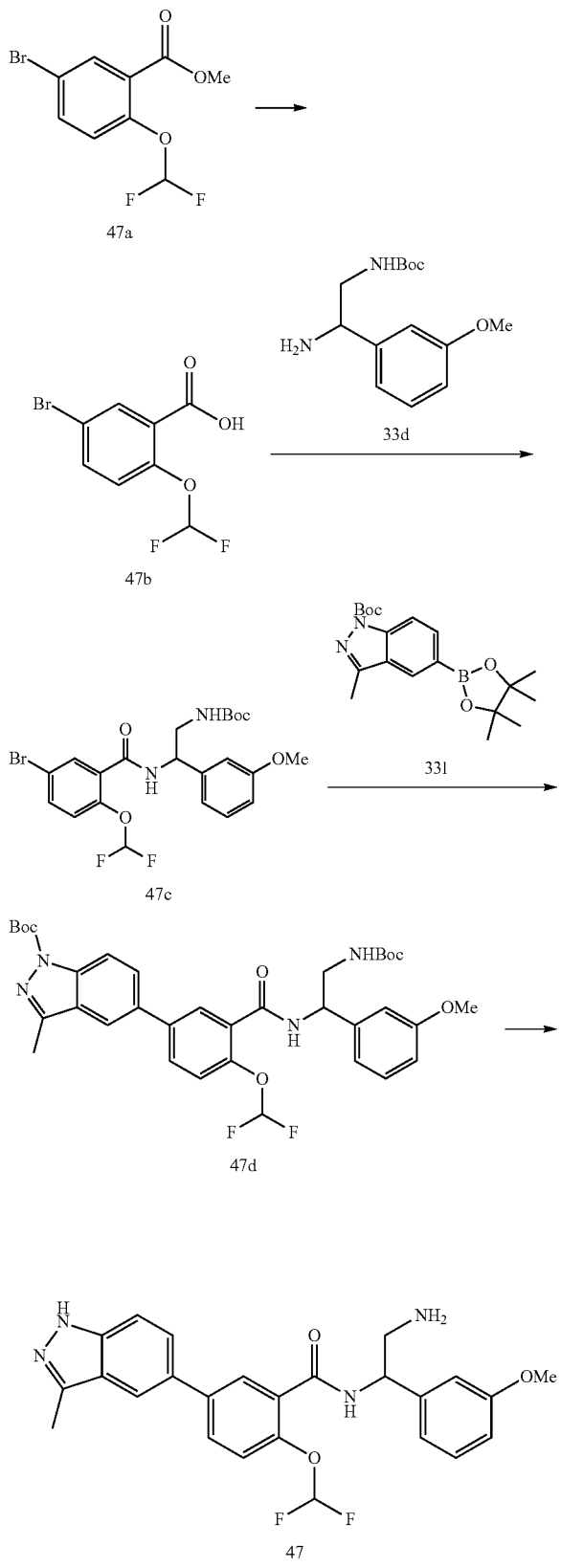

Step 1

Compound 47a (350 mg, 1.25 mmol) was dissolved in tetrahydrofuran (4 mL), water (1 mL) and methanol (1 mL), lithium hydroxide monohydrate (157 mg, 3.74 mmol) was added to the reaction mixture, and the mixture was stirred at 50° C. for 14 hours. After the completion of the reaction, the mixture was concentrated under reduced pressure, water (20 mL) was added to the residue, and the pH value of the solution was acidified to about 6 with dilute hydrochloric acid solution (1 M), a white solid precipitated and the mixture was filtered, the residue was collected to give crude compound 47b.

Step 2

Compound 47b (325 mg, 1.22 mmol) was dissolved in N,N-dimethylformamide (3 mL), and O-(7-azabenzotriazol-1-yl)-N,N,N',N'-tetramethyluronium hexafluorophosphate (694 mg, 1.83 mmol), then compound 33d (329 mg, 1.22 mmol) and N,N-diisopropylethylamine (472 mg, 3.65 mmol, 636 μL) were added to the reaction mixture, the mixture was stirred at 30° C. for 1 hour. After the completion of the reaction, the mixture was concentrated under reduced pressure, and the residue was purified by column chromatography to give compound 47c.

MS-ESI calculated value [M+Na]$^+$ 537 and 539, measured value 537 and 539.

Step 3

Compound 47c (200 mg, 388 μmol), compound 33l (102 mg, 388 μmol) were dissolved in dioxane (4.5 mL) and water (0.5 mL), and [1,1'-bis(diphenylphosphino)ferrocene] palladium dichloride dichloromethane complex (31.7 mg, 38.8 μmol), potassium carbonate (107 mg, 776 μmol) were added thereto under nitrogen protection, the reaction mixture was stirred at 90° C. for 15 hours. After the completion of the reaction, the mixture was concentrated under reduced pressure, and the residue was purified by column chromatography to give compound 47d.

MS-ESI calculated value [M+H]$^+$ 667, measured value 667.

Step 4

Compound 47d (165 mg, 247 μmol) was dissolved in trifluoroacetic acid (3.00 mL), and the reaction mixture was stirred at 20° C. for 1 hour. After the completion of the reaction, the mixture was concentrated under reduced pressure, and the residue was purified by high performance liquid chromatography (hydrochloric acid condition) to give the hydrochloride of compound 47.

MS-ESI calculated value [M+H]+ 467, measured value 467.

$^1$H NMR (400 MHz, DMSO-d$_6$) δ 9.13 (d, J=8.4 Hz, 1H), 8.23 (br, 3H), 8.13-8.04 (m, 2H), 7.88 (dd, J=2.4, 8.8 Hz, 1H), 7.72 (dd, J=1.6, 8.8 Hz, 1H), 7.57 (d, J=8.8 Hz, 1H), 7.37-7.28 (m, 2H), 7.18 (t, J=74.4 Hz, 1H), 7.11-7.02 (m, 2H), 6.93-6.87 (m, 1H), 5.38-5.29 (m, 1H), 3.77 (s, 3H), 3.35-3.10 (m, 2H), 2.55 (s, 3H) ppm.

Embodiment 48

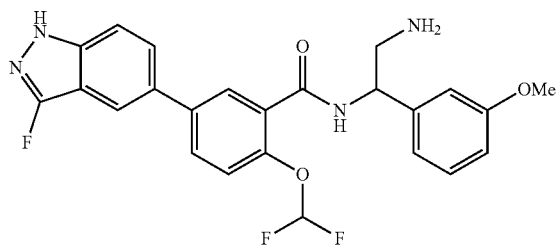

Synthetic Route:

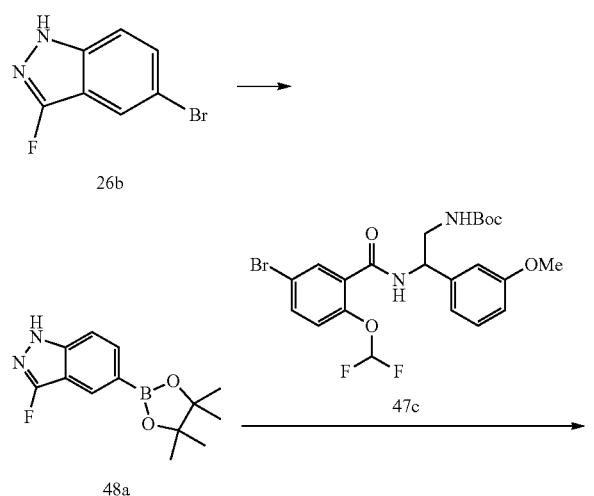

Step 1

Compound 48a was obtained by referring to Step 3 of Embodiment 27.

Step 2

Compound 48b was obtained by referring to Step 3 of Embodiment 47.

MS-ESI calculated value [M+H]$^+$ 571, measured value 571.

Step 3

Hydrochloride of compound 48 as obtained by referring to Step 4 of Embodiment 47.

MS-ESI calculated value [M+H]$^+$ 471, measured value 471.

$^1$H NMR (400 MHz, DMSO-d$_6$) δ 12.72 (s, 1H), 9.11 (d, J=8.0 Hz, 1H), 8.20 (br, 3H), 8.11-8.02 (m, 2H), 7.90 (dd, J=2.4, 8.8 Hz, 1H), 7.84 (dd, J=1.6, 8.8 Hz, 1H), 7.62 (dd, J=1.6, 8.8 Hz, 1H), 7.38-7.28 (m, 2H), 7.18 (t, J=74.4 Hz, 1H), 7.08-6.99 (m, 2H), 6.93-6.87 (m, 1H), 5.40-5.28 (m, 1H), 3.77 (s, 3H), 3.27-3.15 (m, 2H) ppm.

Embodiment 49

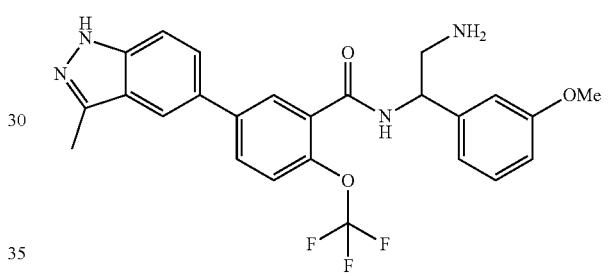

Synthetic Route:

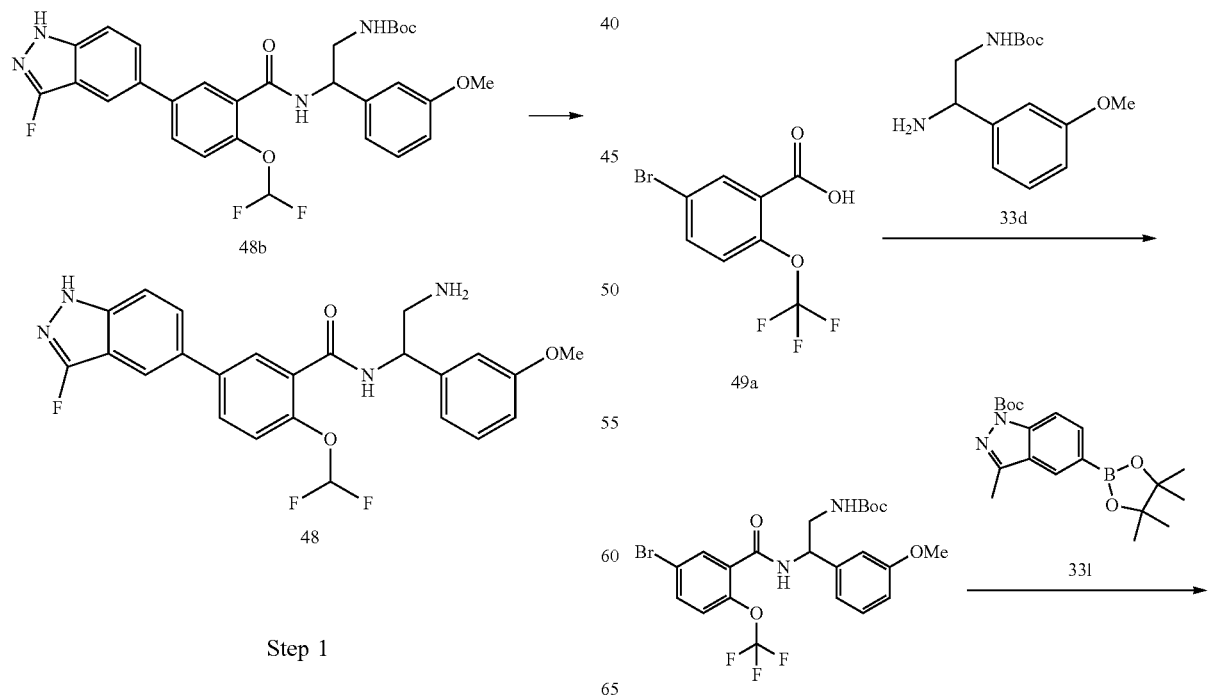

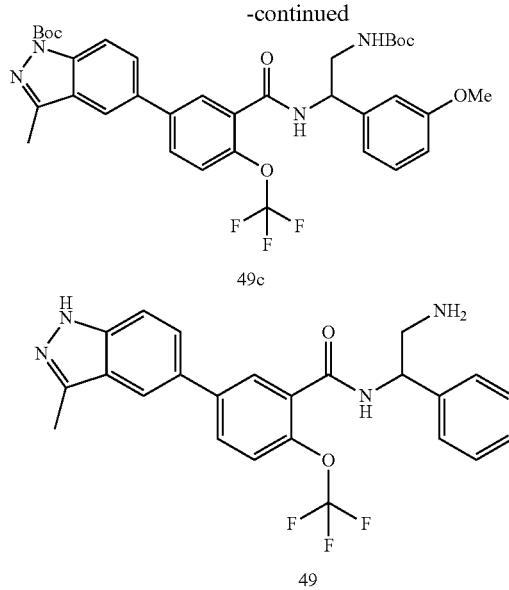

Step 1

Compound 49b was obtained by referring to Step 2 of Embodiment 47.

Step 2

Compound 49c was obtained by referring to Step 6 of Embodiment 35.

MS-ESI calculated value [M+H]⁺ 685, measured value 685.

Step 3

Hydrochloride of compound 49 was obtained by referring to Step 6 of Embodiment 43.

MS-ESI calculated value [M+H]⁺ 485, measured value 485.

¹H NMR (400 MHz, CD$_3$OD) δ 8.20 (s, 1H), 8.10 (d, J=2.4 Hz, 1H), 7.96-7.88 (m, 2H), 7.69 (d, J=8.8 Hz, 1H), 7.49 (dd, J=1.6, 8.8 Hz, 1H), 7.36 (t, J=8.0 Hz, 1H), 7.12-7.05 (m, 2H), 6.99-6.93 (m, 1H), 5.48-5.41 (m, 1H), 3.83 (s, 3H), 3.55-3.46 (m, 1H), 3.44-3.36 (m, 1H), 2.74 (s, 3H) ppm.

Embodiment 50

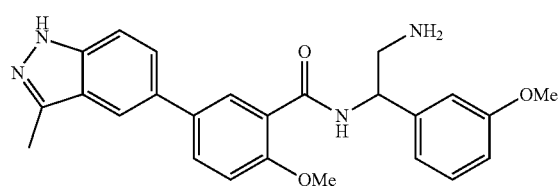

Synthetic Route:

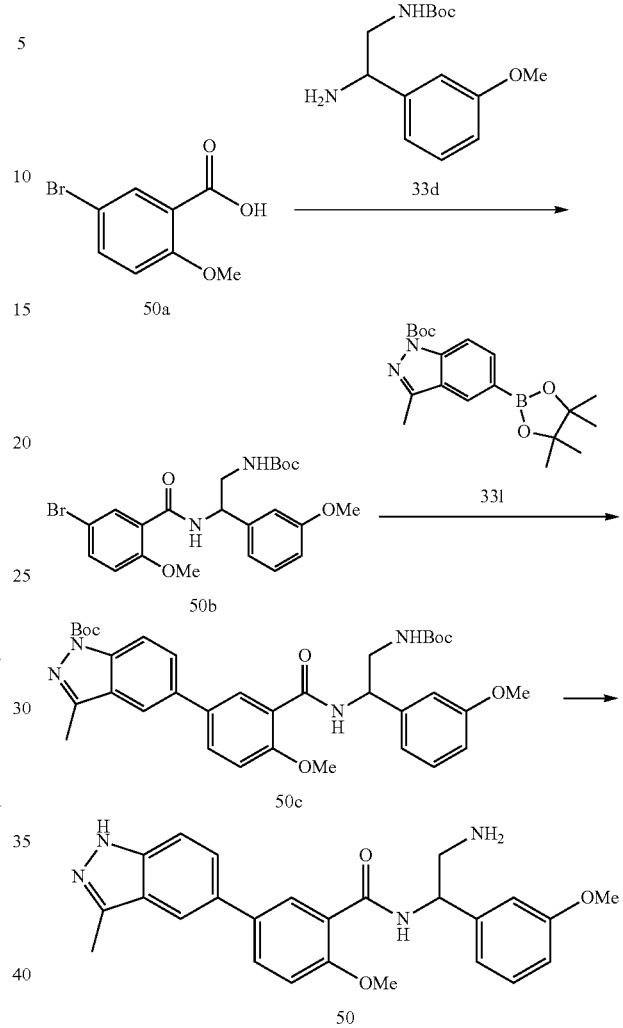

Step 1

Compound 50b was obtained by referring to Step 2 of Embodiment 47.

Step 2

Compound 50c was obtained by referring to Step 6 of Embodiment 35.

MS-ESI calculated value [M+H]⁺ 631, measured value 631.

Step 3

Hydrochloride of compound 50 was obtained by referring to Step 6 of Embodiment 43.

MS-ESI calculated value [M+H]⁺ 431, measured value 431.

¹H NMR (400 MHz, CD$_3$OD) δ 8.28 (d, J=2.4 Hz, 1H), 8.07 (s, 1H), 7.94-7.84 (m, 2H), 7.67 (d, J=, 8.8 Hz, 1H), 7.44-7.36 (m, 1H), 7.31 (d, J=8.8 Hz, 1H), 7.13-7.06 (m, 2H), 7.02-6.95 (m, 1H), 5.53-5.45 (m, 1H), 4.04 (s, 3H), 3.85 (s, 3H), 3.56-3.47 (m, 1H), 3.46-3.38 (m, 1H), 2.73 (s, 3H) ppm.

151
Embodiment 51

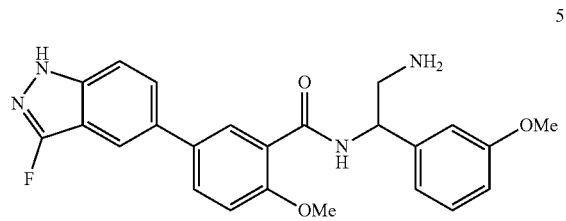

Synthetic Route:

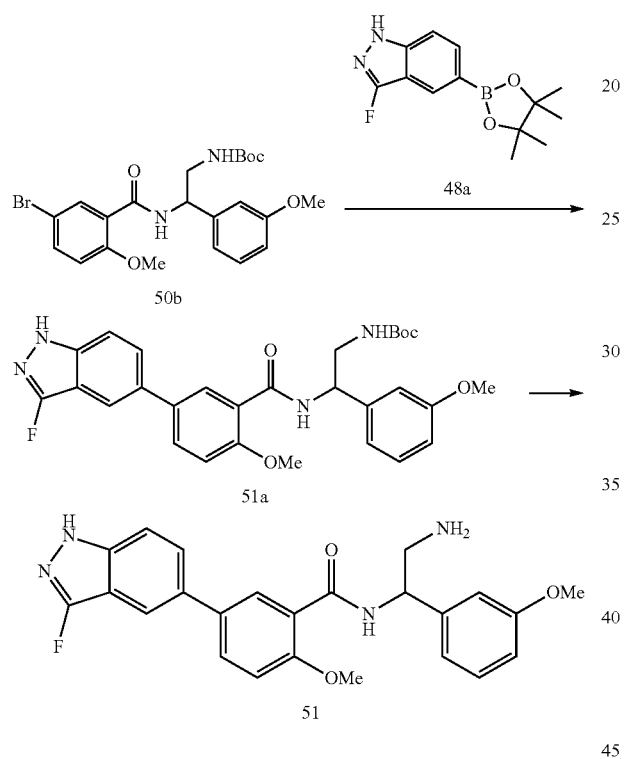

Step 1

Compound 51a was obtained by referring to Step 6 of Embodiment 35.

MS-ESI calculated value [M+H]$^+$ 535, measured value 535.

Step 2

Hydrochloride of compound 51 was obtained by referring to Step 6 of Embodiment 43.

MS-ESI calculated value [M+H]$^+$ 435, measured value 435.

$^1$H NMR (400 MHz, CD$_3$OD) δ 8.24 (d, J=2.4 Hz, 1H), 7.89-7.82 (m, 2H), 7.74 (dd, J=1.6, 8.8 Hz, 1H), 7.53 (dd, J=1.6, 8.8 Hz, 1H), 7.41 (t, J=8.0 Hz, 1H), 7.29 (d, J=8.8 Hz, 1H), 7.15-7.07 (m, 2H), 7.02-6.95 (m, 1H), 5.55-5.47 (m, 1H), 4.05 (s, 3H), 3.86 (s, 3H), 3.56-3.47 (m, 1H), 3.46-3.38 (m, 1H) ppm.

152
Embodiment 52

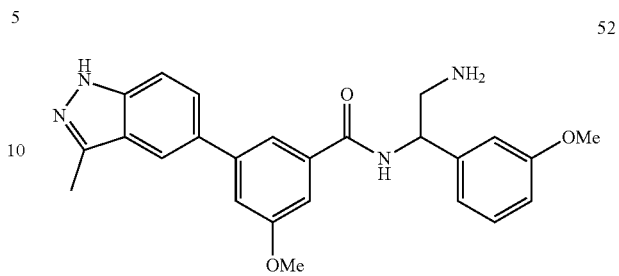

Synthetic Route:

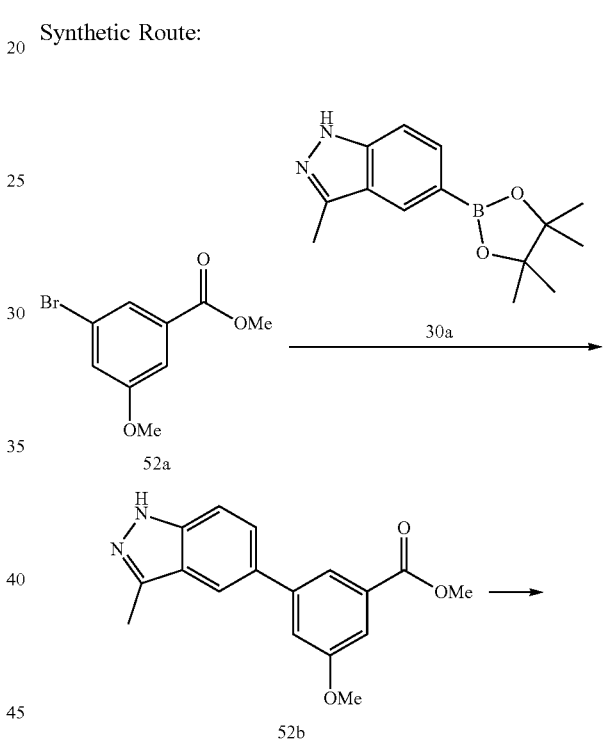

153

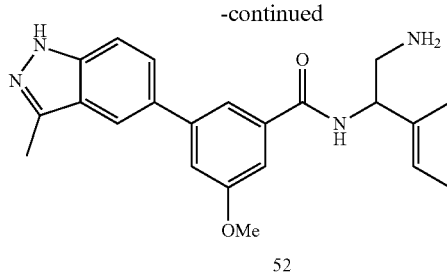

52

Step 1

Compound 52b was obtained by referring to Step 6 of Embodiment 35.

MS-ESI calculated value [M+H]⁺ 297, measured value 297.

Step 2

Compound 52c was obtained by referring to Step 1 of Embodiment 47.

MS-ESI calculated value [M–H]⁺ 281, measured value 281.

Step 3

Compound 52d was obtained by referring to Step 2 of Embodiment 47.

MS-ESI calculated value [M+H]⁺ 531, measured value 531.

Step 3

Hydrochloride of compound 52 was obtained by referring to Step 6 of Embodiment 43.

MS-ESI calculated value [M+H]⁺ 431, measured value 431.

$^1$H NMR (400 MHz, CD$_3$OD) δ 8.19 (s, 1H), 7.95-7.86 (m, 2H), 7.68-7.63 (m, 1H), 7.52-7.47 (m, 1H), 7.46-7.42 (m, 1H), 7.38-7.31 (m, 1H), 7.11-7.05 (m, 2H), 6.95-6.90 (m, 1H), 5.52-5.45 (m, 1H), 3.94 (s, 3H), 3.82 (s, 3H), 3.60-3.51 (m, 1H), 3.46-3.38 (m, 1H), 2.73 (s, 3H) ppm.

Embodiment 53

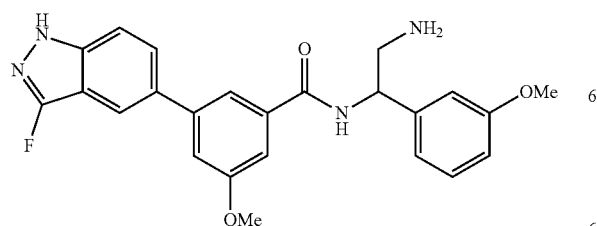

53

154

Synthetic Route:

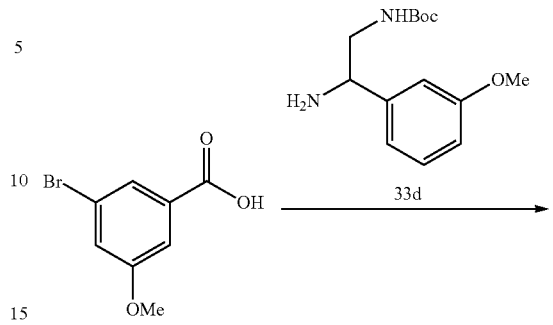

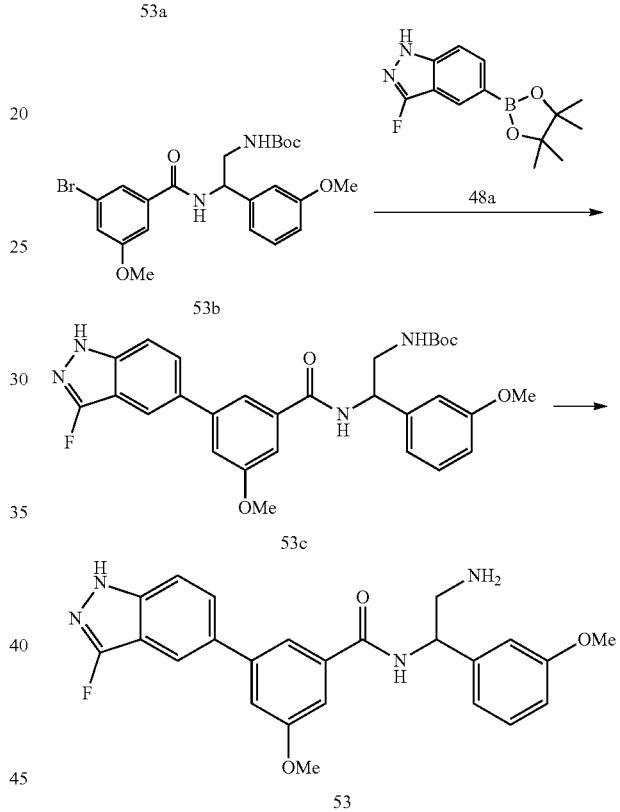

Step 1

Compound 53b was obtained by referring to Step 2 of Embodiment 47.

MS-ESI calculated value [M+H]⁺ 479 and 481, measured value 479 and 481.

Step 2

Compound 53c was obtained by referring to Step 6 of Embodiment 35.

MS-ESI calculated value [M+H]⁺ 535, measured value 535.

Step 3

Hydrochloride of compound 53 was obtained by referring to Step 6 of Embodiment 43.

MS-ESI calculated value [M+H]⁺ 435, measured value 435.

$^1$H NMR (400 MHz, CD$_3$OD) δ 8.00 (s, 1H), 7.85-7.76 (m, 2H), 7.57-7.51 (m, 1H), 7.48-7.44 (m, 1H), 7.43-7.39 (m, 1H), 7.38-7.31 (m, 1H), 7.09-7.02 (m, 2H), 6.96-6.91 (m, 1H), 5.51-5.42 (m, 1H), 3.93 (s, 3H), 3.82 (s, 3H), 3.55-3.39 (m, 2H) ppm.

Embodiment 54

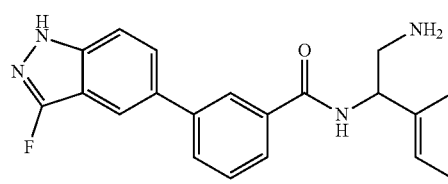

Synthetic Route:

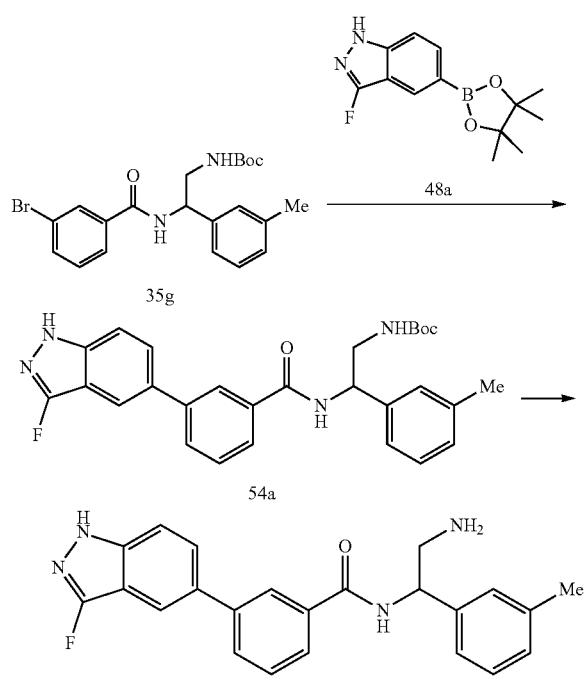

Step 1

Compound 54a was obtained by referring to Step 6 of Embodiment 35.
MS-ESI calculated value [M+H]+ 489, measured value 489.

Step 2

Compound 54a (240 mg, 443 μmol) was dissolved in dichloromethane (5 mL), trifluoroacetic acid (2 mL) was added thereto, and the reaction was stirred at 20° C. for 1 hour. After the completion of the reaction, the reaction mixture was concentrated under reduced pressure. The residue was purified by high performance liquid chromatography (hydrochloric acid condition) to give the hydrochloride of compound 54.

MS-ESI calculated value [M+H]$^+$ 389, measured value 389.
$^1$H NMR (400 MHz, DMSO-d$_6$) δ 12.74 (s, 1H), 9.28 (d, J=8.4 Hz, 1H), 8.39 (s, 1H), 8.31 (br, 3H), 8.11 (s, 1H), 7.98-7.87 (m, 3H), 7.66-7.54 (m, 2H), 7.31-7.24 (m, 3H), 7.17-7.07 (m, 1H), 5.50-5.30 (m, 1H), 3.39-3.38 (m, 1H), 3.25-3.14 (m, 1H), 2.32 (s, 3H) ppm.

Embodiment 55

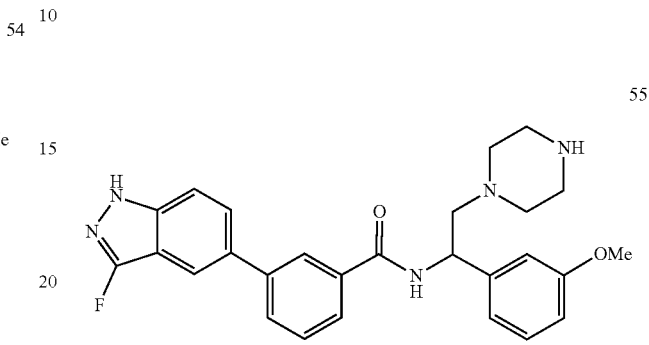

Synthetic Route:

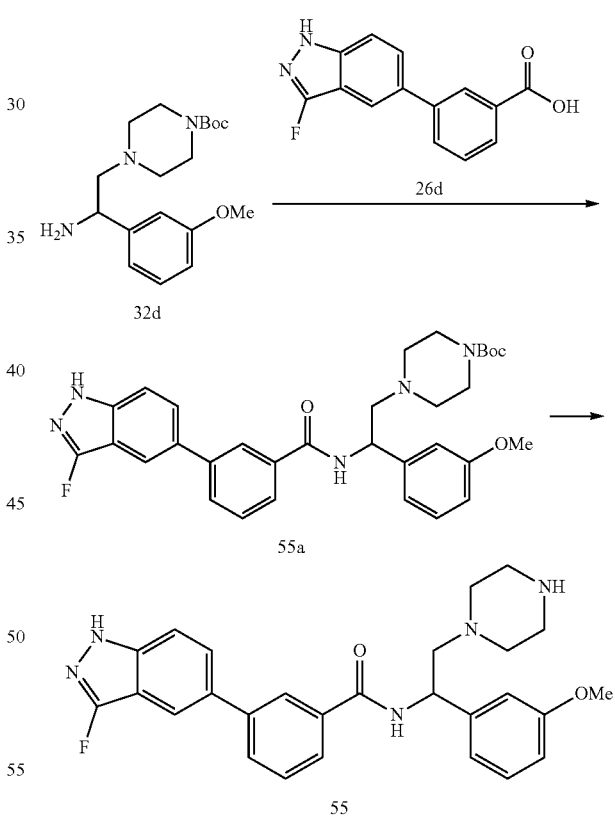

Step 1

Compound 32d (250 mg, 745 μmol) and compound 26d (195 mg, 745 μmol) were dissolved in N,N-dimethylformamide (12 mL), and 1-(3-dimethylaminopropyl-3-ethylcarbodiimide hydrochloride (157 mg, 820 μmol), 1-hydroxybenzotriazole (111 mg, 820 μmol) and N,N-diisopropylethylamine (289 mg, 2.24 mmol, 389.45 μL)

were added to the reaction mixture, the mixture was stirred at 25° C. for 4 hours. After the completion of the reaction, the mixture was diluted with water (120 mL) and extracted with ethyl acetate (70 mL×2). The combined organic phase was washed with saturated brine (100 mL×1), dried over anhydrous sodium sulfate, filtered, and the filtrate was concentrated under reduced pressure. The residue was purified by column chromatography to give compound 55a.

MS-ESI calculated value [M+H]$^+$ 574, measured value 574.

Step 2

Compound 55a (360 mg, 411 μmol) was dissolved in dioxane (5 mL), a solution of hydrogen chloride in dioxane (4 M, 5 mL) was added thereto, and the mixture was stirred at 28° C. for 1 hour. After the completion of the reaction, the reaction mixture was concentrated under reduced pressure. The residue was purified by high performance liquid chromatography (formic acid condition) to give the formate of compound 55.

MS-ESI calculated value [M+H]$^+$ 474, measured value 474.

$^1$H NMR (400 MHz, CD$_3$OD) δ 8.52 (s, 1H), 8.18 (t, J=1.6 Hz, 1H), 7.98 (s, 1H), 7.89-7.86 (m, 2H), 7.80 (dd, J=1.6, 8.8 Hz, 1H), 7.64-7.52 (m, 2H), 7.34-7.26 (m, 1H), 7.08-7.02 (m, 2H), 6.88-6.86 (m, 1H), 5.44-5.33 (m, 1H), 3.82 (s, 3H), 3.27-3.13 (m, 4H), 3.05-2.97 (m, 1H), 2.96-2.86 (m, 2H), 2.84-2.71 (m, 3H) ppm.

Embodiment 56

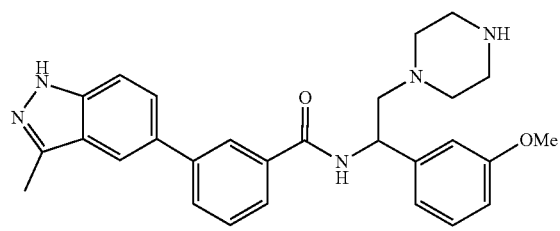

56

Synthetic Route:

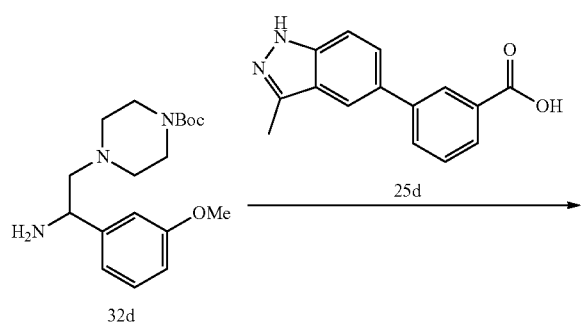

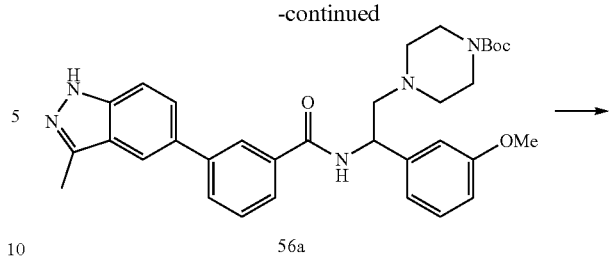

56a

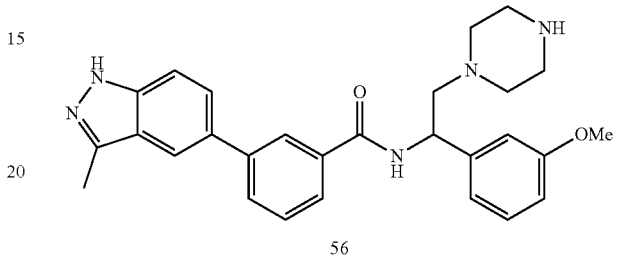

56

Step 1

Compound 56a was obtained by referring to Step 1 of Embodiment 55.

MS-ESI calculated value [M+H]$^+$ 570, measured value 570.

Step 2

Hydrochloride of compound 56 was obtained by referring to the purification of residue obtained in Step 2 of Embodiment 55 by high performance liquid chromatography (hydrochloric acid condition).

MS-ESI calculated value [M+H]$^+$ 470, measured value 470.

$^1$H NMR (400 MHz, DMSO-d$_6$) δ 9.96 (br, 2H), 9.69 (d, J=8.4 Hz, 1H), 8.50 (s, 1H), 8.31 (s, 1H), 8.00-7.89 (m, 2H), 7.83 (dd, J=1.6, 8.4 Hz, 1H), 7.60-7.52 (m, 2H), 7.33-7.25 (m, 1H), 7.24-7.20 (m, 1H), 7.14 (d, J=8.0 Hz, 1H), 6.90-6.82 (m, 1H), 5.70-5.60 (m, 1H), 4.10-4.04 (m, 2H), 3.76 (s, 3H), 3.71-3.45 (m, 8H), 2.60 (s, 3H) ppm.

Embodiment 57

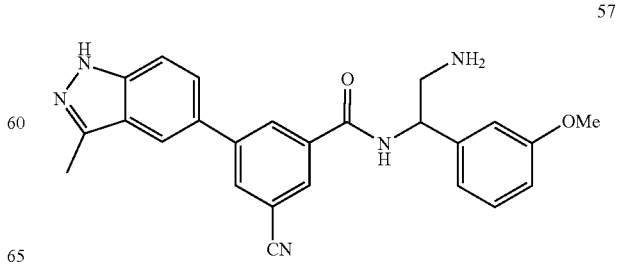

57

Synthetic Route:

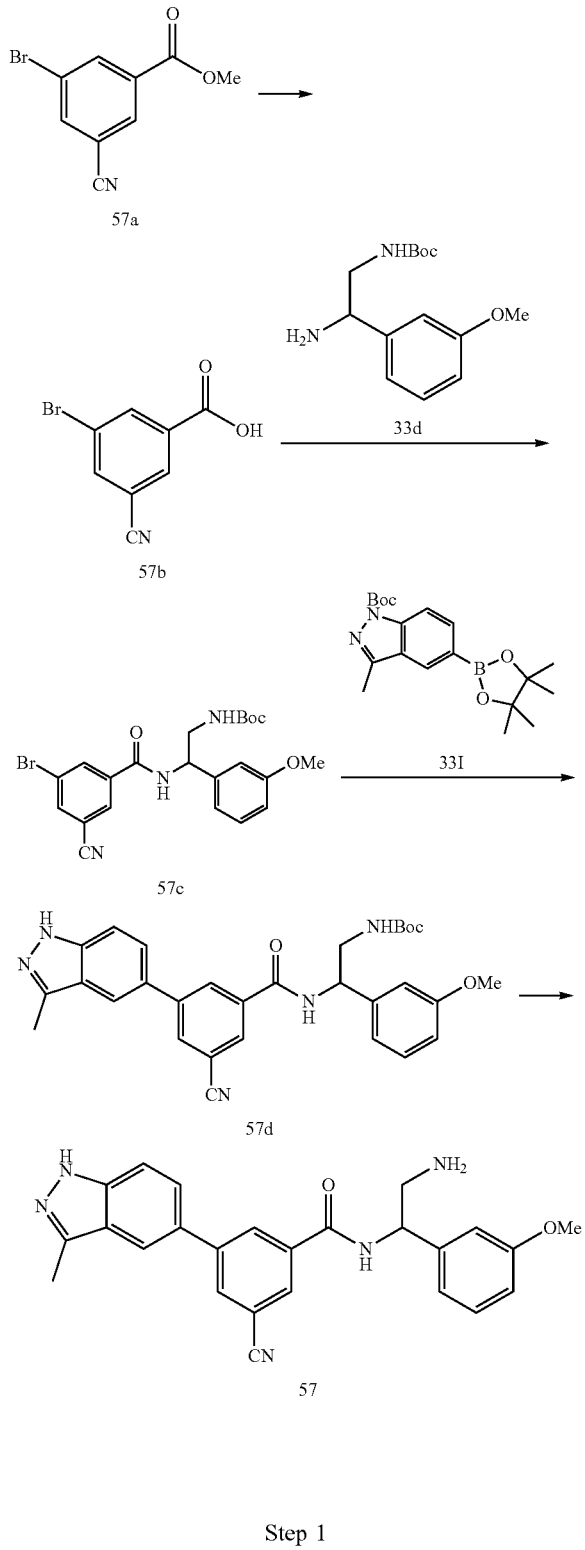

Step 1

Compound 57b was obtained by referring to Step 1 of Embodiment 47.

MS-ESI calculated value [M+H]$^+$ 226 and 228, measured value 226 and 228.

Step 2

Compound 57c was obtained by referring to Step 2 of Embodiment 47.

Step 3

Compound 57d was obtained by referring to Step 3 of Embodiment 47.

MS-ESI calculated value [M+H]$^+$ 526, measured value 526.

Step 4

Hydrochloride of compound 57 was obtained by referring to Step 4 of Embodiment 47.

MS-ESI calculated value [M+H]$^+$ 426, measured value 426.

$^1$H NMR (400 MHz, DMSO-d$_6$) δ 9.69 (d, J=8.4 Hz, 1H), 8.70 (t, J=1.6 Hz, 1H), 8.43-8.43 (m, 1H), 8.41-8.33 (m, 5H), 7.91-7.84 (m, 1H), 7.58 (d, J=8.4 Hz, 1H), 7.32-7.28 (m, 1H), 7.15-7.08 (m, 1H), 7.05 (d, J=7.6 Hz, 1H), 6.92-6.85 (m, 1H), 5.42-5.33 (m, 1H), 3.76 (s, 3H), 3.56-3.40 (m, 1H), 3.22-3.19 (m, 1H), 2.58 (s, 3H) ppm.

Embodiment 58

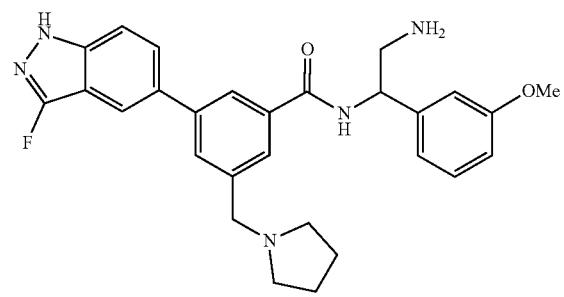

Synthetic Route:

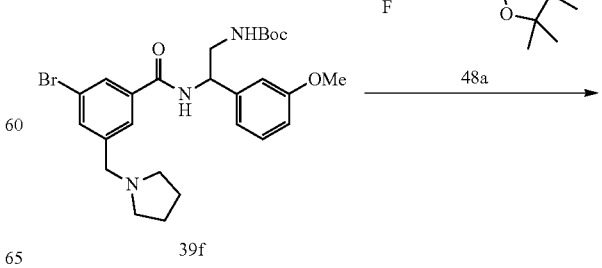

-continued

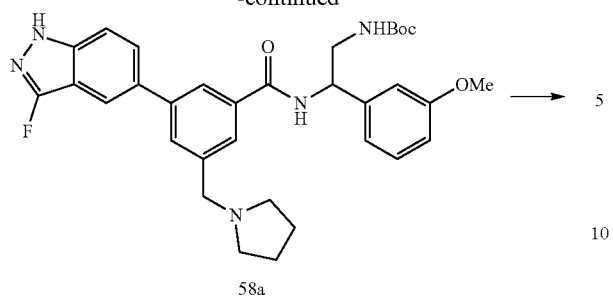

58a

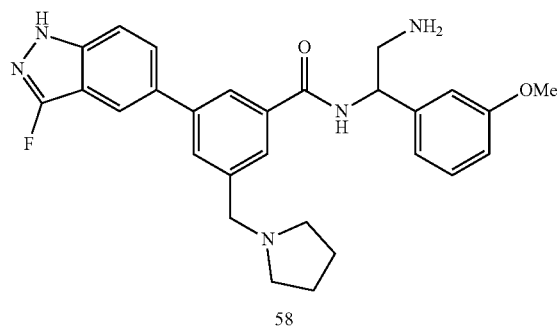

58

Step 1

Compound 39f (150 mg, 282 μmol), compound 48a (111 mg, 423 μmol), tris(dibenzylideneacetone) dipalladium (51.6 mg, 56.3 μmol), 2-dicyclohexylphosphino-2',4',6'-triisopropylbiphenyl (26.9 mg, 56.3 μmol), cesium carbonate (117 mg, 358 μmol) were dissolved in dioxane (5 mL) and water (1 mL), the reaction mixture was stirred at 95° C. for 12 hours. After the completion of the reaction, the reaction mixture was filtered, and the filtrate was concentrated under reduced pressure. The residue was purified by column chromatography to give compound 58a.

MS-ESI calculated value [M+H]$^+$ 588, measured value 588.

Step 2

Compound 58a (280 mg, 430 μmol) was dissolved in dichloromethane (5 mL), then trifluoroacetic acid (2 mL) was added thereto, the mixture was stirred at 20° C. for 1 hour. After their completion of the reaction, the mixture was concentrated under reduced pressure, the residue was purified by high performance liquid chromatography (hydrochloric acid condition) to give the hydrochloride of compound 58.

MS-ESI calculated value [M+H]$^+$ 488, measured value 488.

$^1$H NMR (400 MHz, DMSO-d$_6$) δ 12.83 (s, 1H), 11.43-11.25 (m, 1H), 9.57 (d, J=8.4 Hz, 1H), 8.52 (s, 1H), 8.45 (s, 3H), 8.34 (s, 1H), 8.27 (s, 1H), 8.16 (s, 1H), 8.07 (dd, J=1.6, 8.8 Hz, 1H), 7.63 (dd, J=2.0, 8.8 Hz, 1H), 7.33-7.25 (m, 1H), 7.12 (m, 1H), 7.07 (d, J=7.6 Hz, 1H), 6.89-6.86 (m, 1H), 5.43-5.37 (m, 1H), 4.48 (d, J=5.6 Hz, 2H), 3.76 (s, 3H), 3.50-3.46 (m, 1H), 3.43-3.32 (m, 2H), 3.23-3.17 (m, 1H), 3.17-3.06 (m, 2H), 2.11-1.84 (m, 4H) ppm.

Embodiment 59

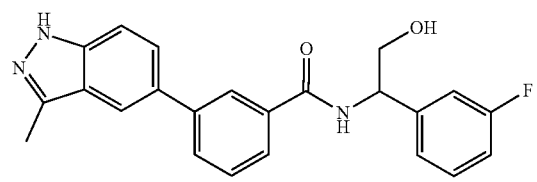

Synthetic Route:

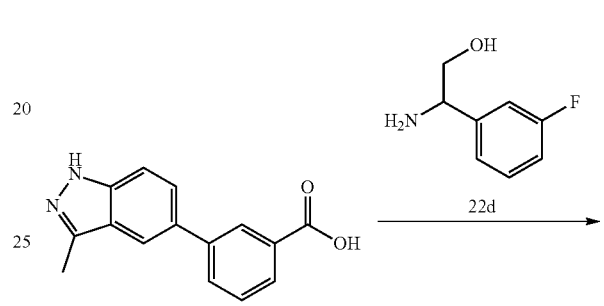

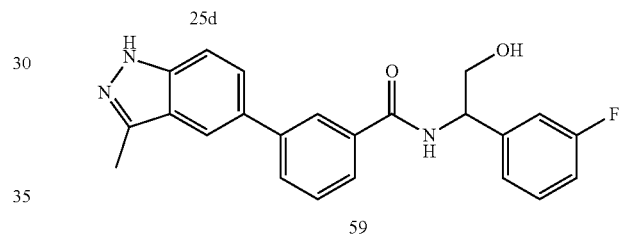

Step 1

Compound 59 was obtained by referring to Step 3 of Embodiment 25.

MS-ESI calculated value [M+H]$^+$ 390, measured value 390.

$^1$H NMR (400 MHz, CD$_3$OD) δ 8.24 (s, 1H), 8.18 (s, 1H), 7.99-7.84 (m, 3H), 7.70 (d, J=8.8 Hz, 1H), 7.61 (t, J=7.6 Hz, 1H), 7.43-7.34 (m, 1H), 7.28 (d, J=7.6 Hz, 1H), 7.24-7.16 (m, 1H), 7.02 (t, J=8.0 Hz, 1H), 5.27 (t, J=6.4 Hz, 1H), 3.92 (d, J=6.4 Hz, 2H), 2.76 (s, 3H) ppm.

Embodiment 60

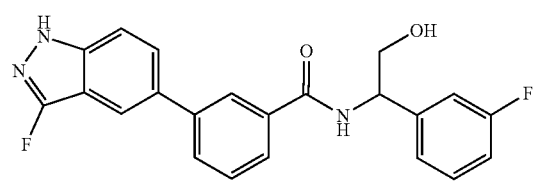

Synthetic Route:

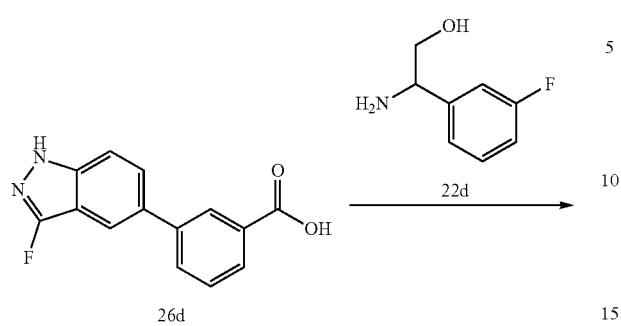

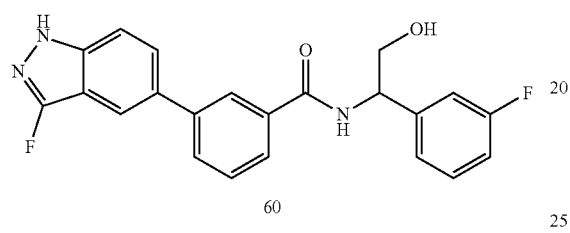

Step 1

Compound 60 was obtained by referring to Step 3 of Embodiment 25.

MS-ESI calculated value [M+H]⁺ 394, measured value 394.

¹H NMR (400 MHz, CD₃OD) δ 8.22 (s, 1H), 8.00 (s, 1H), 7.90-7.85 (m, 2H), 7.82 (dd, J=1.6, 8.8 Hz, 1H), 7.63-7.53 (m, 2H), 7.42-7.35 (m, 1H), 7.28 (d, J=7.8 Hz, 1H), 7.22-7.18 (m, 1H), 7.06-6.98 (m, 1H), 5.26 (t, J=6.4 Hz, 1H), 3.91 (d, J=6.4 Hz, 2H) ppm.

Embodiment 61

61

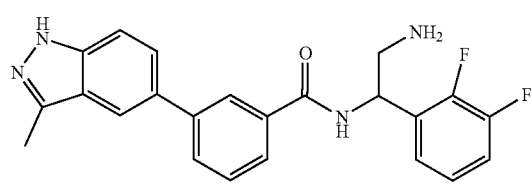

Synthetic Route:

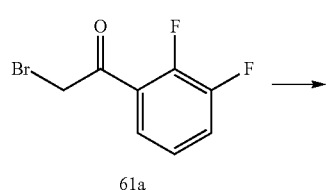

61a

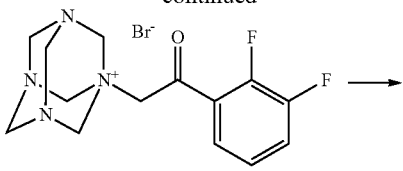

61b

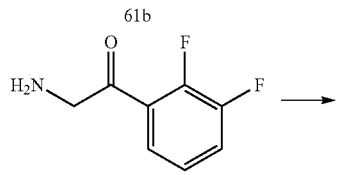

61c

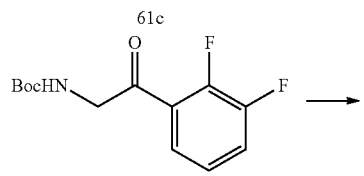

61d

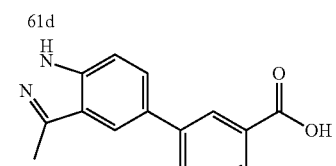

61e

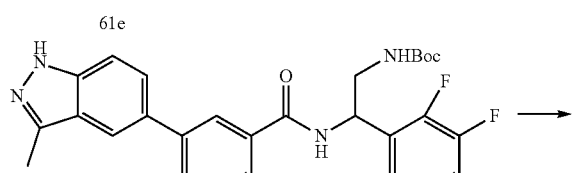

61f

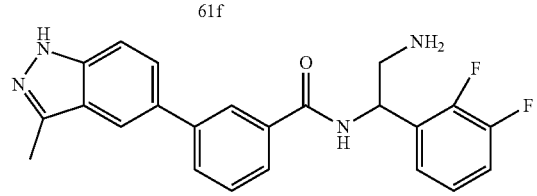

61

Step 1

Compound 61b was obtained by referring to the Step 1 of the preparation of Intermediate 33d in Embodiment 33.

Step 2

Compound 61c was obtained by referring to the Step 2 of the preparation of Intermediate 33d in Embodiment 33.

MS-ESI calculated value [M+H]⁺ 172, measured value 172.

Step 3

Compound 61d was obtained by referring to the Step 3 of the preparation of Intermediate 33d in Embodiment 33.

Step 4

Compound 61e was obtained by referring to the Step 4 of the preparation of Intermediate 33d in Embodiment 33.

MS-ESI calculated value [M+H]$^+$ 273, measured value 273.

Step 5

Compound 61f was obtained by referring to Step 3 of Embodiment 25.

MS-ESI calculated value [M+H]$^+$ 507, measured value 507.

Step 6

Compound 61f (220 mg, 423 μmol) was dissolved in dioxane (2 mL), a solution of hydrogen chloride in dioxane (4 M, 2 mL) was added thereto, and the reaction mixture was stirred at 10° C. for 16 hours. After the completion of the reaction, the mixture was concentrated under reduced pressure, the residue was purified by high performance liquid chromatography (hydrochloric acid condition) to give the hydrochloride of compound 61.

MS-ESI calculated value [M+H]$^+$ 407, measured value 407.

$^1$H NMR (400 MHz, CD$_3$OD) δ 8.36 (s, 1H), 8.30 (s, 1H), 8.04 (d, J=8.8 Hz, 1H), 8.00-7.88 (m, 2H), 7.74 (d, J=8.8 Hz, 1H), 7.67-7.56 (m, 1H), 7.45-7.36 (m, 1H), 7.35-7.20 (m, 2H), 5.90-5.78 (m, 1H), 3.70-3.58 (m, 1H), 3.50-3.40 (m, 1H), 2.80 (s, 3H) ppm.

Embodiment 62

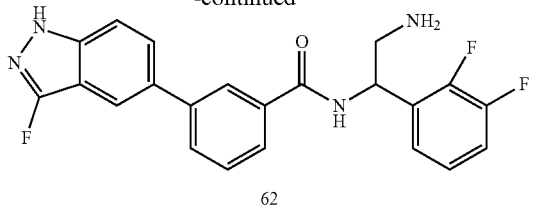

Step 1

Compound 62f was obtained by referring to Step 3 of Embodiment 25.

MS-ESI calculated value [M+H]$^+$ 511, measured value 511.

Step 2

Hydrochloride of compound 62 was obtained by referring to Step 6 of Embodiment 61.

MS-ESI calculated value [M+H]$^+$ 411, measured value 411.

$^1$H NMR (400 MHz, CD$_3$OD) δ 8.26 (t, J=1.6 Hz, 1H), 7.98 (s, 1H), 7.94-7.87 (m, 2H), 7.85-7.78 (m, 1H), 7.66-7.51 (m, 2H), 7.41-7.17 (m, 3H), 5.86-5.78 (m, 1H), 3.66-3.52 (m, 1H), 3.50-3.40 (m, 1H) ppm.

Embodiment 63

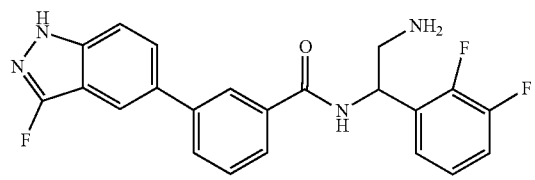

Synthetic Route:

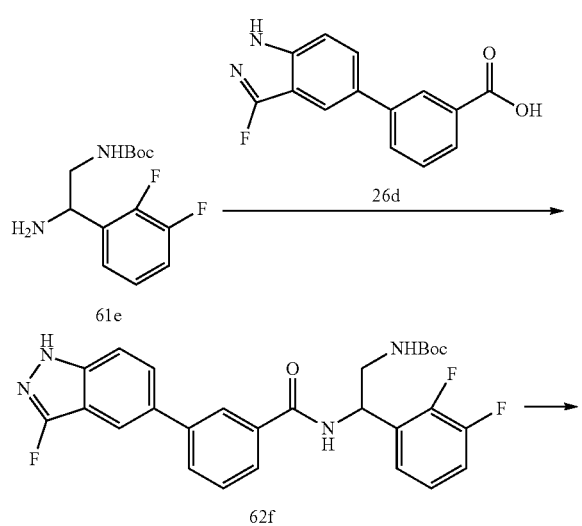

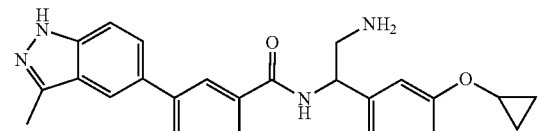

Synthetic Route:

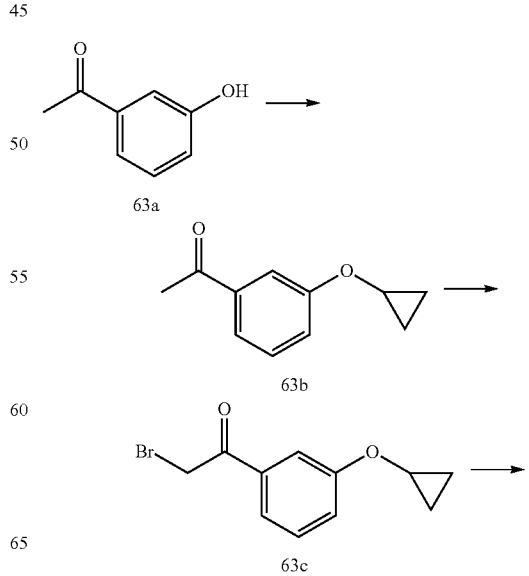

-continued

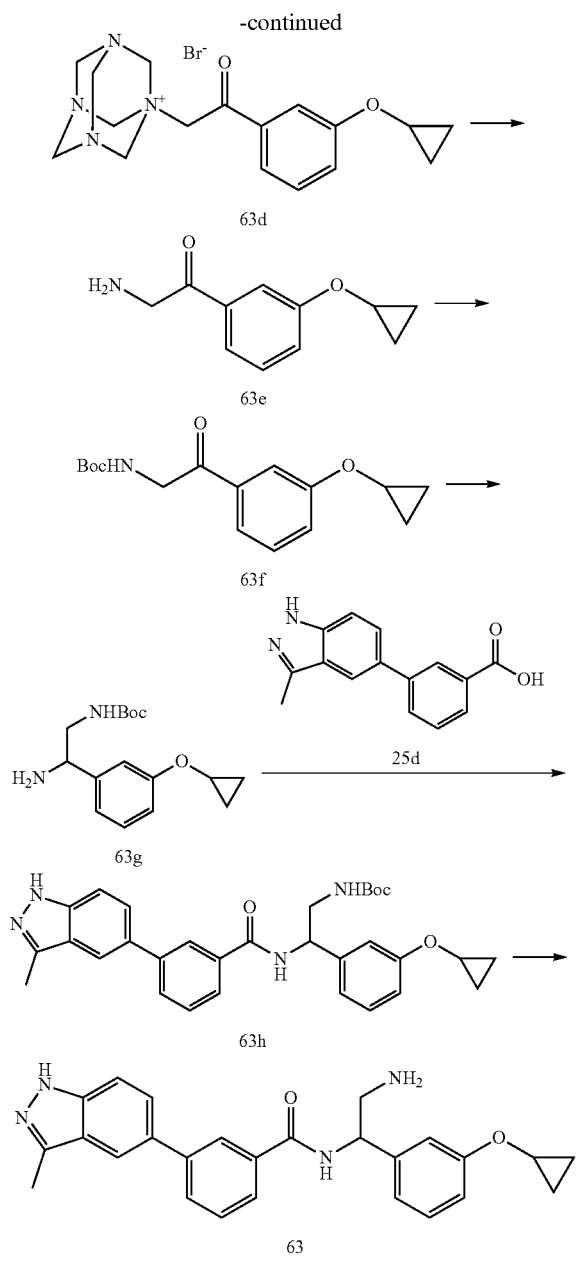

Step 1

Compound 63a (2.00 g, 14.7 mmol) was dissolved in N, N-dimethylformamide (30 mL), cyclopropyl bromide (14.2 g, 118 mmol), cesium carbonate (9.57 g, 29.4 mmol) and potassium iodide (244 mg, 1.47 mmol) were added thereto, the reaction mixture was stirred at 140° C. for 110 hours. After the completion of the reaction, the reaction mixture was filtered with celite and the filter cake was washed with ethyl acetate (100 mL), the filtrate was collected and washed with water (20 mL×3), dried over anhydrous sodium sulfate, filtered, and the filtrate was concentrated under reduced pressure. The residue was purified by column chromatography to give compound 63b.

MS-ESI calculated value [M+H]$^+$ 177, measured value 177.

Step 2

Compound 63b (1.61 g, 9.14 mmol) was dissolved in dichloromethane (5 mL), tetrabutylammonium tribromide (4.63 g, 9.59 mmol) was added thereto, and the reaction solution was stirred at 40° C. for 12 hours. After the completion of the reaction, the reaction solution was concentrated under reduced pressure, and dissolved by adding ethyl acetate (50 mL), then the mixture was washed with water (50 mL×3) and saturated brine (50 mL×2) in sequence. The organic phase was dried over anhydrous sodium sulfate, filtered, and the filtrate was concentrated under reduced pressure to give the crude compound 63c.

MS-ESI calculated value [M+H]$^+$ 255 and 257, measured value 255 and 257.

Step 3

Compound 63d was obtained by referring to the Step 1 of preparation of Intermediate 33d in Embodiment 33.

Step 4

Compound 63e was obtained by referring to the Step 2 of preparation of Intermediate 33d in Embodiment 33.

Step 5

Compound 63f was obtained by referring to the Step 3 of preparation of Intermediate 33d in Embodiment 33.

Step 6

Compound 63g was obtained by referring to the Step 4 of preparation of Intermediate 33d in Embodiment 33.

MS-ESI calculated value [M+H]$^+$ 293, measured value 293.

Step 7

Compound 63h was obtained by referring to Step 1 of Embodiment 41.

MS-ESI calculated value [M+H]$^+$ 527, measured value 527.

Step 8

Trifluoroacetic acid (2 mL) was added to compound 63h (65.0 mg, 123 μmol), and the reaction mixture was stirred at 15° C. for 1 hour. After the completion of the reaction, the reaction mixture was concentrated under reduced pressure, and the residue was prepared by high performance liquid chromatography (hydrochloric acid condition) to give the hydrochloride of compound 63.

MS-ESI calculated value [M+H]$^+$ 427, measured value 427.

$^1$H NMR (400 MHz, DMSO-d$_6$) δ 9.32 (d, J=8.4 Hz, 1H), 8.38 (s, 1H), 8.28 (br, 3H), 8.16 (s, 1H), 7.98-7.88 (m, 2H), 7.77 (dd, J=1.6, 8.4 Hz, 1H), 7.62-7.53 (m, 2H), 7.37-7.27 (m, 1H), 7.15 (d, J=1.6 Hz, 1H), 7.10-6.99 (m, 2H), 5.44-5.33 (m, 1H), 3.86-3.77 (m, 1H), 3.50-3.36 (m, 1H), 3.29-3.15 (m, 1H), 2.57 (s, 3H), 0.82-0.72 (m, 2H), 0.69-0.58 (m, 2H) ppm.

Embodiment 64

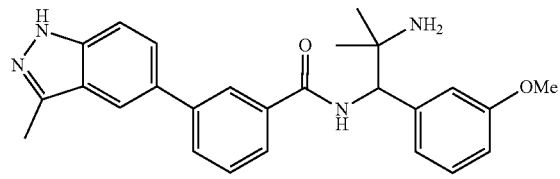

Synthetic Route:

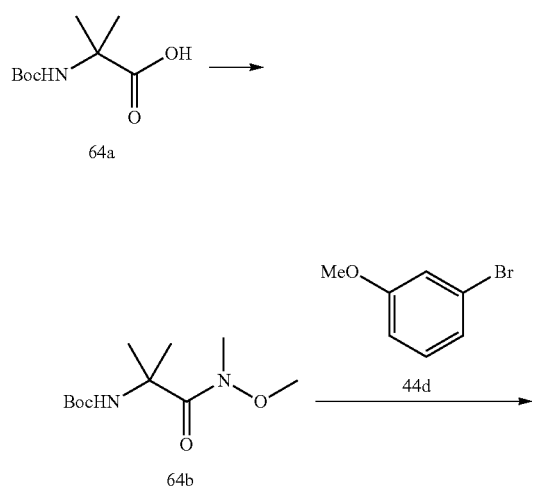

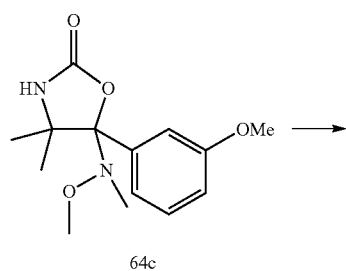

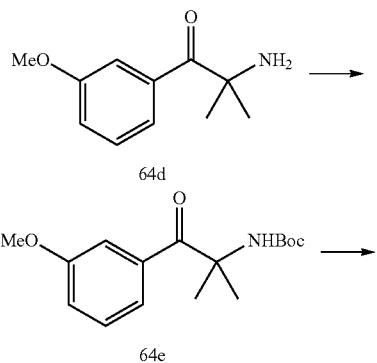

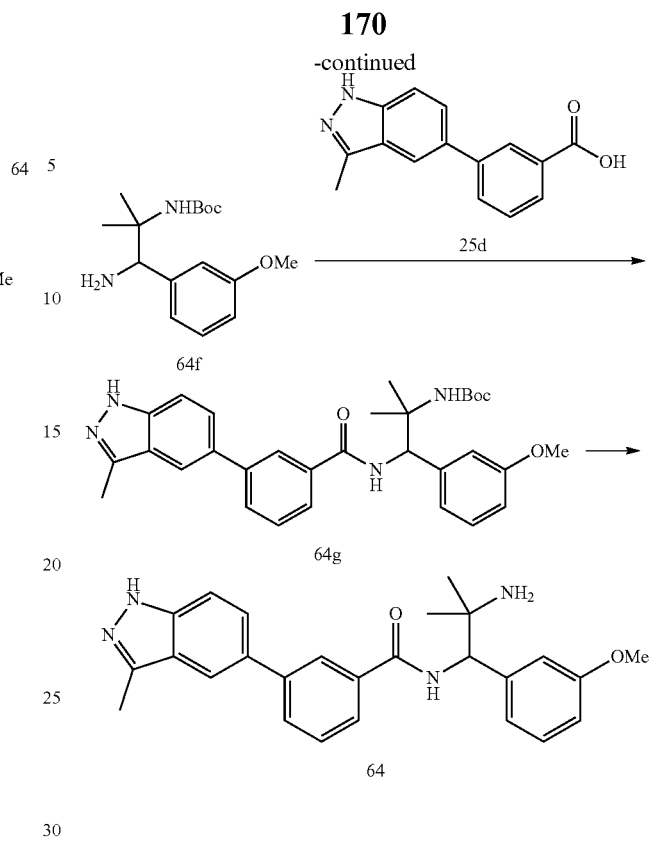

Step 1

Compound 64a (5.00 g, 24.6 mmol) was dissolved in N,N-dimethylformamide (80 mL), O-(7-azabenzotriazol-1-yl)-N,N,N',N'-tetramethyluronium hexafluorophosphate (11.2 g, 29.5 mmol) and N,N-diisopropylethylamine (12.7 g, 98.4 mmol, 17.1 mL) were added to the reaction mixture, and then N-methyl-N-methoxy hydrochloride (2.88 g, 29.5 mmol) was added thereto, and then the mixture was stirred at 20° C. for 12 hours. After the completion of the reaction, the mixture was diluted with water (600 mL) and extracted with ethyl acetate (400 mL×2), the combined organic phase was washed with saturated brine (600 mL×1), dried over anhydrous sodium sulfate, filtered, and the filtrate was concentrated under reduced pressure. The residue was purified by column chromatography to give compound 64b.

Step 2

Compound 44d (4.10 g, 21.9 mmol, 2.80 mL) was dissolved in tetrahydrofuran (40 mL), a solution of n-butyl lithium in n-hexane (2.5 M, 8.2 mL) was slowly added dropwise at −78° C., and the reaction mixture was stirred at −78° C. for 30 minutes. Compound 64b (1.80 g, 7.31 mmol) was dissolved in tetrahydrofuran (15 mL) and was added to the above solution at −78° C., then the temperature of the reaction mixture was slowly raised to 20° C. and stirred for 12 hours. After the completion of the reaction, a saturated aqueous solution of ammonium chloride (40 mL) was added to quench the reaction, then the mixture was diluted with water (80 mL), and extracted with ethyl acetate (100 mL×2), the combined organic phase was washed with saturated brine (100 mL×1), dried over anhydrous sodium sulfate, filtered, and the filtrate was concentrated under reduced pressure. The residue was purified by column chromatography to give compound 64c.

Step 3

Compound 64c (1.70 g, 6.06 mmol) was dissolved in ethanol (15 mL) and water (15 mL), lithium hydroxide monohydrate (1.27 g, 30.3 mmol) was added thereto, and the mixture was stirred at 90° C. for 12 hours. After the completion of the reaction, the mixture was diluted with water (100 mL) and extracted with ethyl acetate (80 mL×2), the combined organic phase was washed with saturated brine (100 mL×1), dried over anhydrous sodium sulfate, filtered, and the filtrate was concentrated under reduced pressure to give crude compound 64d.

MS-ESI calculated value $[M+H]^+$ 194, measured value 194.

Step 4

Compound 64d (1 g, 5.17 mmol) was dissolved in tetrahydrofuran (15 mL) and water (15 mL), di-tert-butyl dicarbonate (1.36 g, 5.17 mmol) and sodium carbonate (1.10 g, 10.35 mmol) were added thereto, the mixture was stirred at 20° C. for 12 hours. After the completion of the reaction, the mixture was diluted with water (100 mL) and extracted with ethyl acetate (70 mL×2). The combined organic phase was washed with saturated brine (100 mL×1) and dried over anhydrous sodium sulfate, filtered, the filtrate was concentrated under reduced pressure. The residue was purified by column chromatography to give compound 64e.

Step 5

Compound 64e (780 mg, 2.66 mmol) was dissolved in methanol (20 mL), sodium cyanoborohydride (167 mg, 2.66 mmol) and ammonium acetate (2.05 g, 26.6 mmol) were added thereto, the reaction mixture was stirred at 70° C. for 12 hours. After the completion of the reaction, the reaction mixture was concentrated under reduced pressure. The residue was purified by column chromatography to give compound 64f.

MS-ESI calculated value $[M+H]^+$ 295, measured value 295.

Step 6

Compound 25d (129 mg, 510 μmol) was dissolved in N,N-dimethylformamide (8 mL), and O-(7-azabenzotriazol-1-yl)-N,N,N',N'-tetramethyluronium hexafluorophosphate (252 mg, 662 μmol) and N,N-diisopropylethylamine (198 mg, 1.53 mmol, 266 μL) were added to the reaction mixture, then compound 64f (150 mg, 510 μmol) were added thereto, and the mixture was stirred for 12 hours at 20° C. After the completion of the reaction, the mixture was diluted with water (100 mL), and extracted with ethyl acetate (50 mL×2), the combined organic phases were washed with saturated brine (100 mL×1), dried over anhydrous sodium sulfate, filtered, and the filtrate was concentrated under reduced pressure. The residue was purified by thin layer chromatography to give compound 64g.

MS-ESI calculated value $[M+H]^+$ 529, measured value 529.

Step 7

Compound 64g (130 mg, 142 μmol) was dissolved in dichloromethane (3 mL), a solution of hydrogen chloride in ethyl acetate (4 M, 3 mL) was added thereto, and the mixture was stirred at 40° C. for 2 hours. After the completion of the reaction, the reaction mixture was concentrated under reduced pressure, and the residue was purified by high performance liquid chromatography to give compound 64.

MS-ESI calculated value $[M+H]^+$ 429, measured value 429.

$^1$H NMR (400 MHz, DMSO-$d_6$) δ 12.88-12.50 (m, 1H), 8.73 (d, J=9.6 Hz, 1H), 8.35 (s, 1H), 8.12 (s, 1H), 8.04 (s, 1H), 7.89 (d, J=8.0 Hz, 1H), 7.81 (d, J=8.0 Hz, 1H), 7.71 (dd, J=2.0, 8.8 Hz, 1H), 7.61-7.54 (m, 2H), 7.26 (t, J=8.0 Hz, 1H), 7.11 (s, 1H), 7.05 (d, J=8.0 Hz, 1H), 6.86 (dd, J=2.0, 8.0 Hz, 1H), 5.08 (d, J=9.6 Hz, 1H), 3.77 (s, 3H), 2.55 (s, 3H), 1.18 (s, 3H), 1.07 (s, 3H) ppm.

Embodiment 65

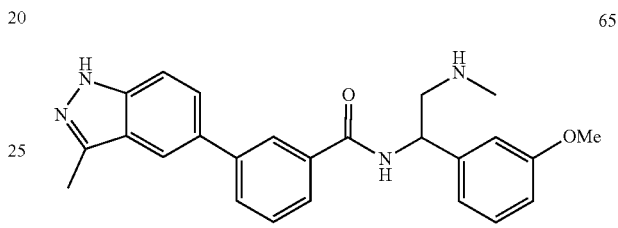

65

Synthetic Route:

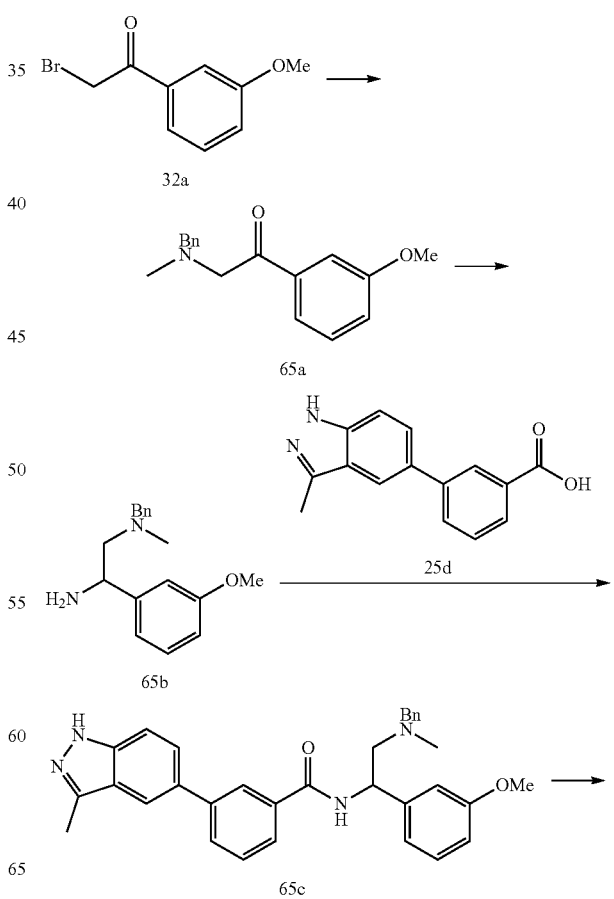

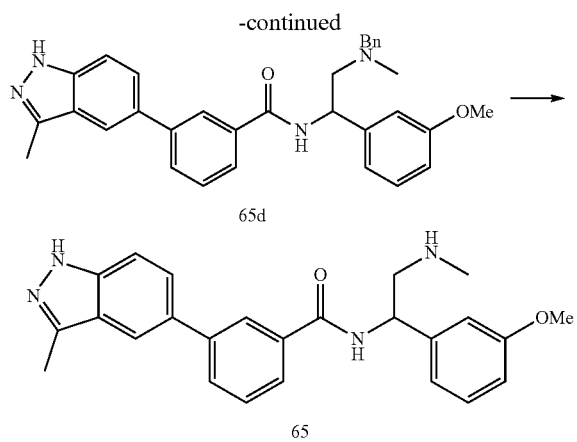

Step 1

N-methylbenzylamine (2.12 g, 17.5 mmol, 2.25 mL) was dissolved in tetrahydrofuran (40 mL), then potassium carbonate (4.83 g, 34.9 mmol) and compound 32a (4.00 g, 17.5 mmol) were added thereto, the mixture was stirred at 10° C. for 1 hour. After the completion of the reaction, the reaction mixture was filtered and the filtrate was concentrated under reduced pressure. The resulting residue was purified by column chromatography to give compound 65a.

Step 2

Compound 65a (4.97 g, 18.5 mmol) was dissolved in methanol (100 mL), then ammonium acetate (14.2 g, 185 mmol) and sodium cyanoborohydride (1.16 g, 18.5 mmol) were added thereto. The reaction mixture was stirred at 50° C. for 12 hours. After the completion of the reaction, the reaction mixture was concentrated under reduced pressure, ethyl acetate (30 mL) was added to the resulting solid, and then the mixture was washed with water (30 mL×1). The organic phase was extracted with hydrochloric acid (1 M, 30 mL×2), the aqueous phases were combined and washed with ethyl acetate (30 mL×1), then the pH value was neutralized to about 8 to 9 by adding saturated sodium carbonate solution, then extracted with ethyl acetate (40 mL×3), and the combined organic phase was concentrated under reduced pressure. The residue was purified by high performance liquid chromatography (neutral condition) to give compound 65b.

Step 3

Compound 65b (250 mg, 925 μmol) and compound 25d (187 mg, 740 μmol) were dissolved in in tetrahydrofuran (5 mL), then O-(7-azabenzotriazol-1-yl)-N,N,N',N'-tetramethyluronium hexafluorophosphate (369 mg, 971 μmol) and N,N-diisopropylethylamine (359 mg, 2.77 mmol, 483 μL) were added thereto. The reaction mixture was stirred at 10° C. for 12 hours. After the completion of the reaction, the mixture was filtered and the filtrate was concentrated under reduced pressure. The residue was purified by thin layer chromatography to give compound 65c.

Step 4

Compound 65c (216 mg, 428 μmol) was dissolved in ethyl acetate (5 mL), then wet palladium on carbon (21.6 mg, 10% purity) and tert-butyl dicarbonate (187 mg, 856 μmol, 197 μL) were added thereto. The reaction mixture was stirred at 60° C. under hydrogen atmosphere (15 psi) for 1 hour. After the completion of the reaction, the mixture was filtered with celite, and the filtrate was concentrated under reduced pressure. The residue was purified by thin layer chromatography to give compound 65d.

Step 5

Compound 65d (140 mg, 272 μmol) was dissolved in ethyl acetate (0.5 mL), and then a solution of hydrogen chloride in ethyl acetate (4 M, 0.5 mL) was added thereto. The reaction mixture was stirred at 10° C. for 1 hour. After the completion of the reaction, the reaction mixture was concentrated under reduced pressure. The residue was purified by high performance liquid chromatography (formic acid condition) to give the formate of compound 65.

MS-ESI calculated value [M+H]$^+$ 415, measured value 415.

$^1$H NMR (400 MHz, CD$_3$OD) δ 8.51 (s, 1H), 8.24 (s, 1H), 8.02 (s, 1H), 7.96-7.85 (m, 2H), 7.79-7.71 (m, 1H), 7.65-7.55 (m, 2H), 7.43-7.33 (m, 1H), 7.18-7.04 (m, 2H), 7.00-6.90 (m, 1H), 5.64-5.51 (m, 1H), 3.84 (s, 3H), 3.67-3.41 (m, 2H), 2.77 (s, 3H), 2.63 (s, 3H) ppm.

Embodiment 66

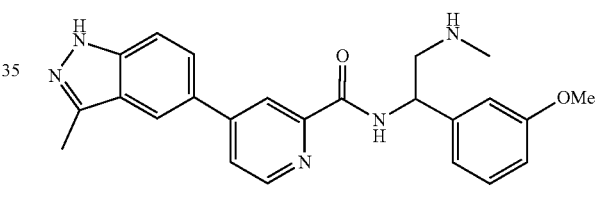

Synthetic Route:

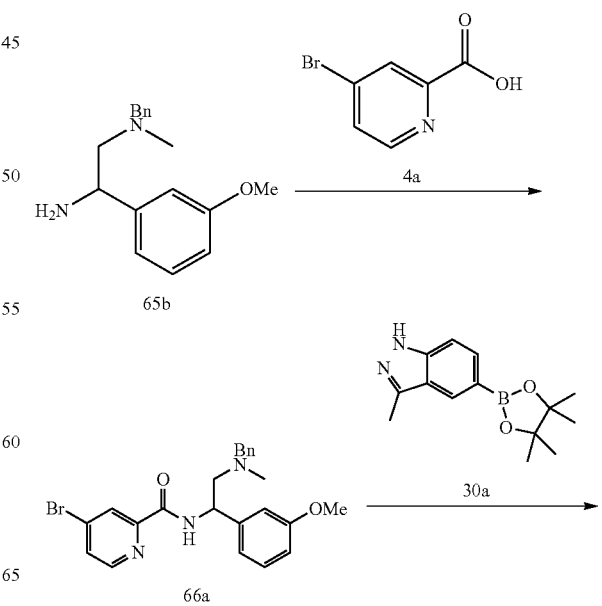

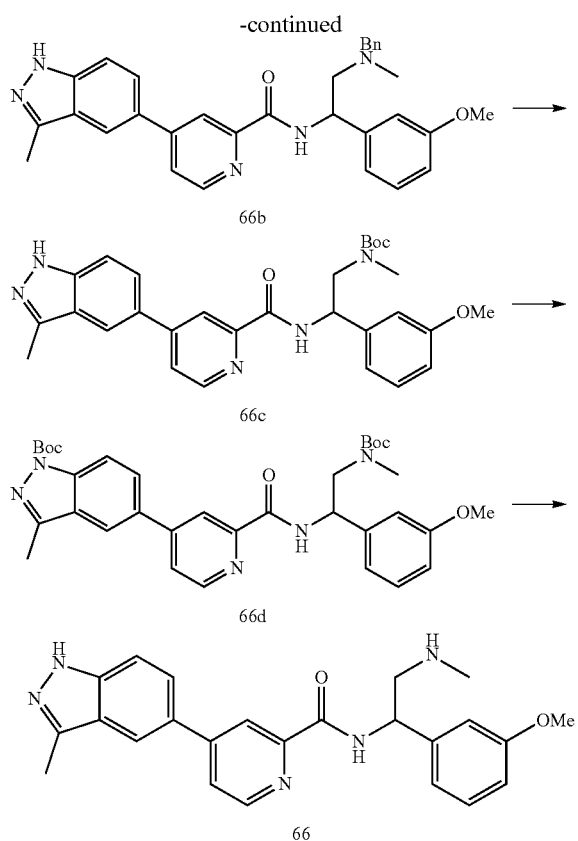

Step 1

Compound 66a was obtained by referring to Step 3 of Embodiment 65.

Step 2

Compound 66b was obtained by referring to Step 3 of Embodiment 34.

Step 3

The crude product of compound 66c was obtained by concentration under reduced pressure referring to Step 4 of Embodiment 65.

Step 4

Compound 66c (500 mg, 970 μmol) was dissolved in acetonitrile (5 mL), then 4-dimethylaminopyridine (9.92 mg, 81.2 μmol) and tert-butyl dicarbonate (177 mg, 812 μmol, 187 μL) were added thereto. The reaction mixture was stirred at 10° C. for 1 hour. After the completion of the reaction, the reaction mixture was concentrated under reduced pressure. The residue was purified by thin layer chromatography to give compound 66d.

Step 5

Compound 66d (176 mg, 286 μmol) was dissolved in dioxane (5 mL), and then a solution of hydrogen chloride in dioxane (4 M, 5 mL) was added thereto. The reaction mixture was stirred at 10° C. for 1 hour and 40 minutes, then concentrated under reduced pressure, and the residue was purified by slurring with ethyl acetate (2 mL) to give the hydrochloride of compound 66.

MS-ESI calculated value [M+H]$^+$ 416, measured value 416.

$^1$H NMR (400 MHz, DMSO-d$_6$) δ 9.13 (s, 1H), 8.83-8.78 (m, 1H), 8.74 (s, 1H), 8.41-8.33 (m, 1H), 8.07 (d, J=8.8 Hz, 1H), 7.65 (d, J=8.8 Hz, 1H), 7.36-7.28 (m, 1H), 7.17 (s, 1H), 7.11 (d, J=8.0 Hz, 1H), 6.90 (dd, J=2.4, 8.0 Hz, 1H), 5.57-5.49 (m, 1H), 3.77 (s, 3H), 3.51-3.46 (m, 2H), 2.65 (s, 3H), 2.62 (s, 3H) ppm.

Embodiment 67

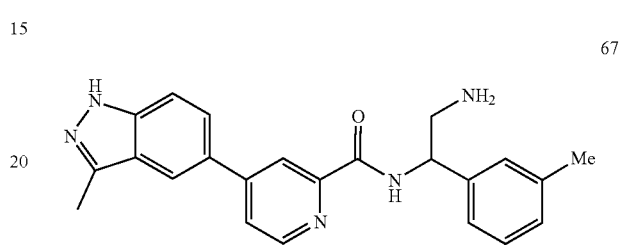

Synthetic Route:

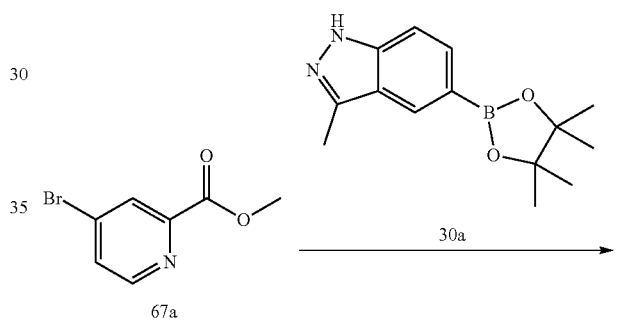

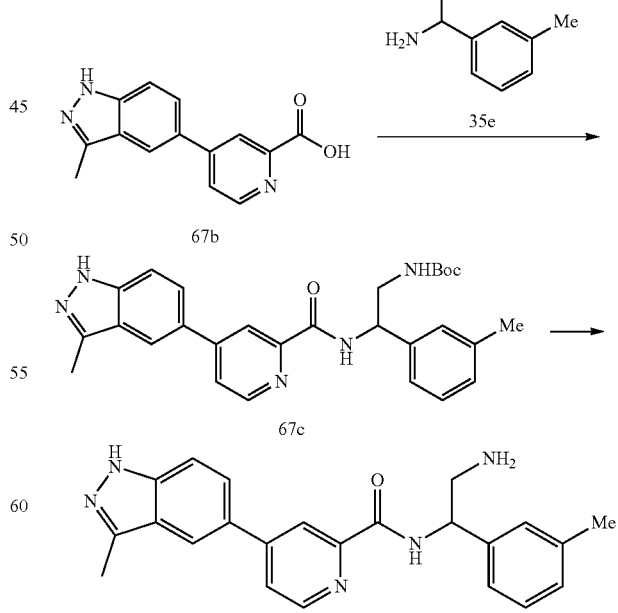

Step 1

Compound 67a (1.67 g, 7.75 mmol), compound 30a (2.00 g, 7.75 mmol), tetrakis(triphenylphosphine)palladium (448 mg, 388 μmol), potassium carbonate (3.21 g, 23.2 mmol) were dissolved in dioxane (40 mL) and water (16 mL), the reaction mixture was stirred at 85° C. for 12 hours. After the completion of the reaction, the reaction mixture was directly filtered, the filtrate was diluted with water (30 mL), and washed with ethyl acetate (30 mL×3). The pH value of the aqueous phase was adjusted to about 5 to 6 with dilute hydrochloric acid solution (2 M), then filtered to give the crude compound 67b.

MS-ESI calculated value [M−H]⁺ 252, measured value 252.

Step 2

Compound 67c was obtained by referring to Step 1 of Embodiment 1.

Step 3

Compound 67c (270 mg, 209 μmol) was dissolved in dichloromethane (5 mL), then trifluoroacetic acid (2 mL) was added thereto, and the mixture was stirred at 20° C. for 0.5 hour. After the completion of the reaction, the reaction mixture was concentrated under reduced pressure, the mixture was purified by high performance liquid chromatography (hydrochloric acid condition) to give the hydrochloride of compound 67.

MS-ESI calculated value [M+H]⁺ 386, measured value 386.

$^1$H NMR (400 MHz, DMSO-$d_6$) δ 9.66 (d, J=8.8 Hz, 1H), 8.75 (d, J=5.2 Hz, 1H), 8.53 (s, 1H), 8.37 (s, 1H), 8.17 (s, 3H), 8.11 (dd, J=1.6, 5.2 Hz, 1H), 7.87 (dd, J=1.6, 8.8 Hz, 1H), 7.63 (d, J=8.8 Hz, 1H), 7.34-7.27 (m, 3H), 7.18-7.10 (m, 1H), 5.44-5.38 (m, 1H), 3.63-3.16 (m, 2H), 2.58 (s, 3H), 2.32 (s, 3H) ppm.

Embodiment 68

68

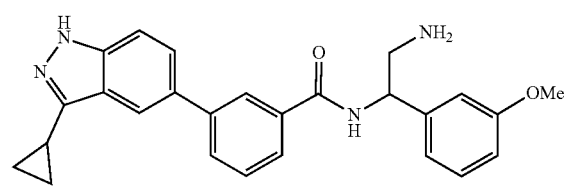

Synthetic Route:

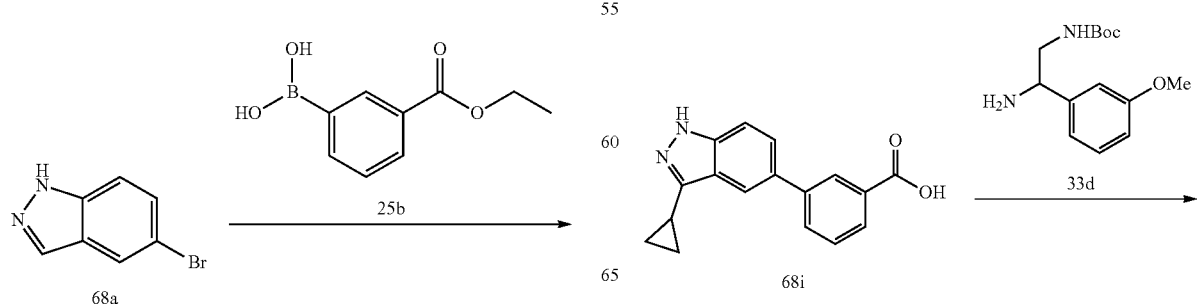

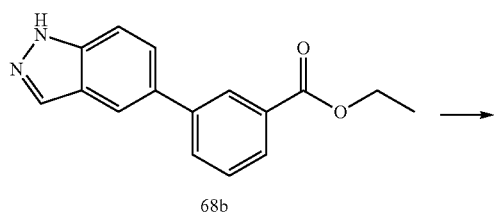

68b

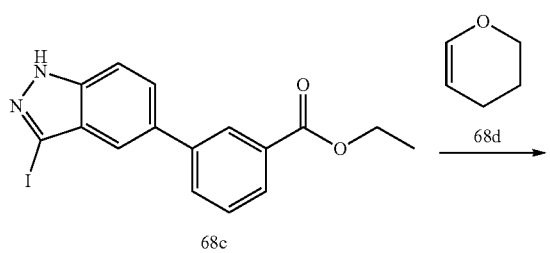

68c

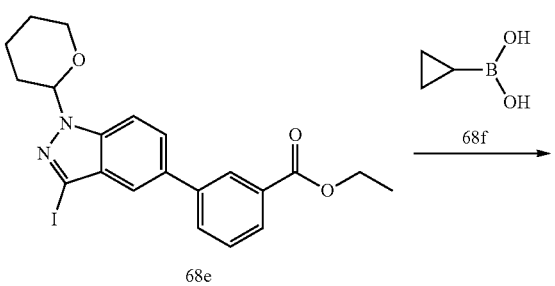

68e

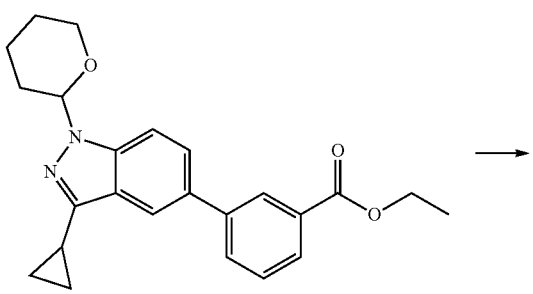

68g

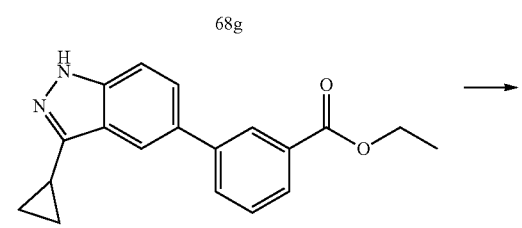

68h

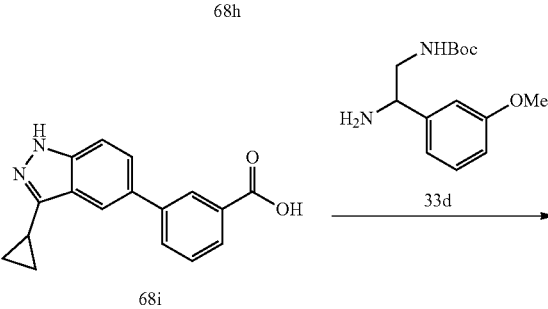

68i

-continued

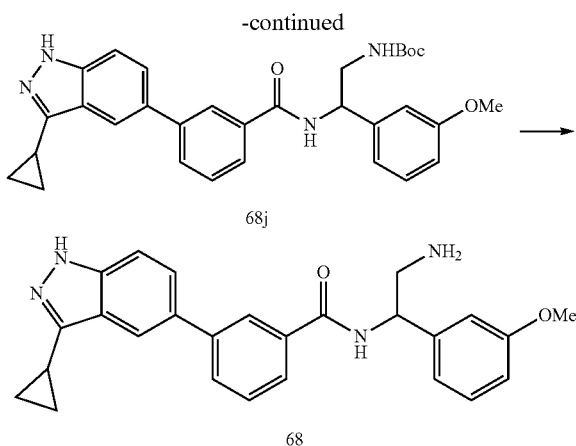

68j

68

Step 1

Compound 68a (2.00 g, 10.2 mmol) and compound 25b (2.56 g, 13.2 mmol) were dissolved in dioxane (40 mL) and water (10 mL), and [1,1'-bis(diphenylphosphino)ferrocene] palladium dichloride (1.11 g, 1.52 mmol) and sodium carbonate (2.15 g, 20.3 mmol) were added thereto. The reaction mixture was stirred at 95° C. for 12 hours. After the completion of the reaction, the reaction mixture was filtered, and the filtrate was concentrated under reduced pressure, the residue was purified by column chromatography to give compound 68b.

Step 2

Compound 68b (900 mg, 3.38 mmol) was dissolved in dichloromethane (20 mL), N-iodosuccinimide (783 mg, 3.48 mmol) was added to the reaction mixture, and the reaction mixture was stirred at 25° C. for 12 hours. After the completion of the reaction, the mixture was diluted with water (20 mL) and extracted with ethyl acetate (20 mL×2). The combined organic phase was washed with saturated brine (20 mL×2), dried over anhydrous sodium sulfate, filtered, the filtrate was concentrated under reduced pressure to give the crude product 68c.

Step 3

Compound 68c (820 mg, 2.09 mmol) and compound 68d (528 mg, 6.27 mmol, 574 µL) were dissolved in dichloromethane (30 mL), and p-toluenesulfonic acid (36.0 mg, 209 µmol) was added to the reaction mixture. The reaction mixture was stirred at 20° C. for 12 hours. After the completion of the reaction, the reaction mixture was concentrated under reduced pressure, and the residue was purified by column chromatography to give compound 68e.

Step 4

Compound 68e (450 mg, 925 µmol) and compound 68f (119 mg, 1.39 mmol) were dissolved in toluene (10 mL) and water (1 mL), and tetrakis(triphenylphosphine) palladium (107 mg, 92.5 µmol) and potassium phosphate (786 mg, 3.70 mmol) were added thereto, the reaction mixture was stirred at 120° C. for 12 hours. After the completion of the reaction, the reaction mixture was diluted with water (20 mL) and extracted with ethyl acetate (20 mL×2). The combined organic phase was washed with saturated brine (20 mL×2), dried over anhydrous sodium sulfate, filtered, and the filtrate was concentrated under reduced pressure. The residue was purified by column chromatography to give compound 68g.

Step 5

Compound 68g (270 mg, 676.48 µmol) was dissolved in a solution of hydrogen chloride in dioxane (4 M, 5 mL) and stirred at 20° C. for 12 hours. After the completion of the reaction, the mixture was concentrated under reduced pressure to give a crude product compound 68h.

Step 6

Compound 68h (160 mg, 467 µmol) was dissolved in tetrahydrofuran (3 mL), methanol (0.75 mL) and water (0.75 mL), lithium hydroxide monohydrate (58.8 mg, 1.40 mmol) was added thereto, and the reaction mixture was stirred at 20° C. for 12 hours. After the completion of the reaction, the pH value was adjusted to about 5 to 6 by adding water (10 mL) and dilute hydrochloric acid solution (2 M), and then the mixture was extracted with ethyl acetate (10 mL×2). The combined organic phase was washed saturated brine (10 mL×2), dried over anhydrous sodium sulfate, filtered, and the filtrate was concentrated under reduced pressure to give a crude product 68i.

Step 7

Compound 68j was obtained by purifying the crude product obtained by referring to Step 3 of Embodiment 25 by thin layer chromatography.

Step 8

Compound 68j (200 mg, 359 µmol) was dissolved in trifluoroacetic acid (5 mL) and stirred at 20° C. for 1 hour. After the completion of the reaction, the mixture was concentrated under reduced pressure, and the residue was purified by high performance liquid chromatography (hydrochloric acid condition) to give the hydrochloride of compound 68.

MS-ESI calculated value [M+H]$^+$ 427, measured value 427.

$^1$H NMR (400 MHz, DMSO-d$_6$) δ 9.29 (d, J=8.4 Hz, 1H), 8.37 (s, 1H), 8.26 (br, 2H), 8.20 (s, 1H), 7.96-7.88 (m, 2H), 7.76 (dd, J=1.6, 8.8 Hz, 1H), 7.61-7.54 (m, 2H), 7.31 (t, J=8.0 Hz, 1H), 7.08 (d, J=2.0 Hz, 1H), 7.04 (d, J=8.0 Hz, 1H), 6.88 (dd, J=2.0, 8.0 Hz, 1H), 5.45-5.30 (m, 1H), 3.76 (s, 3H), 3.51-3.34 (m, 1H), 3.27-3.16 (m, 1H), 2.45-2.39 (m, 1H), 1.06-0.96 (m, 4H) ppm.

Embodiment 69

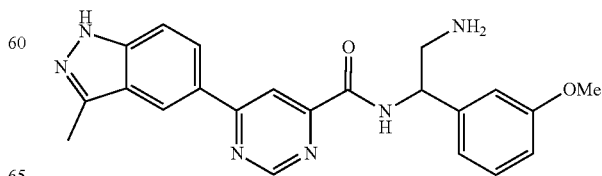

69

Synthetic Route:

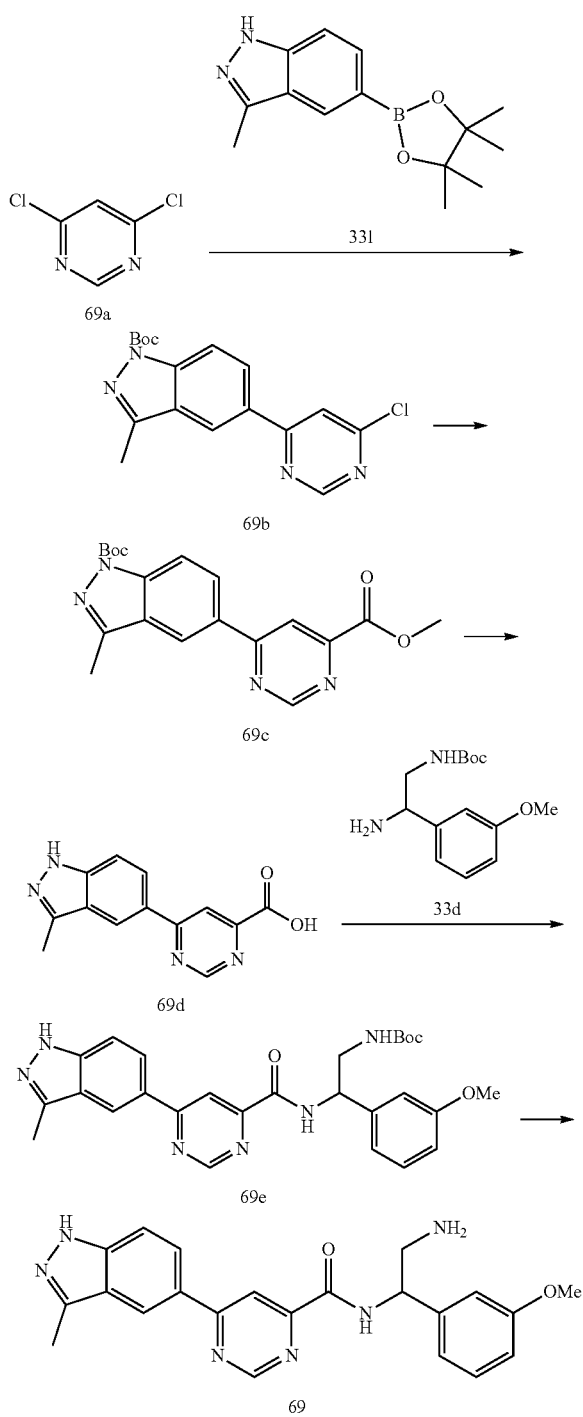

Step 1

Compound 69a (416 mg, 2.79 mmol) and compound 331 (1.00 g, 2.79 mmol) were dissolved in dioxane (20 mL) and water (2 mL), and [1,1'-bis(diphenylphosphino)ferrocene] palladium dichloride (204 mg, 279 μmol) and potassium acetate (822 mg, 8.37 mmol) were added thereto. The reaction mixture was stirred at 85° C. under nitrogen protection for 12 hours, then compound 69a (416 mg, 2.79 mmol) was added to the reaction mixture. The reaction mixture was stirred at 85° C. under nitrogen protection for 12 hours. After the completion of the reaction, the mixture was filtered, and the filtrate was concentrated under reduced pressure. The residue was purified by thin layer chromatography to give compound 69b.

Step 2

Compound 69b (200 mg, 580 μmol) was dissolved in methanol (10 mL), and [1,1'-bis(diphenylphosphino)ferrocene]palladium dichloride (42.4 mg, 58.0 μmol) and triethylamine (176 mg, 1.74 mmol, 242 μL) were added thereto. The reaction mixture was stirred at 70° C. under carbon monoxide atmosphere (40 psi) for 12 hours. After the completion of the reaction, the mixture was filtered, and the filtrate was concentrated under reduced pressure to give the crude compound 69c.

Step 3

Compound 69d was obtained by referring to Step 2 of Embodiment 25.

Step 4

Compound 69e was obtained by referring to Step 3 of Embodiment 25.

Step 5

Compound 69e (50.0 mg, 99.5 μmol) was dissolved in dioxane (0.5 mL), and then a solution of hydrogen chloride in dioxane (4 M, 0.5 mL) was added thereto, the reaction mixture was stirred at 10° C. for 12 hours. After the completion of the reaction, the mixture was concentrated under reduced pressure, the residue was purified by high performance liquid chromatography (basic condition) to give compound 69.

MS-ESI calculated value [M+H]$^+$ 403, measured value 403.

$^1$H NMR (400 MHz, CD$_3$OD) δ 9.30-9.20 (s, 1H), 8.68-8.47 (m, 2H), 8.30-8.17 (m, 1H), 7.63-7.51 (m, 1H), 7.34-7.27 (m, 1H), 7.07-7.01 (m, 2H), 6.91-6.85 (m, 1H), 5.24-5.16 (m, 1H), 3.82 (s, 3H), 3.25-3.07 (m, 2H), 2.63 (s, 3H) ppm.

Embodiment 70

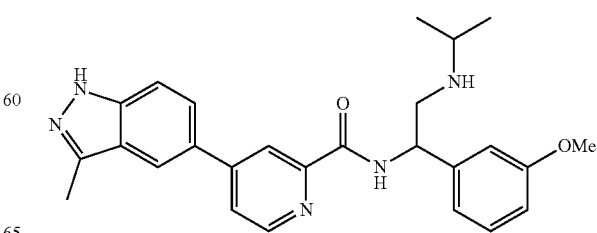

Synthetic Route:

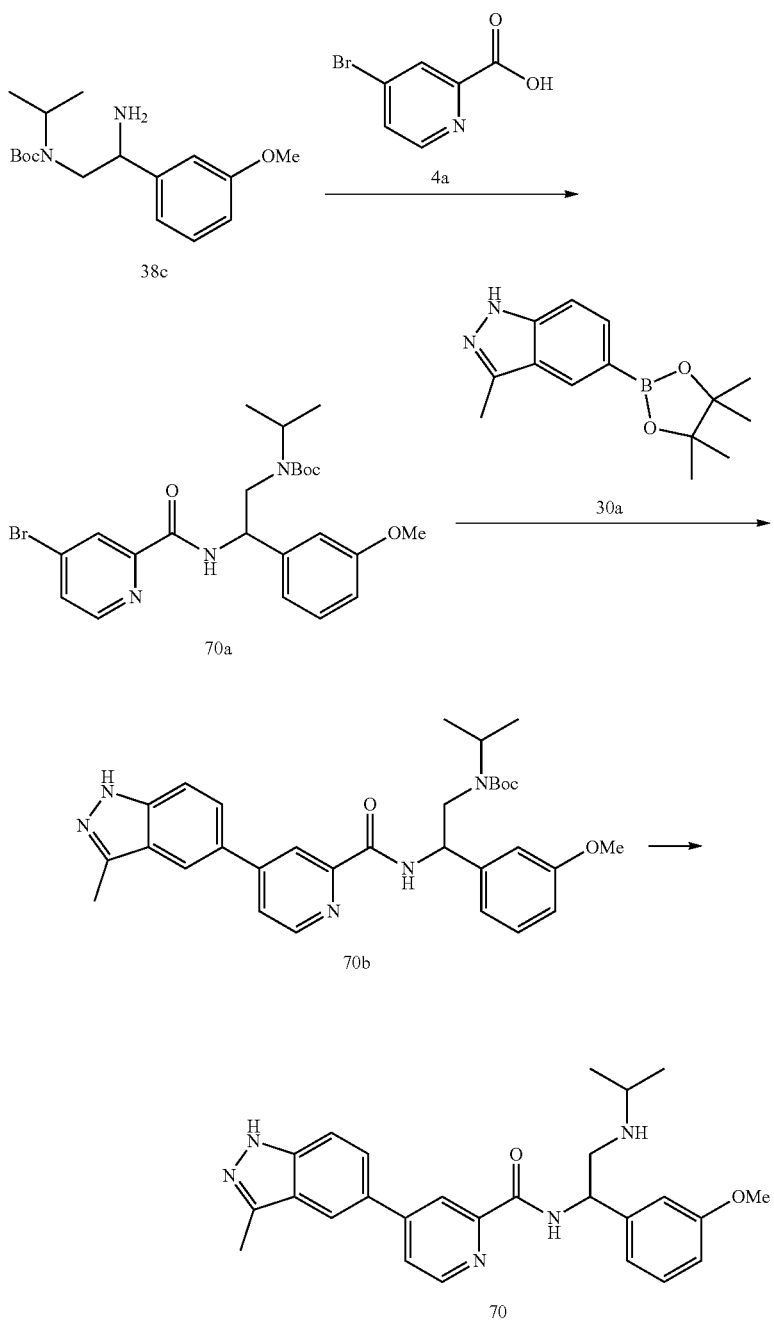

Step 1

Compound 70a was obtained by referring to Step 1 of Embodiment 1.

Step 2

Compound 70b was obtained by referring to Step 6 of Embodiment 35.

MS-ESI calculated value [M+H]$^+$ 544, measured value 544.

Step 3

Compound 70 was obtained by referring to Step 5 of Embodiment 38.

MS-ESI calculated value [M+H]$^+$ 444, measured value 444.

$^1$H NMR (400 MHz, DMSO-d$_6$) δ 10.13 (br, 1H), 9.36 (br, 1H), 8.91 (s, 1H), 8.79 (d, J=5.6 Hz, 1H), 8.73-8.71 (m, 1H), 8.60 (s, 1H), 8.27-8.25 (m, 1H), 7.99 (dd, J=1.6, 8.8 Hz, 1H), 7.64 (d, J=8.8 Hz, 1H), 7.35-7.28 (m, 1H), 7.18 (d, J=1.6 Hz, 1H), 7.11 (d, J=7.6 Hz, 1H), 6.91-6.88 (m, 1H), 5.61-5.50 (m, 1H), 3.77 (s, 4H), 3.46-3.21 (m, 2H), 2.61 (s, 3H), 1.34-1.28 (m, 6H) ppm.

Embodiment 71

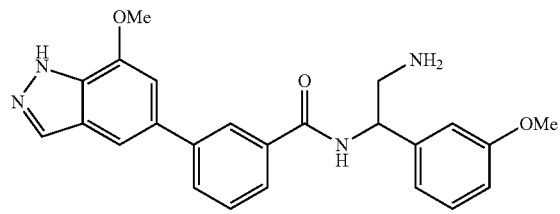 [SMILES: NCC(NC(=O)c1cccc(-c2ccc3[nH]ncc3c2)c1)c1cccc(F)c1]

Synthetic Route:

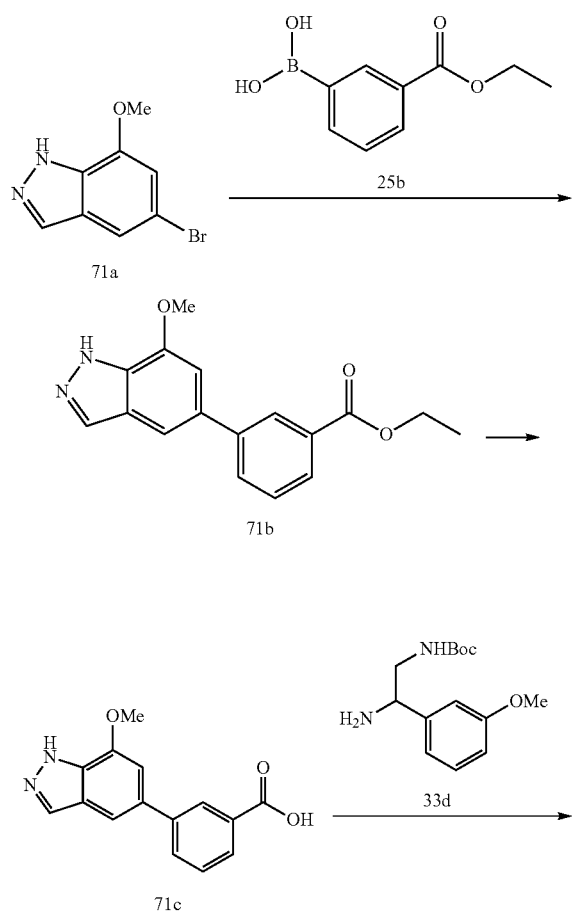

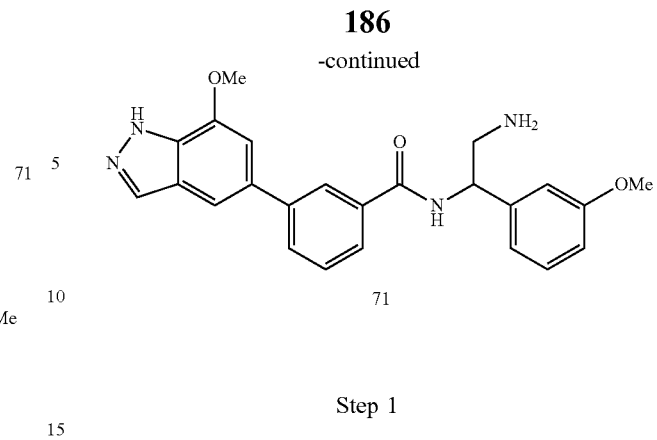

Step 1

Compound 71b was obtained by referring to Step 1 of Embodiment 68.

Step 2

Compound 71c was obtained by referring to Step 6 of Embodiment 68.

Step 3

Compound 71d was obtained by referring to Step 7 of Embodiment 68.

Step 4

Compound 71d (500 mg, 968 μmol) was dissolved in dioxane (5 mL), and then a solution of hydrogen chloride in dioxane (4 M, 5 mL) was added thereto. The reaction mixture was stirred at 10° C. for 12 hours. After the completion of the reaction, the reaction mixture was concentrated under reduced pressure, and the residue was purified by high performance liquid chromatography (basic condition) to give compound 71.

MS-ESI calculated value [M+H]$^+$ 417, measured value 417.

$^1$H NMR (400 MHz, DMSO-d$_6$) δ 8.82 (d, J=8.0 Hz, 1H), 8.22 (s, 1H), 8.14-8.10 (m, 1H), 7.93-7.83 (m, 2H), 7.67 (d, J=1.2 Hz, 1H), 7.61-7.53 (m, 1H), 7.29-7.21 (m, 1H), 7.17-7.13 (m, 1H), 7.02-6.95 (m, 2H), 6.86-6.78 (m, 1H), 5.05-4.91 (m, 1H), 4.06 (s, 3H), 3.75 (s, 3H), 2.97-2.83 (m, 2H) ppm.

Embodiment 72

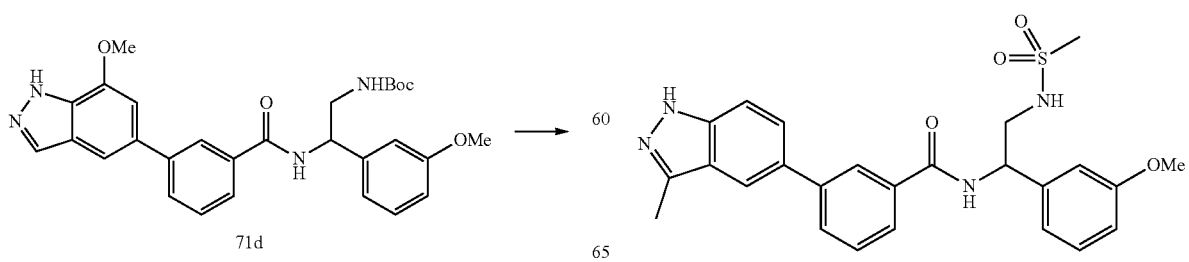

Synthetic Route:

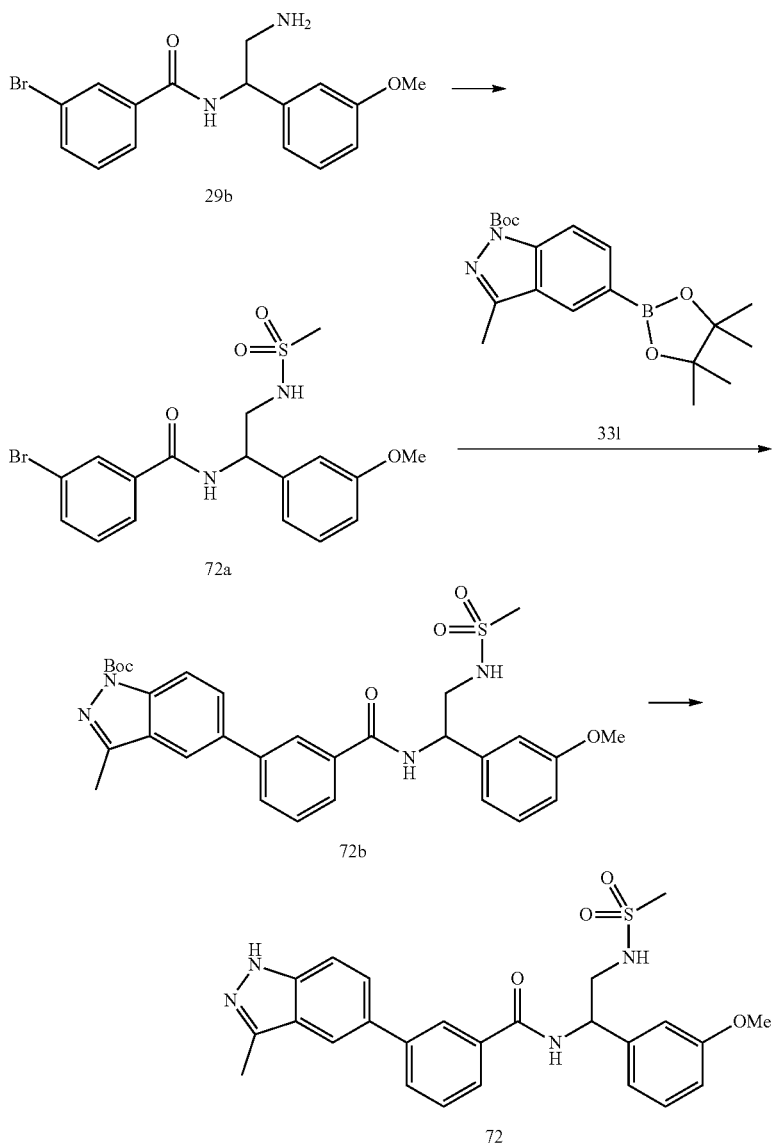

Step 1

Compound 29b (300 mg, 859 μmol) was dissolved in dichloromethane (5 mL), then triethylamine (261 mg, 2.58 mmol, 359 μL) and methanesulfonyl chloride (98.4 mg, 859 μmol, 66.5 μL) were added to the reaction mixture at 0° C., after the addition, the mixture was warmed to 10° C. and stirred for 1 hour. After the completion of the reaction, the mixture was quenched by adding water (10 mL) and extracted with ethyl acetate (10 mL×2). The combined organic phase was washed with saturated brine (10 mL), filtered, and the filtrate was concentrated under reduced pressure to give crude compound 72a.

Step 2

Compound 72b was obtained by referring to Step 6 of Embodiment 35.

Step 3

Hydrochloride of compound 72 was obtained by referring to Step 7 of Embodiment 35.

MS-ESI calculated value [M+H]$^+$ 479, measured value 479.

$^1$H NMR (400 MHz, DMSO-d$_6$) δ 8.89 (d, J=8.8 Hz, 1H), 8.23 (s, 1H), 8.06 (s, 1H), 7.96-7.82 (m, 2H), 7.73 (d, J=8.8 Hz, 1H), 7.64-7.53 (m, 2H), 7.39-7.32 (m, 1H), 7.31-7.25 (m, 1H), 7.10-7.00 (m, 2H), 6.89-6.82 (m, 1H), 5.25-5.17 (m, 1H), 3.76 (s, 3H), 3.50-3.34 (m, 2H), 2.87 (s, 3H), 2.56 (s, 3H) ppm.

Activity Test

1. In Vitro Evaluation of the Inhibitory Activity Against ROCK Protein Kinase

Experimental purpose: to detect the inhibitory IC$_{50}$ value of the compound against ROCK protein kinase.

Experimental Materials:

Assay buffer solution: 20 mM 4-hydroxyethylpiperazine ethanesulfonic acid (pH 7.5), 10 mM magnesium chloride, 1 mM ethylene glycol-bis-(2-aminoethyl)tetraacetic acid, 0.02% polyethylene glycol monododecyl ether, 0.02 mg/mL bovine serum albumin, 0.1 mM sodium vanadate, 2 mM dithiothreitol, 1% DMSO.

Experimental Operation:

The freshly prepared buffer solution was added to ROCK protein kinase substrate (Long S6 Kinase substrate peptide), at a concentration of 20 µM, then 1 nM ROCK protein kinase was added thereto and stirred evenly. Echo550 was used to add a series of DMSO dilutions containing the test compound (starting from 10 µM, serially diluted by 3 times), the solution was pre-incubated at room temperature for 20 minutes, then $^{33}$P-ATP (radiation intensity 10 µCi/µL) was added to initiate the reaction, and the reaction was performed at room temperature for two hours. Then the solution was filtered by P81 ion exchange paper (Whatman #3698-915) and washed with 0.75% phosphoric acid. The radiation intensity was determined by Filter-Binding method.

The protein kinase inhibitory activity of the compound was expressed as the remaining protein kinase activity relative to the blank substrate (simply DMSO). Prism software package (GraphPad Software, San Diego Calif., USA) was used to calculate $IC_{50}$ value and the curve.

Experimental Results:

TABLE 1

ROCK inhibitory activity test results

| Compound | $IC_{50}$ against ROCK1 (nM) | $IC_{50}$ against ROCK2 (nM) |
|---|---|---|
| 1(Hydrochloride) | 1639 | 21 |
| 2(Hydrochloride) | 79 | <1.0 |
| 3(Hydrochloride) | 765 | 11 |
| 4(Hydrochloride) | 288 | 6 |
| 5 | 33 | 6 |
| 6 | 63 | 7 |
| 7(Formate) | 24 | 4 |
| 8(Formate) | 166 | 10 |
| 9 | 25 | 4 |
| 10(Formate) | 79 | 6 |
| 11 | 79 | 5 |
| 12 | 257 | 12 |
| 13 | 139 | 16 |
| 14 | 103 | 8 |
| 15 | 278 | 12 |
| 16 | 259 | 26 |
| 17 | — | 23 |
| 18 | — | 29 |
| 19 | 735 | 35 |
| 20 | 304 | 35 |
| 21 | — | 3 |
| 22(Hydrochloride) | 52 | 6 |
| 23(Hydrochloride) | 29 | 7 |
| 24(Hydrochloride) | 126 | 14 |
| 25 | 89 | 5 |
| 26 | 113 | 16 |
| 27 | 407 | 30 |
| 28(Hydrochloride) | 43 | 13 |
| 29(Hydrochloride) | 65 | 7 |
| 30 | 43 | 3 |
| 31 | 223 | 20 |
| 32(Formate) | 343 | 23 |
| 33(Formate) | — | 16 |
| 34 | 1426 | 17 |
| 35(Hydrochloride) | 317 | 13 |
| 36 | 73 | 10 |
| 37(Hydrochloride) | 290 | 7 |
| 38(Hydrochloride) | 75 | 14 |
| 39(Hydrochloride) | 429 | 15 |
| 40 | 57 | 4 |
| 40-1 | 13 | 2 |
| 41(Hydrochloride) | — | 21 |
| 42(Hydrochloride) | — | 4 |
| 43(Hydrochloride) | 153 | 6 |
| 44(Hydrochloride) | 106 | 4 |
| 45(Hydrochloride) | 1274 | 19 |
| 46(Hydrochloride) | 267 | 8 |
| 47(Hydrochloride) | 67 | 12 |
| 48(Hydrochloride) | 84 | 9 |
| 49(Hydrochloride) | 1204 | 31 |
| 50(Hydrochloride) | 56 | 5 |
| 51(Hydrochloride) | 50 | 7 |
| 52(Hydrochloride) | 182 | 10 |
| 53(Hydrochloride) | 1092 | 20 |
| 54(Hydrochloride) | 180 | 21 |
| 55(Formate) | 4117 | 51 |
| 56(Hydrochloride) | 2300 | 44 |
| 57(Hydrochloride) | 1255 | 58 |
| 58(Hydrochloride) | 1613 | 48 |
| 59 | 94 | 16 |
| 60 | 215 | 44 |
| 61(Hydrochloride) | 253 | 23 |
| 62(Hydrochloride) | 289 | 48 |
| 63(Hydrochloride) | — | 35 |
| 64 | 798 | 46 |
| 65(Formate) | 138 | 4 |
| 66(Hydrochloride) | 193 | 11 |
| 67(Hydrochloride) | 336 | 22 |
| 68(Hydrochloride) | — | 8 |
| 69 | — | 12 |
| 70(Hydrochloride) | — | 24 |
| 71 | 758 | 9 |
| 72(Hydrochloride) | 587 | 12 |

— represents for not tested

Conclusion: The compounds of the present disclosure have a good inhibitory activity against ROCK2, and have certain selectivity to ROCK2 simultaneously.

2. In Vitro Evaluation of the Inhibitory Effect of the Compounds on the Expression of α-SMA Experimental purpose: to detect the inhibitory effect of the compound on the expression of α-SMA.

Experimental Materials:

NIH-3T3 cells were purchased from Shanghai Cell Bank, Chinese Academy of Sciences. TRIzol reagent was purchased from Invitech, genomic DNA removal reverse transcription kit was purchased from Tiangen Biochemical, real-time fluorescent quantitative PCR premix was purchased from Nanjing Novozan, isopropanol and chloroform was purchased from Sinopharm.

Experimental Operation:

The NIH-3T3 cells with a growth confluence of 80% were digested with 0.25% trypsin to form a single cell suspension, and dispensed in a 6-well plate. The cell plate was placed in a 37° C., 5% $CO_2$ incubator for overnight culture. The compound was prepared on the next day, 10 mM of the compound to be tested was diluted to 200 µM, and the solution was added to the 6 well plate in an amount of 10 µL per well and incubated overnight. The final concentration of the compound was 1 µM and the final concentration of DMSO was 1%.

After the drug treatment reached the incubation time, the medium was removed, 1 mL Trizol reagent was added into each well of the 6-well plate, and RNA was extracted according to the instructions. The overall RNA was extracted and quantified. 1 µg RNA was used to perform cDNA synthesis according to the operation method of the reverse transcription kit. After cDNA synthesis was completed, the cDNA template, the forward and reverse primers and the fluorescence quantitative PCR premix were used to prepare qPCR system for reaction. The reaction conditions were as follows: reacting at 50° C. for 2 minutes, reacting at 95° C. for 10 minutes; reacting at 95° C. for 30 seconds and at 60° C. for 30 seconds, and reacting at 95° C. for 30 seconds and at 60° C. for 30 seconds repeatedly for 40 cycles in total. After the completion of the reaction, the CT value of the reaction was derived to calculate the relative expression of the samples.

Data Analysis:

The relative gene expression level $2^{-\Delta\Delta CT}$ was calculated, and two-tailed T test was used for significance analysis (test concentration of the compound was 1 µM).

The experimental results are shown in FIG. 1. (the abscissa shows the number of embodiments, the ordinate shows $2^{-\Delta\Delta CT}$, and in the figure, the "*" indicates that the P value is less than 0.05, the difference is significant; the "" means the P value is less than 0.01, the difference is very significant; the "*" means the P value is less than 0.001, and the difference is quite significant).

Conclusion: The compounds of the present disclosure have a good inhibitory activity on the expression of α-SMA gene.

3. In Vitro Evaluation of the Inhibitory Activity of the Compounds Against the Contraction of Collagen by Fibroblasts Experimental purpose: to detect the ability of the compounds to inhibit the contraction of collagen by fibroblasts, and to evaluate the anti-fibrotic effect of the compounds.

Experimental materials: Human lung fibroblasts HFL-1, rattail type I collagen (Invitrogen, A1048301), 2× Dulbecco's modified Eagle's media (Millipore, SLM-202-B), DMEM medium (Dulbecco's Modified Eagle's Media, Gibco, 11965-092), F-12K medium (Ham's F-12K (Kaighn's) Medium, Gibco, 21127-022), sodium bicarbonate solution (Gibco, 25080-094), penicillin/streptomycin (HyClone, SC30010), 0.25% pancreatin (Gibco, 25200-072), fetal bovine serum (HyClone, SV30087.03), bovine serum albumin (Absin, abs49001012b), Dulbecco's phosphate buffered saline, (Corning, 21-031-CVR).

Experimental Operation:

3.1 Reagent Preparation (1) 5 mL of sodium bicarbonate solution was added to 45 mL of 2× Dulbecco's modified Eagle's media.

(2) HFL-1 culture medium: 10% (v/v) fetal bovine serum and 1% (v/v) penicillin/streptomycin were added to F-12K medium.

3.2 Coating of HFL-1 Cells with Collagen (1) A48-well cell culture plate was coated with Dulbecco's phosphate buffered saline containing 2% bovine serum albumin at 37° C. for 2 hours in an amount of 600 µL liquid per well, and was washed twice with Dulbecco's phosphate buffered saline.

(2) The cultured cells were taken out, the culture medium was discarded, and the cells were rinsed with Dulbecco's phosphate buffered saline. The culture flask was added with 4 mL trypsin, followed by digestion in a 37° C. incubator for 3 minutes. The digestion was terminated by adding culture medium, and the mixture was centrifuged at 300 g for 3 minutes.

(3) The cells were resuspended with Dulbecco's modified Eagle's media and counted, and the cell concentration was adjusted to 6*10⁵ cells/mL. The cell suspension, 2× Dulbecco's modified Eagle's media, and rat tail type I collagen were mixed at a ratio of 1:2:1, and added to the culture plate in an amount of 300 µL per well, and the culture plate was placed in a 37° C. 5% $CO_2$ incubator for 1 hour.

3.3 Addition of Drugs (1) The compound was prepared to a required concentration and added to the culture medium.

(2) The culture plate was removed from the incubator, the collagen had already solidified at this time, and 300 µL of the culture medium containing the compound was added to the collagen, followed by incubation at 37° C. for 17 hours.

Data Analysis:

Gel imager was used for taking pictures, ImageJ software was used for measuring the contraction area of collagen, and Prism software was used for processing the data.

Figure 2:
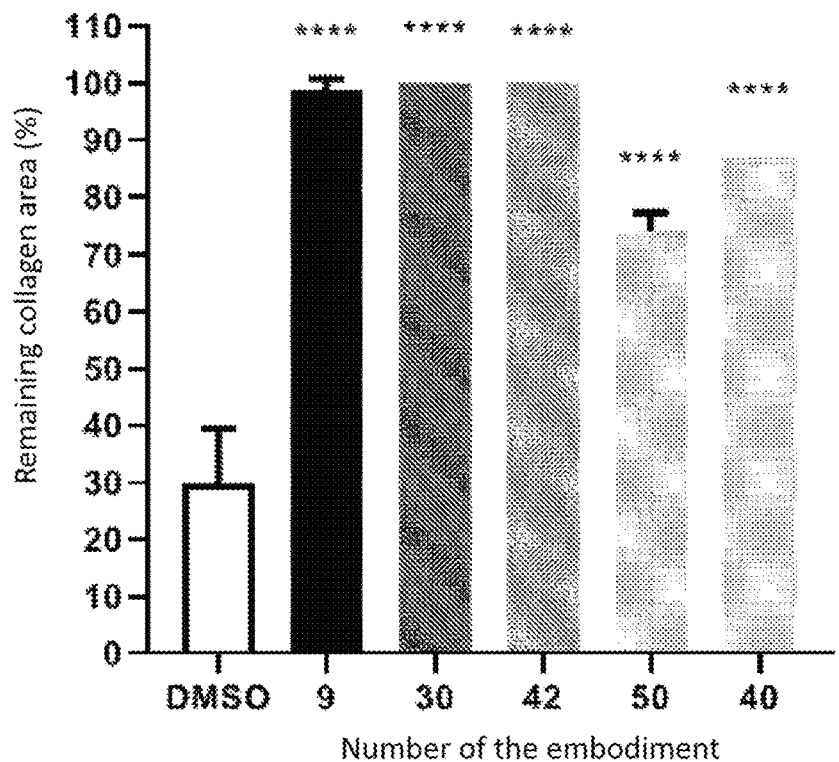
FIG. 2 shows the inhibitory effect of the embodiments 9, 30, 40, 42 and 50 of the present disclosure on collagen contraction induced by fibroblasts.

The experimental results are shown in FIG. 2. (the abscissa shows the number of embodiments, the ordinate shows the proportion of remaining area of collagen, and the significance analysis was performed by One-way ANOVA, wherein the "*" indicates that the P value is less than 0.05, the difference is significant; the "" means the P value is less than 0.01, the difference is very significant; the "*" means the P value is less than 0.001, and the difference is quite significant; and the "****" means the P value is less than 0.0001, and the difference is extremely significant).

Conclusion: The compound of the present disclosure can significantly inhibit collagen contraction caused by fibroblasts, and has good cytoskeleton regulation and anti-fibrosis activity.

4. Evaluation of the Pharmacokinetics of the Compound

Experimental purpose: to study the pharmacokinetics of the compounds in SD rats in vivo Experimental Materials:

SD rat (male, 7 to 10 weeks old, WTLH/SLAC)

Experimental Operation:

The rodent pharmacokinetic characteristics of the compounds after intravenous injection and oral administration were tested by standard protocols. In the experiment, the candidate compounds were formulated into 0.2 mg/mL clear solutions and were given to the rats by a single intravenous injection and oral administration. The vehicles of the intravenous injection and oral administration were both 5% DMSO/95% (10% hydroxypropyl β-cyclodextrin) aqueous solution. This project used four male SD rats and two of them were administered by intravenous injection at a dosage of 1 mg/kg, plasma samples were collected at 0.0833, 0.25, 0.5, 1, 2, 4, 6, 8, and 24 hours after administration, the other two rats were administered orally and intragastrically at a dosage of 2 mg/kg, plasma samples were collected at 0.25, 0.5, 1, 2, 3, 4, 6, 8, 24 hours after administration. The whole blood samples were collected within 24 hours and centrifuged at 3000 g for 15 minutes, and the supernatants were separated to give plasma samples. The plasma samples were added with an acetonitrile solution containing internal standard to precipitate protein, mixed thoroughly and centrifuged, and the supernatants were taken for injection. The blood drug concentration was quantitatively analyzed by LC-MS/MS analysis method, and the pharmacokinetic parameters (such as peak concentration ($C_{max}$), clearance rate (CL), half-life ($T_{1/2}$), tissue distribution (Vdss), area under the drug-time curve ($AUC_{0\text{-}last}$), and bioavailability (F), etc.) were calculated.

The pharmacokinetic parameters of the embodiments of the present disclosure in rats in vivo are shown in Table 2 below.

TABLE 2

Pharmacokinetic test results

| Compound | Peak concentration $C_{max}$ (nM) | Clearance rate CL (mL/min/kg) | Tissue distribution Vdss (L/kg) | Half-life $T_{1/2}$ (IV, h) | Area under the drug-time curve $AUC_{0-last}$ PO (nM · hr) | Bioavailability F (%) |
|---|---|---|---|---|---|---|
| 25 | 1180 | 6.24 | 1.15 | 2.91 | 6297 | 45 |
| 26 | 752 | 14 | 1.72 | 2.5 | 3043 | 51 |
| 35 (Hydrochloride) | 117 | 25.0 | 6.78 | 3.83 | 734 | 21 |
| 36 | 36.4 | 50.9 | 5.05 | 1.33 | 156 | 10 |
| 40 | 117 | 23.4 | 6 | 3.58 | 758 | 21 |
| 49 (Hydrochloride) | 157 | 23.1 | 8.31 | 4.82 | 1331 | 60 |
| 61 (Hydrochloride) | 55.6 | 30.8 | 4.72 | 2.37 | 266 | 11 |
| 64 | 17 | 88.3 | 16.4 | 2.83 | 100 | 12 |
| 66 (Hydrochloride) | 50.7 | 50.8 | 10.5 | 2.74 | 306 | 20.9 |
| 72 (Hydrochloride) | 99.4 | 55.7 | 1.79 | 0.62 | 148 | 11 |

Conclusion: The compounds of the present disclosure have good pharmacokinetic properties, including good oral bioavailability, oral exposure, half-life, and clearance rate, etc.

5. In Vivo Efficacy Test

Experimental purpose: To test the therapeutic effect of the compound on bleomycin-induced pulmonary fibrosis in SD rats.

Experimental Materials:

Animals: male SD rats.

Model: unilateral pulmonary fibrosis model of left lung in SD rats: bleomycin (3 mg/kg in 1.5 mL/kg) was administrated to the rats via tracheal injection for inducing pulmonary fibrosis model.

Modeling agent: bleomycin (BLM).

Experiment Operation:

1. Experimental grouping: the experimental grouping is shown in Table 3 below, there are three groups in total, namely the model group (the first group, n=8, vehicle group), the positive control drug (the second group, n=8, nintedanib, BIBF), test compound 25 (the third group, n=8, compound 25).

TABLE 3

Experimental grouping of pulmonary fibrosis induced by bleomycin

| Grouping | Number of Bleomycin animals (3.0 mg/kg) | Dosing compound | Dosage and frequency |
|---|---|---|---|
| First group | 8 injection | N/A | N/A |
| Second group | 8 injection | Nintedanib | 100 mpk, once a day |
| Third group | 8 injection | 25 | 10 mpk, once a day |

2. Experimental Operation:

After the animals were purchased, they were adaptively fed for 4 days before modeling. The animals were weighed and anesthetized by isoflurane inhalation. After the anesthesia of the animals was confirmed, the neck thereof was disinfected, the neck skin was cut open, blunt dissection of muscles were performed to expose the main trachea, a small opening was cut between the tracheal rings, a PE-20 tube was inserted to the left main bronchus, bleomycin was directly injected, and the trachea and skin was sutured. After the operation, the animals were kept warm on an electric blanket at 37° C. till they were completely awake, and were returned to the cage and fed normally after they were confirmed to be able to eat and drink freely. On the 8th day of modeling, the compound was administered orally and the treatment continued for 14 days. All animals were euthanized 24 hours after the last administration; the lungs were collected after systemic perfusion of low-temperature PBS through heart, and were reperfused with formalin to fullness, the tissues were fixed in 10% formalin solution for subsequent histopathological analysis.

3. Physiological Observation of Experimental Animals:

From the day of modeling, the weight changes of the animals were recorded every 2 days; the mental conditions of the animals were closely observed during the experiment, if the animal was found dead, a detailed death record and a death report were required.

Test Result Determination:

Histopathological examination of left lung: pathological evaluation by H&E staining: 1) pathological changes of terminal bronchioles and arterioles of the left lung, and, 2) pulmonary fibrosis area of the left lung, 3) pulmonary fibrosis Ashcroft score of left lung.

Figure 3:
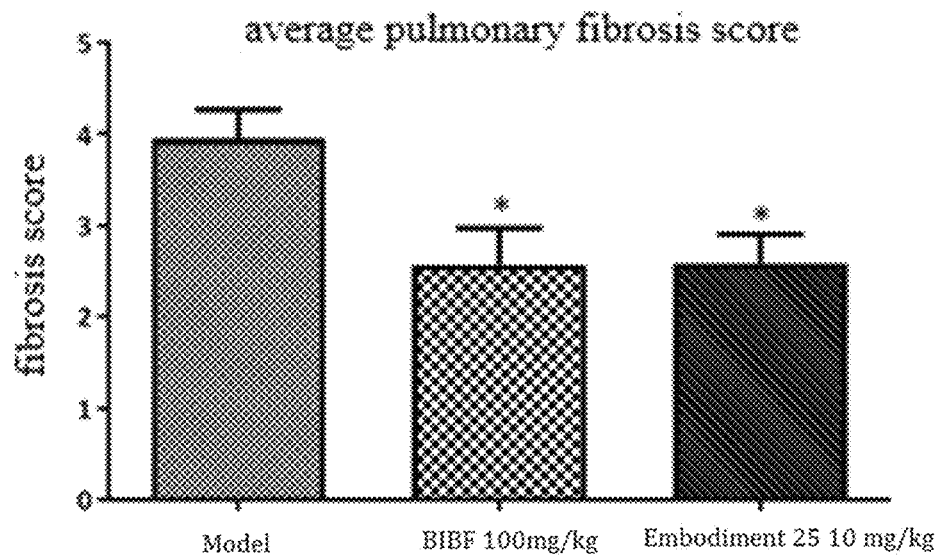
FIG. 3 shows the pulmonary fibrosis score of the embodiment 25 of the present disclosure.
Figure 4:
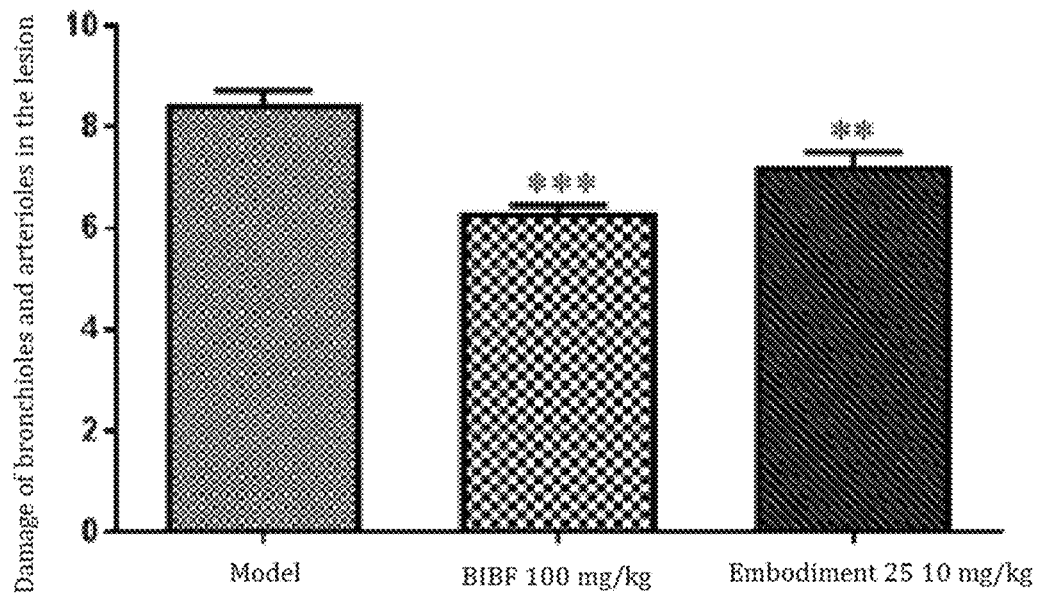
FIG. 4 shows the effect of the embodiment 25 of the present disclosure to the damage of bronchioles and arterioles in the lesion.
Figure 5:
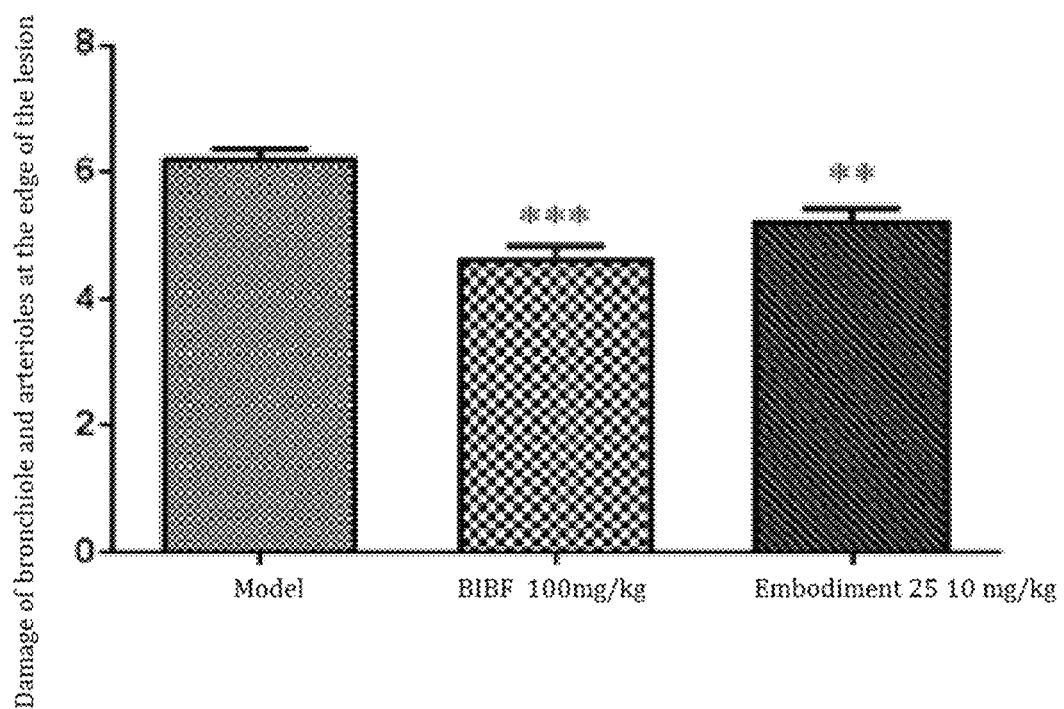
FIG. 5 shows the effect of the embodiment 25 of the present disclosure to the damage of bronchiole and arterioles at the edge of the lesion.

The experimental results are shown in FIG. 3, FIG. 4 and FIG. 5 (two-tailed T test was used for significance analysis of the experimental data. The "*" in the three figures indicates that the P value is less than 0.05, the difference is significant; the "" means the P value is less than 0.01, the difference is very significant; and the "*" means the P value is less than 0.001, and the difference is quite significant);

Conclusion: The compounds of the present disclosure can significantly improve the damage of the bronchioles and arterioles inside the lesion or at the edge of the lesion (FIG. 4 and FIG. 5), and can also reduce the pulmonary fibrosis score (FIG. 3), they can achieve the same efficacy as nintedanib (100 mpk) at a lower dosage (10 mpk).

What is claimed is:

1. A compound represented by formula (I-1), a pharmaceutically acceptable salt thereof or an isomer thereof, (I-1)

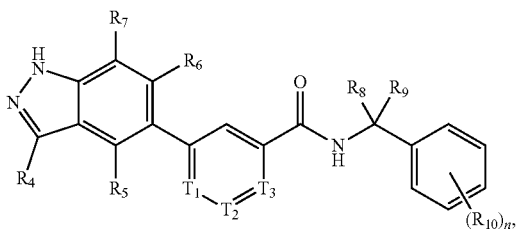

T₁ is N or CR₁; T₂ is N or CR₂; T₃ is N or CR₃;

R₁, R₂ and R₃ are each independently H, F, Cl, Br, CN, —OR_a, —C(═O)NR_bR_c or C₁₋₆ alkyl, wherein the C₁₋₆ alkyl is optionally substituted by 1, 2 or 3 substituents independently selected from F, Cl, Br, I, —OH, —OCH₃, —CN, —NH₂, —NO₂ or 5-membered heterocycloalkyl;

or, R₂ and R₃ with the carbon atoms to which they are attached are linked together so that the moiety

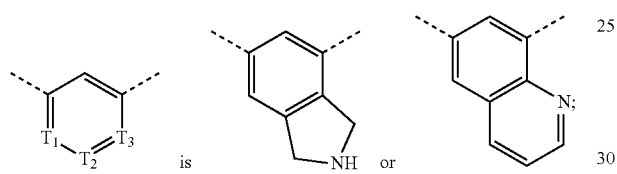

is

R₄, R₅, R₆ and R₇ are each independently H, F, Cl, Br, CN, —OR_a, —C(═O)NR_bR_c, —NR_dR_e, C₁₋₆ alkyl or C₃₋₆ cycloalkyl, wherein the C₁₋₆ alkyl and C₃₋₆ cycloalkyl are optionally substituted by 1, 2 or 3 substituents independently selected from F, Cl, Br, I, —OH, —OCH₃, —CN, —NO₂ or C₁₋₄ alkyl;

R₈ and R₉ are each independently H, F, Cl, C₁₋₆ alkyl, or R₈ and R₉ together with the carbon atom to which they are attached form a 5- to 6-membered heterocycloalkyl, wherein the C₁₋₆ alkyl and 5- to 6-membered heterocycloalkyl are optionally substituted by 1, 2 or 3 substituents independently selected from F, Cl, Br, CN, —OR_a or —NR_dR_e;

each of R₁₀ is independently F, Cl, Br, CN, —OR_a, C₁₋₆ alkyl or C₃₋₆ cycloalkyl, wherein the C₁₋₆ alkyl and C₃₋₆ cycloalkyl are optionally substituted by 1, 2 or 3 substituents independently selected from F, Cl, Br, I, —OH, —OCH₃, —CN, —NH₂, —NO₂ or C₁₋₄ alkyl;

R_a, R_b and R_c are each independently H, C₁₋₆ alkyl or C₃₋₄ cycloalkyl, wherein the C₁₋₆ alkyl and C₃₋₄ cycloalkyl are optionally substituted by 1, 2 or 3 substituents independently selected from F, Cl, Br, —OH, —OCH₃, —CN, —NH₂ or —NO₂;

R_d and R_e are each independently H, C₁₋₆ alkyl, —S(═O)₂C₁₋₃ alkyl, or R_d and R_e together with the N atom to which they are attached form a 4- to 8-membered heterocycloalkyl, wherein the C₁₋₆ alkyl and 4- to 8-membered heterocycloalkyl are optionally substituted by 1, 2 or 3 substituents independently selected from F, Cl, Br, —OH, —OCH₃, —CN, —NH₂, C₁₋₆ alkylamino or —NO₂;

n is 0, 1, 2, 3 or 4;

the 5-membered heterocycloalkyl, 5- to 6-membered heterocycloalkyl and 4- to 8-membered heterocycloalkyl contains 1, 2, 3 or 4 heteroatoms or heteroatomic groups independently selected from N, —O—, —S— and —NH—.

2. The compound, the pharmaceutically acceptable salt thereof or the isomer thereof as defined in claim 1, wherein R_a, R_b and R_e are each independently H, methyl, ethyl, n-propyl, isopropyl or cyclopropyl, wherein the methyl, ethyl, n-propyl, isopropyl and cyclopropyl are optionally substituted by 1, 2 or 3 substituents independently selected from F, Cl, Br, I, —OH, —OCH₃, CN, —NH₂ or —NO₂;

and/or, R₄, R₅, R₆ and R₇ are each independently H, F, Cl, Br, CN, —OH, —OCH₃, —OCH₂CH₃, —C(═O)NH₂, —NH₂, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH₃, CN, —NH₂, —NO₂, methyl, ethyl or propyl;

and/or, R₁, R₂ and R₃ are each independently H, F, Cl, Br, CN, —OH, —OCH₃, —OCHF₂, —OCF₃, —C(═O)NH₂, methyl, ethyl, n-propyl or isopropyl, wherein the methyl, ethyl, n-propyl and isopropyl are optionally substituted by 1, 2 or 3 substituents independently selected from F, Cl, Br, I, —OH, —OCH₃, CN, —NH₂, —NO₂ or pyrrolidyl;

and/or, the moiety

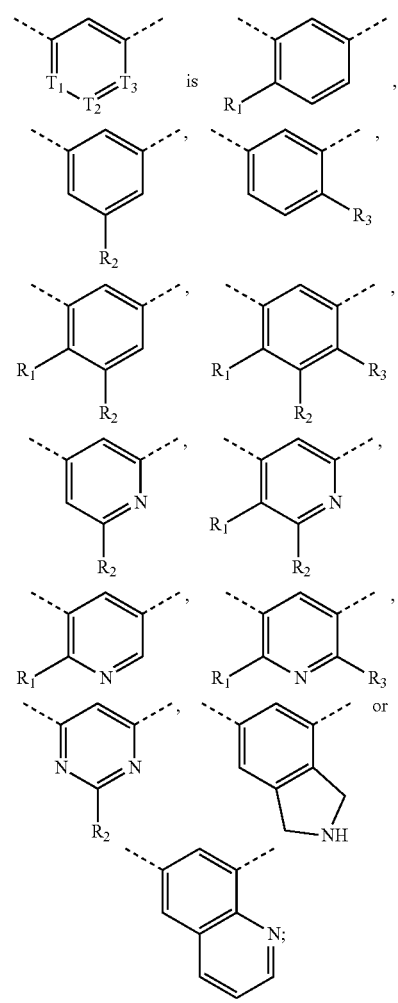

and/or, $R_d$ and $R_e$ are each independently H, methyl, ethyl, n-propyl, isopropyl,

or $R_d$ and $R_e$ together with the N atom to which they are attached form a 5- to 6-membered heterocycloalkyl, wherein the methyl, ethyl, n-propyl, isopropyl, and 5- to 6-membered heterocycloalkyl are optionally substituted by 1, 2 or 3 substituents independently selected from F, Cl, Br, I, —OH, —OCH$_3$, CN, —NH$_2$, C$_{1-3}$ alkylamino or —NO$_2$;

and/or, each of $R_{10}$ is independently F, Cl, Br, CN, —OH, —OCH$_3$, methyl, ethyl, n-propyl, isopropyl, cyclopropyl, cyclopentyl or cyclohexyl, wherein the methyl, ethyl, n-propyl, isopropyl, cyclopropyl, cyclopentyl and cyclohexyl are optionally substituted by 1, 2 or 3 substituents independently selected from F, Cl, Br, I, —OH, —OCH$_3$, CN, —NH$_2$, —NO$_2$, methyl, ethyl or propyl;

and/or, the moiety

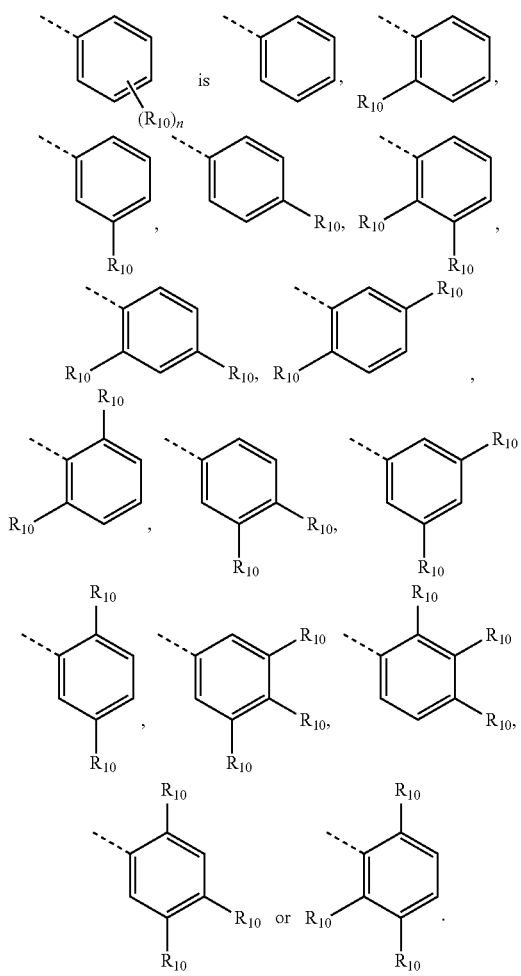

3. The compound, the pharmaceutically acceptable salt thereof or the isomer thereof as defined in claim 2, wherein, $R_a$, $R_b$ and $R_c$ are each independently H, methyl, ethyl, n-propyl, isopropyl,

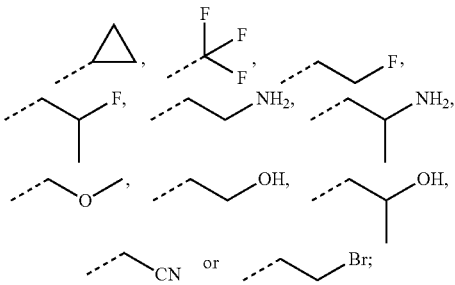

and/or, $R_4$, $R_5$, $R_6$ and $R_7$ are each independently H, F, Cl, Br, CN, —OH, —OCH$_3$, —OCH$_2$CH$_3$, —C(=O)NH$_2$, —NH$_2$, methyl, ethyl, n-propyl, isopropyl,

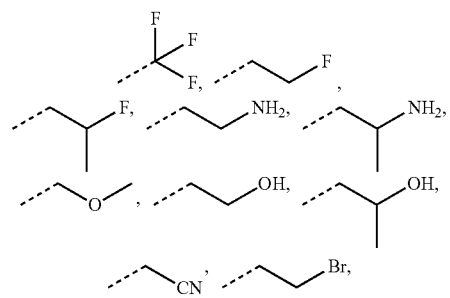

cyclopropyl, cyclopentyl, cyclohexyl,

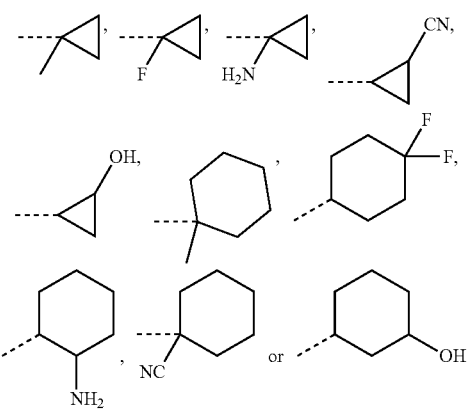

and/or, $R_1$, $R_2$ and $R_3$ are each independently H, F, Cl, Br, CN, —OH, —OCH$_3$, —OCHF$_2$, —OCF$_3$, —C(=O)NH$_2$, methyl, ethyl, n-propyl, isopropyl,

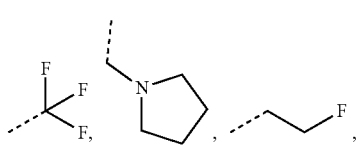

-continued

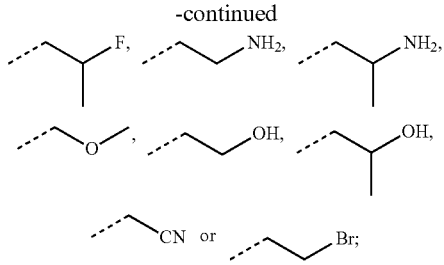

and/or, the moiety

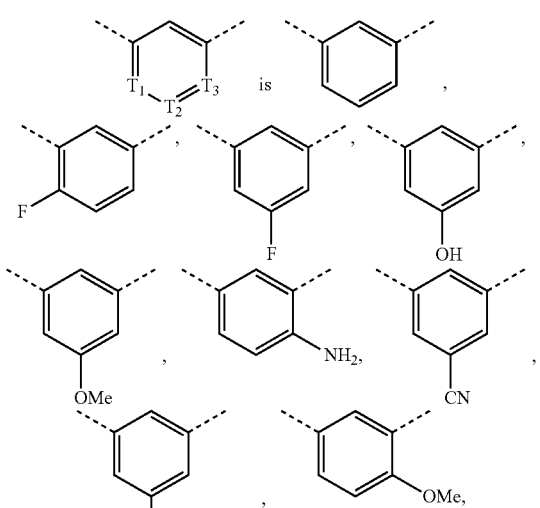

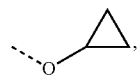

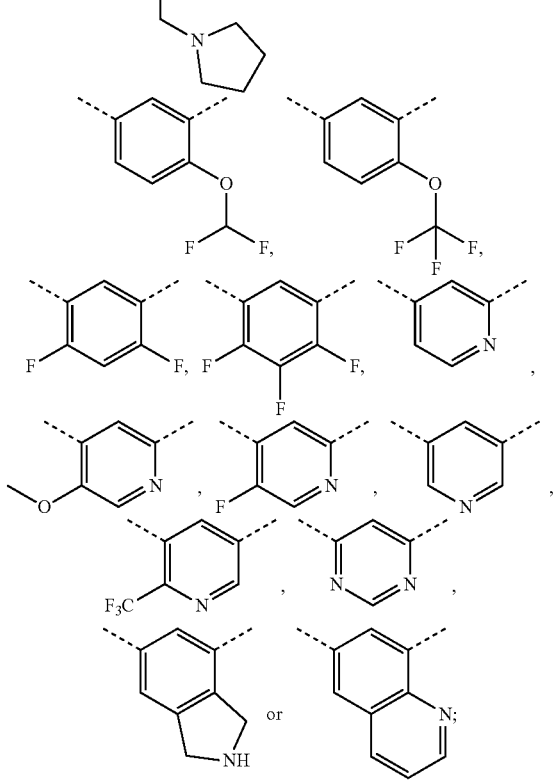

and/or, $R_d$ and $R_e$ are each independently H, methyl, ethyl, n-propyl, isopropyl,

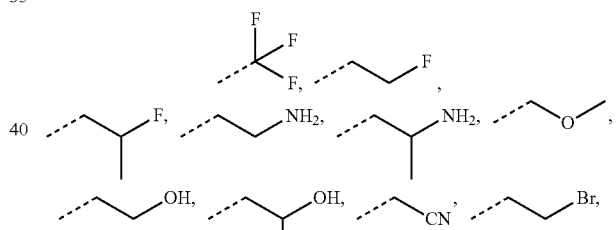

or $R_d$ and $R_e$ together with the N atom to which they are attached form a pyrrolidyl, piperazinyl or piperidyl, wherein the pyrrolidyl, piperazinyl and piperidyl are optionally substituted by 1, 2 or 3 substituents independently selected from F, Cl, Br, I, —OH, —OCH$_3$, CN, —NH$_2$, C$_{1-3}$ alkylamino or —NO$_2$;

and/or, each of $R_{10}$ is independently F, Cl, Br, CN, —OH, —OCH$_3$, —OCH$_2$CH$_3$, methyl, ethyl, n-propyl, isopropyl, cyclopropyl, cyclopentyl, cyclohexyl,

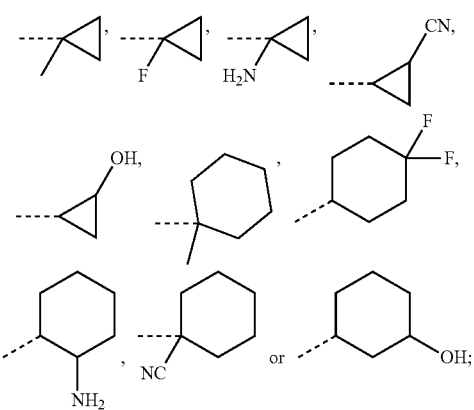

and/or, the moiety
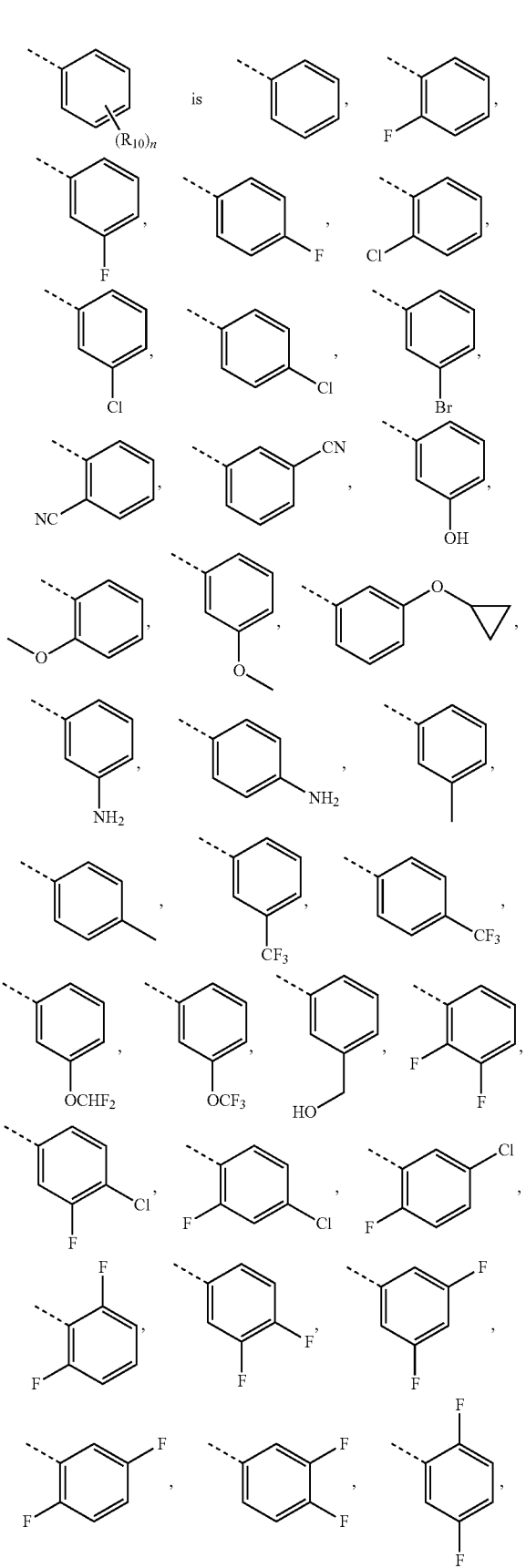
is
4. The compound, the pharmaceutically acceptable salt thereof or the isomer thereof as defined in claim 1, wherein $R_8$ and $R_9$ are each independently H, F, Cl, methyl, ethyl, n-propyl, isopropyl,
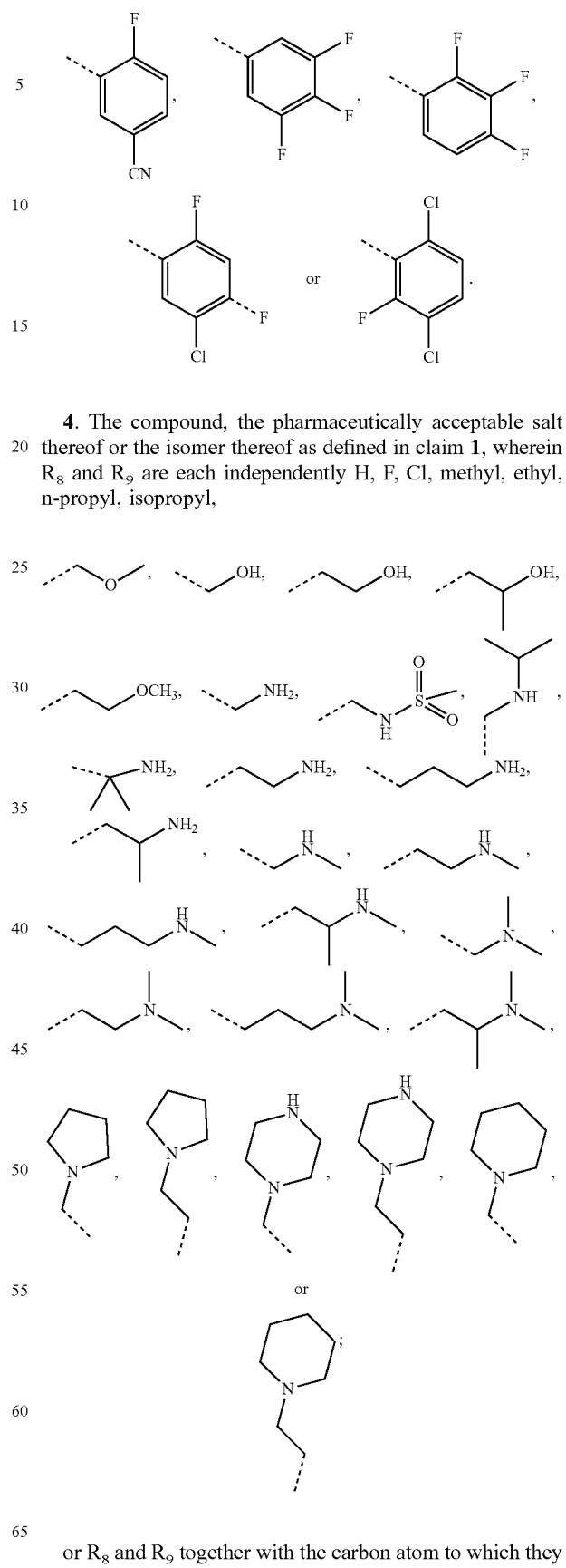
or $R_8$ and $R_9$ together with the carbon atom to which they are attached form

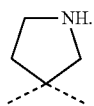

5. The compound, the pharmaceutically acceptable salt thereof or the isomer thereof as defined in claim 1, wherein the compound is represented by formula (I-2') to (I-5'), (I-2')

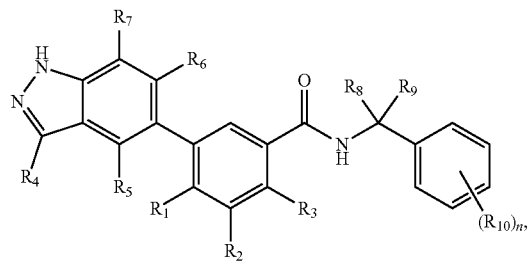

(I-3')

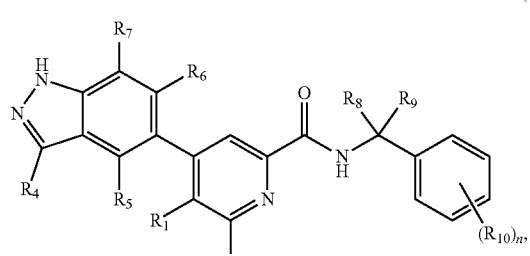

(I-4')

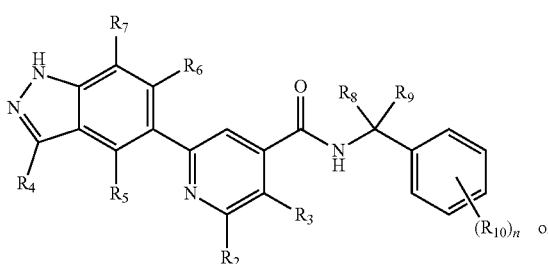

or (I-5')

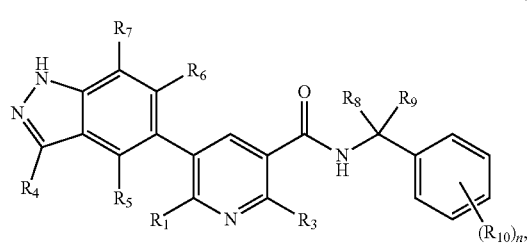

wherein, $R_1, R_2, R_3, R_4, R_5, R_6, R_7, R_8, R_9, R_{10}$ and n are as defined in claim 1.

6. The compound, the pharmaceutically acceptable salt thereof or the isomer thereof as defined in claim 1, wherein the compound is represented by formula (I-2) to (I-5), (I-2)

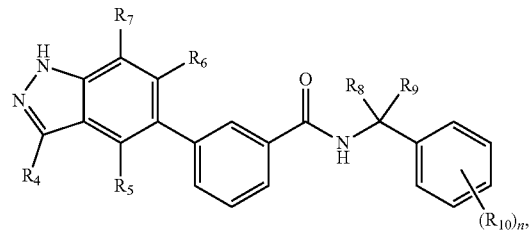

(I-3)

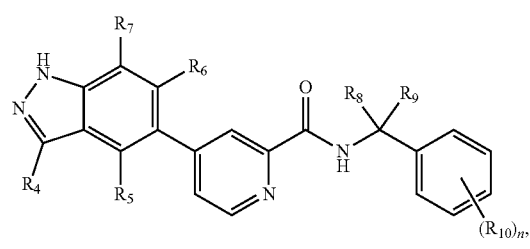

(I-4)

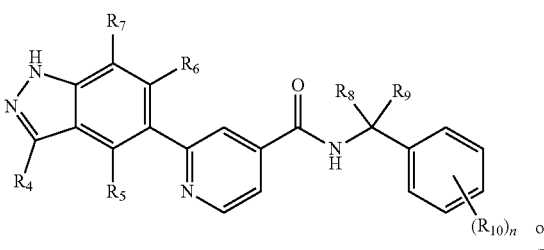

or (I-5)

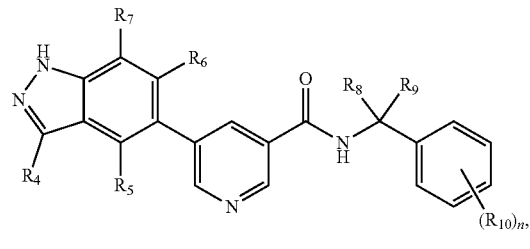

wherein, $R_4, R_5, R_6, R_7, R_8, R_9, R_{10}$ and n are as defined in claim 1.

7. The compound, the pharmaceutically acceptable salt thereof or the isomer thereof as defined in claim 6, wherein the compound is represented by formula (II-1) to (II-4), (II-1)

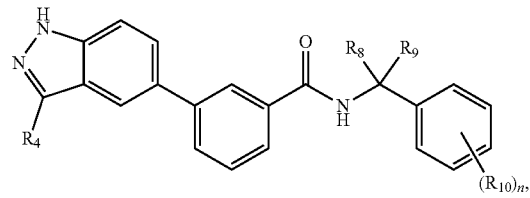

(II-2)

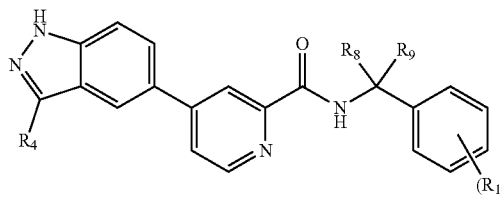

(II-3)

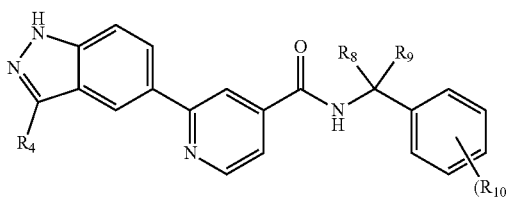

or (II-4)

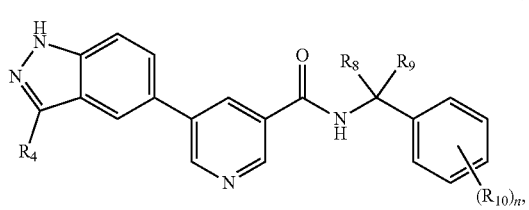

wherein, $R_4$, $R_8$, $R_9$, $R_{10}$ and n are as defined in claim 6.

8. The compound, the pharmaceutically acceptable salt thereof or the isomer thereof as defined in claim 7, wherein the compound is represented by formula (I-6) to (I-9), (I-6)

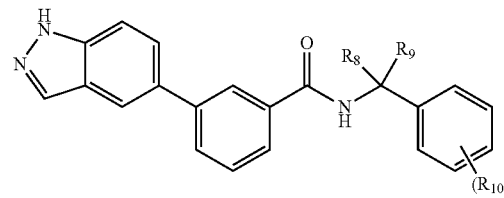

(I-7)

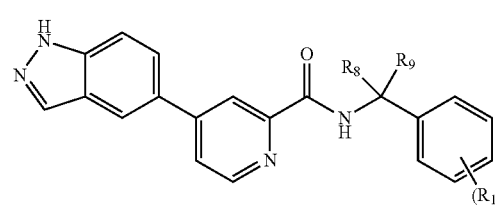

(I-8)

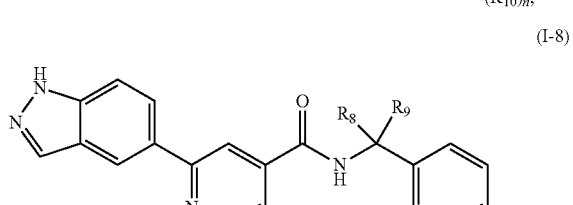

(I-9)

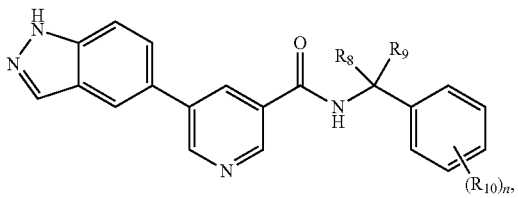

or, the compound is represented by formula (I-14) to (I-17), (I-14)

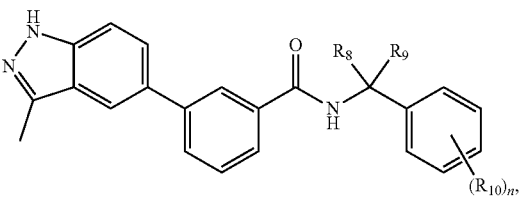

(I-15)

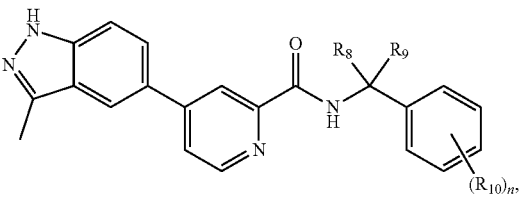

(I-16)

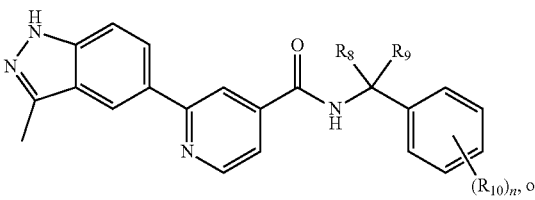

or (I-17)

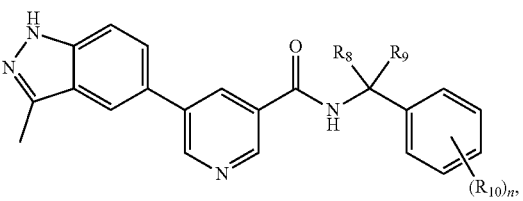

wherein, $R_8$, $R_9$, $R_{10}$ and n are as defined in claim 7.

9. The compound, the pharmaceutically acceptable salt thereof or the isomer thereof as defined in claim 8, wherein the compound is represented by formula (I-10) to (I-13),

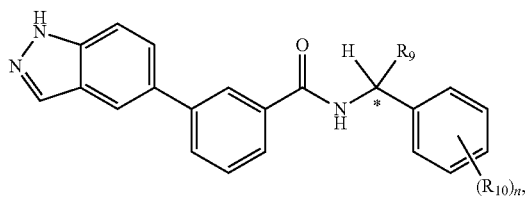
(I-10)
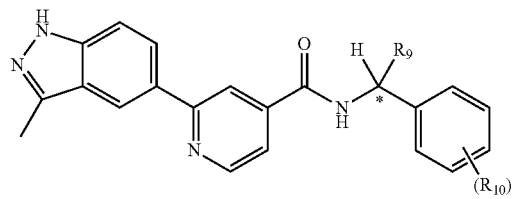
(I-20)
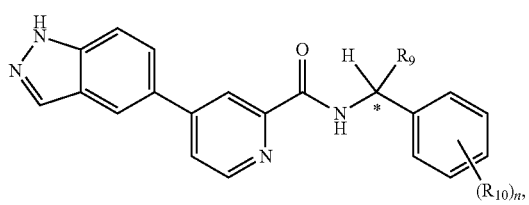
(I-11)
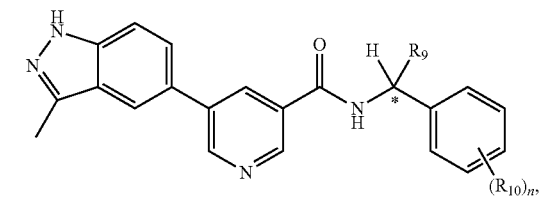
(I-21)
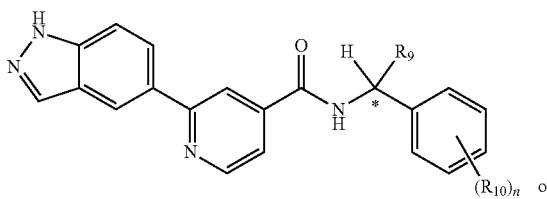
(I-12)
wherein, the carbon atom labeled with "*" is a chiral carbon atom, and exists in the form of (R) or (S) single enantiomer or enriched in one enantiomer;
$R_9$ is F, Cl, methyl, ethyl, n-propyl, isopropyl,
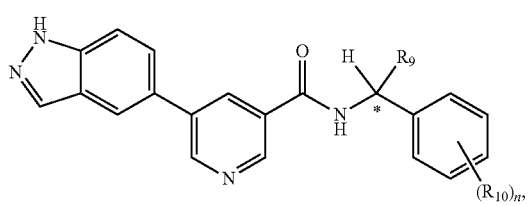
(I-13)
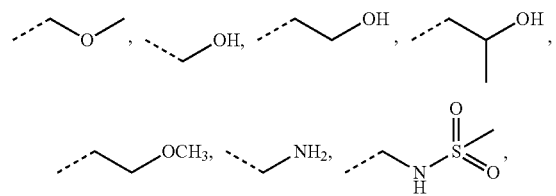
or, the compound is represented by formula (I-18) to (I-21),
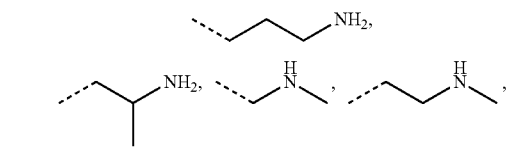
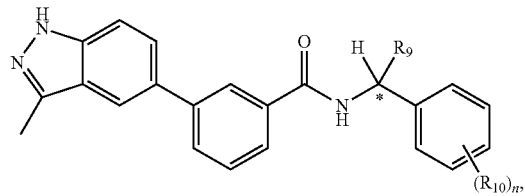
(I-18)
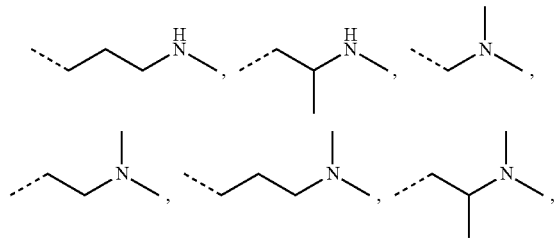
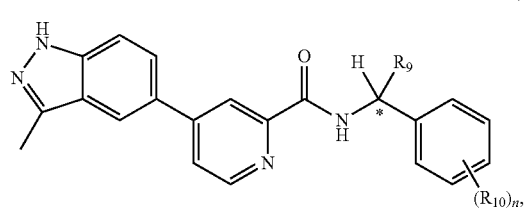
(I-19)
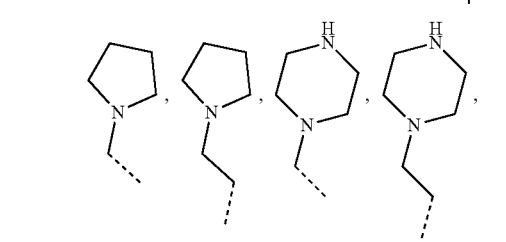

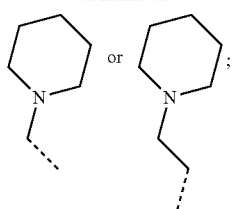 or 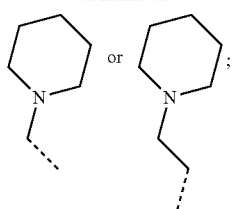;
R₁₀ and n are as defined in claim 8.
10. A compound represented by the following formula, a pharmaceutically acceptable salt thereof or an isomer thereof:
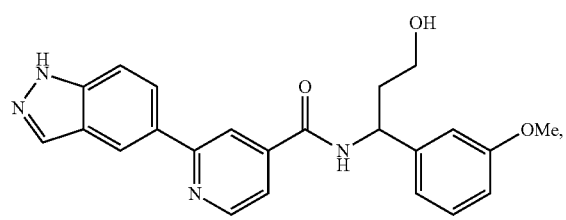
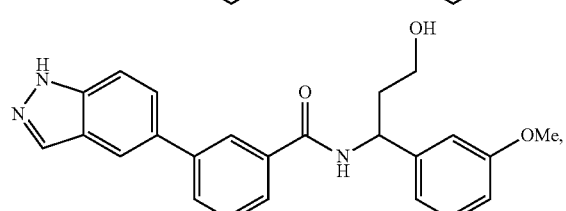
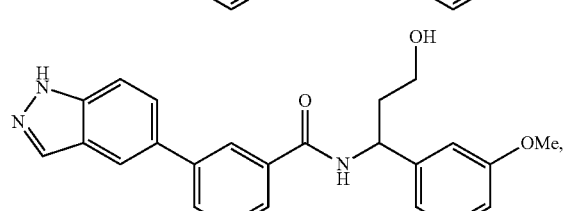
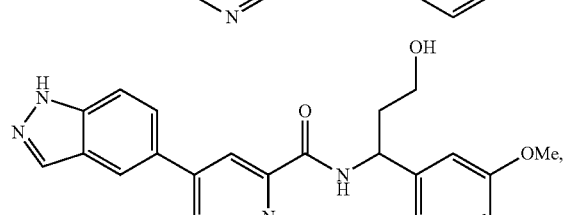
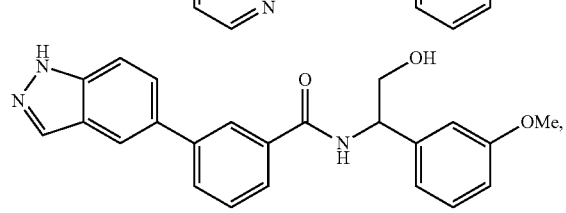
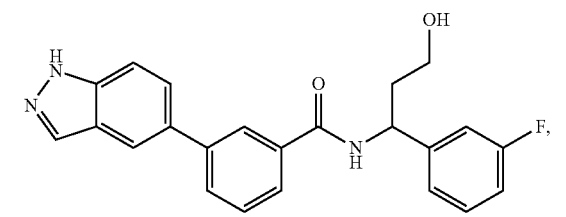
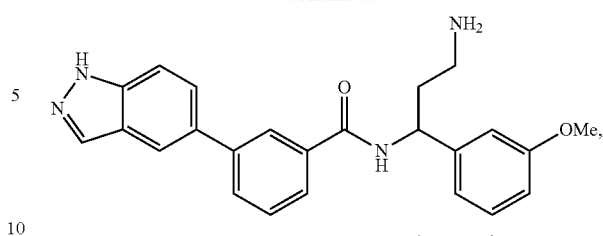
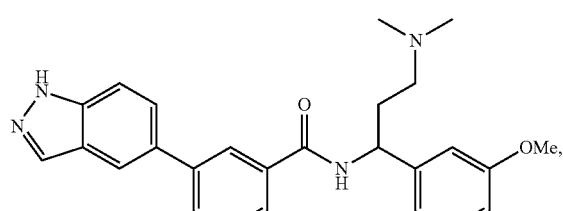
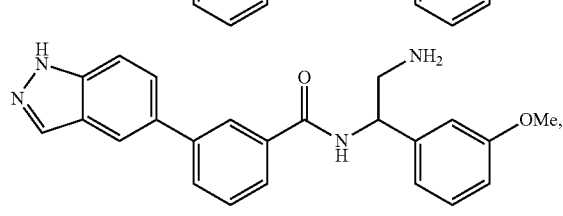
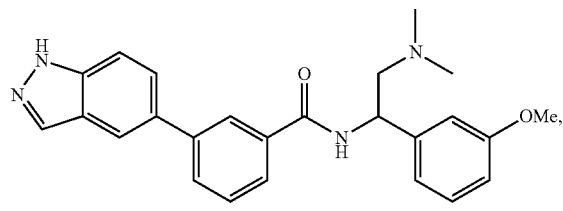
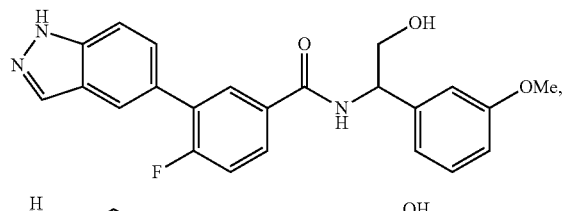
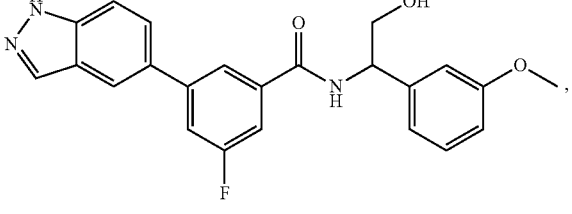
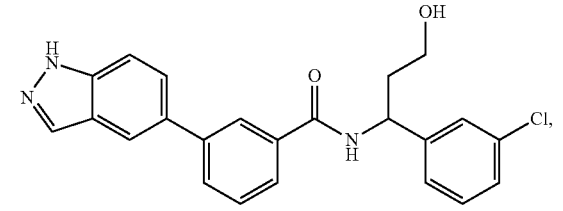
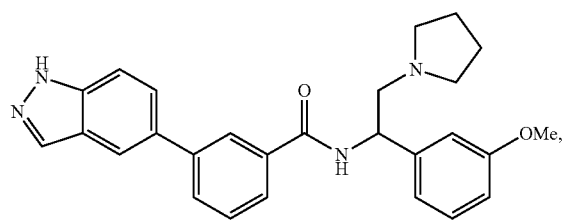

211
-continued
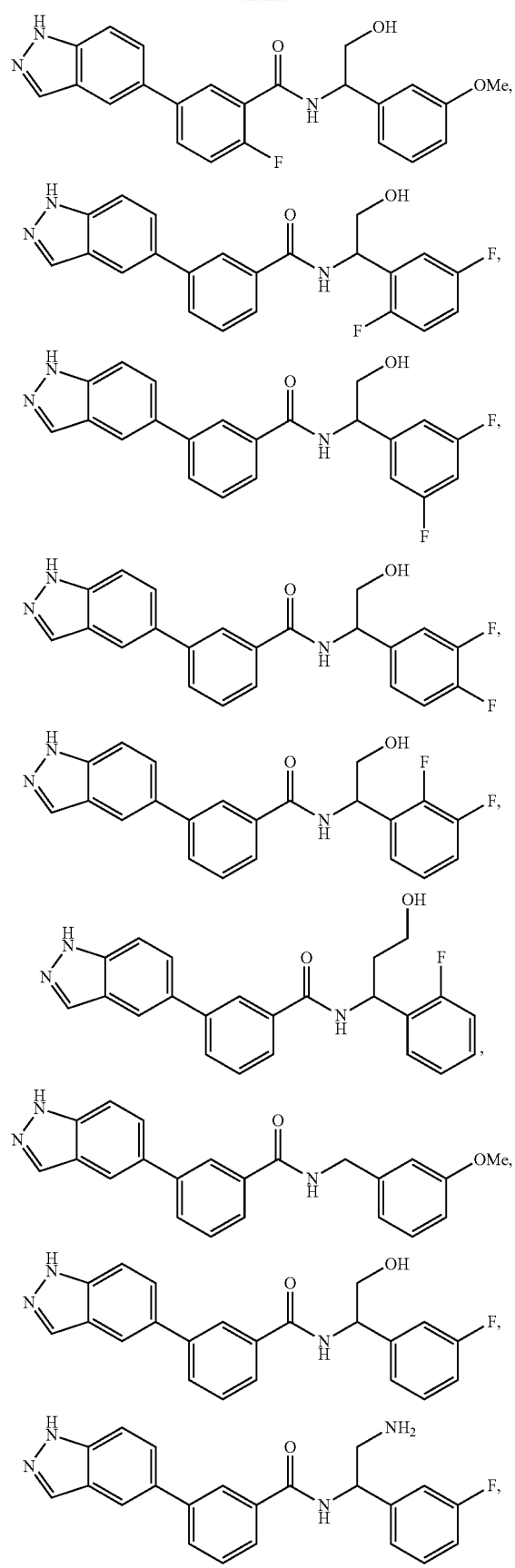
212
-continued
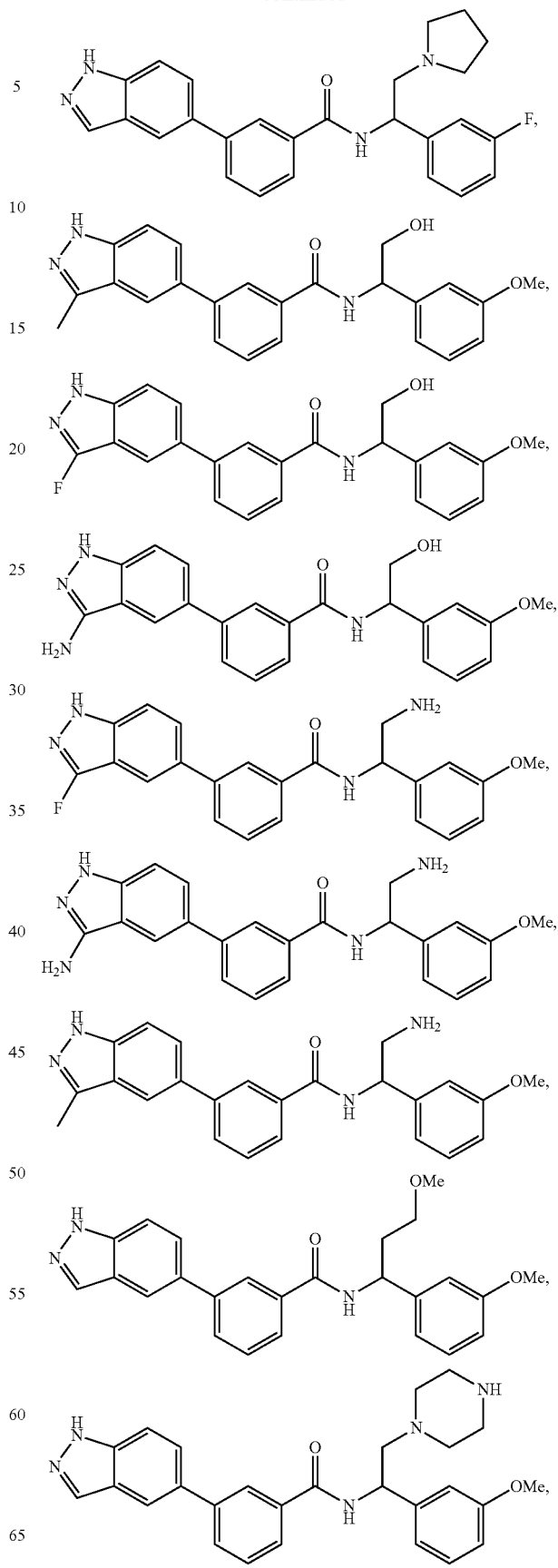

213
-continued
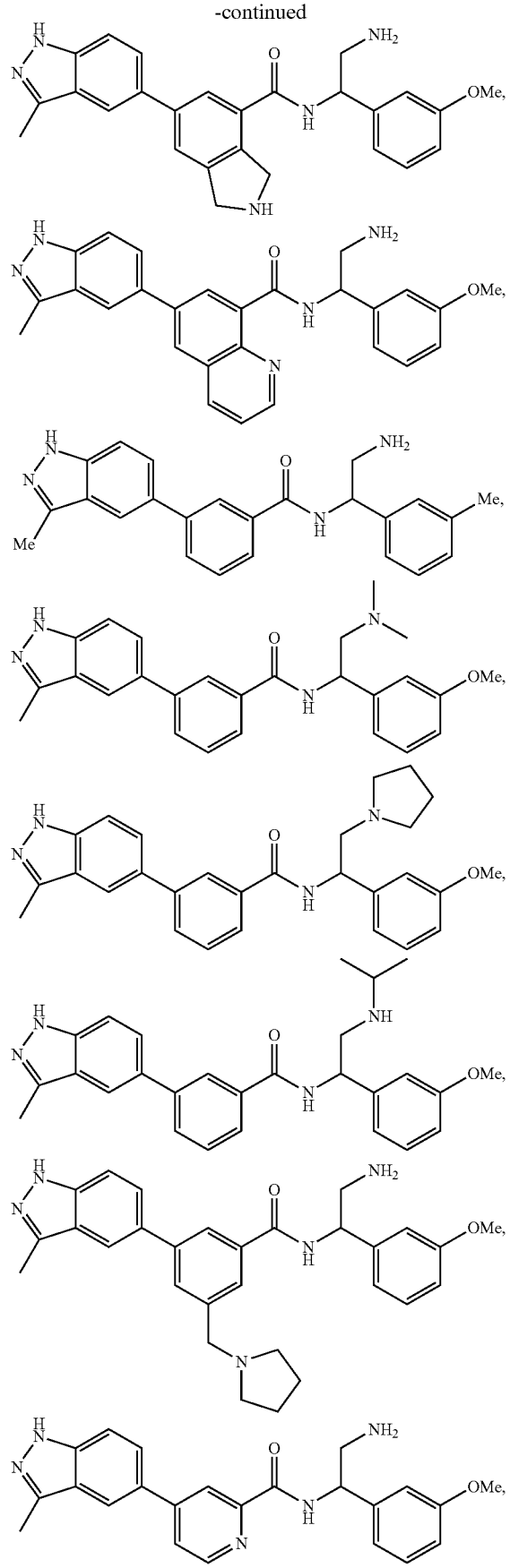
214
-continued
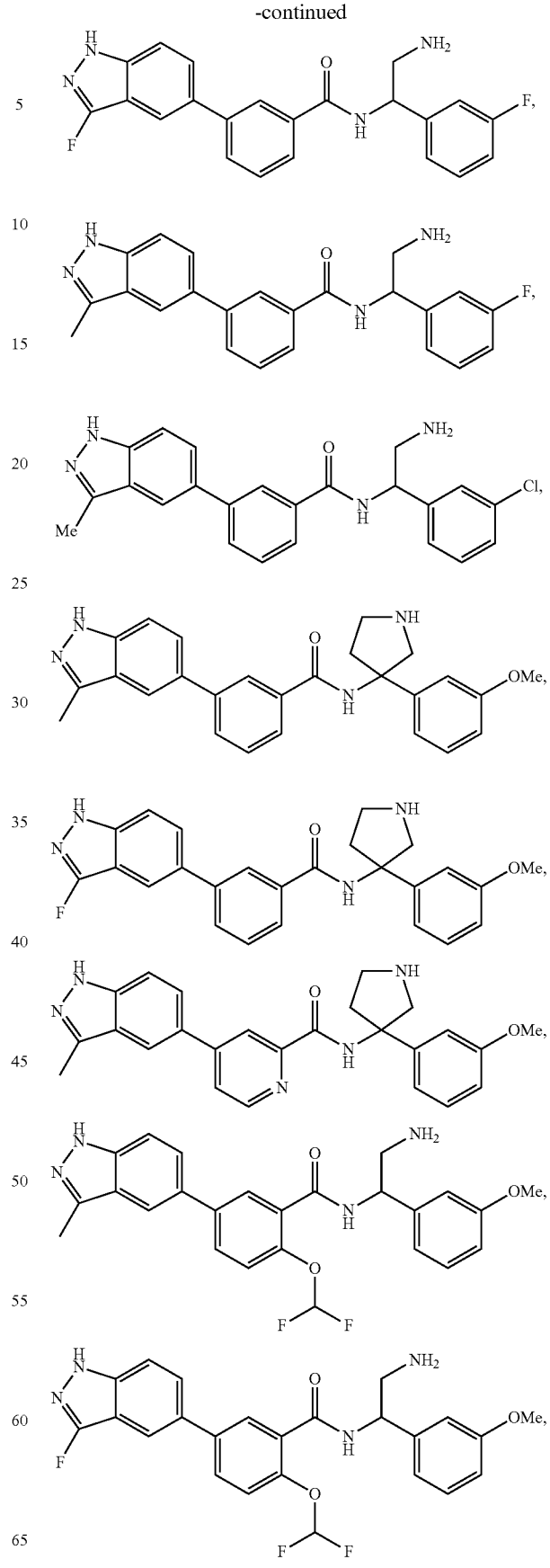

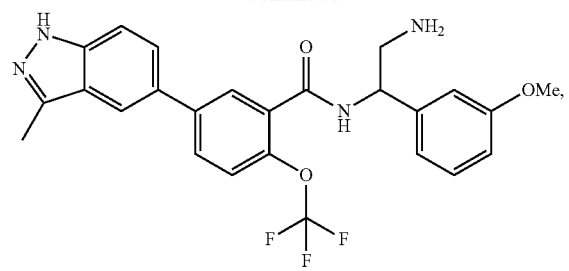
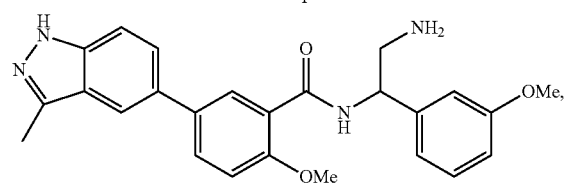
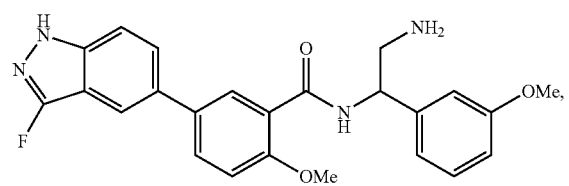
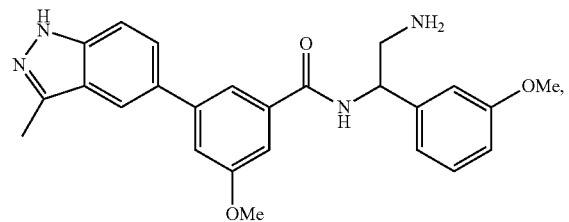
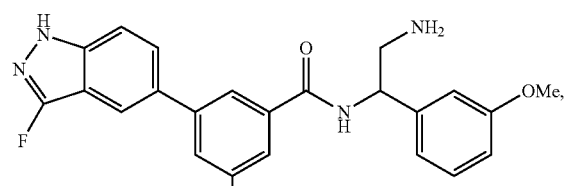
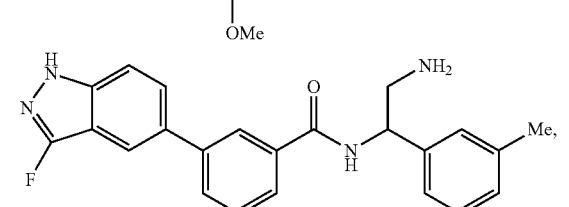
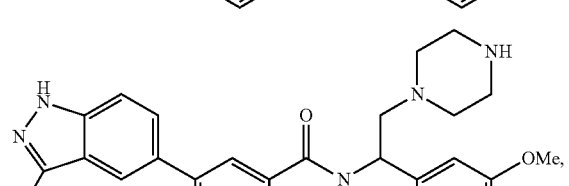
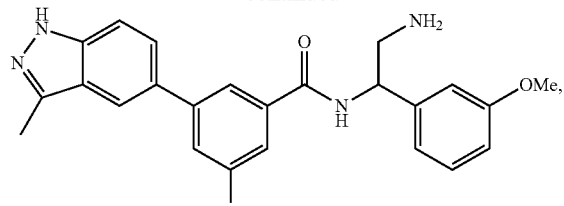
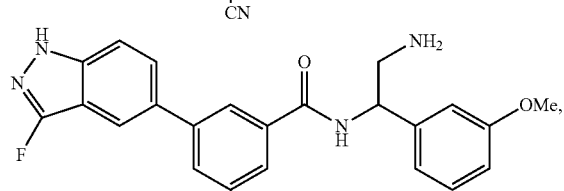
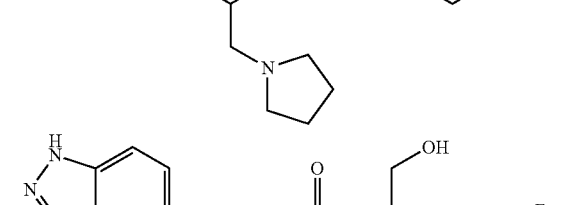
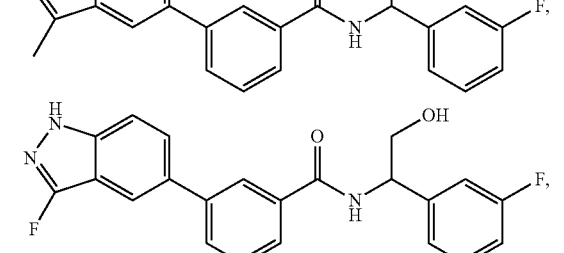
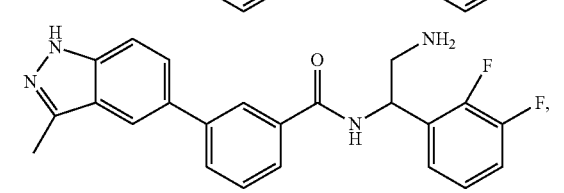
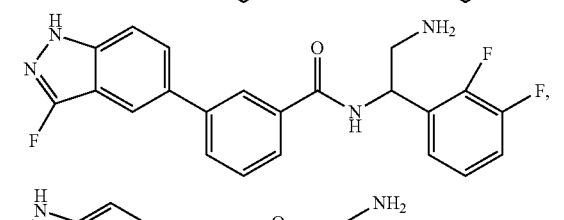
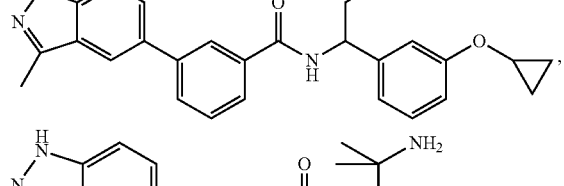

217
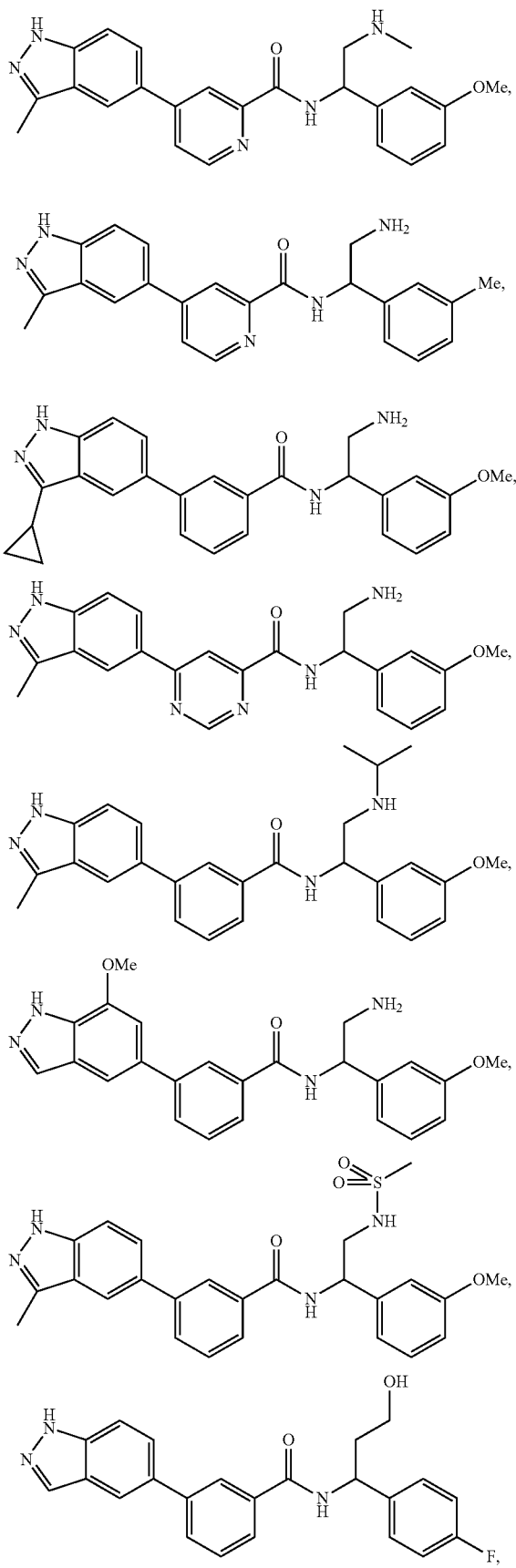
218
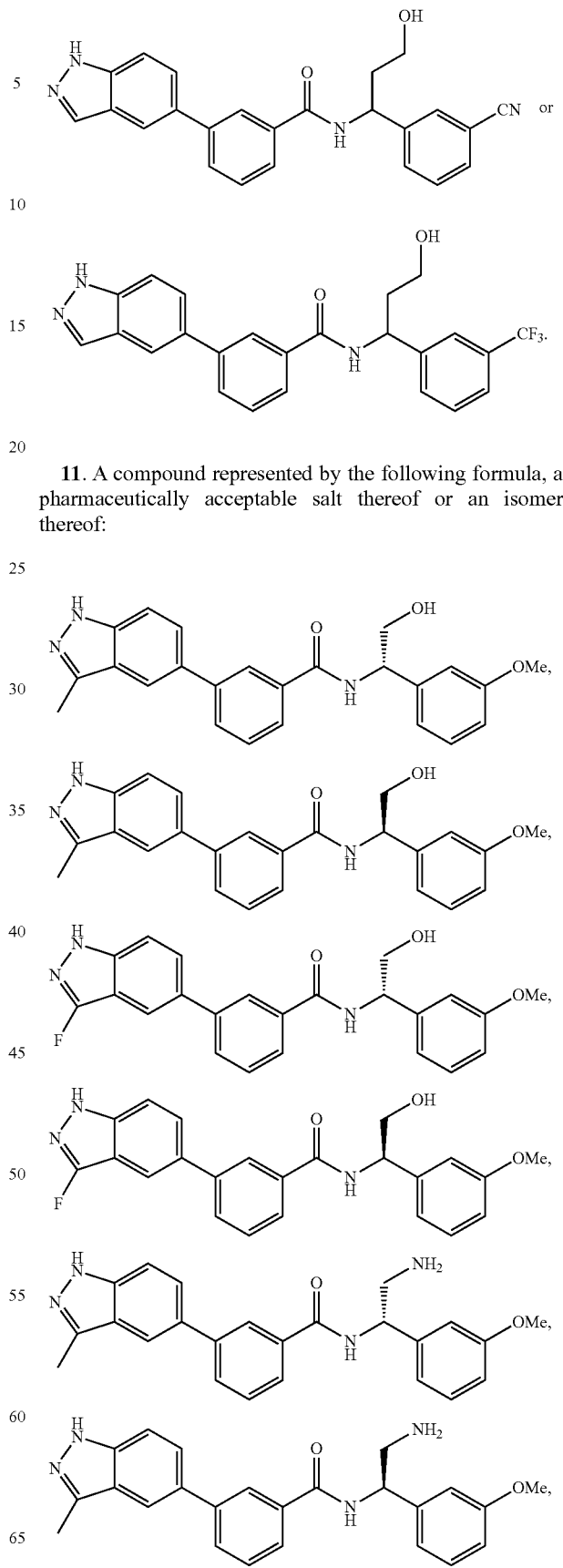
11. A compound represented by the following formula, a pharmaceutically acceptable salt thereof or an isomer thereof:

219
-continued

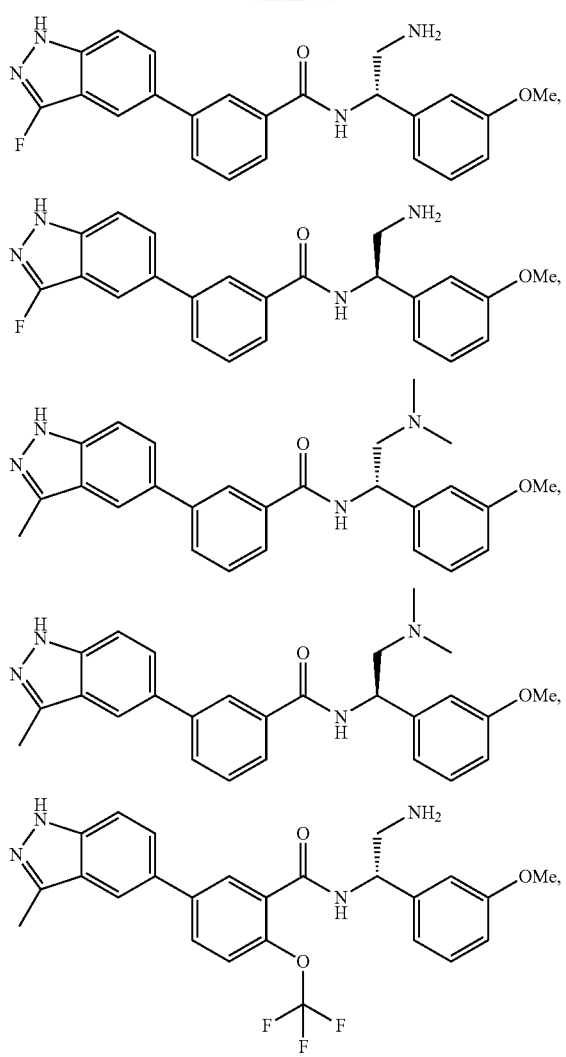

220
-continued

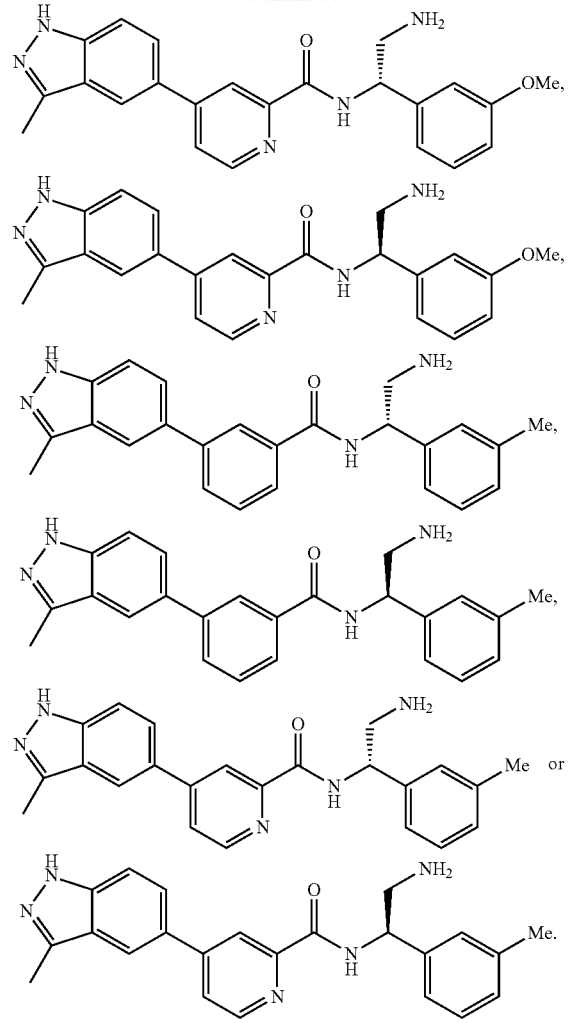

12. The compound, the pharmaceutically acceptable salt thereof or the isomer thereof as defined in claim 1, wherein the pharmaceutically acceptable salt is formate or hydrochloride.

13. A pharmaceutical composition comprising a therapeutically effective amount of the compound, the pharmaceutically acceptable salt thereof or the isomer thereof as defined in claim 1 as an active ingredient, and a pharmaceutically acceptable carrier.

14. A method for inhibiting RHO in vivo, in vitro or ex vivo, comprising contacting the compound, the pharmaceutically acceptable salt thereof or the isomer thereof as defined in claim 1 with the RHO.

15. A method for treating pulmonary fibrosis and radiation pulmonary fibrosis in a subject in need thereof, comprising administering an effective amount of the compound, the pharmaceutically acceptable salt thereof or the isomer thereof as defined in claim 1 to the subject.

16. A method for inhibiting RHO in vivo, in vitro or ex vivo, comprising contacting the compound, the pharmaceutically acceptable salt thereof or the isomer thereof as defined in claim 10 with the RHO.

17. A method for treating pulmonary fibrosis and radiation pulmonary fibrosis in a subject in need thereof, comprising administering an effective amount of the compound, the pharmaceutically acceptable salt thereof or the isomer thereof as defined in claim 10 to the subject.

18. A method for inhibiting RHO in vivo, in vitro or ex vivo, comprising contacting the compound, the pharmaceutically acceptable salt thereof or the isomer thereof as defined in claim 11 with the RHO.

19. A method for treating pulmonary fibrosis and radiation pulmonary fibrosis in a subject in need thereof, comprising administering an effective amount of the compound, the pharmaceutically acceptable salt thereof or the isomer thereof as defined in claim 11 to the subject.

\* \* \* \* \*